United States Patent
Boyle et al.

(10) Patent No.: US 10,010,547 B2
(45) Date of Patent: Jul. 3, 2018

(54) PHARMACEUTICAL COMPOUNDS

(71) Applicant: CASCADIAN THERAPEUTICS, INC., Seattle, WA (US)

(72) Inventors: Robert George Boyle, Cambridge (GB); David Winter Walker, Linton (GB); Richard Justin Boyce, Newmarket (GB); Scott Peterson, Woodinville, WA (US); Francine Farouz, San Carlos, CA (US); Cong Hung Vo, Mill Creek, WA (US)

(73) Assignee: Cascadian Therapeutics, Inc., Seattle, WA (US)

( * ) Notice: Subject to any disclaimer, the term of this patent is extended or adjusted under 35 U.S.C. 154(b) by 0 days.

(21) Appl. No.: 15/118,072

(22) PCT Filed: Feb. 9, 2015

(86) PCT No.: PCT/US2015/015030
§ 371 (c)(1),
(2) Date: Aug. 10, 2016

(87) PCT Pub. No.: WO2015/120390
PCT Pub. Date: Aug. 13, 2015

(65) Prior Publication Data
US 2016/0361310 A1    Dec. 15, 2016

Related U.S. Application Data

(60) Provisional application No. 62/083,687, filed on Nov. 24, 2014.

(30) Foreign Application Priority Data

Feb. 10, 2014    (GB) .................................. 1402277.6

(51) Int. Cl.

| | | |
|---|---|---|
| C07D 403/12 | (2006.01) |
| A61K 31/497 | (2006.01) |
| A61K 45/06 | (2006.01) |
| A61K 31/4155 | (2006.01) |
| C07D 401/14 | (2006.01) |
| C07D 405/14 | (2006.01) |
| C07D 413/14 | (2006.01) |
| C07D 403/14 | (2006.01) |
| A61K 31/454 | (2006.01) |
| A61K 31/5377 | (2006.01) |
| A61K 31/551 | (2006.01) |
| C07D 401/10 | (2006.01) |

(52) U.S. Cl.
CPC ........ *A61K 31/497* (2013.01); *A61K 31/4155* (2013.01); *A61K 31/454* (2013.01); *A61K 31/5377* (2013.01); *A61K 31/551* (2013.01); *A61K 45/06* (2013.01); *C07D 401/10* (2013.01); *C07D 401/14* (2013.01); *C07D 403/12* (2013.01); *C07D 403/14* (2013.01); *C07D 405/14* (2013.01); *C07D 413/14* (2013.01)

(58) Field of Classification Search
CPC ........................... C07D 403/12; A61K 31/497
See application file for complete search history.

(56) References Cited

U.S. PATENT DOCUMENTS

| | | | |
|---|---|---|---|
| 8,314,108 B2 | 11/2012 | Farouz et al. | |
| 8,716,287 B2 | 5/2014 | Boyle et al. | |
| 9,067,920 B2 | 6/2015 | Joseph et al. | |
| 9,630,931 B2 | 4/2017 | Boyle et al. | |
| 2007/0167449 A1* | 7/2007 | Bold ................... | C07D 231/38 514/235.5 |
| 2011/0144126 A1 | 6/2011 | Farouz et al. | |
| 2013/0065900 A1 | 3/2013 | Boyle et al. | |

FOREIGN PATENT DOCUMENTS

| | | |
|---|---|---|
| EP | 1706385 B1 | 6/2010 |
| WO | WO 2005/009435 A1 | 2/2005 |
| WO | WO 2010/077758 A1 | 7/2010 |
| WO | 2012/064548 A1 | 5/2012 |
| WO | 2015120390 A1 | 8/2015 |
| WO | 2017/105982 A1 | 6/2017 |

OTHER PUBLICATIONS

PCT International Search Report and Written Opinion, PCT International Application No. PCT/US2015/015030, Apr. 29, 2015, 13 Pages.
PCT Written Opinion, PCT Application No. PCT/US2015/015030, Feb. 19, 2016, 8 Pages.
PCT International Preliminary Report on Patentability, PCT Application No. PCT/US2015/015030, Jun. 20, 2016, 53 Pages.
Foloppe, N., et al., "Structure-Based Design of Novel Chk1 Inhibitors: Insights into Hydrogen Bonding and Protein-Ligand Affinity," J. Med. Chem., 2005, pp. 4332-4345, vol. 48.
European Application No. 15746362.1, Extended European Search Report dated Jul. 13, 2017, 10 pages.
Teng et al., "Structure-Based Design of (5-Arylamino-2H-pyrazol-3-yl)-biphenyl-2',4'-diols as Novel and Potent Human CHK1 Inhibitors," J. Med. Chem., vol. 50, No. 22, web-publication Sep. 21, 2007, pp. S1-S24, DOI:10.1021/jm0704604.
United Kingdom Application No. 1402277.6, filed Feb. 10, 2014, 79 pages.
Al-Ahmadie, et al., Synthetic Lethality in ATM-Deficient RAD50-Mutant Tumors Underlies Outlier Response to Cancer Therapy, Cancer Discovery, American Association for Cancer Research, Jun. 16, 2014, pp. 1014-1022.
Ashwell, et al., Dna Damage Detection and Repair Pathways—Recent Advances with Inhibitors of Checkpoint Kinases in Cancer Therapy, Molecular Pathways, Clin Cancer Res vol. 14(13), Jul. 1, 2008, pp. 4032-4037.

(Continued)

*Primary Examiner* — Craig D Ricci
*Assistant Examiner* — Christopher R Stone
(74) *Attorney, Agent, or Firm* — Kilpatrick Townsend & Stockton LLP

(57) ABSTRACT

This invention relates to compounds that inhibit or modulate the activity of Chk-1 kinase. Also provided are pharmaceutical compositions containing the compounds and the therapeutic uses of the compounds.

23 Claims, No Drawings

(56) References Cited

OTHER PUBLICATIONS

Ashwell, et al., Keeping checkpoint kinases in line: new selective inhibitors in clinical trials, Expert Opinion on Investigational Drugs. vol. 17(9), Oct. 2008, pp. 1331-1340.
Bao, et al., Glioma stem cells promote radio resistance by preferential activation of the DNA damage response, Nature, vol. 444, Dec. 2006, pp. 756-760.
Berge, et al., Pharmaceutical Salts, Journal of Pharmaceutical Sciences, vol. 66, No. 1, Jan. 1977, 19 pages.
Blasina, et al., Breaching the DNA damage checkpoint via PF-00477736, a novel small-molecule inhibitor of checkpoint kinase 1, Molecular Cancer Therapeutics, vol. 7(8), Aug. 2008, pp. 2394-2404.
Bristow, et al., Hypoxia, DNA repair and genetic instability, Nature Reviews, Cancer, vol. 8, Mar. 2008, pp. 180-192.
Cavelier, et al., Constitutive Activation of the DNA Damage Signaling Pathway in Acute Myeloid Leukemia with Complex Karyotype: Potential Importance for Checkpoint Targeting Therapy, Cancer Research, vol. 69 (2), Oct. 20, 2009, pp. 8652-8661.
Chaudary, et al., Hypoxia and Metastasis, Clin. Cancer Res, vol. 13(7), Apr. 1, 2007, pp. 1947-1949.
Chaudhuri, et al., CHK1 and WEE1 inhibition combine synergistically to enhance therapeutic efficacy in acute myeloid leukemia ex vivo, Haematologica, vol. 99(4), 2014, pp. 688-696.
Chen, et al., CHK1 inhibition as a strategy for targeting fanconi anemia (FA) DNA repair pathway deficient tumors, Molecular Cancer, vol. 8 (24), Apr. 16, 2009, pp. 1-16.
Dai, et al., Disruption of Src function potentiates Chk1-inhibitor-induced apoptosis in human multiple myeloma cells in vitro and in vivo, Blood, vol. 117, No. 6, Feb. 10, 2011, pp. 1947-1957.
Dai, et al., Farnesyltransferase inhibitors interact synergistically with the Chk1 inhibitor UCN-01 to induce apoptosis in human leukemia cells through interruption of both Akt and MEK/ERK pathways and activation of SEK1/JNK, Blood, vol. 105 (4), Feb. 15, 2005, 12 pages.
Dai, et al., Interruption of the Ras/MEK/ERK signaling cascade enhances Chk1 inhibitor-induced DNA damage in vitro and in vivo in human multiple myeloma cells, Blood, vol. 112(6), Sep. 15, 2008, pp. 2439-2449.
Dai, et al., New Insights into Checkpoint Kinase 1 (Chk1) in the DNA Damage Response (DDR) Signaling Network: Rationale for Employing Chk1 Inhibitors in Cancer Therapeutics, Clin Cancer Res., vol. 16(2), Jan. 15, 2010 , pp. 376-383.
Duan, et al., Fanconi anemia repair pathway dysfunction, a potential therapeutic target in lung cancer, Original Research Article, Frontiers in Oncology, Thoracic Oncology, vol. 4 Article 368, Dec. 19, 2014, pp. 1-8.
Hahn, et al., Rapamycin and UCN-01 synergistically induce apoptosis in human leukemia cells through a process that is regulated by the Raf-1/MEK/ERK, Akt, and JNK signal transduction pathways, Molecular Cancer Therapeutics, vol. 4 (3), Mar. 2005, pp. 457-470.
Hahn, et al., Rules for Making Human Tumor Cells, Mechanisms of Disease, N Engl J Med, vol. 347, No. 20, Nov. 14, 2002, pp. 1593-1603.
Höglund, et al, Therapeutic implications for the induced levels of Chk1 in Myc-expressing cancer cells, Clinical Cancer Research, Sep. 20, 2011, 36 pages.
Marcus, et al., CVP chemotherapy plus rituximab compared with CVP as first-line treatment for advanced follicular lymphoma, Blood, vol. 105 (4), Feb. 15, 2005, pp. 1417-1423.
McCabe, et al., Deficiency in the Repair of DNA Damage by Homologous Recombination and Sensitivity to Poly (ADP-Ribose) Polymerase Inhibition , Cancer Research, vol. 66 (16), Aug. 15, 2006, pp. 8109-8115.
Mitchell, et al., In Vitro and In Vivo Radiation Sensitization of Human Tumor Cells by a Novel Checkpoint Kinase Inhibitor, AZD7762, Clin. Cancer Res., vol. 16 (7), Apr. 1, 2010, pp. 2076-2084.
Nomi, et al., Clinical Significance and Therapeutic Potential of the Programmed Death-1 Ligand/Programmed Death-1 Pathway in Human Pancreatic Cancer, Cancer Therapy: Preclinical, Clin. Cancer Res., vol. 13 (7), Apr. 1, 2007, pp. 2151-2157.
Pires, et al., Exposure to acute hypoxia induces a transient DNA damage response which includes Chk1 and TLK1, Cell Cycle, vol. 9 (13), 2010, pp. 2502-2507.
Retraction: Glioma-Associated Cancer-Initiating Cells Induce Immunosuppression, Clinical Cancer Research, vol. 21, Issue 9, May 2015, 2 pages.
Singapore Application No. 11201606553X, Search Report and Written Opinion dated Sep. 25, 2017, 9 pages.
Sinha, et al., Nanotechnology in cancer therapeutics: bio conjugated nanoparticles for drug delivery, Mol. Cancer Ther., vol. 5(8), Aug. 2006, pp. 1909-1917.
Strickley, Robert G. Solubilizing Excipients in Oral and Injectable Formulations, Pharmaceutical Research, vol. 21, No. 2, Feb. 2004, pp. 201-230.

* cited by examiner

PHARMACEUTICAL COMPOUNDS

This invention relates to compounds that inhibit or modulate the activity of Chk-1 kinase. Also provided are pharmaceutical compositions containing the compounds and the therapeutic uses of the compounds.

BACKGROUND OF THE INVENTION

Chk-1 is a serine/threonine kinase involved in the induction of cell cycle checkpoints in response to DNA damage and replicative stress [*Clin. Can. Res.* 2007; 13(7)]. Cell cycle checkpoints are regulatory pathways that control the order and timing of cell cycle transitions. Most cancer cells have impaired G1 checkpoint activation due to a defective p53 tumor suppressor protein. Hahn et al., "Rules for making human tumor cells" *N. Engl. J. Med.* 2002; 347: 1593-603 and Hollstein et al., "p53 mutations in human cancers" *Science* 1991; 253: 49-53) have reported that tumours are associated with mutations in the p53 gene, a tumour suppressor gene found in about 50% of all human cancers.

Chk-1 inhibition abrogates the intra S and G2/M checkpoints and has been shown to selectively sensitise tumour cells to well known DNA damaging agents. Examples of DNA damaging agents where this sensitising effect has been demonstrated include Gemcitabine, Pemetrexed, Cytarabine, Irinotecan, Camptothecin, Cisplatin, Carboplatin [*Clin. Cancer Res.* 2010, 16, 376], Temozolomide [*Journal of Neurosurgery* 2004, 100, 1060], Doxorubicin [*Bioorg. Med. Chem. Lett.* 2006; 16:421-6], Paclitaxel [WO2010149394], Hydroxy urea [*Nat. Cell. Biol.* 2005 February; 7(2):195-20], the nitroimidazole hypoxia-targetted drug TH-302 (Meng et al., AACR, 2013 Abstract No. 2389) and ionising radiation [*Clin. Cancer Res.* 2010, 16, 2076]. See also the review article by McNeely, S., et al., "CHEK again: Revisiting the development of CHK1 inhibitors for cancer therapy, *Pharmacology & Therapeutics* (2014), http://dx.doi.orq/10.1016/j.pharmthera.2013.10.005.

Recently published data have also shown that Chk-1 inhibitors may act synergistically with PARP inhibitors [*Cancer Res.;* 66: (16)], Mek inhibitors [*Blood.* 2008 Sep. 15; 112(6): 2439-2449], Farnesyltransferase inhibitors [*Blood.* 2005 Feb. 15; 105(4):1706-16], Rapamycin [*Mol. Cancer Ther.* 2005 March; 4(3):457-70], Src inhibitors [*Blood.* 2011 Feb. 10; 117(6):1947-57] and WEE1 inhibitors (Chaudhuri et al., *Haematologica,* 2013.093187).

Resistance to chemotherapy and radiotherapy, a clinical problem for conventional therapy, has been associated with activation of the DNA damage response in which Chk-1 has been implicated (Chk-1 activation is associated with radioresistence in glioblastoma [*Nature;* 2006; 444(7):756-760] and the inhibition of Chk-1 sensitises lung cancer brain metastases to radiotherapy [*Biochem. Biophys. Res. Commun.* 2011 Mar. 4; 406(1):53-8]).

It is also envisaged that Chk-1 inhibitors, either as single agents or in combination, may be useful in treating tumour cells in which constitutive activation of DNA damage and checkpoint pathways drive genomic instability. This phenotype is associated with complex karyotypes in samples from patients with acute myeloid leukemia (AML) [*Cancer Research* 2009, 89, 8652]. In vitro antagonisation of the Chk-1 kinase with a small molecule inhibitor or by RNA interference strongly reduces the clonogenic properties of high-DNA damage level AML samples. In contrast Chk-1 inhibition has no effect on normal hematopoietic progenitors. Furthermore, recent studies have shown that the tumour microenvironment drives genetic instability [*Nature;* 2008; (8):180-192] and loss of Chk-1 sensitises cells to hypoxia/reoxygenation [*Cell Cycle;* 2010; 9(13):2502]. In neuroblastoma, a kinome RNA interference screen demonstrated that loss of Chk-1 inhibited the growth of eight neuroblastoma cell lines. Tumour cells deficient in Fanconi anemia DNA repair have shown sensitivity to Chk-1 inhibition [*Molecular Cancer* 2009, 8:24]. It has been shown that the Chk-1 specific inhibitor PF-00477736 inhibits the growth of thirty ovarian cancer cell lines [Bukczynska et al, 23$^{rd}$ Lorne Cancer Conference] and triple negative negative breast cancer cells [*Cancer Science* 2011, 102, 882]. Also, PF-00477736 has displayed selective single agent activity in a MYC oncogene driven murine spontaneous cancer model [Ferrao et al, *Oncogene* (15 Aug. 2011)]. Chk-1 inhibition, by either RNA interference or selective small molecule inhibitors, results in apoptosis of MYC-overexpressing cells both in vitro and in an in vivo mouse model of B-cell lymphoma [Hoglund et al., *Clinical Cancer Research*, Online First Sep. 20, 2011]. The latter data suggest that Chk-1 inhibitors would have utility for the treatment of MYC-driven malignancies such as B-cell lymphoma/leukemia, neuroblastoma and some breast and lung cancers. Ewing sarcoma cell lines have also been reported to be sensitive to Chk kinase inhibitors (McCalla et al., Kinase Targets in Ewing's Sarcoma Cell Lines using RNAi-based & Investigational Agents Screening Approaches, Molecular Targets 2013, Boston, USA).

It has also been reported that mutations that reduce the activity of DNA repair pathways can result in synthetically lethal interactions with Chk1 inhibition. For example, mutations that disrupt the RAD50 complex and ATM signaling increase responsiveness to Chk1 inhibition [Al-Ahmadie et al., Synthetic lethality in ATM-deficient RAD50-mutant tumors underlie outlier response to cancer therapy]. Likewise, deficiencies in the Fanconi anemia homologous DNA repair pathway lead to sensitivity to Chk1 inhibition [Chen et al., Chk1 inhibition asd a strategy for targeting fanconi anemia (FA) DNA repair pathway deficient tumors. Mol. Cancer 2009 8:24, Duan et al., Fanconi anemia repair pathway dysfunction, a potential therapeutic target in lung cancer. Frontiers in Oncology 2014 4:1]. Also, human cells that have loss of function in the Rad17 gene product are sensitive to Chk1 suppression [Shen et al., Synthetic lethal interaction between tumor suppressor RAD17 and Chk1 kinase in human cancer cells. 2014 SACNAS National Conference Abstract].

Various attempts have been made to develop inhibitors of Chk-1 kinase. For example, WO 03/10444 and WO 2005/072733 (both in the name of Millennium) disclose aryl/heteroaryl urea compounds as Chk-1 kinase inhibitors. US2005/215556 (Abbott) discloses macrocyclic ureas as kinase inhibitors. WO 02/070494, WO2006014359 and WO2006021002 (all in the name of Icos) disclose aryl and heteroaryl ureas as Chk-1 inhibitors. Our earlier applications WO/2011/141716 and WO/2013/072502 both disclose substituted pyrazinyl-phenyl ureas as Chk-1 kinase inhibitors. WO2005/009435 (Pfizer) and WO2010/077758 (Eli Lilly) disclose aminopyrazoles as Chk-1 kinase inhibitors.

The Invention

The present invention provides compounds having activity as Chk-1 kinase inhibitors. Accordingly, in a first embodiment (Embodiment 1.0), the invention provides a compound of the formula (0):

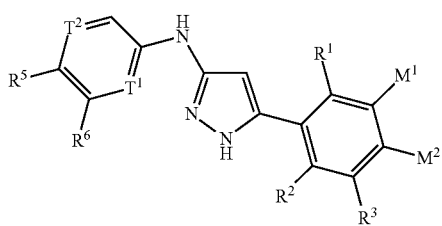

or a salt, N-oxide or tautomer thereof, wherein:

$T^1$ is selected from N and CH;
$T^2$ is selected from N, CH and CF;
$R^1$ is selected from hydrogen, fluorine, $C_{1-4}$ hydrocarbyl and $C_{1-4}$ hydrocarbyloxy;
$R^2$ is selected from hydrogen, fluorine, $C_{1-4}$ hydrocarbyl and $C_{1-4}$ hydrocarbyloxy;
$R^3$ is selected from hydrogen, methyl, fluorine, chlorine and bromine;
one of $M^1$ and $M^2$ is a group $R^4$ selected from hydrogen, methyl, fluorine, chlorine and bromine; and the other of $M^1$ and $M^2$ is a moiety -A-$R^7$;
$R^5$ is selected from hydrogen, cyano, $C_{1-3}$ alkyl, cyclopropyl, chlorine, carboxy, and $C_{1-3}$-alkoxy-carbonyl;
$R^6$ is selected from hydrogen, fluorine, $C_{1-4}$ alkyl; and $C_{1-4}$ alkoxy optionally substituted with $NR^dR^e$ where $R^d$ and $R^e$ are the same or different and each is selected from hydrogen and $C_{1-4}$ alkyl, or $NR^dR^e$ forms a 4 to 7 membered saturated heterocyclic ring optionally containing a second heteroatom ring member selected from N, O and S and oxidized forms of S, the saturated heterocyclic ring being optionally substituted with one or more substituents selected from oxo, methyl, hydroxy and fluorine;
A is selected from:
  (i) a bond;
  (ii) $(CR^pR^q)_x$ where $R^p$ and $R^q$ are each independently hydrogen or methyl and x is 1 to 4;
  (iii) an oxygen atom;
  (iv) a group $NR^r$ wherein $R^r$ is hydrogen or methyl; and
  (v) a saturated chain of 2 to 10 chain members in length containing at least one carbon atom chain member, at least one heteroatom chain member selected from nitrogen and oxygen, and optionally one or more further carbon atom chain members and/or heteroatom chain members selected from nitrogen, oxygen, sulphur, sulphinyl and sulphonyl; the saturated chain being optionally substituted with one or more substituents selected from =O, $C_{1-4}$ hydrocarbyl, fluoro-$C_{1-4}$ hydrocarbyl, hydroxy-$C_{1-4}$ hydrocarbyl, $C_{1-2}$-alkoxy-$C_{1-4}$ hydrocarbyl, and fluorine wherein two hydrocarbyl substituents on the same carbon atom may optionally link to form a ring of three to five ring members;
$R^7$ is selected from hydrogen; $R^{11}SO_2$—; amino; NH-$Hyd^1$; N($Hyd^1$)$_2$; and a group $Cyc^1$ wherein $Cyc^1$ is a carbocyclic or heterocyclic aromatic or non-aromatic group of 3 to 10 ring members of which 0 to 3 are selected from O, N and S and oxidised forms thereof, the carbocyclic or heterocyclic aromatic or non-aromatic group being optionally substituted with one or more substituents $R^8$; provided that when A is a bond, $(CR^pR^q)_x$, an oxygen atom or $NR^r$, then $R^7$ is other than hydrogen; and provided also that when $R^7$ is hydrogen, then A has a chain length of at least four chain members and contains at least two heteroatom chain members;

$R^8$ is selected from:
  halogen;
  oxo;
  cyano;
  nitro;
  a carbocyclic or heterocyclic group having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^9$; and
  a group $R^a$-$R^b$;
$R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$;
$R^b$ is:
  hydrogen;
  a carbocyclic and heterocyclic group having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^9$;
  an acyclic $C_{1-12}$ hydrocarbyl group optionally substituted with one or more substituents selected from hydroxy; oxo; halogen; cyano; nitro; carboxy; amino; mono- or di-$C_{1-8}$ non-aromatic hydrocarbylamino; and carbocyclic and heterocyclic groups having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^9$; wherein one or more but not all of the carbon atoms of the acyclic $C_{1-12}$ hydrocarbyl group may optionally be replaced by O, S, SO, $SO_2$, $NR^c$, $X^1C(X^2)$, $C(X^2)X^1$ or $X^1C(X^2)X^1$;
$R^c$ is:
  hydrogen;
  a carbocyclic and heterocyclic group having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^9$;
  an acyclic $C_{1-12}$ hydrocarbyl group optionally substituted with one or more substituents selected from hydroxy; oxo; halogen; cyano; nitro; carboxy; amino;
  mono- or di-$C_{1-8}$ non-aromatic hydrocarbylamino; and carbocyclic and heterocyclic groups having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^9$; wherein one or more but not all of the carbon atoms of the acyclic $C_{1-12}$ hydrocarbyl group may optionally be replaced by O, S, SO, $SO_2$, NH, N—$C_{1-4}$ alkyl, C(O)O, OC(O), NH(CO), C(O)NH, NH(CO)NH, N($C_{1-4}$alkyl)C(O), C(O)N($C_{1-4}$ alkyl)
$X^1$ is O, S or $NR^c$; and
$X^2$ is =O, =S or =$NR^c$;
wherein $R^9$ is selected from $R^8$ provided that when the substituents $R^9$ contain a carbocyclic or heterocyclic group, the said carbocyclic or heterocyclic group is unsubstituted or substituted with one or more substituents $R^{10}$;
$R^{10}$ is selected from halogen, oxo, cyano, and an acyclic $C_{1-6}$ hydrocarbyl group optionally substituted with one or more substituents selected from hydroxy; oxo; halogen; cyano; carboxy; amino; mono- or di-$C_{1-2}$ alkylamino; wherein one but not all of the carbon atoms of the acyclic $C_{1-6}$ hydrocarbyl group may optionally be replaced by O, S, SO, $SO_2$, NH or NMe;

$R^{11}$ is selected from amino, $Hyd^1$, NH-$Hyd^1$, N($Hyd^1$)$_2$; and $Cyc^1$;

$Hyd^1$ is a non-aromatic $C_{1-6}$ hydrocarbyl group optionally substituted by one or more substituents selected from halogen, cyano, hydroxy, amino and $Cyc^1$, wherein one or two of the carbon atoms of the non-aromatic $C_{1-6}$ hydrocarbyl group may optionally be replaced by O, NH, N-$Hyd^2$, C(=O), S, SO or $SO_2$, provided that at least one carbon atom of the hydrocarbyl group remains;

$Hyd^2$ is a $C_{1-4}$ hydrocarbyl group;

and wherein in any group consisting of or containing a hydrocarbyl moiety, the hydrocarbyl moiety is a hydrocarbon group optionally containing one or more single, double or triple carbon-carbon bonds or combinations thereof.

Particular embodiments of the invention are as set out below in Embodiments 1.01 to 1.107.

1.01 A compound according to Embodiment 1.0 wherein $T^2$ is N.

1.02 A compound according to Embodiment 1.01 wherein both $T^1$ and $T^2$ are N.

1.03 A compound according to any one of Embodiments 1.0 to 1.02 wherein $M^2$ is a moiety -A-$R^7$.

1.04 A compound according to any one of Embodiments 1.0 to 1.03 wherein $R^5$ is selected from hydrogen, cyano, $C_{1-3}$ alkyl, cyclopropyl and chlorine.

1.05 A compound according to Embodiment 1.04 wherein $R^5$ is selected from hydrogen, cyano, $C_{1-3}$ alkyl and cyclopropyl.

1.06 A compound according to Embodiment 1.05 wherein $R^5$ is selected from hydrogen, cyano and methyl.

1.07 A compound according to any one of Embodiments 1.0 to 1.06 wherein $R^6$ is selected from hydrogen, $C_{1-4}$ alkyl; and $C_{1-4}$ alkoxy optionally substituted with $NR^dR^e$ where $R^d$ and $R^e$ are the same or different and each is selected from hydrogen and $C_{1-4}$ alkyl, or $NR^dR^e$ forms a 4 to 7 membered saturated heterocyclic ring optionally containing a second heteroatom ring member selected from N, O and S and oxidized forms of S, the saturated heterocyclic ring being optionally substituted with one or more substituents selected from oxo, methyl, hydroxy and fluorine.

1.08 A compound according to any one of Embodiments 1.0 to 1.07 wherein A is selected from:
(i) a bond;
(ii) $(CR^pR^q)_x$ where $R^p$ and $R^q$ are each independently hydrogen or methyl and x is 1 to 4;
(iii) an oxygen atom;
(iv) a group $NR^r$ wherein $R^r$ is hydrogen or methyl; and
(v) a saturated chain of 2 to 10 chain members in length containing at least one carbon atom chain member, at least one heteroatom chain member selected from nitrogen and oxygen, and optionally one or more further carbon atom chain members and/or heteroatom chain members selected from nitrogen, oxygen, sulphur, sulphinyl and sulphonyl; the saturated chain being optionally substituted with one or more substituents selected from =O, $C_{1-4}$ hydrocarbyl and fluorine wherein two hydrocarbyl substituents on the same carbon atom may optionally link to form a ring of three to five ring members.

1.09 A compound according to any one of Embodiments 1.0 to 1.08 wherein A is selected from:
(i) a bond;
(ii) $CH_2$;
(iii) an oxygen atom; and
(iv) a saturated chain of 2 to 10 chain members in length containing at least one carbon atom chain member, at least one heteroatom chain member selected from nitrogen and oxygen, and optionally one or more further carbon atom chain members and/or heteroatom chain members selected from nitrogen, oxygen, sulphur, sulphinyl and sulphonyl; the saturated chain being optionally substituted with one or more substituents selected from =O, $C_{1-4}$ hydrocarbyl and fluorine wherein two hydrocarbyl substituents on the same carbon atom may optionally link to form a ring of three to five ring members.

1.1 A compound according to Embodiment 1.0 wherein the compound is of the formula (1):

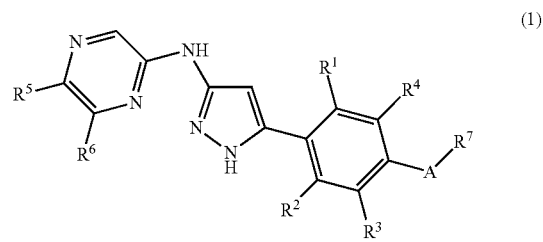

(1)

or a salt, N-oxide or tautomer thereof, wherein:

A is selected from:
a bond; and
(ii) a saturated chain of 2 to 10 chain members in length containing at least one carbon atom chain member, at least one heteroatom chain member selected from nitrogen and oxygen, and optionally one or more further carbon atom chain members and/or heteroatom chain members selected from nitrogen, oxygen, sulphur, sulphinyl and sulphonyl; the saturated chain being optionally substituted with one or more substituents selected from =O, $C_{1-4}$ hydrocarbyl and fluorine wherein two hydrocarbyl substituents on the same carbon atom may optionally link to form a ring of three to five ring members;

$R^1$ is selected from hydrogen, fluorine, $C_{1-4}$ hydrocarbyl and $C_{1-4}$ hydrocarbyloxy;

$R^2$ is selected from hydrogen, fluorine, $C_{1-4}$ hydrocarbyl and $C_{1-4}$ hydrocarbyloxy;

$R^3$ is selected from hydrogen, methyl, chlorine and bromine;

$R^4$ is selected from hydrogen, methyl, chlorine and bromine;

$R^5$ is selected from hydrogen, cyano and methyl;

$R^6$ is selected from hydrogen, $C_{1-4}$ alkyl; and $C_{1-4}$ alkoxy optionally substituted with $NR^dR^e$ where $R^d$ and $R^e$ are the same or different and each is selected from hydrogen and $C_{1-4}$ alkyl, or $NR^dR^e$ forms a 4 to 7 membered saturated heterocyclic ring optionally containing a second heteroatom ring member selected from N, O and S and oxidized forms of S, the saturated heterocyclic ring being optionally substituted with one or more substituents selected from oxo, methyl, hydroxy and fluorine;

$R^7$ is selected from hydrogen; $R^{11}SO_2$—; amino, NH-$Hyd^1$, N($Hyd^1$)$_2$; and a group $Cyc^1$ wherein $Cyc^1$ is a carbocyclic or heterocyclic aromatic or non-aromatic group of 3 to 10 ring members of which 0 to 3 are selected from O, N and S and oxidised forms thereof, the carbocyclic or heterocyclic aromatic or non-aromatic group being optionally substituted with one or more substituents $R^8$; provided that when A is a bond, then $R^7$ is $Cyc^1$; and provided also that when $R^7$ is hydrogen, then A has a chain length of at least four chain members and contains at least two heteroatom chain members;

$R^8$ is selected from:
  halogen;
  oxo;
  cyano;
  nitro;
  a carbocyclic or heterocyclic group having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^9$; and
  a group $R^a$-$R^b$;

$R^a$ is a bond, O, CO, $X^1C(X^2)$; $C(X^2)X^1$; $X^1C(X^2)X^1$; S, SO, $SO_2$, $NR^c$, $SO_2NR^c$ or $NR^cSO_2$;

$R^b$ is:
  hydrogen;
    a carbocyclic and heterocyclic group having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^9$;
    an acyclic $C_{1-12}$ hydrocarbyl group optionally substituted with one or more substituents selected from hydroxy; oxo; halogen; cyano; nitro; carboxy; amino; mono- or di-$C_{1-8}$ non-aromatic hydrocarbylamino; and carbocyclic and heterocyclic groups having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^9$; wherein one or more but not all of the carbon atoms of the acyclic $C_{1-12}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is:
  hydrogen;
    a carbocyclic and heterocyclic group having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^9$;
    an acyclic $C_{1-12}$ hydrocarbyl group optionally substituted with one or more substituents selected from hydroxy; oxo; halogen; cyano; nitro; carboxy; amino;
  mono- or di-$C_{1-8}$ non-aromatic hydrocarbylamino; and carbocyclic and heterocyclic groups having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^9$; wherein one or more but not all of the carbon atoms of the acyclic $C_{1-12}$ hydrocarbyl group may optionally be replaced by O, S, SO, $SO_2$, NH, N—$C_{1-4}$ alkyl, C(O)O, OC(O), NH(CO), C(O)NH, NH(CO)NH, N($C_{1-4}$alkyl)C(O), C(O)N($C_{1-4}$ alkyl)

$X^1$ is O, S or $NR^c$; and
$X^2$ is =O, =S or =$NR^c$;

wherein $R^9$ is selected from $R^8$ provided that when the substituents $R^9$ contain a carbocyclic or heterocyclic group, the said carbocyclic or heterocyclic group is unsubstituted or substituted with one or more substituents $R^{10}$;

$R^{10}$ is selected from halogen, oxo, cyano, and an acyclic $C_{1-6}$ hydrocarbyl group optionally substituted with one or more substituents selected from hydroxy; oxo; halogen; cyano; carboxy; amino; mono- or di-$C_{1-2}$ alkylamino; wherein one but not all of the carbon atoms of the acyclic $C_{1-6}$ hydrocarbyl group may optionally be replaced by O, S, SO, $SO_2$, NH or NMe;

$R^{11}$ is selected from amino, $Hyd^1$, NH-$Hyd^1$, N($Hyd^1$)$_2$; and $Cyc^1$;

$Hyd^1$ is a non-aromatic $C_{1-6}$ hydrocarbyl group optionally substituted by one or more substituents selected from halogen, cyano, hydroxy, amino and $Cyc^1$, wherein one or two of the carbon atoms of the non-aromatic $C_{1-6}$ hydrocarbyl group may optionally be replaced by O, NH, N-$Hyd^2$, C(=O), S, SO or $SO_2$, provided that at least one carbon atom of the hydrocarbyl group remains;

$Hyd^2$ is a $C_{1-4}$ hydrocarbyl group;

and wherein in any group consisting of or containing a hydrocarbyl moiety, the hydrocarbyl moiety is a hydrocarbon group optionally containing one or more single, double or triple carbon-carbon bonds or combinations thereof.

1.2 A compound according to any one of Embodiments 1.0 to 1.1 wherein $R^1$ is selected from hydrogen, fluorine, $C_{1-3}$ hydrocarbyl and $C_{1-3}$ hydrocarbyloxy.

1.3 A compound according to Embodiment 1.2 wherein $R^1$ is selected from hydrogen, fluorine, $C_{1-2}$ hydrocarbyl and $C_{1-2}$ hydrocarbyloxy.

1.4 A compound according to Embodiment 1.3 wherein $R^1$ is selected from hydrogen, fluorine, methyl and methoxy.

1.5 A compound according to Embodiment 1.1 wherein $R^1$ is selected from hydrogen and $C_{1-4}$ hydrocarbyloxy.

1.6 A compound according to Embodiment 1.5 wherein $R^1$ is selected from hydrogen and methoxy.

1.7 A compound according to Embodiment 1.6 wherein $R^1$ is hydrogen.

1.8 A compound according to Embodiment 1.6 wherein $R^1$ is methoxy.

1.9 A compound according to any one of Embodiments 1.0 to 1.8 wherein $R^2$ is selected from hydrogen, fluorine, $C_{1-3}$ hydrocarbyl and $C_{1-3}$ hydrocarbyloxy.

1.9 A compound according to Embodiment 1.9 wherein $R^2$ is selected from hydrogen, fluorine and $C_{1-3}$ hydrocarbyloxy.

1.10 A compound according to Embodiment 1.9 wherein $R^2$ is selected from hydrogen, fluorine, $C_{1-2}$ hydrocarbyl and $C_{1-2}$ hydrocarbyloxy.

1.11 A compound according to Embodiment 1.10 wherein $R^2$ is selected from hydrogen, fluorine, methyl and methoxy.

1.12 A compound according to any one of Embodiments 1.0 to 1.8 wherein $R^2$ is selected from hydrogen and $C_{1-4}$ hydrocarbyloxy.

1.13 A compound according to Embodiment 1.12 wherein $R^2$ is selected from hydrogen and methoxy.

1.14 A compound according to Embodiment 1.13 wherein $R^2$ is hydrogen.

1.15 A compound according to Embodiment 1.13 wherein $R^2$ is methoxy.

1.16 A compound according to any one of Embodiments 1.0 to 1.1 wherein one of $R^1$ and $R^2$ is hydrogen and the other is methoxy.

1.17 A compound according to Embodiment 1.1 wherein both of $R^1$ and $R^2$ are methoxy.

1.18 A compound according to any one of Embodiments 1.0 to 1.1 wherein both of $R^1$ and $R^2$ are hydrogen.

1.19 A compound according to any one of Embodiments 1.0 to 1.18 wherein $R^3$ is selected from hydrogen and chlorine.

1.20 A compound according to any one of Embodiments 1.0 to 1.19 wherein $R^4$ is selected from hydrogen, methyl and chlorine.

1.21 A compound according to Embodiment 1.19 or Embodiment 1.20 wherein one of $R^3$ and $R^4$ is hydrogen and the other is chlorine.

1.22 A compound according to Embodiment 1.19 or Embodiment 1.20 wherein both of $R^3$ and $R^4$ are hydrogen.

1.23 A compound according to any one of Embodiments 1.0 to 1.1 wherein $R^1$ is methoxy and $R^2$, $R^3$ and $R^4$ are all hydrogen.

1.24 A compound according to any one of Embodiments 1.0 to 1.1 wherein $R^1$ and $R^2$ are both methoxy and $R^3$ and $R^4$ are both hydrogen.

1.25 A compound according to any one of Embodiments 1.0 to 1.1 wherein $R^1$, $R^2$, $R^3$ and $R^4$ are all hydrogen.

1.26 A compound according to any one of Embodiments 1.0 to 1.1 wherein $R^1$ is methoxy, $R^2$ is hydrogen, $R^3$ is chlorine and $R^4$ is hydrogen.

1.27 A compound according to any one of Embodiments 1.0 to 1.26 wherein $R^5$ is selected from hydrogen and cyano.

1.28 A compound according to Embodiment 1.27 wherein $R^5$ is cyano.

1.29 A compound according to Embodiment 1.27 wherein $R^5$ is hydrogen.

1.30 A compound according to any one of Embodiments 1.0 to 1.29 wherein $R^6$ is selected from hydrogen, methyl and methoxy.

1.30 A compound according to Embodiment 1.30 wherein $R^6$ is hydrogen.

1.30B A compound according to any one of Embodiments 1.1 to 1.30A wherein A is selected from:
  (i) a bond;
  (ii) $(CR^pR^q)_x$ where $R^p$ and $R^q$ are each independently hydrogen or methyl and x is 1 to 3;
  (iii) an oxygen atom;
  (iv) a group $NR^r$ wherein $R^r$ is hydrogen or methyl; and
  (v) a saturated chain of 2 to 8 chain members in length containing at least one carbon atom chain member, at least one heteroatom chain member selected from nitrogen and oxygen, and optionally one or more further carbon atom chain members and/or heteroatom chain members selected from nitrogen, oxygen, sulphur, sulphinyl and sulphonyl; the saturated chain being optionally substituted with one or more substituents selected from =O, $C_{1-4}$ hydrocarbyl, hydroxy-$C_{1-4}$ hydrocarbyl, $C_{1-2}$-alkoxy-$C_{1-4}$ hydrocarbyl, and fluorine wherein two hydrocarbyl substituents on the same carbon atom may optionally link to form a ring of three to five ring members;
  provided that when A is a bond, $CR^pR^q$ or an oxygen atom, then $R^7$ is other than hydrogen; and provided also that when $R^7$ is hydrogen, then A has a chain length of at least four chain members and contains at least two heteroatom chain members.

1.30C A compound according to Embodiment 1.30B wherein A is selected from:
  (i) a bond;
  (ii) $(CR^pR^q)_x$ where $R^p$ and $R^q$ are each independently hydrogen or methyl and x is 1 to 3;
  (iii) an oxygen atom;
  (iv) a group $NR^r$ wherein $R^r$ is hydrogen or methyl; and
  (v) a saturated chain of 2 to 6 chain members in length containing at least one carbon atom chain member, at least one heteroatom chain member selected from nitrogen and oxygen, and optionally one or more further carbon atom chain members and/or heteroatom chain members selected from nitrogen, oxygen, sulphur, sulphinyl and sulphonyl; the saturated chain being optionally substituted with one or more substituents selected from =O, $C_{1-4}$ hydrocarbyl, hydroxy-$C_{14}$ hydrocarbyl, $C_{1-2}$-alkoxy-$C_{1-4}$ hydrocarbyl, and fluorine wherein two hydrocarbyl substituents on the same carbon atom may optionally link to form a ring of three to five ring members;
  provided that when A is a bond, $CR^pR^q$ or an oxygen atom, then $R^7$ is other than hydrogen; and provided also that when $R^7$ is hydrogen, then A has a chain length of at least four chain members and contains at least two heteroatom chain members.

1.30D A compound according to Embodiment 1.30C wherein A is selected from:
  (i) a bond;
  (ii) $(CR^pR^q)_x$ where $R^p$ and $R^q$ are each independently hydrogen or methyl and x is 1;
  (iii) an oxygen atom;
  (iv) a group $NR^r$ wherein $R^r$ is hydrogen or methyl; and
  (v) a saturated chain of 2 to 6 chain members in length containing at least one carbon atom chain member, at least one heteroatom chain member selected from nitrogen and oxygen, and optionally one or more further carbon atom chain members and/or heteroatom chain members selected from nitrogen, oxygen, sulphur, sulphinyl and sulphonyl; the saturated chain being optionally substituted with one or more substituents selected from =O, $C_{1-4}$ hydrocarbyl, and fluorine wherein two hydrocarbyl substituents on the same carbon atom may optionally link to form a ring of three to five ring members;
  provided that when A is a bond, $CR^pR^q$ or an oxygen atom, then $R^7$ is other than hydrogen; and provided also that when $R^7$ is hydrogen, then A has a chain length of at least four chain members and contains at least two heteroatom chain members 1.30E A compound according to Embodiment 1.30D wherein A is selected from:
  (i) a bond;
  (ii) $CR^pR^q$ where $R^p$ and $R^q$ are each independently hydrogen or methyl;
  (iii) an oxygen atom; and
  (v) a saturated chain of 2 to 6 chain members in length containing at least one carbon atom chain member, at least one heteroatom chain member selected from nitrogen and oxygen, and optionally one or more further carbon atom chain members and/or heteroatom chain members selected from nitrogen, oxygen, sulphur, sulphinyl and sulphonyl; the saturated chain being optionally substituted with one or more substituents selected from =O, $C_{1-4}$ hydrocarbyl and fluorine wherein two hydrocarbyl substituents on the same carbon atom may optionally link to form a ring of three to five ring members;
  provided that when A is a bond, $CR^pR^q$ or an oxygen atom, then $R^7$ is other than hydrogen; and provided also that when $R^7$ is hydrogen, then A has a chain length of at least four chain members and contains at least two heteroatom chain members.

1.30F A compound according to Embodiment 1.30E wherein A is selected from:
  (i) a bond;
  (ii) $CR^pR^q$ where $R^p$ and $R^q$ are each independently hydrogen or methyl;
  (iii) an oxygen atom; and (v) a saturated chain of 2 to 5 chain members in length containing at least one carbon atom chain member, at least one heteroatom chain member selected from nitrogen and oxygen, and optionally one or more further carbon atom chain members and/or heteroatom chain members selected from nitrogen, oxygen, sulphur, sulphinyl and sulphonyl; the saturated chain being optionally substituted with one or more substituents selected from =O, $C_{1-4}$ hydrocarbyl and fluorine wherein two hydrocarbyl substituents on the same carbon atom may optionally link to form a ring of three to five ring members;

provided that when A is a bond, $CR^pR^q$ or an oxygen atom, then $R^7$ is other than hydrogen; and provided also that when $R^7$ is hydrogen, then A has a chain length of at least four chain members and contains at least two heteroatom chain members.

1.30G A compound according to Embodiment 1.30F wherein A is selected from:
(i) a bond;
(ii) $CH_2$;
(iii) an oxygen atom; and
(v) a saturated chain of 2 to 5 chain members in length containing a single heteroatom chain member which is nitrogen or oxygen; the saturated chain being optionally substituted with one or more substituents selected from =O, $C_{1-4}$ hydrocarbyl and fluorine;

provided that when A is a bond, $CH_2$ or an oxygen atom, then $R^7$ is other than hydrogen; and provided also that when $R^7$ is hydrogen, then A has a chain length of at least four chain members and contains at least two heteroatom chain members.

1.30H A compound according to Embodiment 1.30G wherein A is selected from:
(i) a bond;
(ii) $CH_2$;
(iii) an oxygen atom; and
(v) a saturated chain of 2 to 5 chain members in length having the formula $-(CR^vR^w)_m-J-(CR^xR^y)_n-$; wherein J is $NR^z$, O or $NHC(=O)$; $R^v$, $R^w$, $R^x$, $R^y$ and $R^z$ are each hydrogen or methyl; m is 0, 1, 2 or 3 and n is 0, 1, 2 or 3 wherein the sum of m and n is no greater than 4 or, when J is $NH(=O)$, the sum of m and n is no greater than 3;
provided that $R^7$ is other than hydrogen.

1.30J A compound according to Embodiment 1.30H wherein A is selected from:
(i) a bond;
(ii) $CH_2$;
(iii) an oxygen atom; and
(v) a saturated chain of 2 to 4 chain members in length having the formula $-(CR^vR^w)_m-J-(CR^xR^y)_n-$; wherein J is $NR^z$, O or $NHC(=O)$; $R^v$, $R^w$, $R^y$ and $R^z$ are each hydrogen or methyl; m is 0, 1 or 2 and n is 0, 1 or 2 wherein the sum of m and n is no greater than 3 or, when J is $NH(=O)$, the sum of m and n is no greater than 2;
provided that $R^7$ is other than hydrogen.

1.30K A compound according to any one of Embodiments 1.0 to 1.30C wherein, when A is $(CR^pR^q)_x$, then x is 1, 2 or 3.

1.30L A compound according to any one of Embodiments 1.0 to 1.30C wherein, when A is $(CR^pR^q)_x$, then x is 1 or 2.

1.30M A compound according to any one of Embodiments 1.0 to 1.30C wherein, when A is $(CR^pR^q)_x$, then x is 1.

1.31 A compound according to Embodiment 1.30B wherein A is selected from:
(i) a bond; and
(ii) a saturated chain of 2 to 8 chain members in length containing at least one carbon atom chain member, at least one heteroatom chain member selected from nitrogen and oxygen, and optionally one or more further carbon atom chain members and/or heteroatom chain members selected from nitrogen, oxygen, sulphur, sulphinyl and sulphonyl; the saturated chain being optionally substituted with one or more substituents selected from =O, $C_{1-4}$ hydrocarbyl and fluorine wherein two hydrocarbyl substituents on the same carbon atom may optionally link to form a ring of three to five ring members;
provided that when A is a bond, then $R^7$ is $Cyc^1$; and provided also that when $R^7$ is hydrogen, then A has a chain length of at least four chain members and contains at least two heteroatom chain members.

1.32 A compound according to Embodiment 1.31 wherein A is selected from:
(i) a bond; and
(ii) a saturated chain of 2 to 6 chain members in length containing at least one carbon atom chain member, at least one heteroatom chain member selected from nitrogen and oxygen, and optionally one or more further carbon atom chain members and/or heteroatom chain members selected from nitrogen, oxygen, sulphur, sulphinyl and sulphonyl; the saturated chain being optionally substituted with one or more substituents selected from =O, $C_{1-4}$ hydrocarbyl and fluorine wherein two hydrocarbyl substituents on the same carbon atom may optionally link to form a ring of three to five ring members;
provided that when A is a bond, then $R^7$ is $Cyc^1$; and provided also that when $R^7$ is hydrogen, then A has a chain length of at least four chain members and contains at least two heteroatom chain members.

1.33 A compound according to Embodiment 1.32 wherein A is selected from:
(i) a bond; and
(ii) a saturated chain of 2 to 5 chain members in length containing at least one carbon atom chain member, at least one heteroatom chain member selected from nitrogen and oxygen, and optionally one or more further carbon atom chain members and/or heteroatom chain members selected from nitrogen, oxygen, sulphur, sulphinyl and sulphonyl; the saturated chain being optionally substituted with one or more substituents selected from =O, $C_{1-4}$ hydrocarbyl and fluorine wherein two hydrocarbyl substituents on the same carbon atom may optionally link to form a ring of three to five ring members;
provided that when A is a bond, then $R^7$ is $Cyc^1$; and provided also that when $R^7$ is hydrogen, then A has a chain length of at least four chain members and contains at least two heteroatom chain members.

1.34 A compound according to Embodiment 1.33 wherein A is selected from:
(i) a bond; and
(ii) a saturated chain of 2 to 5 chain members in length containing a single heteroatom chain member which is nitrogen or oxygen; the saturated chain being optionally substituted with one or more substituents selected from =O, $C_{1-4}$ hydrocarbyl and fluorine; provided that when A is a bond, then $R^7$ is $Cyc^1$; and provided also that $R^7$ is other than hydrogen.

1.35 A compound according to Embodiment 1.34 wherein A is selected from:
(i) a bond; and
(ii) a saturated chain of 2 to 5 chain members in length containing a single heteroatom chain member which is nitrogen; the saturated chain being optionally substituted with one or more substituents selected from =O, $C_{1-4}$ hydrocarbyl and fluorine; provided that when A is a bond, then $R^7$ is $Cyc^1$; and provided also that $R^7$ is other than hydrogen.

1.36 A compound according to Embodiment 1.35 wherein A is selected from:
(i) a bond; and
(ii) a saturated chain of 2 to 5 chain members in length containing a single heteroatom chain member which is nitrogen; the saturated chain being optionally substituted with one or more substituents selected from methyl and fluorine; provided that when A is a bond, then $R^7$ is $Cyc^1$; and provided also that $R^7$ is other than hydrogen.

1.37 A compound according to Embodiment 1.36 wherein A is selected from:
(i) a bond; and
(ii) a saturated chain of 2 to 5 chain members in length containing a single heteroatom chain member which is nitrogen; the saturated chain being optionally substituted with one or more methyl groups; provided that when A is a bond, then $R^7$ is $Cyc^1$; and provided also that $R^7$ is other than hydrogen.

1.38 A compound according to Embodiment 1.37 wherein A is selected from:
(i) a bond; and
(ii) a saturated chain of 2 to 5 chain members in length having the formula —$(CR^vR^w)_m$—NH—$(CR^xR^y)_n$—; wherein $R^v$, $R^w$, $R^x$ and $R^y$ are each hydrogen or methyl; m is 0, 1, 2 or 3 and n is 0, 1, 2 or 3 wherein the sum of m and n is no greater than 4; provided that when A is a bond, then $R^7$ is $Cyc^1$; and provided also that $R^7$ is other than hydrogen.

1.39 A compound according to Embodiment 1.38 wherein A is selected from:
(i) a bond; and
(ii) a saturated chain of 2 to 4 chain members in length having the formula —$(CR^vR^w)_m$—NH—$(CR^xR^y)_n$—; wherein $R^v$, $R^w$, $R^x$ and $R^y$ are each hydrogen or methyl; m is 0, 1 or 2 and n is 0, 1 or 2 wherein the sum of m and n is no greater than 3; provided that when A is a bond, then $R^7$ is $Cyc^1$; and provided also that $R^7$ is other than hydrogen.

1.40 A compound according to any one of Embodiments 1.30H, 1.30J, 1.38 and 1.39 wherein no more than two $R^v$, $R^w$, $R^x$ or $R^y$ groups are methyl.

1.41 A compound according to any one of Embodiments 1.30B, 1.30C, 1.30K, 1.30L, 1.38 and 1.39 wherein all of $R^v$, $R^w$, $R^x$ and $R^y$ are hydrogen.

1.42 A compound according to Embodiment 1.41 wherein one $R^v$, $R^w$, $R^x$ or $R^y$ group is methyl and the others are all hydrogen.

1.43 A compound according to any one of Embodiments 1.0 to 1.42 wherein A is a saturated chain.

1.43 A compound according to any one of Embodiments 1.0 to 1.30A wherein A is selected from a bond; —$CH_2$—NH—C(=O)—; —NH—$CH_2$—; —$(CH_2)$—NH—$(CH_2)$—; —$(CH_2)$—N(Me)-$(CH_2)$—$(CH_2)$—; —$(CH_2)$—NH—$(CH_2)$—$(CH_2)$—; —$(CH_2)$—$(CH_2)$—NH—$(CH_2)$—; —$(CH_2)$—NH—(CHMe)—; —$(CH_2)$—NH—(CHMe)—$(CH_2)$—; —NH—$CH_2$—$CH_2$—; —$(CH_2)$—NH—$(CMe_2)$—$(CH_2)$—; —O—; —O—$(CH_2)$—; —$(CH_2)$—NH—; —$(CH_2)$—NMe—; and —$CH_2$—.

1.44 A compound according to any one of Embodiments 1.0 to 1.30A wherein A is selected from a bond; —NH—$CH_2$—; —$(CH_2)$—NH—$(CH_2)$—; —$(CH_2)$—N(Me)—$(CH_2)$—; —$(CH_2)$—NH—$(CH_2)$—$(CH_2)$—; —$(CH_2)$—$(CH_2)$—NH—$(CH_2)$—; and —$(CH_2)$—NH—(CHMe)—.

1.45 A compound according to Embodiment 1.44 wherein A is a bond.

1.46 A compound according to Embodiment 1.44 wherein A is selected from —NH—$CH_2$—; —$(CH_2)$—NH—$(CH_2)$—; —$(CH_2)$—NH—$(CH_2)$—$(CH_2)$—; —$(CH_2)$—$(CH_2)$—NH—$(CH_2)$—; and —$(CH_2)$—NH—(CHMe)—.

1.47 A compound according to Embodiment 1.46 wherein A is selected from —$(CH_2)$—NH—$(CH_2)$—; —$(CH_2)$—NH—$(CH_2)$—$(CH_2)$—; —$(CH_2)$—$(CH_2)$—NH—$(CH_2)$—; and —$(CH_2)$—NH—(CHMe)—.

1.48 A compound according to Embodiment 1.47 wherein A is —$(CH_2)$—NH—$(CH_2)$—.

1.49 A compound according to Embodiment 1.47 wherein A is —$(CH_2)$—NH—$(CH_2)$—$(CH_2)$—.

1.50 A compound according to Embodiment 1.47 wherein A is —$(CH_2)$—$(CH_2)$—NH—$(CH_2)$—.

1.51 A compound according to Embodiment 1.47 wherein A is —$(CH_2)$—NH—(CHMe)—.

1.51A A compound according to Embodiment 1.43A wherein A is —$CH_2$—NH—C(=O)—.

1.51B A compound according to Embodiment 1.43A wherein A is —NH—$CH_2$—.

1.51C A compound according to Embodiment 1.43A wherein A is —$(CH_2)$—N(Me)—$(CH_2)$—$(CH_2)$—.

1.51D A compound according to Embodiment 1.43A wherein A is —$(CH_2)$—NH—(CHMe)—$(CH_2)$—.

1.51E A compound according to Embodiment 1.43A wherein A is —NH—$CH_2$—$CH_2$—.

1.51F A compound according to Embodiment 1.43A wherein A is —$(CH_2)$—NH—$(CMe_2)$—$(CH_2)$—.

1.51G A compound according to Embodiment 1.43A wherein A is —O—.

1.51H A compound according to Embodiment 1.43A wherein A is —O—$(CH_2)$—.

1.51J A compound according to Embodiment 1.43A wherein A is —$(CH_2)$—NH—.

1.51K A compound according to Embodiment 1.43A wherein A is —$(CH_2)$—NMe—.

1.51L A compound according to Embodiment 1.43A wherein A is —$CH_2$—.

1.51M A compound according to any one of Embodiments 1.0 to 1.30A wherein A is a group $NR^r$ wherein $R^r$ is hydrogen or methyl.

1.51N A compound according to Embodiment 1.51M wherein $R^7$ is hydrogen.

151P A compound according to any one of Embodiments 1.0 to 1.51N wherein $R^7$ is selected from hydrogen; $R^{11}SO_2$—; amino; NH-$Hyd^1$; N($Hyd^1$)$_2$; and a group $Cyc^1$ wherein $Cyc^1$ is a carbocyclic or heterocyclic aromatic or non-aromatic group of 3 to 9 ring members of which 0 to 3 are selected from O, N and S and oxidised forms thereof, the carbocyclic or heterocyclic aromatic or non-aromatic group being optionally substituted with one or more substituents $R^8$; provided that when A is a bond, $(CR^pR^q)_x$, an oxygen atom or $NR^r$, then $R^7$ is other than hydrogen; and provided also that when $R^7$ is hydrogen, then A has a chain length of at least four chain members and contains at least two heteroatom chain members;

1.52 A compound according to Embodiment 1.51P wherein $R^7$ is selected from hydrogen; $R^{11}SO_2$—; amino, NH-$Hyd^1$, N(Hyd$^1$)$_2$; and a group Cyc$^1$ which is a carbocyclic or heterocyclic aromatic or non-aromatic group of 3 to 9 ring members of which 0 to 3 are selected from O, N and S and oxidised forms thereof, the carbocyclic or heterocyclic aromatic or non-aromatic group being optionally substituted with one or more substituents R$^8$.

1.53 A compound according to Embodiment 1.52 wherein R$^7$ is selected from hydrogen; R$^{11}$SO$_2$—; amino, NH-Hyd$^1$, N(Hyd$^1$)$_2$; and a group Cyc$^1$ which is a carbocyclic or heterocyclic aromatic or non-aromatic group of 3 to 8 ring members of which 0 to 3 are selected from O, N and S and oxidised forms thereof, the carbocyclic or heterocyclic aromatic or non-aromatic group being optionally substituted with one or more substituents R$^8$.

1.54 A compound according to Embodiment 1.53 wherein R$^7$ is selected from hydrogen; R$^{11}$SO$_2$—; amino, NH-Hyd$^1$, N(Hyd$^1$)$_2$; and a group Cyc$^1$ which is a carbocyclic or heterocyclic aromatic or non-aromatic group of 3 to 7 ring members of which 0 to 3 are selected from O, N and S and oxidised forms thereof, the carbocyclic or heterocyclic aromatic or non-aromatic group being optionally substituted with one or more substituents R$^8$.

1.55 A compound according to Embodiment 1.54 wherein R$^7$ is selected from hydrogen; R$^{11}$SO$_2$—; amino, NH-Hyd$^1$, N(Hyd$^1$)$_2$; and a group Cyc$^1$ which is a carbocyclic or heterocyclic aromatic or non-aromatic group of 5 or 6 ring members of which 0 to 2 are selected from O, N and S and oxidised forms thereof, the carbocyclic or heterocyclic aromatic or non-aromatic group being optionally substituted with one or more substituents R$^8$.

1.56 A compound according to Embodiment 1.54 wherein R$^7$ is selected from R$^{11}$SO$_2$—; amino, NH-Hyd$^1$, N(Hyd$^1$)$_2$; and a group Cyc$^1$ which is a carbocyclic or heterocyclic aromatic or non-aromatic group of 5, 6 or 7 ring members of which 0 to 2 are selected from O, N and S and oxidised forms thereof, the carbocyclic or heterocyclic aromatic or non-aromatic group being optionally substituted with one or more substituents R$^8$.

1.57 A compound according to any one of Embodiments 1.0 to 1.56 wherein R$^7$ is a group Cyc$^1$.

1.57A A compound according to Embodiment 1.57 wherein Cyc$^1$ is a carbocyclic or heterocyclic aromatic or non-aromatic group of 3 to 9 ring members of which 0 to 3 are selected from O, N and S and oxidised forms thereof, the carbocyclic or heterocyclic aromatic or non-aromatic group being optionally substituted with one or more substituents R$^8$.

1.57B A compound according to Embodiment 1.57A wherein Cyc$^1$ is a carbocyclic or heterocyclic aromatic or non-aromatic group of 3 to 8 ring members of which 0 to 3 are selected from O, N and S and oxidised forms thereof, the carbocyclic or heterocyclic aromatic or non-aromatic group being optionally substituted with one or more substituents R$^8$.

1.57C A compound according to Embodiment 1.57B wherein Cyc$^1$ is a carbocyclic or heterocyclic aromatic or non-aromatic group of 3 to 7 ring members of which 0 to 3 are selected from O, N and S and oxidised forms thereof, the carbocyclic or heterocyclic aromatic or non-aromatic group being optionally substituted with one or more substituents R$^8$.

1.57D A compound according to Embodiment 1.57C wherein Cyc$^1$ is a carbocyclic or heterocyclic aromatic or non-aromatic group of 3 to 7 ring members of which 0 to 2 are selected from 0 and N, the carbocyclic or heterocyclic aromatic or non-aromatic group being optionally substituted with one or more substituents R$^8$.

1.57E A compound according to Embodiment 1.57D wherein Cyc$^1$ is a carbocyclic or heterocyclic aromatic or non-aromatic group selected from cyclopropane, phenyl, tetrahydrofuran, tetrahydropyran, azetidine, pyrrolidine, piperidine, piperazine, morpholine and 1,4-diazepane, the carbocyclic or heterocyclic aromatic or non-aromatic group being optionally substituted with one or more substituents R$^8$.

1.58 A compound according to Embodiment 1.56 wherein R$^7$ is selected from R$^{11}$SO$_2$—; amino, NH-Hyd$^1$ and N(Hyd$^1$)$_2$.

1.59 A compound according to Embodiment 1.56 wherein R$^7$ is R$^{11}$SO$_2$—.

1.60 A compound according to Embodiment 1.56 wherein R$^7$ is selected from amino, NH-Hyd$^1$ and N(Hyd$^1$)$_2$.

1.61 A compound according to any one of Embodiments 1.0 to 1.57 wherein the moiety A-R$^7$ is other than an optionally substituted biphenyl group.

1.61A A compound according to any one of Embodiments 1.0 to 1.57 wherein, when A is a bond and R$^7$ is Cyc$^1$, Cyc$^1$ is a non-aromatic carbocyclic or heterocyclic group.

1.61B A compound according to any one of Embodiments 1.0 to 1.57, 1.61 and 1.61A wherein Cyc$^1$ is a carbocyclic or heterocyclic aromatic group of 5 to 9 ring members of which 0 to 3 are selected from O, N and S and oxidised forms thereof, the carbocyclic or heterocyclic aromatic group being optionally substituted with one or more substituents R$^8$.

1.62 A compound according to any one of Embodiments 1.57, 1.61, 1.61A and 1.61B wherein Cyc$^1$ is a benzene ring which is optionally substituted with one or more substituents R$^8$.

1.63 A compound according to any one of Embodiments 1.57, 1.61, 1.61A and 1.61B wherein Cyc$^1$ is a heterocyclic aromatic group of 5 to 9 ring members of which 0 to 3 are selected from O, N and S and oxidised forms thereof, the heterocyclic aromatic group being optionally substituted with one or more substituents R$^8$.

1.64 A compound according to any one of Embodiments 1.57, 1.61, 1.61A and 1.61B wherein Cyc$^1$ is a heterocyclic non-aromatic group of 4 to 7 ring members of which 1 or 2 are selected from O, N and S and oxidised forms thereof, the heterocyclic non-aromatic group being optionally substituted with one or more substituents R$^8$.

1.65 A compound according to Embodiment 1.64 wherein Cyc$^1$ is a heterocyclic non-aromatic group of 5, 6 or 7 ring members of which 1 or 2 are selected from O, N and S and oxidised forms thereof, the heterocyclic non-aromatic group being optionally substituted with one or more substituents R$^8$.

1.66 A compound according to Embodiment 1.64 wherein Cyc$^1$ is a heterocyclic non-aromatic group selected from azetidine, pyrrolidine, piperidine, piperazine, morpholine, thiomorpholine, thiomorpholine-S—S-dioxide, azepane, diazepane, tetrahydrofuran and tetrahydropyran the heterocyclic non-aromatic group being optionally substituted with one or more substituents R$^8$.

1.67 A compound according to Embodiment 1.66 wherein Cyc$^1$ is selected from pyrrolidine, piperidine, piperazine, morpholine, azepane and diazepane, the heterocyclic non-aromatic group being optionally substituted with one or more substituents R$^8$.

1.68 A compound according to Embodiment 1.67 wherein Cyc$^1$ is selected from pyrrolidine, piperidine, piperazine and morpholine, the heterocyclic non-aromatic group being optionally substituted with one or more substituents R$^8$.

1.69 A compound according to Embodiment 1.68 wherein Cyc$^1$ is selected from piperidine and morpholine, the heterocyclic non-aromatic group being optionally substituted with one or more substituents R$^8$.

1.70 A compound according to Embodiment 1.69 wherein Cyc$^1$ is piperidine which is optionally substituted with one or more substituents R$^8$.

1.71 A compound according to Embodiment 1.69 wherein Cyc$^1$ is morpholine which is optionally substituted with one or more substituents R$^8$.

1.71A A compound according to Embodiment 1.68 wherein Cyc$^1$ is piperazine optionally substituted with one or more substituents R$^8$.

1.72 A compound according to any one of Embodiments 1.57, 1.61, 1.61A and 1.61B wherein Cyc$^1$ is selected from a benzene ring, piperidine and morpholine, each being optionally substituted with one or more substituents R$^8$.

1.73 A compound according to any one of Embodiments 1.1 to 1.57 and 1.61 to 1.72 wherein R$^8$ is selected from:
  fluorine;
  chlorine;
  bromine;
  oxo;
  cyano;
  a carbocyclic or heterocyclic group having from 3 to 7 ring members, of which 0, 1, 2 or 3 are heteroatom ring members selected from O, N and S and oxidised forms thereof, the carbocyclic or heterocyclic group being optionally substituted with one or more substituents R$^9$; and
  a group R$^a$—R$^b$.

1.74 A compound according to Embodiment 1.73 wherein R$^8$ is selected from:
  fluorine;
  chlorine;
  bromine;
  oxo;
  cyano;
  a carbocyclic group having from 3 to 6 ring members, the carbocyclic group being optionally substituted with one or more substituents R$^9$;
  a heterocyclic group having from 4 to 7 ring members, of which 1, 2 or 3 are heteroatom ring members selected from O, N and S and oxidised forms thereof, the heterocyclic group being optionally substituted with one or more substituents R$^9$; and
  a group R$^a$—R$^b$.

1.75 A compound according to any one of Embodiments 1.1 to 1.57 and 1.61 to 1.74 wherein R$^8$ is selected from:
  fluorine;
  chlorine;
  bromine;
  oxo;
  cyano;
  a carbocyclic or heterocyclic group having from 3 to 7 ring members, of which 0, 1 or 2 are heteroatom members selected from O, N and S and oxidised forms thereof, the carbocyclic or heterocyclic group being optionally substituted with one or more substituents R$^9$; and
  a group R$^a$—R$^b$;
R$^a$ is a bond, O, CO, X$^1$C(X$^2$), C(X$^2$)X$^1$, X$^1$C(X$^2$)X$^1$, S, SO, SO$_2$, NR$^c$, SO$_2$NR$^c$ or NR$^c$SO$_2$;
R$^b$ is:
  hydrogen;
  a carbocyclic and heterocyclic group having from 3 to 7 ring members, of which 0, 1 or 2 are heteroatom ring members selected from O, N and S and oxidised forms thereof, the carbocyclic or heterocyclic group being optionally substituted with one or more substituents R$^9$;
  an acyclic C$_{1-6}$ hydrocarbyl group optionally substituted with one or more substituents selected from hydroxy; oxo; fluorine; cyano; carboxy; amino; mono- or di-C$_{1-2}$ hydrocarbylamino; and carbocyclic and heterocyclic groups having from 3 to 7 ring members, of which 0, 1 or 2 are heteroatom ring members selected from O, N and S and oxidised forms thereof, the carbocyclic or heterocyclic group being optionally substituted with one or more substituents R$^9$; wherein one or two but not all of the carbon atoms of the acyclic C$_{1-6}$ hydrocarbyl group may optionally be replaced by O, S, SO, SO$_2$, NH, NMe, CO$_2$, OC(=O), CONH, NHCO; CON(Me) and N(Me)CO;
R$^c$ is hydrogen or C$_{1-4}$ hydrocarbyl;
X$^1$ is O, S or NR$^c$; and
X$^2$ is =O, =S or =NR$^c$;
wherein R$^9$ is selected from R$^8$ provided that the substituents R$^9$ do not contain a carbocyclic or heterocyclic group.

1.76 A compound according to Embodiment 1.75 wherein R$^8$ is selected from:
  fluorine;
  chlorine;
  bromine;
  oxo;
  cyano;
  a carbocyclic group having 3 to 6 ring members, the carbocylic group being optionally substituted with one or more substituents R$^9$;
  a heterocyclic group having from 4 to 7 ring members, of which 1 or 2 are heteroatom ring members selected from O, N and S and oxidised forms thereof, the carbocyclic or heterocyclic group being optionally substituted with one or more substituents R$^9$; and
  a group R$^a$—R$^b$;
R$^a$ is a bond, O, CO, OC(O), C(O)O, NR$^c$C(O), C(O)NR$^c$, NR$^c$C(O)NR$^c$, S, SO, SO$_2$, NR$^c$, SO$_2$NR$^c$ or NR$^c$SO$_2$;
R$^b$ is:
  hydrogen;
  a carbocyclic group having 3 to 6 ring members, the carbocyclic group being optionally substituted with one or more substituents R$^9$;
  a heterocyclic group having from 4 to 7 ring members, of which 0, 1 or 2 are heteroatom ring members selected from O, N and S and oxidised forms thereof, the carbocyclic or heterocyclic group being optionally substituted with one or more substituents R$^9$;
  an acyclic C$_{1-4}$ hydrocarbyl group optionally substituted with one or more substituents selected from hydroxy; oxo; fluorine; cyano; carboxy; amino; mono- or di-C$_{1-2}$ hydrocarbylamino; and carbocyclic groups having from 3 to 6 ring members and heterocyclic groups having from 4 to 7 ring members, of which 1 or 2 are heteroatom ring members selected from O, N and S and oxidised forms thereof, the carbocyclic or heterocyclic groups being optionally substituted with one or more substituents R$^9$; wherein one but not all of the carbon atoms of the acyclic C$_{1-6}$ hydrocarbyl group may optionally be replaced by O, S, SO, SO$_2$, NH, NMe, CO$_2$, OC(=O), CONH, NHCO; CON(Me) and N(Me) CO;

$R^c$ is hydrogen or $C_{1-4}$ alkyl;

$X^1$ is O, S or $NR^c$; and $X^2$ is =O, =S or =$NR^c$;

wherein $R^9$ is selected from fluorine, chlorine, bromine, oxo, cyano, $C_{1-4}$ alkyl, $C_{3-4}$ cycloalkyl, cyclopropylmethyl, $C_{1-4}$ alkoxy, hydroxy, amino, mon- or di-$C_{1-4}$ alkylamino, carbamoyl, mono- or di$C_{1-4}$alkylcarbamoyl, aminosulphonyl, mono- or di-$C_{1-4}$alkylaminosulphonyl, $C_{1-4}$alkylsulphonamido, and when $R^9$ consists of or contains a $C_{1-4}$ alkyl group, the $C_{1-4}$ alkyl group is optionally substituted with one or more fluorine atoms or by $C_{1-2}$ alkoxy.

1.77 A compound according to Embodiment 1.76 wherein $R^8$ is selected from:
fluorine;
chlorine;
bromine;
oxo;
cyano;
a carbocyclic group having 3 to 6 ring members, the carbocylic group being optionally substituted with one or more substituents $R^9$;
a heterocyclic group having from 4 to 7 ring members, of which 1 or 2 are heteroatom ring members selected from O, N and S and oxidised forms thereof, the carbocyclic or heterocyclic group being optionally substituted with one or more substituents $R^9$; and
a group $R^a$—$R^b$;

$R^a$ is a bond, O, CO, OC(O), C(O)O, $NR^cC(O)$, $C(O)NR^c$, $NR^cC(O)NR^c$, S, SO, $SO_2$, $NR^c$, $SO_2NR^c$ or $NR^cSO_2$;

$R^b$ is:
hydrogen;
a carbocyclic group having 3 to 6 ring members, the carbocyclic group being optionally substituted with one or more substituents $R^9$;
a heterocyclic group having from 4 to 7 ring members, of which 0, 1 or 2 are heteroatom ring members selected from O, N and S and oxidised forms thereof, the carbocyclic or heterocyclic group being optionally substituted with one or more substituents $R^9$;
an acyclic $C_{1-4}$ hydrocarbyl group optionally substituted with one or more substituents selected from hydroxy; oxo; fluorine; cyano; carboxy; amino; mono- or di-$C_{1-2}$ hydrocarbylamino; and carbocyclic groups having from 3 to 6 ring members and heterocyclic groups having from 4 to 7 ring members, of which 1 or 2 are heteroatom ring members selected from O, N and S and oxidised forms thereof, the carbocyclic or heterocyclic groups being optionally substituted with one or more substituents $R^9$; wherein one but not all of the carbon atoms of the acyclic $C_{1-6}$ hydrocarbyl group may optionally be replaced by O, S, SO, $SO_2$, NH, NMe, $CO_2$, OC(=O), CONH, NHCO; CON(Me) and N(Me)CO;

$R^c$ is hydrogen or $C_{1-4}$ alkyl;

$X^1$ is O, S or $NR^c$; and $X^2$ is =O, =S or =$NR^c$;

wherein $R^9$ is selected from fluorine, chlorine, bromine, oxo, cyano, $C_{1-4}$ alkyl, $C_{3-4}$ cycloalkyl, cyclopropylmethyl, $C_{1-4}$ alkoxy, hydroxy, amino, mon- or di-$C_{1-4}$ alkylamino, carbamoyl, mono- or di$C_{1-4}$alkylcarbamoyl, aminosulphonyl, mono- or di-$C_{1-4}$alkylaminosulphonyl, $C_{1-4}$alkylsulphonamido, and when $R^9$ consists of or contains a $C_{1-4}$ alkyl group, the $C_{1-4}$ alkyl group is optionally substituted with one or more fluorine atoms or by $C_{1-2}$ alkoxy.

1.78 A compound according to Embodiment 1.77 wherein $R^8$ is selected from:
fluorine;
chlorine;
bromine;
oxo;
cyano;
a carbocyclic group having 3 to 5 ring members;
a heterocyclic group having from 5 to 6 ring members, of which 1 or 2 are heteroatom ring members selected from O, N and S and oxidised forms thereof, the carbocyclic or heterocyclic group being optionally substituted with one or more substituents $R^9$; and
a group $R^a$—$R^b$;

$R^a$ is a bond, O, CO, OC(O), C(O)O, $NR^cC(O)$, $C(O)NR^c$, $NR^cC(O)NR^c$, S, SO, $SO_2$, $NR^c$, $SO_2NR^c$ or $NR^cSO_2$;

$R^b$ is:
hydrogen;
a carbocyclic group having 3 to 5 ring members;
a heterocyclic group having from 5 to 6 ring members, of which 1 or 2 are heteroatom ring members selected from O, N and S and oxidised forms thereof, the carbocyclic or heterocyclic group being optionally substituted with one or more substituents $R^9$;
a $C_{1-4}$ alkyl group optionally substituted with one or more substituents selected from hydroxy; oxo; fluorine; cyano; amino; mono- or di-methylamino; carbocyclic groups having from 3 to 5 ring members and heterocyclic groups having from 5 to 6 ring members, of which 1 or 2 are heteroatom ring members selected from O, N and S and oxidised forms thereof, the carbocyclic or heterocyclic groups being optionally substituted with one or more substituents $R^9$;

$R^c$ is hydrogen or methyl;

wherein, (i) when the carbocyclic or heterocylic groups are non-aromatic, $R^9$ is selected from fluorine, oxo, cyano, $C_{1-4}$ alkyl, $C_{3-4}$ cycloalkyl, cyclopropylmethyl, $C_{1-4}$ alkoxy, hydroxy, amino, mon- or di-$C_{1-4}$ alkylamino, carbamoyl, mono- or di$C_{1-4}$alkylcarbamoyl, aminosulphonyl, mono- or di-$C_{1-4}$alkylaminosulphonyl, $C_{1-4}$alkylsulphonamido, and when $R^9$ consists of or contains a $C_{1-4}$ alkyl group, the $C_{1-4}$ alkyl group is optionally substituted with $C_{1-2}$ alkoxy; and (ii) when the carbocyclic or heterocyclic groups are aromatic, $R^9$ is selected from fluorine, chlorine, bromine, cyano, $C_{1-4}$ alkyl, $C_{3-4}$ cycloalkyl, cyclopropylmethyl, $C_{1-4}$ alkoxy, hydroxy, amino, mon- or di-$C_{1-4}$ alkylamino, carbamoyl, mono- or di$C_{1-4}$alkylcarbamoyl, aminosulphonyl, mono- or di-$C_{1-4}$alkylaminosulphonyl, $C_{1-4}$alkylsulphonamido, and when $R^9$ consists of or contains a $C_{1-4}$ alkyl group, the $C_{1-4}$ alkyl group is optionally substituted with one or more fluorine atoms or by $C_{1-2}$ alkoxy.

1.79 A compound according to Embodiment 1.78 wherein $R^8$ is selected from:
fluorine;
chlorine;
bromine;
oxo;
cyano;
a heterocyclic group having from 5 to 6 ring members, of which 1 or 2 are heteroatom ring members selected from O, N and S, the carbocyclic or heterocyclic group being optionally substituted with one or more substituents $R^9$; and
a group $R^a$—$R^b$;

$R^a$ is a bond, O, CO or $SO_2$;
$R^b$ is:
  cyclopropyl;
  a heterocyclic group having from 5 to 6 ring members, of which 1 or 2 are heteroatom ring members selected from O, N and S, the carbocyclic or heterocyclic group being optionally substituted with one or more methyl substituents $R^9$;
  a $C_{1-4}$ alkyl group optionally substituted with one or more substituents selected from oxo; fluorine; cyano; amino; mono- or di-methylamino; cyclopropyl; heterocyclic groups having from 5 to 6 ring members, of which 1 or 2 are heteroatom ring members selected from O, N and S, the carbocyclic or heterocyclic groups being optionally substituted with one or more methyl substituents $R^9$;

1.79A A compound according to Embodiment 1.76 wherein $R^8$ is selected from:
  fluorine;
  chlorine;
  oxo;
  cyano;
  a group $R^a$—$R^b$;
$R^a$ is a bond, O, CO or $SO_2$;
$R^b$ is selected from:
  cyclopropyl; and
  a $C_{1-4}$ alkyl group optionally substituted with one or more substituents selected from hydroxy; methoxy; oxo; fluorine; cyano; amino; mono- or di-methylamino; cyclopropyl.

1.79B A compound according to Embodiment 1.79 wherein $R^8$ is selected from fluorine, $C_{1-3}$ alkyl, cyclopropylcarbonyl, dimethylaminoacetyl, aminocarbonylmethyl and hydroxyethyl.

1.79C A compound according to Embodiment 1.79 wherein $R^8$ is selected from $C_{1-4}$ alkyl.

1.79D A compound according to Embodiment 1.79C wherein $R^8$ is selected from $C_{1-3}$ alkyl.

1.79E A compound according to Embodiment 1.79D wherein $R^8$ is selected from methyl, ethyl and isopropyl.

1.79F A compound according to Embodiment 1.79E wherein $R^8$ is methyl.

1.79G A compound according to Embodiment 1.79E wherein $R^8$ is ethyl.

1.79H A compound according to Embodiment 1.79E wherein $R^8$ is isopropyl.

1.80 A compound according to Embodiment 1.77 wherein:
(i) $Cyc^1$ is a non-aromatic group and $R^8$ is absent or is selected from $C_{1-4}$ hydrocarbyl, $C_{1-4}$hydrocarbylsulfonyl, oxo, di-$C_{1-4}$hydrocarbylamino-$C_{1-4}$alkanoyl; and $C_{1-4}$ hydrocarbylcarbonyl; or
(ii) $Cyc^1$ is an aromatic group and $R^8$ is absent or is selected from $C_{1-4}$ hydrocarbyl; halogen; $C_{1-4}$ hydrocarbyloxy; cyano; methylenedioxy; carbamoyl; mono- or di-$C_{1-4}$ alkylcarbamoyl; a 5- or 6-membered saturated heterocyclic ring containing 1 or 2 heteroatoms selected from O, N and S, the heterocyclic ring being optionally substituted with one or more $C_{1-4}$ alkyl group substituents; wherein the hydrocarbyl moieties in each of the $C_{1-4}$ hydrocarbyl and $C_{1-4}$ hydrocarbyloxy groups are optionally substituted with one or more substituents selected from fluorine, hydroxy, amino, mono- or di-$C_{1-4}$ alkylamino, oxo and $C_{1-2}$ alkyl.

1.81 A compound according to Embodiment 1.80 wherein:
(i) $Cyc^1$ is a non-aromatic group and $R^8$ is absent or is selected from $C_{1-4}$ hydrocarbyl, $C_{1-4}$hydrocarbylsulfonyl, oxo, di-$C_{1-4}$hydrocarbylaminoacetyl and $C_{1-4}$ hydrocarbylcarbonyl; or
(ii) $Cyc^1$ is an aromatic group and $R^8$ is absent or is selected from $C_{1-4}$ hydrocarbyl, halogen, $C_{1-4}$ hydrocarbyloxy, cyano, morpholinyl, piperazinyl, N-methylpiperazinyl and methylenedioxy, wherein the hydrocarbyl moieties in each of the $C_{1-4}$ hydrocarbyl and $C_{1-4}$ hydrocarbyloxy groups are optionally substituted with one or more substituents selected from fluorine, hydroxy, amino, mono- or di-$C_{1-4}$ alkylamino, oxo and $C_{1-2}$ alkyl.

1.82 A compound according to Embodiment 1.81 wherein:
(i) $Cyc^1$ is a non-aromatic group and $R^8$ is absent or is selected from $C_{1-4}$ alkyl, $C_{1-4}$alkylsulfonyl, oxo, di-$C_{1-4}$alkylaminoacetyl and cyclopropylcarbonyl; or
(ii) $Cyc^1$ is an aromatic group and $R^8$ is absent or is selected from $C_{1-4}$ alkyl, halogen, $C_{1-4}$ alkoxy, trifluoromethyl, trifluoromethoxy, morpholinyl, piperazinyl, N-methylpiperazinyl and methylenedioxy.

1.83 A compound according to Embodiment 1.82 wherein:
(i) $Cyc^1$ is a non-aromatic group and $R^8$ is absent or is selected from methyl, methylsulfonyl, oxo, N,N-dimethylaminoacetyl and cyclopropylcarbonyl; or
(ii) $Cyc^1$ is an aromatic group and $R^8$ is absent or is selected from fluorine, chlorine, methoxy, trifluoromethyl, trifluoromethoxy, morpholinyl, piperazinyl, N-methylpiperazinyl and methylenedioxy.

1.84 A compound according to Embodiment 1.83 wherein:
(i) $Cyc^1$ is a non-aromatic heterocyclic group and $R^8$ is absent or is selected from methyl and cyclopropylcarbonyl; or
(ii) $Cyc^1$ is a benzene ring and $R^8$ is absent or is selected from fluorine.

1.85 A compound according to any one of Embodiments 1.0 to 1.57E and 1.61 to 1.84 wherein 0, 1, 2, 3 or 4 substituents $R^8$ are present in $R^7$.

1.86 A compound according to Embodiment 1.85 wherein 0, 1, 2 or 3 substituents $R^8$ are present in $R^7$.

1.87 A compound according to Embodiment 1.86 wherein 0, 1 or 2 substituents $R^8$ are present in $R^7$.

1.88 A compound according to Embodiment 1.87 wherein 0 substituents $R^8$ are present in $R^7$.

1.89 A compound according to Embodiment 1.87 wherein 1 substituent $R^8$ is present in $R^7$.

1.90 A compound according to Embodiment 1.87 wherein 2 substituents $R^8$ are present in $R^7$.

1.91 A compound according to Embodiment 1.86 wherein 3 substituents $R^8$ are present in $R^7$.

1.92 A compound according to any one of Embodiments 1.0 to 1.57 wherein $R^7$ is selected from:
  (i) phenyl optionally substituted with one or more substituents selected from methyl, fluorine, chlorine, methoxy, cyano, trifluoromethyl, trifluoromethoxy, difluoromethyl, difluoromethoxy, methylenedioxy, morpholinyl, piperazinyl, N-methylpiperazinyl, acetyl, carbamoyl, methylcarbamoyl and dimethylcarbamoyl;
  (ii) cyclohexyl, morpholin-4-yl, morpholin-2-yl, 4-cyclopropylcarbonylmorpholin-2-yl, N-methylpiperazinyl, N-ethylpiperazinyl, N-isopropylpiperazinyl, piperidin-1-yl, piperidin-3-yl, piperidin-4-yl, 1-methylsulfonylpiperidin-4-yl, 1-cyclopropylcarbonylpiperidin-1-yl, 1,4-diazepanyl, 4-methyl-diazepan-1-yl, 4,4-difluoropiperidinyl, pyrrolidinyl, 3,3-difluoropyrrolidinyl, pyrrolidon-1-yl and tetrahydropyran-4-yl.

1.92A A compound according to any one of Embodiments 1.0 to 1.57 wherein $R^7$ is selected from:
  (phenyl optionally substituted with one or more substituents selected from methyl, fluorine, chlorine, methoxy, cyano, trifluoromethyl, trifluoromethoxy, difluoromethyl, difluoromethoxy, methylenedioxy, morpholinyl, piperazinyl, N-methylpiperazinyl, acetyl, carbamoyl, methylcarbamoyl and dimethylcarbamoyl;

(ii) cyclopropyl, cyclohexyl, pyridyl, methylazetidinyl, fluoro-methyl-azetidinyl, morpholinyl, cyclopropylcarbonylmorpholinyl, piperazinyl, methylpiperazinyl, dimethylpiperazinyl, ethyl-methyl-piperazinyl, ethyl-piperazinyl, isopropylpiperazinyl, piperidinyl, methyl-piperidinyl, fluoropiperidinyl, difluoropiperidinyl, fluoro-ethyl-piperidin, fluoro-methyl-piperidinyl, difluoro-methyl-piperidinyl, difluoro-ethyl-piperidinyl, fluoro-isopropyl-piperidinyl, dimethyl-piperidinyl, ethyl-piperidinyl, methoxyethyl-piperidinyl, hydroxyethyl-piperidinyl, isopropyl-piperidinyl, aminocarbonylmethyl-piperidinyl, methylsulfonyl-piperidinyl, cyclopropylcarbonylpiperidinyl, diazepanyl, methyl-diazepanyl, ethyl-diazepanyl, isopropyl-diazepanyl, pyrrolidinyl, methyl-pyrrolidinyl, isopropyl-pyrrolidinyl, difluoropyrrolidinyl, pyrrolidonyl, tetrahydrofuranyl, tetrahydropyranyl, ethylamino, N-isopropyl-N-methylamino 1.928 A compound according to Embodiment 1.92A wherein $R^7$ is selected from phenyl; cyclopropyl, 2-pyridyl, 1-methyl-azetidin-3-yl, 3-fluoro-1-methyl-azetidin-3-yl, morpholin-4-yl, morpholin-2-yl, 4-cyclopropylcarbonyl-morpholin-4-yl, piperazinyl, 2-methyl-piperazin-4-yl, 1,2-dimethyl-piperazin-4-yl, 1-ethyl-2-methyl-piperazin-4-yl, N-methylpiperazinyl, N-ethylpiperazinyl, N-isopropylpiperazinyl, piperidin-1-yl, piperidin-1-yl, piperidin-2-yl, 1-methyl-piperidin-2-yl, piperidin-3-yl, 1-methyl-piperidin-3-yl, piperidin-4-yl, 4-fluoro-piperidin-4-yl, 1-methyl-piperidin-4-yl, 4-fluoro-1-ethyl-piperidin-4-yl, 3-fluoro-1-ethyl-piperidin-4-yl, 3-fluoro-1-methyl-piperidin-4-yl, 3,3-difluoro-1-methyl-piperidin-4-yl, 3,3-difluoro-1-ethyl-piperidin-4-yl, 4-fluoro-1-isopropyl-piperidin-4-yl, 3-fluoro-1-isopropyl-piperidin-4-yl, 2,6-dimethyl-piperidin-4-yl, 1-ethyl-piperidin-4-yl, 1-(2-methoxyethyl)-piperidin-4-yl, 1-(2-hydroxyethyl)piperidin-4-yl, 1-isopropyl-piperidin-4-yl, 1-aminocarbonylmethyl-piperidin-4-yl, 1-methylsulfonyl-piperidin-4-yl, 1-cyclopropylcarbonylpiperidin-1-yl, 1,4-diazepanyl, 4-methyl-diazepan-1-yl, 4-ethyl-diazepan-1-yl, 4-isopropyl-diazepan-1-yl, 4,4-difluoropiperidinyl, pyrrolidinyl, 1-methyl-pyrrolidin-3-yl, 1-isopropyl-pyrrolidin-3-yl, 3,3-difluoropyrrolidinyl, pyrrolidon-1-yl, tetrahydrofuran-3-yl, tetrahydropyran-4-y, ethylamino and N-isopropyl-N-methylamino. 1.93 A compound according to Embodiment 1.92 wherein $R^7$ is selected from phenyl, fluorophenyl, 4-morpholinyl, 1-methyl-4-piperidinyl and 1-cyclopropylcarbonyl-piperidin-4-yl.

1.94 A compound according to Embodiment 1.1 wherein:
$R^1$ is hydrogen or methoxy;
$R^2$ is hydrogen or methoxy;
$R^3$ is hydrogen;
$R^4$ is hydrogen;
$R^5$ is hydrogen or cyano;
$R^6$ is hydrogen;
A is selected from a bond, —NH—CH$_2$—; —(CH$_2$)—NH—(CH$_2$)—; —(CH$_2$)—NH—(CH$_2$)—(CH$_2$)—; —(CH$_2$)—(CH$_2$)—NH—(CH$_2$)—; and —(CH$_2$)—NH—(CHMe)—; and
$R^7$ is selected from phenyl, 4-fluorophenyl, 4-morpholinyl, 1-methyl-4-piperidinyl and 1-cyclopropylcarbonyl-piperidin-4-yl.

1.95 A compound according to Embodiment 1.1 wherein:
$R^1$ is methoxy;
$R^2$ is hydrogen or methoxy;
$R^3$ is hydrogen;
$R^4$ is hydrogen;
$R^5$ is cyano;
$R^6$ is hydrogen;
A is selected from a bond, —NH—CH$_2$—; —(CH$_2$)—NH—(CH$_2$)—; —(CH$_2$)—NH—(CH$_2$)—(CH$_2$)—; —(CH$_2$)—(CH$_2$)—NH—(CH$_2$)—; and —(CH$_2$)—NH—(CHMe)—; and
$R^7$ is selected from phenyl, 4-fluorophenyl, 4-morpholinyl, 1-methyl-4-piperidinyl and 1-cyclopropylcarbonyl-piperidin-4-yl.

1.96 A compound according to Embodiment 1.95 wherein:
$R^1$ is methoxy;
$R^2$ is hydrogen or methoxy;
$R^3$ is hydrogen;
$R^4$ is hydrogen;
$R^5$ is cyano;
$R^6$ is hydrogen;
A is selected from a bond, —(CH$_2$)—NH—(CH$_2$)—; —(CH$_2$)—NH—(CH$_2$)—(CH$_2$)—; —(CH$_2$)—(CH$_2$)—NH—(CH$_2$)—; and —(CH$_2$)—NH—(CHMe)—; and
$R^7$ is selected from phenyl, 4-fluorophenyl, 4-morpholinyl, 1-methyl-4-piperidinyl and 1-cyclopropylcarbonyl-piperidin-4-yl.

1.97 A compound according to Embodiment 1.96 wherein:
$R^1$ is methoxy;
$R^2$ is hydrogen or methoxy;
$R^3$ is hydrogen;
$R^4$ is hydrogen;
$R^5$ is cyano;
$R^6$ is hydrogen; and
(i) when A is a bond, $R^7$ is 1-methyl-4-piperidinyl; or
(ii) when A is —(CH$_2$)—NH—(CH$_2$)—, $R^7$ is selected from phenyl, 4-fluorophenyl and 1-cyclopropylcarbonyl-piperidin-4-yl; or
(iii) when A is (CH$_2$)—NH—(CH$_2$)—(CH$_2$)—, $R^7$ is 4-morpholinyl; or
(iv) when A is —(CH$_2$)—(CH$_2$)—NH—(CH$_2$)—, $R^7$ is phenyl; or
(v) when A is —(CH$_2$)—NH—(CHMe)—, $R^7$ is 4-fluorophenyl.

1.97A A compound according to Embodiment 1.0 wherein:
$R^1$ is methoxy;
$R^2$ is hydrogen;
$R^3$ is hydrogen;
$R^4$ is hydrogen;
$R^5$ is cyano;
$R^6$ is hydrogen;
A is a bond; and
$R^7$ is piperazinyl optionally substituted with one or two $C_{1-4}$ alkyl substituents.

1.978 A compound according to Embodiment 1.97A wherein $R^7$ is piperazinyl optionally substituted with one or two $C_{1-4}$ alkyl substituents provided that the aggregate number of carbon atoms present in the substituents does not exceed four.

1.97C A compound according to Embodiment 1.97A or 1.978 wherein $R^7$ is piperazinyl which is (i) unsubstituted; or (ii) monosubstituted with a substituent selected from methyl, ethyl and isopropyl; or (iii) is disubstituted with two methyl substituents.

1.97D A compound according to Embodiment 1.97A or 1.978 wherein $R^7$ is piperazinyl which is (ii) monosubstituted with a substituent selected from methyl, ethyl and isopropyl; or (iii) is disubstituted with two methyl substituents.

1.97E A compound according to Embodiment 1.97D wherein $R^7$ is piperazinyl which is monosubstituted on a nitrogen atom thereof with a substituent selected from methyl, ethyl and isopropyl.

1.97F A compound according to Embodiment 1.97D wherein $R^7$ is piperazinyl which is monosubstituted on a carbon atom thereof with a substituent selected from methyl, ethyl and isopropyl.

1.97G A compound according to Embodiment 1.97C which is disubstituted on a single carbon atom thereof with two methyl substituents.

1.98 A compound according to Embodiment 1.0 or Embodiment 1.1 which is selected from:

5-[5-(4-benzylamino-2,6-dimethoxy-phenyl)-1H-pyrazol-3-ylamino]-pyrazine-2-carbonitrile;

5-[5-(4-benzylamino-2-methoxy-phenyl)-1H-pyrazol-3-ylamino]-pyrazine-2-carbonitrile;

5-{5-[4-(benzylamino-methyl)-2-methoxy-phenyl]-1H-pyrazol-3-ylamino}-pyrazine-2-carbonitrile (e.g. the hydrochloride salt);

5-{5-[4-(2-benzylamino-ethyl)-2-methoxy-phenyl]-1H-pyrazol-3-ylamino}-pyrazine-2-carbonitrile (e.g. the hydrochloride salt);

5-{5-[4-(benzylamino-methyl)-phenyl]-1H-pyrazol-3-ylamino}-pyrazine-2-carbonitrile (e.g. the hydrochloride salt);

5-[5-(4-{[(S)-1-(4-fluoro-phenyl)-ethylamino]-methyl}-2-methoxy-phenyl)-1H-pyrazol-3-ylamino]-pyrazine-2-carbonitrile (e.g. the hydrochloride salt);

5-[5-(4-{[(R)-1-(4-fluoro-phenyl)-ethylamino]-methyl}-2-methoxy-phenyl)-1H-pyrazol-3-ylamino]-pyrazine-2-carbonitrile (e.g. the hydrochloride salt);

5-(5-{4-[(4-fluoro-benzylamino)-methyl]-2-methoxy-phenyl}-1H-pyrazol-3-ylamino)-pyrazine-2-carbonitrile (e.g. the hydrochloride salt);

5-(5-{2-methoxy-4-[(2-morpholin-4-yl-ethylamino)-methyl]-phenyl}-1H-pyrazol-3-ylamino)-pyrazine-2-carbonitrile (e.g. the hydrochloride salt);

(5-{2-methoxy-4-[(2-morpholin-4-yl-ethylamino)-methyl]-phenyl}-1H-pyrazol-3-yl)-pyrazin-2-yl-amine (e.g. the hydrochloride salt);

5-{5-[2-methoxy-4-(1-methyl-piperidin-4-yl)-phenyl]-1H-pyrazol-3-ylamino}-pyrazine-2-carbonitrile (e.g. the hydrochloride salt);

5-[5-(4-{[(1-cyclopropane-carbonyl-piperidin-4-ylmethyl)-amino]-methyl}-2-methoxy-phenyl)-1 H-pyrazol-3-ylamino]-pyrazine-2-carbonitrile (e.g. the hydrochloride salt);

N-[[4-[3-[(5-cyanopyrazin-2-yl)amino]-1H-pyrazol-5-yl]-3-methoxy-phenyl]methyl]cyclopropanecarboxamide;

5-[[5-[2-methoxy-4-[(tetrahydropyran-4-ylamino)methyl]phenyl]-1H-pyrazol-3-yl]amino]pyrazine-2-carbonitrile;

5-[[5-[2-methoxy-4-[[methyl(2-morpholinoethyl)amino]methyl]phenyl]-1H-pyrazol-3-yl]amino]pyrazine-2-carbonitrile;

5-[[5-[2-methoxy-4-(2-morpholinoethylamino)phenyl]-1H-pyrazol-3-yl]amino]pyrazine-2-carbonitrile;

5-[[5-[4-1-[2-(dimethylamino)acetyl]-4-piperidyl]-2-methoxy-phenyl]-1H-pyrazol-3-yl]amino]pyrazine-2-carbonitrile;

5-[[5-[2-methoxy-4-[[[(1R)-1-methyl-2-morpholino-ethyl]amino]methyl]phenyl]-1H-pyrazol-3-yl]amino]pyrazine-2-carbonitrile;

5-[[5-[4-[[(1,1-dimethyl-2-morpholino-ethyl)amino]methyl]-2-methoxy-phenyl]-1H-pyrazol-3-yl]amino]pyrazine-2-carbonitrile;

5-[[5-[2-methoxy-4-(4-piperidyl)phenyl]-1H-pyrazol-3-yl]amino]pyrazine-2-carbonitrile;

5-[[5-[2-fluoro-4-(1-methyl-4-piperidyl)phenyl]-1H-pyrazol-3-yl]amino]pyrazine-2-carbonitrile;

5-[[5-[2-methoxy-4-(4-methylpiperazin-1-yl)phenyl]-1H-pyrazol-3-yl]amino]pyrazine-2-carbonitrile;

5-[[5-[2-methoxy-4-(4-methyl-1,4-diazepan-1-yl)phenyl]-1H-pyrazol-3-yl]amino]pyrazine-2-carbonitrile;

5-[[5-[2-methoxy-4-(1-methyl-4-piperidyl)phenyl]-1H-pyrazol-3-yl]amino]pyridine-2-carbonitrile;

6-[[5-[2-methoxy-4-(1-methyl-4-piperidyl)phenyl]-1H-pyrazol-3-yl]amino]pyridine-3-carbonitrile;

N-[5-[2-methoxy-4-(1-methyl-4-piperidyl)phenyl]-1H-pyrazol-3-yl]-5-methyl-pyrazin-2-amine;

5-[[5-[4-(1-methyl-4-piperidyl)phenyl]-1H-pyrazol-3-yl]amino]pyrazine-2-carbonitrile;

5-[[5-[2-methoxy-4-[(1-methyl-4-piperidyl)oxy]phenyl]-1H-pyrazol-3-yl]amino]pyrazine-2-carbonitrile;

5-[[5-[2-methoxy-4-[(1-methyl-4-piperidyl)methoxy]phenyl]-1H-pyrazol-3-yl]amino]pyrazine-2-carbonitrile;

2-fluoro-4-[[5-[2-methoxy-4-(1-methyl-4-piperidyl)phenyl]-1H-pyrazol-3-yl]amino]benzonitrile;

5-[[5-[2-methoxy-4-[(2-pyridylamino)methyl]phenyl]-1H-pyrazol-3-yl]amino]pyrazine-2-carbonitrile;

5-[[5-[5-fluoro-2-methoxy-4-(1-methyl-4-piperidyl)phenyl]-1H-pyrazol-3-yl]amino]pyrazine-2-carbonitrile;

5-[[5-[2-methoxy-4-[(3S)-pyrrolidin-3-yl]oxy-phenyl]-1H-pyrazol-3-yl]amino]pyrazine-2-carbonitrile;

5-[[5-[2-methoxy-4-(pyrrolidin-2-ylmethoxy)phenyl]-1H-pyrazol-3-yl]amino]pyrazine-2-carbonitrile;

5-[[5-[2-methoxy-4-[(1-methylpyrrolidin-2-yl)methoxy]phenyl]-1H-pyrazol-3-yl]amino]pyrazine-2-carbonitrile;

5-[[5-[2-methoxy-4-(4-piperidylmethoxy)phenyl]-1H-pyrazol-3-yl]amino]pyrazine-2-carbonitrile;

5-[[5-[2-methoxy-4-[[(1-methyl-4-piperidyl)amino]methyl]phenyl]-1H-pyrazol-3-yl]amino]pyrazine-2-carbonitrile;

5-[[5-[2-isopropoxy-4-(1-methyl-4-piperidyl)phenyl]-1H-pyrazol-3-yl]amino]pyrazine-2-carbonitrile;

5-[[5-[2-methoxy-4-(3-piperidyl)phenyl]-1H-pyrazol-3-yl]amino]pyrazine-2-carbonitrile;

5-[[5-[2-methoxy-4-(1-methyl-3-piperidyl)phenyl]-1H-pyrazol-3-yl]amino]pyrazine-2-carbonitrile;

5-[[5-[2-methoxy-4-(1-methyl-2-piperidyl)phenyl]-1H-pyrazol-3-yl]amino]pyrazine-2-carbonitrile;

5-[[5-[2-methoxy-4-[(3S)-1-methylpyrrolidin-3-yl]oxy-phenyl]-1H-pyrazol-3-yl]amino]pyrazine-2-carbonitrile;

5-chloro-N-[5-[2-methoxy-4-(4-piperidyl)phenyl]-1H-pyrazol-3-yl]pyrazin-2-amine;

5-chloro-N-[5-[2-methoxy-4-(1-methyl-4-piperidyl)phenyl]-1H-pyrazol-3-yl]pyrazin-2-amine;

5-[[5-[2-methoxy-4-(4-piperidyl)phenyl]-1H-pyrazol-3-yl]amino]pyrazine-2-carboxylic acid;

5-[[5-(2-methoxy-4-piperazin-1-yl-phenyl)-1H-pyrazol-3-yl]amino]pyrazine-2-carbonitrile;

5-[[5-[4-[(2S,6S)-2,6-dimethyl-4-piperidyl]-2-methoxy-phenyl]-1H-pyrazol-3-yl]amino]pyrazine-2-carbonitrile;

5-[[5-(2-methoxy-4-tetrahydropyran-4-yl-phenyl)-1H-pyrazol-3-yl]amino]pyrazine-2-carbonitrile;

2-fluoro-4-[[5-[2-methoxy-4-(4-piperidyl)phenyl]-1H-pyrazol-3-yl]amino]benzonitrile;

6-[[5-[2-methoxy-4-(4-piperidyl)phenyl]-1H-pyrazol-3-yl]amino]pyridine-3-carbonitrile;

5-[[5-[2-fluoro-4-(4-piperidyl)phenyl]-1H-pyrazol-3-yl]amino]pyrazine-2-carbonitrile;

5-[[5-[2-methoxy-4-(4-piperidyl)phenyl]-1H-pyrazol-3-yl]amino]pyridine-2-carbonitrile;

5-[[5-[2-isopropoxy-4-(4-piperidyl)phenyl]-1H-pyrazol-3-yl]amino]pyrazine-2-carbonitrile;
5-[[5-[4-(1,4-diazepan-1-yl)-2-methoxy-phenyl]-1H-pyrazol-3-yl]amino]pyrazine-2-carbonitrile;
N-[5-[2-methoxy-4-(4-piperidyl)phenyl]-1H-pyrazol-3-yl]-5-methyl-pyrazin-2-amine;
5-[[5-[4-(4-piperidyl)phenyl]-1H-pyrazol-3-yl]amino]pyrazine-2-carbonitrile;
5-[[5-[2-methoxy-4-(4-piperidyloxy)phenyl]-1H-pyrazol-3-yl]amino]pyrazine-2-carbonitrile;
5-[[5-[5-fluoro-2-methoxy-4-(4-piperidyl)phenyl]-1H-pyrazol-3-yl]amino]pyrazine-2-carbonitrile;
5-[[5-[4-[(isopropylamino)methyl]-2-methoxy-phenyl]-1H-pyrazol-3-yl]amino]pyrazine-2-carbonitrile;
5-[[5-[4-(1-ethyl-4-piperidyl)-2-methoxy-phenyl]-1H-pyrazol-3-yl]amino]pyrazine-2-carbonitrile;
5-[[5-[4-(1-isopropyl-4-piperidyl)-2-methoxy-phenyl]-1H-pyrazol-3-yl]amino]pyrazine-2-carbonitrile;
2-[4-[4-[3-[(5-cyanopyrazin-2-yl)amino]-1H-pyrazol-5-yl]-3-methoxy-phenyl]-1-piperidyl]acetamide;
5-[[5-[2-methoxy-4-[[methyl(tetra hydropyran-4-yl)amino]methyl]phenyl]-1H-pyrazol-3-yl]amino]pyrazine-2-carbonitrile;
5-[[5-[4-(4-fluoro-1-methyl-4-piperidyl)-2-methoxy-phenyl]-1H-pyrazol-3-yl]amino]pyrazine-2-carbonitrile;
5-[[5-[2-methoxy-4-(1-methylazetidin-3-yl)phenyl]-1H-pyrazol-3-yl]amino]pyrazine-2-carbonitrile;
5-[[5-[4-(3-fluoro-1-methyl-azetidin-3-yl)-2-methoxy-phenyl]-1H-pyrazol-3-yl]amino]pyrazine-2-carbonitrile;
5-[[5-[5-chloro-2-methoxy-4-(1-methyl-4-piperidyl)phenyl]-1H-pyrazol-3-yl]amino]pyrazine-2-carbonitrile;
5-[[5-[5-chloro-2-methoxy-4-(4-piperidyl)phenyl]-1H-pyrazol-3-yl]amino]pyrazine-2-carbonitrile;
5-[[5-[3-chloro-2-methoxy-4-(1-methyl-4-piperidyl)phenyl]-1H-pyrazol-3-yl]amino]pyrazine-2-carbonitrile;
5-[[5-[3-chloro-2-methoxy-4-(4-piperidyl)phenyl]-1H-pyrazol-3-yl]amino]pyrazine-2-carbonitrile;
methyl 5-[[5-[2-methoxy-4-(4-piperidyl)phenyl]-1H-pyrazol-3-yl]amino]pyrazine-2-carboxylate;
5-[[5-[2-methoxy-4-[(tetrahydrofuran-3-ylamino)methyl]phenyl]-1H-pyrazol-3-yl]amino]pyrazine-2-carbonitrile;
5-[[5-[2-methoxy-4-[[methyl(tetra hydrofuran-3-yl)amino]methyl]phenyl]-1H-pyrazol-3-yl]amino]pyrazine-2-carbonitrile;
5-[[5-[2-methoxy-4-(tetrahydropyran-4-ylmethylamino)phenyl]-1H-pyrazol-3-yl]amino]pyrazine-2-carbonitrile;
5-[[5-[2-methoxy-4-(tetrahydropyran-4-ylmethoxy)phenyl]-1H-pyrazol-3-yl]amino]pyrazine-2-carbonitrile;
5-[[5-[4-(4-fluoro-4-piperidyl)-2-methoxy-phenyl]-1H-pyrazol-3-yl]amino]pyrazine-2-carbonitrile;
5-[[5-[4-(3-fluoroazetidin-3-yl)-2-methoxy-phenyl]-1H-pyrazol-3-yl]amino]pyrazine-2-carbonitrile;
5-[[5-[2-methoxy-4-[(3R)-1-methylpyrrolidin-3-yl]oxy-phenyl]-1H-pyrazol-3-yl]amino]pyrazine-2-carbonitrile;
5-[[5-(2-methoxy-4-morpholino-phenyl)-1H-pyrazol-3-yl]amino]pyrazine-2-carbonitrile;
5-[[5-[4-(4-ethylpiperazin-1-yl)-2-methoxy-phenyl]-1H-pyrazol-3-yl]amino]pyrazine-2-carbonitrile;
5-[[5-[4-(4-isopropylpiperazin-1-yl)-2-methoxy-phenyl]-1H-pyrazol-3-yl]amino]pyrazine-2-carbonitrile;
5-[[5-[2-methoxy-4-[(3R)-3-methylpiperazin-1-yl]phenyl]-1H-pyrazol-3-yl]amino]pyrazine-2-carbonitrile;
5-[[5-[4-(4-ethyl-1,4-diazepan-1-yl)-2-methoxy-phenyl]-1H-pyrazol-3-yl]amino]pyrazine-2-carbonitrile;
5-[[5-[4-(4-isopropyl-1,4-diazepan-1-yl)-2-methoxy-phenyl]-1H-pyrazol-3-yl]amino]pyrazine-2-carbonitrile;
5-[[5-[4-(1-ethyl-4-fluoro-4-piperidyl)-2-methoxy-phenyl]-1H-pyrazol-3-yl]amino]pyrazine-2-carbonitrile;
5-[[5-[4-(4-fluoro-1-isopropyl-4-piperidyl)-2-methoxy-phenyl]-1H-pyrazol-3-yl]amino]pyrazine-2-carbonitrile;
5-[[5-[4-(1-ethyl-3-fluoro-4-piperidyl)-2-methoxy-phenyl]-1H-pyrazol-3-yl]amino]pyrazine-2-carbonitrile;
5-[[5-[4-(3-fluoro-1-isopropyl-4-piperidyl)-2-methoxy-phenyl]-1H-pyrazol-3-yl]amino]pyrazine-2-carbonitrile;
5-[[5-[2-methoxy-4-[1-(2-methoxyethyl)-4-piperidyl]phenyl]-1H-pyrazol-3-yl]amino]pyrazine-2-carbonitrile;
5-[[5-[4-(ethylaminomethyl)-2-methoxy-phenyl]-1H-pyrazol-3-yl]amino]pyrazine-2-carbonitrile;
5-[[5-[4-[(cyclopropylamino)methyl]-2-methoxy-phenyl]-1H-pyrazol-3-yl]amino]pyrazine-2-carbonitrile;
5-[[5-[4-[(3R)-3,4-dimethylpiperazin-1-yl]-2-methoxy-phenyl]-1H-pyrazol-3-yl]amino]pyrazine-2-carbonitrile;
5-[[5-[4-[(3R)-4-ethyl-3-methyl-piperazin-1-yl]-2-methoxy-phenyl]-1H-pyrazol-3-yl]amino]pyrazine-2-carbonitrile;
5-[[5-[4-[(3S)-1-isopropylpyrrolidin-3-yl]oxy-2-methoxy-phenyl]-1H-pyrazol-3-yl]amino]pyrazine-2-carbonitrile;
5-[[5-[4-[(3R)-1-isopropylpyrrolidin-3-yl]oxy-2-methoxy-phenyl]-1H-pyrazol-3-yl]amino]pyrazine-2-carbonitrile;
5-[[5-[4-[(3(R,S),4(R,S))-3-fluoro-1-methyl-4-piperidyl]-2-methoxy-phenyl]-1H-pyrazol-3-yl]amino]pyrazine-2-carbonitrile;
5-[[5-[4-(3,3-difluoro-1-methyl-4-piperidyl)-2-methoxy-phenyl]-1H-pyrazol-3-yl]amino]pyrazine-2-carbonitrile;
5-[[5-[4-(1-ethyl-3,3-difluoro-4-piperidyl)-2-methoxy-phenyl]-1H-pyrazol-3-yl]amino]pyrazine-2-carbonitrile;
5-[[5-[4-[1-(2-hydroxyethyl)-4-piperidyl]-2-methoxy-phenyl]-1H-pyrazol-3-yl]amino]pyrazine-2-carbonitrile;
5-[[5-[4-[[isopropyl(methyl)amino]methyl]-2-methoxy-phenyl]-1H-pyrazol-3-yl]amino]pyrazine-2-carbonitrile;
5-[[5-[2-methoxy-4-(pyrrolidin-1-ylmethyl)phenyl]-1H-pyrazol-3-yl]amino]pyrazine-2-carbonitrile;
5-[[5-[2-methoxy-4-(morpholinomethyl)phenyl]-1H-pyrazol-3-yl]amino]pyrazine-2-carbonitrile;
5-[[5-[2-methoxy-4-[[(2R)-1-methylpyrrolidin-2-yl]methoxy]phenyl]-1H-pyrazol-3-yl]amino]pyrazine-2-carbonitrile hydrochloride;
5-[[5-[2-methoxy-4-[[(2S)-1-methyl pyrrolidin-2-yl]methoxy]phenyl]-1H-pyrazol-3-yl]amino]pyrazine-2-carbonitrile hydrochloride;
5-[[5-[2-methoxy-4-(oxazol-4-ylmethoxy)phenyl]-1H-pyrazol-3-yl]amino]pyrazine-2-carbonitrile;
5-[[5-[4-[1-(2-fluoroethyl)-4-piperidyl]-2-methoxy-phenyl]-1H-pyrazol-3-yl]amino]pyrazine-2-carbonitrile;
5-[[5-[2-methoxy-4-[(1-methyl-4-piperidyl)methylamino]phenyl]-1H-pyrazol-3-yl]amino]pyrazine-2-carbonitrile;
5-[[5-[4-[(1-ethyl-4-piperidyl)methylamino]-2-methoxy-phenyl]-1H-pyrazol-3-yl]amino]pyrazine-2-carbonitrile;
5-[[5-[4-[(1-isopropyl-4-piperidyl)methylamino]-2-methoxy-phenyl]-1H-pyrazol-3-yl]amino]pyrazine-2-carbonitrile;
5-[[5-[2-methoxy-4-[(1-methyl-4-piperidyl)amino]phenyl]-1H-pyrazol-3-yl]amino]pyrazine-2-carbonitrile;
5-[[5-[4-[(1-ethyl-4-piperidyl)amino]-2-methoxy-phenyl]-1H-pyrazol-3-yl]amino]pyrazine-2-carbonitrile;
5-[[5-[4-[(1-isopropyl-4-piperidyl)amino]-2-methoxy-phenyl]-1H-pyrazol-3-yl]amino]pyrazine-2-carbonitrile;
5-[[5-[2-methoxy-4-[(1-methyl-4-piperidyl)oxymethyl]phenyl]-1H-pyrazol-3-yl]amino]pyrazine-2-carbonitrile;
5-[[5-[4-[(1-ethyl-4-piperidyl)oxymethyl]-2-methoxy-phenyl]-1H-pyrazol-3-yl]amino]pyrazine-2-carbonitrile;
5-[[5-[4-[(1-isopropyl-4-piperidyl)oxymethyl]-2-methoxy-phenyl]-1H-pyrazol-3-yl]amino]pyrazine-2-carbonitrile;

5-[[5-(2-fluoro-6-methoxy-4-piperazin-1-yl-phenyl)-1H-pyrazol-3-yl]amino]pyrazine-2-carbonitrile;
5-[[5-[2-methoxy-4-[(2R)-4-methylmorpholin-2-yl]phenyl]-1H-pyrazol-3-yl]amino]pyrazine-2-carbonitrile;
5-[[5-[2-methoxy-4-[(2R)-4-ethylmorpholin-2-yl]phenyl]-1H-pyrazol-3-yl]amino]pyrazine-2-carbonitrile;
5-[[5-[2-methoxy-4-[(2S)-4-methylmorpholin-2-yl]phenyl]-1H-pyrazol-3-yl]amino]pyrazine-2-carbonitrile;
5-[[5-[2-methoxy-4-[(2S)-4-ethylmorpholin-2-yl]phenyl]-1H-pyrazol-3-yl]amino]pyrazine-2-carbonitrile;
5-[[5-(2,6-dimethoxy-4-piperazin-1-yl-phenyl)-1H-pyrazol-3-yl]amino]pyrazine-2-carbonitrile;
5-[[5-[2,6-dimethoxy-4-(4-methylpiperazin-1-yl)phenyl]-1H-pyrazol-3-yl]amino]pyrazine-2-carbonitrile;
5-[[5-[4-[[(3R)-3-fluoropyrrolidin-1-yl]methyl]-2-methoxy-phenyl]-1H-pyrazol-3-yl]amino]pyrazine-2-carbonitrile;
5-[[5-[2-methoxy-4-[[(3S)-3-methoxypyrrolidin-1-yl]methyl]phenyl]-1H-pyrazol-3-yl]amino]pyrazine-2-carbonitrile;
5-[[5-[2-methoxy-4-[[(3R)-3-methoxypyrrolidin-1-yl]methyl]phenyl]-1H-pyrazol-3-yl]amino]pyrazine-2-carbonitrile;
5-[[5-[4-[[(2R)-1-ethylpyrrolidin-2-yl]methoxy]-2-methoxy-phenyl]-1H-pyrazol-3-yl]amino]pyrazine-2-carbonitrile;
5-[[5-[4-[[(2R)-1-isopropylpyrrolidin-2-yl]methoxy]-2-methoxy-phenyl]-1H-pyrazol-3-yl]amino]pyrazine-2-carbonitrile;
5-[[5-[4-[[(2S)-1-ethyl pyrrolidin-2-yl]methoxy]-2-methoxy-phenyl]-1H-pyrazol-3-yl]amino]pyrazine-2-carbonitrile;
5-[[5-[4-[[(2S)— 1-isopropylpyrrolidin-2-yl]methoxy]-2-methoxy-phenyl]-1H-pyrazol-3-yl]amino]pyrazine-2-carbonitrile;
5-[[5-[4-[(cyclopropylmethylamino)methyl]-2-methoxy-phenyl]-1H-pyrazol-3-yl]amino]pyrazine-2-carbonitrile;
5-[[5-[2-methoxy-4-[[[(3R)-tetrahydrofuran-3-yl]amino]methyl]phenyl]-1H-pyrazol-3-yl]amino]pyrazine-2-carbonitrile;
5-[[5-[2-methoxy-4-[[[(3S)-tetrahydrofuran-3-yl]amino]methyl]phenyl]-1H-pyrazol-3-yl]amino]pyrazine-2-carbonitrile;
5-[[5-[4-[(3R)-4-isopropyl-3-methyl-piperazin-1-yl]-2-methoxy-phenyl]-1H-pyrazol-3-yl]amino]pyrazine-2-carbonitrile;
5-[[5-[4-[(1-ethyl-4-piperidyl)oxy]-2-methoxy-phenyl]-1H-pyrazol-3-yl]amino]pyrazine-2-carbonitrile;
5-[[5-[4-[(1-isopropyl-4-piperidyl)oxy]-2-methoxy-phenyl]-1H-pyrazol-3-yl]amino]pyrazine-2-carbonitrile;
5-[[5-[4-(4-ethylpiperazin-1-yl)-2-fluoro-6-methoxy-phenyl]-1H-pyrazol-3-yl]amino]pyrazine-2-carbonitrile;
5-[[5-[4-(4-isopropylpiperazin-1-yl)-2-fluoro-6-methoxy-phenyl]-1H-pyrazol-3-yl]amino]pyrazine-2-carbonitrile;
5-[[5-[4-[[(3S)-1-ethyl pyrrolidin-3-yl]oxymethyl]-2-methoxy-phenyl]-1H-pyrazol-3-yl]amino]pyrazine-2-carbonitrile;
5-[[5-[4-[[(3S)-1-isopropylpyrrolidin-3-yl]oxymethyl]-2-methoxy-phenyl]-1H-pyrazol-3-yl]amino]pyrazine-2-carbonitrile;
5-[[5-[4-[[(3R)-1-ethyl pyrrolidin-3-yl]oxymethyl]-2-methoxy-phenyl]-1H-pyrazol-3-yl]amino]pyrazine-2-carbonitrile;
5-[[5-[4-[[(3R)-1-isopropylpyrrolidin-3-yl]oxymethyl]-2-methoxy-phenyl]-1H-pyrazol-3-yl]amino]pyrazine-2-carbonitrile;
5-[[5-[4-(4-isobutylpiperazin-1-yl)-2-methoxy-phenyl]-1H-pyrazol-3-yl]amino]pyrazine-2-carbonitrile;
5-[[5-[4-[(1-ethyl-4-piperidyl)methyl]-2-methoxy-phenyl]-1H-pyrazol-3-yl]amino]pyrazine-2-carbonitrile;
5-[[5-[4-[(1-isopropyl-4-piperidyl)methyl]-2-methoxy-phenyl]-1H-pyrazol-3-yl]amino]pyrazine-2-carbonitrile;
5-[[5-[4-[(1-ethyl-4-piperidyl)methyl-methyl-amino]-2-methoxy-phenyl]-1H-pyrazol-3-yl]amino]pyrazine-2-carbonitrile;
5-[[5-[4-[(isobutylamino)methyl]-2-methoxy-phenyl]-1H-pyrazol-3-yl]amino]pyrazine-2-carbonitrile;
5-[[5-[4-[(2R)-4-isopropylmorpholin-2-yl]-2-methoxy-phenyl]-1H-pyrazol-3-yl]amino]pyrazine-2-carbonitrile;
5-[[5-[4-[(1-isopropyl-4-piperidyl)methyl-methyl-amino]-2-methoxy-phenyl]-1H-pyrazol-3-yl]amino]pyrazine-2-carbonitrile;
5-[[5-[4-[[(2R)-1-ethyl pyrrolidin-2-yl]methyl]-2-methoxy-phenyl]-1H-pyrazol-3-yl]amino]pyrazine-2-carbonitrile;
5-[[5-[4-[(2S)-4-isopropylmorpholin-2-yl]-2-methoxy-phenyl]-1H-pyrazol-3-yl]amino]pyrazine-2-carbonitrile;
5-[[5-[4-[[(2R)-1-isopropylpyrrolidin-2-yl]methyl]-2-methoxy-phenyl]-1H-pyrazol-3-yl]amino]pyrazine-2-carbonitrile;
5-[[5-[4-[[(2S)-1-ethyl pyrrolidin-2-yl]methyl]-2-methoxy-phenyl]-1H-pyrazol-3-yl]amino]pyrazine-2-carbonitrile;
5-[[5-(2-methoxy-4-piperazin-1-yl-phenyl)-1H-pyrazol-3-yl]amino]pyrazine-2-carbonitrile;
5-[[5-[4-[[(2S)-1-isopropylpyrrolidin-2-yl]methyl]-2-methoxy-phenyl]-1H-pyrazol-3-yl]amino]pyrazine-2-carbonitrile;
5-[[5-[4-[[(3S)-1-isopropylpyrrolidin-3-yl]amino]-2-methoxy-phenyl]-1H-pyrazol-3-yl]amino]pyrazine-2-carbonitrile;
5-[[5-[4-[[(3R)-1-isopropylpyrrolidin-3-yl]amino]-2-methoxy-phenyl]-1H-pyrazol-3-yl]amino]pyrazine-2-carbonitrile;
5-[[5-[4-[[(3R)-1-ethylpyrrolidin-3-yl]amino]-2-methoxy-phenyl]-1H-pyrazol-3-yl]amino]pyrazine-2-carbonitrile;
5-[[5-[4-[[(3S)-1-ethylpyrrolidin-3-yl]amino]-2-methoxy-phenyl]-1H-pyrazol-3-yl]amino]pyrazine-2-carbonitrile;
5-[[5-[2-methoxy-4-[(3S)-3-methylpiperazin-1-yl]phenyl]-1H-pyrazol-3-yl]amino]pyrazine-2-carbonitrile;
5-[[5-[4-[(3R)-3-ethylpiperazin-1-yl]-2-methoxy-phenyl]-1H-pyrazol-3-yl]amino]pyrazine-2-carbonitrile;
5-[[5-[4-[(3S)-3-isopropylpiperazin-1-yl]-2-methoxy-phenyl]-1H-pyrazol-3-yl]amino]pyrazine-2-carbonitrile;
5-[[5-[4-[(3R)-3-isopropylpiperazin-1-yl]-2-methoxy-phenyl]-1H-pyrazol-3-yl]amino]pyrazine-2-carbonitrile;
5-[[5-[4-(3,3-dimethylpiperazin-1-yl)-2-methoxy-phenyl]-1H-pyrazol-3-yl]amino]pyrazine-2-carbonitrile;
and salts and tautomers thereof.

1.99 A compound according to any one of Embodiments 1.1 to 1.98 having a molecular weight of up to 1000, for example less than 750.

1.100 A compound according to Embodiment 1.99 having a molecular weight of less than 700.

1.101 A compound according to Embodiment 1.100 having a molecular weight of less than 650.

1.102 A compound according to Embodiment 1.101 having a molecular weight of less than 600 or less than 550.

1.103 A compound according to Embodiment 1.102 having a molecular weight of less than 530, for example up to 525.

1.104 A compound according to Embodiment 1.1 which is the title compound of any one of Examples 1 to 12 below.

1.105 A compound according to any one of Embodiments 1.1 to 1.104 which is in the form of a salt.

1.106 A compound according to Embodiment 1.105 wherein the salt is an acid addition salt.

1.107 A compound according to Embodiment 1.105 or Embodiment 1.106 wherein the salt is a pharmaceutically acceptable salt.

Definitions

In this application, the following definitions apply, unless indicated otherwise.

The term "non-aromatic carbocyclic or heterocyclic group" embraces unsaturated ring systems without aromatic character, partially saturated and fully saturated carbocyclic and heterocyclic ring systems. The terms "unsaturated" and "partially saturated" refer to rings wherein the ring structure (s) contains atoms sharing more than one valence bond i.e. the ring contains at least one multiple bond e.g. a C=C, C≡C or N=C bond. The term "fully saturated" refers to rings where there are no multiple bonds between ring atoms. Saturated carbocyclic groups include cycloalkyl groups as defined below. Partially saturated carbocyclic groups include cycloalkenyl groups as defined below, for example cyclopentenyl, cycloheptenyl and cyclooctenyl.

Examples of non-aromatic heterocyclic groups include morpholine, thiomorpholine and its S-oxide and S,S-dioxide, piperidine, N-alkyl piperidines, piperidone, pyrrolidine, pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran, imidazoline, imidazolidinone, oxazoline, thiazoline, 2-pyrazoline, pyrazolidine, piperazone, piperazine, and N-alkyl piperazines.

Examples of non-aromatic carbocyclic groups include cycloalkane groups such as cyclohexyl and cyclopentyl, cycloalkenyl groups such as cyclopentenyl, cyclohexenyl, and cycloheptenyl.

The term "hydrocarbyl" as used herein is used in its standard IUPAC sense to refer to moieties consisting of carbon and hydrogen atoms, i.e. hydrocarbon moieties.

In addition to carbon-hydrogen bonds, the hydrocarbyl groups can contain one or more single, double or triple carbon-carbon bonds. The hydrocarbyl groups can be aromatic or non-aromatic. Examples of non-aromatic hydrocarbyl groups include alkyl, alkenyl, alkynyl, cycloalkyl, cycloalkenyl, cycloalkylalkyl, cycloakenylalkyl, cycloalkylalkenyl and cycloalkylalkynyl groups.

The term "alkyl" covers both straight chain and branched chain alkyl groups. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers.

Examples of alkenyl groups include, but are not limited to, ethenyl (vinyl), 1-propenyl, 2-propenyl (allyl), isopropenyl, butenyl, buta-1,4-dienyl, pentenyl, and hexenyl.

Examples of alkynyl groups include, but are not limited to, ethynyl and 2-propynyl (propargyl) groups.

Examples of cycloalkyl groups are those derived from cyclopropane, cyclobutane, cyclopentane, cyclohexane and cycloheptane.

Examples of cycloalkenyl groups include, but are not limited to, cyclopropenyl, cyclobutenyl, cyclopentenyl, cyclopentadienyl and cyclohexenyl.

Examples of aromatic hydrocarbyl groups are phenyl and naphthyl.

Examples of halogen substituents include fluorine, chlorine, bromine and iodine. Fluorine and chlorine are particularly preferred. When attached to a non-aromatic moiety, fluorine is preferred.

Salts

The compounds of the invention may be presented in the form of salts.

The salts (as defined in Embodiments 1.105 to 1.107) are typically acid addition salts.

The salts can be synthesized from the parent compound by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free base form of the compound with the acid in water or in an organic solvent, or in a mixture of the two; generally, nonaqueous media such as ether, ethyl acetate, ethanol, isopropanol, or acetonitrile are used.

Acid addition salts (as defined in Embodiment 1.106) may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic, (±)-DL-lactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, p-toluenesulphonic, undecylenic and valeric acids, as well as acylated amino acids and cation exchange resins.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Geometric Isomers and Tautomers

The compounds of the invention may exist in a number of different geometric isomeric, and tautomeric forms and references to the compounds of formula (0) or formula (1) as defined in Embodiments 1.0 to 1.107 include all such forms. For the avoidance of doubt, where a compound can exist in one of several geometric isomeric or tautomeric forms and only one is specifically described or shown, all others are nevertheless embraced by formula (0) or formula (1) or subgroups, subsets, preferences and examples thereof.

For example, the compounds of formula (0) may exist in either or both of tautomeric forms A and B below.

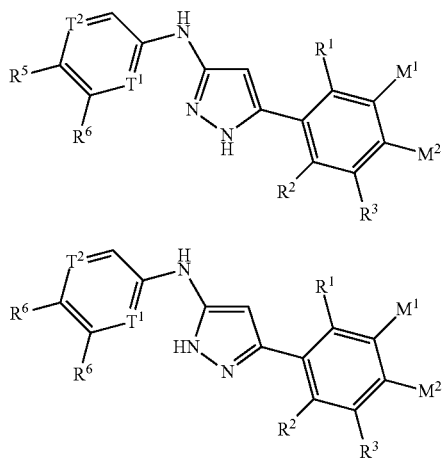

Although only tautomeric form A is shown in the formula drawings in this application, it should be understood that formula (0) and the other formulae in this application are intended to cover both tautomeric forms.

Optical Isomers

Where compounds of the formula contain one or more chiral centres, and can exist in the form of two or more optical isomers, references to the compounds include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the invention exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound having one or more chiral centres, wherein at least 55% (e.g. at least 60%, 65%, 70%, 75%, 80%, 85%, 90% or 95%) of the compound of the formula (0) or formula (1) is present as a single optical isomer (e.g. enantiomer or diastereoisomer). In one general embodiment, 99% or more (e.g. substantially all) of the total amount of the compound of the formula (0) or formula (1) may be present as a single optical isomer (e.g. enantiomer or diastereoisomer).

Isotopes

The compounds of the invention as defined in any one of Embodiments 1.0 to 1.107 may contain one or more isotopic substitutions, and a reference to a particular element includes within its scope all isotopes of the element. For example, a reference to hydrogen includes within its scope $^{1}$H, $^{2}$H (D), and $^{3}$H (T). Similarly, references to carbon and oxygen include within their scope respectively $^{12}$C, $^{13}$C and $^{14}$C and $^{16}$O and $^{18}$O.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Solvates

Compounds of the formula (0) or formula (1) as defined in any one of Embodiments 1.0 to 1.107 may form solvates.

Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates.

Particularly preferred solvates are hydrates, and examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Prodrugs

The compounds of the formula (0) or formula (1) as defined in any one of Embodiments 1.0 to 1.107 may be presented in the form of a pro-drug.

By "prodrugs" is meant for example any compound that is converted in vivo into a biologically active compound of the formula (0) or formula (1), as defined in any one of Embodiments 1.0 to 1.107.

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Complexes and Clathrates

Also encompassed by formula (0) or formula (1) or subgroups, subsets, preferences and examples thereof are complexes (e.g. inclusion complexes or clathrates with compounds such as cyclodextrins, or complexes with metals) of the compounds.

Biological Activity

The compounds of the formulae (1) and sub-groups thereof are potent inhibitors of Chk-1 and consequently are expected to be beneficial alone or in combination with various chemotherapeutic agents or radiation for treating a wide spectrum of proliferative disorders.

Preferred compounds of the formula (0) or formula (1) are those compounds that have $IC_{50}$ values of less than 0.1 µM against Chk-1 kinase. Particularly preferred compounds are those that have $IC_{50}$ values of less than 0.01 µM against Chk-1 kinase. Still more preferred compounds are those that have $IC_{50}$ values of less than 0.001 µM against Chk-1 kinase.

Accordingly, in further embodiments (Embodiments 2.1 to 2.14), the invention provides:

2.1 A compound of the formula (0) or formula (1) as defined in any one of Embodiments 1.0 to 1.107 for use in medicine or therapy.

2.2 A compound of the formula (0) or formula (1) as defined in any one of Embodiments 1.0 to 1.107 for for use as a Chk-1 kinase inhibitor.

2.3 A compound of the formula (0) or formula (1) for use as defined in Embodiment 2.2 wherein the compound has an $IC_{50}$ values of less than than 1 µM against Chk-1 kinase (e.g. when determined according the assays described herein).

2.4 A compound of the formula (0) or formula (1) for use as defined in Embodiment 2.3 wherein the compound has an $IC_{50}$ value of less than 0.1 µM against Chk-1 kinase.

2.5 A compound of the formula (0) or formula (1) for use as defined in Embodiment 2.3 wherein the compound has an $IC_{50}$ value of less than 0.01 µM against Chk-1 kinase.

2.6 A compound of the formula (0) or formula (1) for use as defined in Embodiment 2.3 wherein the compound has an $IC_{50}$ value of less than 0.001 µM against Chk-1 kinase.

2.7 A compound of the formula (0) or formula (1) as defined in any one of Embodiments 1.0 to 1.107 or 2.3 to 2.6 for use in enhancing a therapeutic effect of radiation therapy or chemotherapy in the treatment of a proliferative disease such as cancer.

2.8 A compound of the formula (0) or formula (1) as defined in any one of Embodiments 1.0 to 1.107 or 2.3 to 2.6 for use in the treatment of a proliferative disease such as cancer.

2.9 The use of a compound of the formula (0) or formula (1) as defined in any one of Embodiments 1.0 to 1.107 or 2.3 to 2.6 for the manufacture of a medicament for enhancing a therapeutic effect of radiation therapy or chemotherapy in the treatment of a proliferative disease such as cancer.

2.10 The use of a compound of the formula (0) or formula (1) as defined in any one of Embodiments 1.0 to 1.107 or 2.3 to 2.6 for the manufacture of a medicament for the treatment of a proliferative disease such as cancer.

2.11 A method for the prophylaxis or treatment of a proliferative disease such as cancer, which method comprises administering to a patient in combination with radiotherapy or chemotherapy a compound of the formula (0) or formula (1) as defined in any one of Embodiments 1.0 to 1.107 or 2.3 to 2.6.

2.12 A method for the prophylaxis or treatment of a proliferative disease such as cancer, which method comprises administering to a patient a compound of the formula (0) or formula (1) as defined in any one of Embodiments 1.0 to 1.107 or 2.3 to 2.6.

2.13 A compound for use, use or method as defined in any one of Embodiments 2.7 to 2.12 wherein the cancer is selected from carcinomas, for example carcinomas of the bladder, breast, colon, kidney, epidermis, liver, lung, oesophagus, gall bladder, ovary, pancreas, stomach, cervix, thyroid, prostate, gastrointestinal system, or skin, hematopoieitic tumours such as leukaemia, B-cell lymphoma, T-cell lymphoma, Hodgkin's lymphoma, non-Hodgkin's lymphoma, hairy cell lymphoma, or Burkett's lymphoma; hematopoieitic tumours of myeloid lineage, for example acute and chronic myelogenous leukaemias, myelodysplastic syndrome, or promyelocytic leukaemia; thyroid follicular cancer; tumours of mesenchymal origin, for example fibrosarcoma or habdomyosarcoma; tumours of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; Ewing's sarcoma or Kaposi's sarcoma.

2.14 A compound for use, use or method according to Embodiment 2.13 wherein the cancer is selected from breast cancer, colon cancer, lung cancer, ovarian cancer, pancreatic cancer, prostate cancer, glioma, Ewing's sarcoma and leukemia.

It is also envisaged that the Chk-1 inhibitors of the invention may be useful in treating tumours in which there is a defective DNA repair mechanism or a defective cell cycle, for example a cancer in which mutations (e.g. in p53) have led to the G1/S DNA damage checkpoint being lost (see the introductory section of this application). The Chk-1 inhibitors of the invention may also be useful in treating RAD17 mutant tumours, ATM-deficient RAD50-mutant tumours and fanconi anaemia. Accordingly in further embodiments (Embodiments 2.15 to 2.24), the invention provides:

2.15 A compound for use, use or method as defined in any one of Embodiments 2.7 to 2.14 wherein the cancer is one which is characterized by a defective DNA repair mechanism or defective cell cycle.

2.16 A compound for use, use or method according to Embodiment 2.15 wherein the cancer is a p53 negative or mutated tumour.

2.17 A compound for use, use or method as defined in any one of Embodiments 2.7 to 2.14 wherein the cancer is an MYC oncogene-driven cancer.

2.18 A compound for use, use or method according to Embodiment 2.16 wherein the MYC oncogene-driven cancer is a B-cell lymphoma, leukemia, neuroblastoma, breast cancer or lung cancer.

2.19 A compound of the formula (0) or formula (1) as defined in any one of Embodiments 1.0 to 1.107 for use in the treatment of a patient suffering from a p53 negative or mutated tumour (e.g. a cancer selected from breast cancer, colon cancer, lung cancer, ovarian cancer, pancreatic cancer, prostate cancer, glioma, and leukemia) in combination with radiotherapy or chemotherapy.

2.20 A compound for use according to any one of Embodiments 2.7 to 2.19 wherein, in addition to administration of a compound of the formula (0) or formula (1) as defined in any one of Embodiments 1.0 to 1.107, the treatment comprises administration to a patient of a chemotherapeutic agent selected from cytarabine, etoposide, gemcitabine and SN-38.

2.21 The use of a compound of the formula (0) or formula (1) as defined in any one of Embodiments 1.0 to 1.107 or 2.3 to 2.6 for the manufacture of a medicament for the treatment of a patient suffering from a cancer which is characterised by a defective DNA repair mechanism or defective cell cycle.

2.22 The use according to Embodiment 2.21 wherein the cancer is a p53 negative or mutated tumour.

2.23 A method for the treatment of a patient (e.g. a human patient) suffering from a cancer which is characterised by a defective DNA repair mechanism or defective cell cycle, which method comprises administering to the patient a therapeutically effective amount of a compound of the formula (0) or formula (1) as defined in any one of Embodiments 1.0 to 1.107 or 2.3 to 2.6.

2.24 A method according to Embodiment 2.23 wherein the cancer is a p53 negative or mutated tumour.

2.25 A compound for use, use or method as defined in any one of Embodiments 2.7 to 2.14 wherein the cancer is a RAD17-mutant tumour or an ATM-deficient RAD50-mutant tumour.

2.26 A compound of the formula (0) or formula (1) as defined in any one of Embodiments 1.0 to 1.107 or 2.3 to 2.6 for use in the treatment of Fanconi anaemia.

2.27 The use of a compound of the formula (0) or formula (1) as defined in any one of Embodiments 1.0 to 1.107 or 2.3 to 2.6 for the manufacture of a medicament for the treatment of Fanconi anaemia.

2.28 A method of treating Fanconi anaemia in a subject (e.g. a human subject) in need thereof, which method comprises administering to the subject a therapeutically effective amount of a compound of the formula (0) or formula (1) as defined in any one of Embodiments 1.0 to 1.107 or 2.3 to 2.6.

The Chk-1 inhibitor compounds of the invention may be used alone or they may be used in combination with DNA-damaging anti-cancer drugs and/or radiation therapy to treat subjects with multi-drug resistant cancers. A cancer is considered to be resistant to a drug when it resumes a normal rate of tumour growth while undergoing treatment with the drug after the tumour had initially responded to the drug. A tumour is considered to "respond to a drug" when it exhibits a decrease in tumor mass or a decrease in the rate of tumour growth.

Methods for the Preparation of Compounds of the Formulae (O) and (1)

Compounds of the formulae (O) and (1) can be prepared in accordance with synthetic methods well known to the skilled person and as described herein.

Accordingly, in another embodiment (Embodiment 3.1), the invention provides a process for the preparation of a compound as defined in any one of Embodiments 1.0 to 1.107, which process comprises:

(A) the reaction of a compound of formula (11):

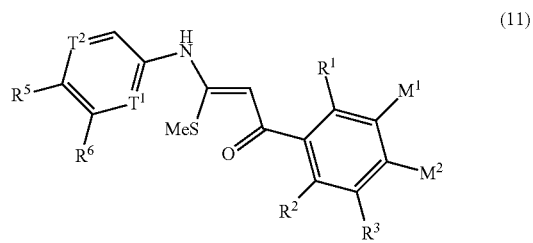

(11)

or a protected form thereof, wherein $R^1$ to $R^6$, $T^1$ and $T^2$ are as hereinbefore defined; with hydrazine, followed by removal of any protecting groups present, where required; or (B) the reaction of a compound of the formula (12):

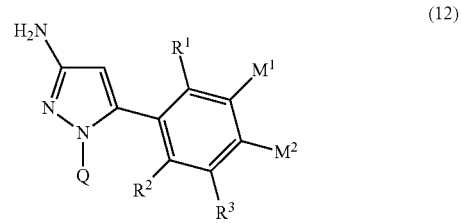

(12)

(or its pyrazole-ring tautomer) wherein $R^1$ to $R^3$, $M^1$ and $M^2$ are as hereinbefore defined, and Q is hydrogen or a protecting group PG; with a compound of the formula (13):

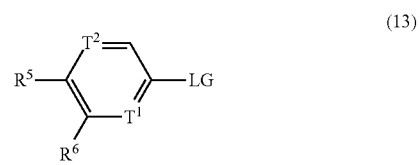

(13)

where $R^5$ and $R^6$ are as hereinbefore defined and LG is a leaving group or atom such as bromine, in the presence of a base such as a metal hydride base (e.g. sodium hydride), followed by removal of any protecting group PG where necessary; and thereafter:

(C) optionally converting one compound of the formula (0) or (1), into another compound of the formula (0) or (1).

In formula (11), a nitrogen atom forming part of the moiety A in $M^1$ or $M^2$ may be protected by an amino group protecting group. The protecting group, when present, is a group capable of protecting the amino function against unwanted side reactions and examples of such protecting groups are well known to the skilled person, see the reference book (*Protective Groups in Organic Synthesis* (Greene and Wuts) referred to below.

A particularly preferred protecting group is the tert-butoxycarbonyl (Boc) group. The Boc group may readily be removed when required by treatment with an acid such as hydrochloric acid or trifluoroacetic acid.

In process variant (A), the reaction of the compound of formula (11) with hydrazine is typically carried out in a polar solvent such as ethanol or aqueous ethanol in the presence of acetic acid, with moderate heating, for example to a temperature of about 60° C.

Compounds of the formula (11) wherein $R^1$ to $R^4$, A and $R^7$ are as defined in formula (1), can be prepared by the sequence of reactions shown in Scheme 1.

Scheme 1

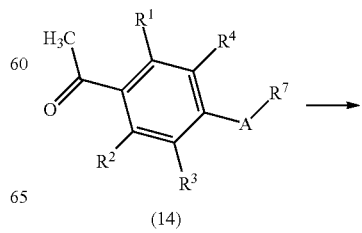

(14)

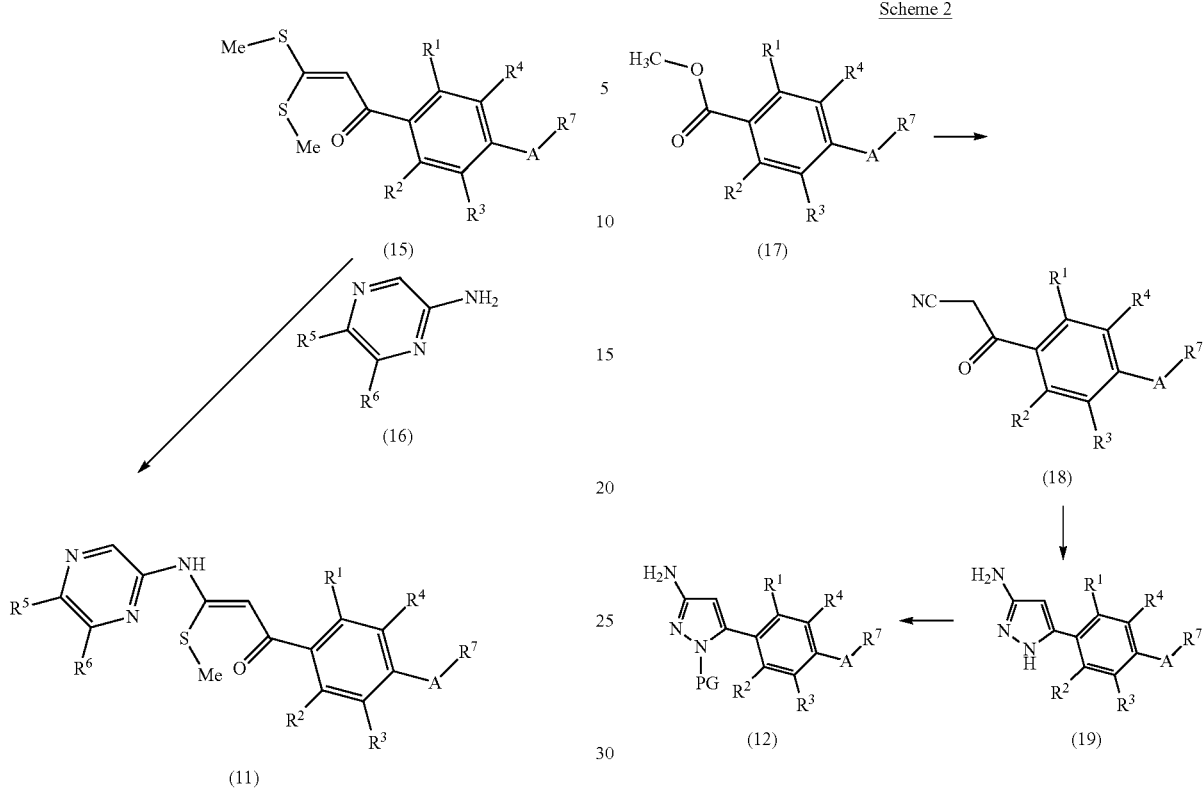

Compounds of the formula (14) can be prepared by the methods described below in the Examples section below or by methods analogous thereto. The compound of formula (14) is reacted with carbon disulfide and iodomethane in the presence of a metal hydride base such as sodium hydride in a polar solvent such as dimethyl sulfoxide, THF or DMF to give the intermediate (15). The intermediate (15) is then reacted with the aminopyrazine (16) in the presence of a metal hydride base (such as sodium hydride) in a polar solvent such as THF to give the compound (11).

In process variant (B), the compound of formula ((12) is typically reacted with the pyrazine compound (13) in the presence of a metal hydride base such as sodium hydride in a non-protic polar solvent such as THF. The reaction is typically carried out at low temperature, for example around 0° C. The leaving group LG is typically a halogen such as bromine. When a metal hydride base is used, the moiety Q is preferably a protecting group PG such as a Boc group. As an alternative to using a metal hydride base, a non-nucleophilic (or poorly nucleophilic) base such as N,N-diisopropylethylamine (DIPEA) can be used, in which case a protecting group can be omitted from the pyrazole ring (i.e. Q=hydrogen).

Compounds of the formula (12) wherein $R^1$ to $R^4$, A and $R^7$ are as defined in formula (1) and PG is a protecting group can be prepared by the sequence of reactions shown in Scheme 2.

Compounds of the formula (17) can be prepared by the methods described below in the Examples section or by methods analogous thereto. The compound of formula (17) is reacted with acetonitrile in the presence of an alkyl lithium base such as butyl lithium to give the cyano compound of formula (18). The reaction is typically carried out in an inert non-polar aprotic solvent such as toluene at a low temperature, for example about −78° C.

The cyano compound of formula (18) is then reacted with hydrazine in a polar solvent such as ethanol in the presence of acetic acid to give the pyrazole (19). The nitrogen atom at the 1-position of the pyrazole ring is then protected with a tert-butyloxycarbonyl (Boc) protecting group by reaction with Boc-anhydride in THF in the presence of a metal hydride base such as sodium hydride to give the pyrazole intermediate (12) where PG is Boc. The reaction is typically carried out at a low temperature, for example a temperature of about 0° C.

Once formed, one compound of the formula (0) or (1), or a protected derivative thereof, can be converted into another compound of the formula (0) or (1) by methods well known to the skilled person. Examples of synthetic procedures for converting one functional group into another functional group are set out in standard texts such as *Advanced Organic Chemistry and Organic Syntheses* (see references above) or *Fiesers' Reagents for Organic Synthesis*, Volumes 1-17, John Wiley, edited by Mary Fieser (ISBN: 0-471-58283-2).

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Greene and P. Wuts; 3rd Edition; John Wiley and Sons, 1999).

Compounds made by the foregoing methods may be isolated and purified by any of a variety of methods well known to those skilled in the art and examples of such methods include recrystallisation and chromatographic techniques such as column chromatography (e.g. flash chromatography) and HPLC.

Many of the synthetic intermediates of the formulae (11) to (19) described above and in the reaction schemes and examples below are novel and, as such, represent a further aspect of the invention.

Pharmaceutical Formulations

While it is possible for the active compound to be administered alone, it is preferable to present it as a pharmaceutical composition (e.g. formulation).

Accordingly, in another embodiment (Embodiment 4.1) of the invention, there is provided a pharmaceutical composition comprising at least one compound of the formula (0) or formula (1) as defined in any one of Embodiments 1.0 to 1.107 together with a pharmaceutically acceptable excipient.

The pharmaceutically acceptable excipient can be, for example, a carrier (e.g. a solid, liquid or semi-solid carrier), a diluent or bulking agent, a granulating agent, coating agent, binding agent, disintegrant, lubricating agent, preservative, antioxidant, buffering agent, suspending agent, thickening agent, flavouring agent, sweetener, taste masking agent or any other excipient conventionally used in pharmaceutical compositions. Examples of excipients for various types of pharmaceutical compositions are set out in more detail below.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacteriostats, co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

A drug molecule that is ionizable can be solubilized to the desired concentration by pH adjustment if the drug's $pK_a$ is sufficiently away from the formulation pH value. The acceptable range is pH 2-12 for intravenous and intramuscular administration, but subcutaneously the range is pH 2.7-9.0. The solution pH is controlled by either the salt form of the drug, strong acids/bases such as hydrochloric acid or sodium hydroxide, or by solutions of buffers which include but are not limited to buffering solutions formed from glycine, citrate, acetate, maleate, succinate, histidine, phosphate, tris(hydroxymethyl)-aminomethane (TRIS), or carbonate.

The combination of an aqueous solution and a water-soluble organic solvent/surfactant (i.e., a cosolvent) is often used in injectable formulations. The water-soluble organic solvents and surfactants used in injectable formulations include but are not limited to propylene glycol, ethanol, polyethylene glycol 300, polyethylene glycol 400, glycerin, dimethylacetamide (DMA), N-methyl-2-pyrrolidone (NMP; Pharmasolve), dimethylsulphoxide (DMSO), Solutol HS 15, Cremophor EL, Cremophor RH 60, and polysorbate 80. Such formulations can usually be, but are not always, diluted prior to injection.

Propylene glycol, PEG 300, ethanol, Cremophor EL, Cremophor RH 60, and polysorbate 80 are the entirely organic water-miscible solvents and surfactants used in commercially available injectable formulations and can be used in combinations with each other. The resulting organic formulations are usually diluted at least 2-fold prior to IV bolus or IV infusion.

Alternatively increased water solubility can be achieved through molecular complexation with cyclodextrins.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound of formula (0) or formula (1) or acid addition salt thereof. Lyophilisation refers to the procedure of freeze-drying a composition. Freeze-drying and lyophilisation are therefore used herein as synonyms. A typical process is to solubilise the compound and the resulting formulation is clarified, sterile filtered and aseptically transferred to containers appropriate for lyophilisation (e.g. vials). In the case of vials, they are partially stoppered with lyo-stoppers. The formulation can be cooled to freezing and subjected to lyophilisation under standard conditions and then hermetically capped forming a stable, dry lyophile formulation. The composition will typically have a low residual water content, e.g. less than 5% e.g. less than 1% by weight based on weight of the lyophile.

The lyophilisation formulation may contain other excipients for example, thickening agents, dispersing agents, buffers, antioxidants, preservatives, and tonicity adjusters. Typical buffers include phosphate, acetate, citrate and glycine. Examples of antioxidants include ascorbic acid, sodium bisulphite, sodium metabisulphite, monothioglycerol, thiourea, butylated hydroxytoluene, butylated hydroxyl anisole, and ethylenediaminetetraacetic acid salts. Preservatives may include benzoic acid and its salts, sorbic acid and its salts, alkyl esters of para-hydroxybenzoic acid, phenol, chlorobutanol, benzyl alcohol, thimerosal, benzalkonium chloride and cetylpyridinium chloride. The buffers mentioned previously, as well as dextrose and sodium chloride, can be used for tonicity adjustment if necessary.

Bulking agents are generally used in lyophilisation technology for facilitating the process and/or providing bulk and/or mechanical integrity to the lyophilized cake. Bulking agent means a freely water soluble, solid particulate diluent that when co-lyophilised with the compound or salt thereof, provides a physically stable lyophilized cake, a more optimal freeze-drying process and rapid and complete reconstitution. The bulking agent may also be utilised to make the solution isotonic.

The water-soluble bulking agent can be any of the pharmaceutically acceptable inert solid materials typically used for lyophilisation. Such bulking agents include, for example, sugars such as glucose, maltose, sucrose, and lactose; polyalcohols such as sorbitol or mannitol; amino acids such as glycine; polymers such as polyvinylpyrrolidine; and polysaccharides such as dextran.

The ratio of the weight of the bulking agent to the weight of active compound is typically within the range from about 1 to about 5, for example of about 1 to about 3, e.g. in the range of about 1 to 2.

Alternatively they can be provided in a solution form which may be concentrated and sealed in a suitable vial. Sterilisation of dosage forms may be via filtration or by autoclaving of the vials and their contents at appropriate stages of the formulation process. The supplied formulation may require further dilution or preparation before delivery for example dilution into suitable sterile infusion packs.

Extemporaneous injection solutions and suspensions may be prepared from sterile powders, granules and tablets.

In one preferred embodiment of the invention, the pharmaceutical composition is in a form suitable for i.v. administration, for example by injection or infusion.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing compounds of the formula (I) can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable cross-linked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The compound of formula (0) or formula (1), as defined in any one of Embodiments 1.0 to 1.107, or a prodrug thereof, may be formulated with a carrier and administered in the form of nanoparticles. Nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (0) or formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 miligrams to 1 gram, of active compound.

The active compound will be administered to a patient in need thereof (for example a human or animal patient) in an amount sufficient to achieve the desired therapeutic effect.

Methods of Treatment

It is envisaged that the compounds of the formula (0) or formula (1) as defined in any one of Embodiments 1.0 to 1.107 as defined herein will be useful either alone or in combination therapy with chemotherapeutic agents (particularly DNA-damaging agents) or radiation therapy in the prophylaxis or treatment of a range of proliferative disease states or conditions. Examples of such disease states and conditions are set out above.

The compounds of formula (0) or formula (1), whether administered alone, or in combination with DNA damaging agents and other anti-cancer agents and therapies, are generally administered to a subject in need of such administration, for example a human or animal patient, preferably a human.

According to another embodiment of the invention, Embodiment 5.1, there is provided a combination of a compound of formula (0) or formula (1) as defined in any one of Embodiments 1.0 to 1.107 together with another chemotherapeutic agent, for example an anticancer drug.

Examples of chemotherapeutic agents that may be co-administered with the compounds of formula (0) or formula (1) as defined in any one of Embodiments 1.0 to 1.107 include:

Topoisomerase I inhibitors
Antimetabolites
Tubulin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferases
Cytokines and retinoids
Hypoxia triggered DNA damaging agents (e.g. Tirapazamine, TH-302)

Particular examples of chemotherapeutic agents that may be administered in combination with the compounds of formula (0) or formula (1) as defined in any one of Embodiments 1.0 to 1.107 include:
nitrogen mustards such as mechlorethamine, cyclophosphamide, ifosfamide, melphalan and chlorambucil;
nitrosoureas such as carmustine, lomustine and semustine;
ethyleneimine/methylmelamine compounds such as triethylenemelamine, triethylene thiophosphoramide and hexamethylmelamine;
alkyl sulphonates such as busulfan;
triazines such as dacarbazine
Antimetabolites such as folates, methotrexate, trimetrexate, 5-fluorouracil, fluorodeoxyuridine, gemcitabine, cytosine arabinoside, 5-azacytidine, 2, 2'-difluorodeoxycytidine, 6-mercaptopurine, 6-thioguanine, azathioprine, 2'-deoxycoformycin, erythrohydroxynonyl-adenine, fludarabine phosphate and 2-chlorodeoxyadenosine;
type I topoisomerase inhibitors such as camptothecin, topotecan and irinotecan;
type II topoisomerase inhibitors such as the epipodophylotoxins (e.g. etoposide and teniposide);
antimitotic drugs such as paclitaxel, Taxotere, *Vinca* alkaloids (e.g. vinblastine, vincristine, vinorelbine) and estramustine (e.g. estramustine phosphate);
antibiotics such as actimomycin D, daunomycin (rubidomycin), doxorubicin (adriamycin), mitoxantrone, idarubicine, bleomycin, mithramycin, mitomycin C and dactinomycin enzymes such as L-asparaginase;
cytokines and biological response modifiers such as interferon ($\alpha,\beta,\gamma$), interleukin-2G-CSF and GM-CSF:
retinoids such as retinoic acid derivatives (e.g. bexarotene);
radiosensitisers such as metronidazole, misonidazole, desmethylmisonidazole, pimonidazole, etanidazole, nimorazole, nicotinamide, 5-bromodeoxyuridine, 5-iododeoxyuridine and bromodeoxycytidine;
platinum compounds such as cisplatin, carboplatin, spiroplatin, iproplatin, onnaplatin, tetraplatin and oxaliplatin;
anthracenediones such as mitoxantrone;
ureas such as hydroxyurea;
hydrazine derivatives such as N-methylhydrazine and procarbazine;
adrenocortical suppressants such as mitotane and aminoglutethimide;
adrenocorticosteroids and antagonists such as prednisone, dexamethasone and aminoglutethimide;
progestins such as hydroxyprogesterone (e.g. hydroxyprogesterone caproate), medroxyprogesterone (e.g. medroxyprogesterone acetate) and megestrol (e.g. megestrol acetate);
oestrogens such as diethylstilbestrol and ethynyl estradiol;
anti-oestrogens such as tamoxifen;
androgens such as testosterone (e.g. testosterone propionate) and fluoxymesterone;
anti-androgens such as flutamide and leuprolide;
nonsteroidal anti-androgens such as flutamide; and
signal transduction inhibitors such as PARP inhibitors [e.g. as disclosed in *Cancer Res.;* 66: (16)], Mek inhibitors [e.g as disclosed in *Blood.* 2008 Sep. 15; 112(6): 2439-2449], farnesyltransferase inhibitors [e.g. as disclosed in *Blood.* 2005 Feb. 15; 105(4):1706-16], wee1 inhibitors [e.g. as disclosed in Haematologica 2013.093187 (epub ahead of print)], rapamycin and Src inhibitors [e.g as disclosed in *Blood.* 2011 Feb. 10; 117(6):1947-57].

Examples of the chemotherapeutic agents than may be used in combination with the Chk-1 inhibitor compounds of Embodiments 1.0 to 1.107 as defined herein include the chemotherapeutic agents described in Blasina et al., Mol. Cancer Ther., 2008, 7(8), 2394-2404, Ashwell et al., Clin. Cancer Res., 2008, 14(13), 4032-4037, Ashwell et al., Expert Opin. Investig. Drugs, 2008, 17(9), 1331-1340, Trends in Molecular Medicine February 2011, Vol. 17, No. 2 and Clin Cancer Res; 16(2) Jan. 15, 2010.

Particular examples of chemotherapeutic agents that may be used in combination with the Chk-1 inhibitor compounds of Embodiments 1.0 to 1.107 as defined herein include antimetabolites (such as capecitabine, cytarabine, fludarabine, gemcitabine and pemetrexed), Topoisomerase-I inhibitors (such as SN38, topotecan, irinotecan), platinum compounds (such as carboplatin, oxaloplatin and cisplatin), Topoisomerase-II inhibitors (such as daunorubicin, doxorubicin and etoposide), thymidylate synthase inhibitors (such as 5-fluoruracil), mitotic inhibitors (such as docetaxel, paclitaxel, vincristine and vinorelbine), and alkylating agents (such as mitomycin C).

A further set of chemotherapeutic agents that may be used in combination with the Chk-1 inhibitor compounds of Embodiments 1.0 to 1.107 as defined herein includes agents that induce stalled replication forks (see Ashwell et al., Clin. Cancer Res., above), and examples of such compounds include gemcitabine, 5-fluorouracil and hydroxyurea.

The compounds of the invention and combinations with chemotherapeutic agents or radiation therapies as described above may be administered over a prolonged term to maintain beneficial therapeutic effects or may be administered for a short period only. Alternatively they may be administered in a pulsatile or continuous manner.

The compounds of the invention will be administered in an effective amount, i.e. an amount which is effective to bring about the desired therapeutic effect either alone (in monotherapy) or in combination with one or more chemotherapeutic agents or radiation therapy. For example, the "effective amount" can be a quantity of compound which, when administered alone or together with a DNA-damaging drug or other anti-cancer drug to a subject suffering from cancer, slows tumour growth, ameliorates the symptoms of the disease and/or increases longevity. More particularly, when used in combination with radiation therapy, with a DNA-damaging drug or other anti-cancer drug, an effective amount of the Chk-1 inhibitor of the invention is the quantity in which a greater response is achieved when the Chk-1 inhibitor is co-administered with the DNA damaging anti-cancer drug and/or radiation therapy compared with when the DNA damaging anti-cancer drug and/or radiation therapy is administered alone. When used as a combination therapy, an "effective amount" of the DNA damaging drug and/or an "effective" radiation dose are administered to the subject, which is a quantity in which anti-cancer effects are normally achieved. The Chk-1 inhibitors of the invention and the DNA damaging anti-cancer drug can be co-administered to the subject as part of the same pharmaceutical composition or, alternatively, as separate pharmaceutical compositions.

When administered as separate pharmaceutical compositions, the Chk-1 inhibitor of the invention and the DNA-damaging anti-cancer drug (and/or radiation therapy) can be administered simultaneously or at different times, provided that the enhancing effect of the Chk-1 inhibitor is retained.

In one embodiment, a compound of any one of Embodiments 1.0 to 1.107 as defined herein is administered before (e.g by up to 8 hours or up to 12 hours or up to one day before) administration of the DNA-damaging anticancer drug.

In another embodiment, a compound of any one of Embodiments 1.0 to 1.107 as defined herein is administered after (e.g by up to 8 hours or up to 12 hours or up to 24 hours or up to 30 hours or up to 48 hours after) administration of the DNA-damaging anticancer drug. In another embodiment, a first dose of a compound of any one of Embodiments 1.0 to 1.107 as defined herein is administered one day after administration of the DNA-damaging anticancer drug and a second dose of the said compound is administered two days after administration of the DNA-damaging anticancer drug.

In a further embodiment, a first dose of a compound of any one of Embodiments 1.0 to 1.107 as defined herein is administered one day after administration of the DNA-damaging anticancer drug, a second dose of the said compound is administered two days after administration of the DNA-damaging anticancer drug, and third dose of the said compound is administered three days after administration of the DNA-damaging anticancer drug.

Particular dosage regimes comprising the administration of a compound of any one of Embodiments 1.0 to 1.107 as defined herein and a DNA-damaging anticancer drug may be as set out in WO2010/118390 (Array Biopharma), the contents of which are incorporated herein by reference.

The amount of Chk-1 inhibitor compound of the invention and (in the case of combination therapy) the DNA damaging anti-cancer drug and radiation dose administered to the subject will depend on the nature and potency of the DNA damaging anti-cancer drug, the type and severity of the disease or condition and on the characteristics of the subject, such as general health, age, sex, body weight and tolerance to drugs. The skilled person will be able to determine appropriate dosages depending on these and other factors. Effective dosages for commonly used anti-cancer drugs and radiation therapy are well known to the skilled person.

A typical daily dose of the compound of formula (0) or formula (1), whether administered on its own in monotherapy or administered in combination with a DNA damaging anticancer drug, can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound can be administered on a daily basis or on a repeat basis every 2, or 3, or 4, or 5, or 6, or 7, or 10 or 14, or 21, or 28 days for example.

Ultimately, however, the quantity of compound administered and the type of composition used will be commensurate with the nature of the disease or physiological condition being treated and will be at the discretion of the physician.

Methods of Diagnosis

Prior to administration of a compound of the formula (0) or formula (1) as defined in any one of Embodiments 1.0 to 1.107, a patient may be screened to determine whether a cancer from which the patient is or may be suffering is one which would be susceptible to treatment with either a Chk-1 kinase inhibitor compound or a combination of a chemotherapeutic agent (such as a DNA-damaging agent) and a Chk-1 kinase inhibitor compound.

More particularly, a patient may be screened to determine whether a cancer from which the patient is or may be suffering is one which is characterised by a defective DNA repair mechanism or a defective cell cycle, for example a defective cell cycle due to a p53 mutation or is a p53 negative cancer.

Cancers which are characterised by p53 mutations or the absence of p53 can be identified, for example, by the methods described in Allred et al., J. Nat. Cancer Institute, Vol. 85, No. 3, 200-206 (1993) and the methods described in the articles listed in the introductory part of this application. For example, p53 protein may be detected by immunohistochemical methods such as immuno-staining.

The diagnostic tests are typically conducted on a biological sample selected from tumour biopsy samples, blood samples (isolation and enrichment of shed tumour cells), stool biopsies, sputum, chromosome analysis, pleural fluid, peritoneal fluid, or urine.

In addition to p53, mutations to other DNA repair factors such as RAD17, RAD50, and members of the Fanconi's anaemia complementation group may be predictive of response to Chk1 inhibitors alone, or in combination with chemotherapy. Cancers which contain mutations in these DNA repair pathways may be identified by DNA sequence analysis of tumor biopsy tissue or circulating tumor DNA (ctDNA) or, in the case of Fanconi's anaemia, by evaluating DNA foci formation in tumor biopsy specimens using an antibody to FANCD2, as described in Duan et al., Frontiers in Oncology vol. 4, 1-8 (2014).

Thus, the compounds of any one of Embodiments 1.0 to 1.107 may be used to treat members of a sub-population of patients who have been screened (for example by testing one or more biological samples taken from the said patients) and have been found to be suffering from a cancer characterised by p53 mutation or a p53 negative cancer, or a cancer containing a RAD17 or RAD50 mutation, or a mutation in a member of the Fanconi's anaemia complementation group.

EXAMPLES

The invention will now be illustrated, but not limited, by reference to the specific embodiments described in the following examples.

In the examples, the following abbreviations are used.
ACN acetonitrile
Ac$_2$O acetic anhydride
AcOH acetic acid
AIBN azobisisobutyronitrile
AlCl$_3$ aluminium chloride
aq aqueous
Boc$_2$O di-tert-butyl dicarbonate
BINAP 2,2'-bis(diphenylphosphino)-1,1'-binaphthyl
DAST Diethylaminosulfur trifluoride
DCM dichloromethane
DEAD diethyl azodicarboxylate
DIPEA diisopropylethylamine
DMF dimethylformamide
DMSO dimethylsulfoxide
EDCl 1-ethyl-3-(3-dimethylaminopropyl)carbodiimide
Et$_3$N triethylamine
Et$_2$O diethyl ether
EtOAc ethyl acetate
EtOH ethanol
HCl hydrogen chloride
HPLC high performance liquid chromatography
LCMS liquid chromatography-mass spectrometry
LiHMDS lithium bis(trimethylsilyl)amide
MeCN acetonitrile
MeOH methanol
Mesyl methanesulfonyl
NaBH$_4$ sodium borohydride
NaBH(AcO)$_3$ sodium triacetoxyborohydride
NaH sodium hydride
NaHCO$_3$ sodium hydrogen carbonate
NaOH sodium hydroxide
Na$_2$SO$_4$ sodium sulfate
NBS N-bromosuccinimide
NH$_3$ ammonia
NH$_4$Cl ammonium chloride
NMR nuclear magnetic resonance
PdCl$_2$(dppf).DCM [1,1'-Bis(diphenylphosphino)ferrocene]dichloropalladium(II), complex with dichloromethane
TBAF tetrabutylammonium fluoride
TBDMS tert-butyldimethylsilyl
THF tetrahydrofuran
TMOA trimethylorthoacetate
TMS trimethylsilyl Proton magnetic resonance ($^1$H NMR) spectra were recorded on a Bruker 400 instrument operating at 400 MHz, in DMSO-d$_6$ or MeOH-d$_4$ (as indicated) at 27° C., unless otherwise stated and are reported as follows: chemical shift δ/ppm (multiplicity where s=singlet, d=doublet, dd, double doublet, t=triplet, q=quartet, m=multiplet, br=broad, number of protons). The residual protic solvent was used as the internal reference.

Liquid chromatography and mass spectroscopy analyses were carried out using the system and operating conditions set out below. Where atoms with different isotopes are present and a single mass quoted, the mass quoted for the compound is the monoisotopic mass (i.e. $^{35}$Cl; $^{79}$Br etc.)

LCMS Conditions

The LCMS data given in the following examples were obtained using Method A or Method B as set out below.

LCMS Method A

Samples were analysed by reverse phase HPLC-MS using a Waters 2795 Alliance HT HPLC, a Micromass ZQ mass spectrometer and a Waters 996 photodiode array UV detector. The LCMS used electrospray ionisation and the chromatography system as follows:

| Mass Spectrometer: | | |
|---|---|---|
| Ionization mode: | Positive | Negative |
| Capillary Voltage: | 3.20 kV | −3.00 kV |
| Cone Voltage: | 30 V | −30 V |
| Source Temperature: | 110° C. | 110° C. |
| Desolvation Temperature: | 350° C. | 350° C. |
| Cone Gas Flow: | 30 L/Hr | 30 L/Hr |
| Desolvation Gas Flow: | 400 L/Hr | 400 L/Hr |
| Scan duration: | 0.50 seconds | 0.50 seconds |
| Interscan delay: | 0.20 seconds | 0.20 seconds |
| Mass range: | 80 to 1000 AMU | 80 to 1000 AMU |

LCMS was carried using a BEH C18×2.1 mm, 1.7 micron column. Column flow was 0.55 ml/min and the mobile phase used were 0.1% formic acid in water and 5 mM ammonium acetate (A) and 0.1% formic acid in acetonitrile (B), with an injection volume of 10 μL.

The gradient was as described below.

| Time (min) | % A | % B |
|---|---|---|
| 0.01 | 95 | 5 |
| 0.40 | 95 | 5 |
| 0.80 | 65 | 35 |
| 1.20 | 45 | 55 |
| 2.50 | 0 | 100 |
| 3.30 | 0 | 100 |
| 3.31 | 95 | 5 |
| 4.00 | 95 | 5 |

LCMS Method B

Samples were analysed by reverse phase HPLC-MS using a Waters 2795 Alliance HPLC, an Acquity QDA mass spectrometer and a Waters 996 photodiode array UV detector. The LCMS used electrospray ionisation and the chromatography system as follows:

| Mass Spectrometer: | | |
|---|---|---|
| Ionization mode: | Positive | Negative |
| Capillary Voltage: | 1.50 kV | −0.80 kV |
| Cone Voltage: | 10 V | −30 V |
| Source Temperature: | 120° C. | 120° C. |
| Desolvation Temperature: | 600° C. | 600° C. |
| Scan duration: | 0.50 seconds | 0.50 seconds |
| Interscan delay: | 0.10 seconds | 0.10 seconds |
| Mass range: | 100 to 700 AMU | 100 to 700 AMU |

LCMS was carried using a X-BRIDGE C18 100×4.6 mm, 5 micron column. Column flow was 1.0 ml/min and the mobile phase used were 0.1% formic acid in water (A) and methanol (B), with an injection volume of 10 μL.

The gradient was as described below.

| Time (min) | % A | % B |
|---|---|---|
| 0.01 | 90 | 10 |
| 3.00 | 10 | 90 |
| 6.00 | 0 | 100 |

-continued

| Time (min) | % A | % B |
|---|---|---|
| 7.01 | 90 | 10 |
| 10.00 | 90 | 10 |

Examples 1 to 163

The compounds of Examples 1 to 163 shown in Table 1 below have been prepared. Their NMR and LCMS properties are set out in Table 2.

TABLE 1

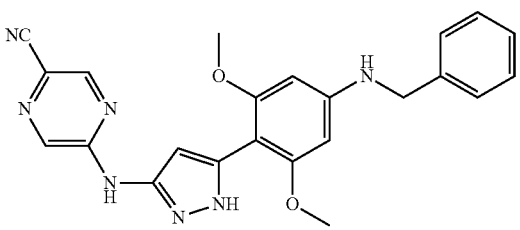 [SMILES: COc1cc(NCc2ccccc2)cc(OC)c1-c1cc(Nc2cnc(C#N)cn2)n[nH]1]

Example 1

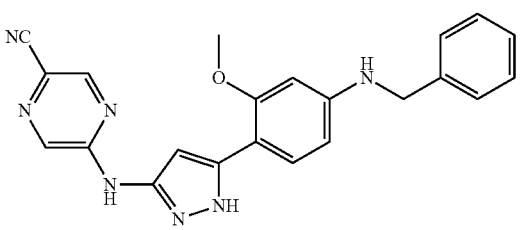 [SMILES: COc1cc(NCc2ccccc2)ccc1-c1cc(Nc2cnc(C#N)cn2)n[nH]1]

Example 2

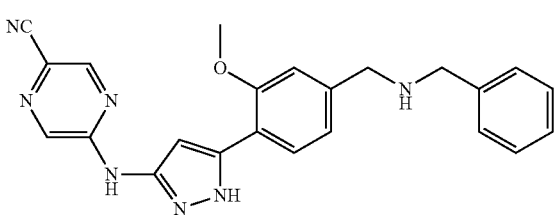 [SMILES: COc1cc(CNCc2ccccc2)ccc1-c1cc(Nc2cnc(C#N)cn2)n[nH]1]

Example 3

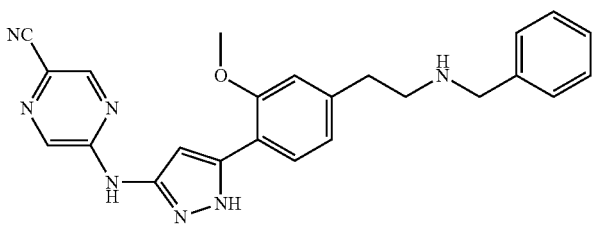 [SMILES: COc1cc(CCNCc2ccccc2)ccc1-c1cc(Nc2cnc(C#N)cn2)n[nH]1]

Example 4

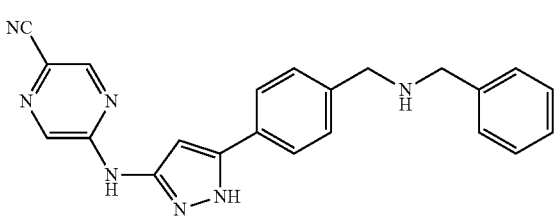 [SMILES: N#Cc1cnc(Nc2cc(-c3ccc(CNCc4ccccc4)cc3)[nH]n2)cn1]

Example 5

TABLE 1-continued
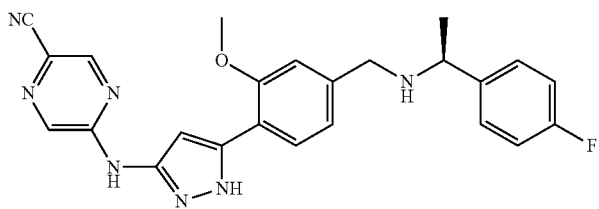 [SMILES: COc1cc(CN[C@@H](C)c2ccc(F)cc2)ccc1-c1cc(Nc2cnc(C#N)cn2)n[nH]1]
Example 6
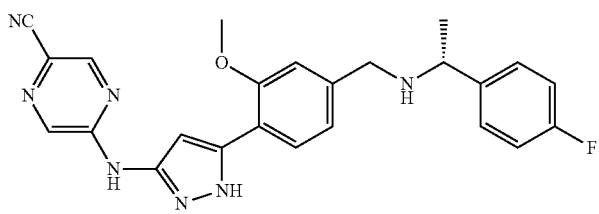 [SMILES: COc1cc(CN[C@H](C)c2ccc(F)cc2)ccc1-c1cc(Nc2cnc(C#N)cn2)n[nH]1]
Example 7
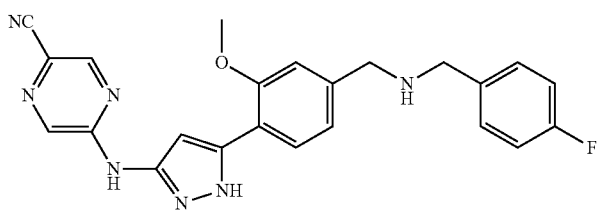 [SMILES: COc1cc(CNCc2ccc(F)cc2)ccc1-c1cc(Nc2cnc(C#N)cn2)n[nH]1]
Example 8
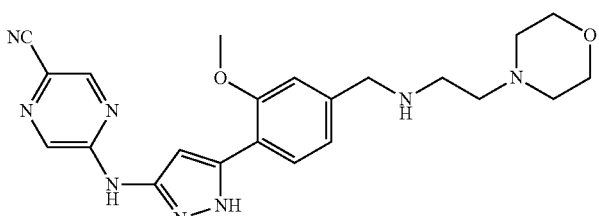
Example 9
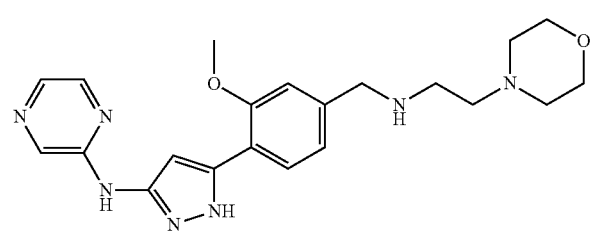 [SMILES: COc1cc(CNCCN2CCOCC2)ccc1-c1cc(Nc2cnccn2)n[nH]1]
Example 10
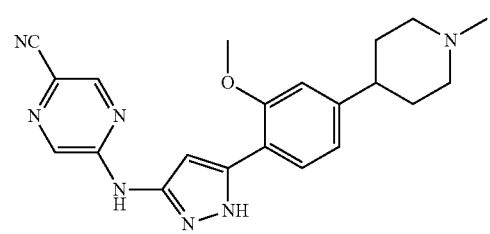 [SMILES: COc1cc(C2CCN(C)CC2)ccc1-c1cc(Nc2cnc(C#N)cn2)n[nH]1]
Example 11
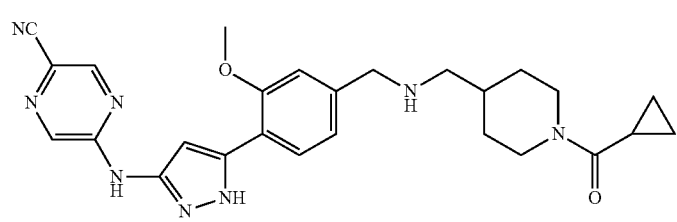 [SMILES: COc1cc(CNCC2CCN(C(=O)C3CC3)CC2)ccc1-c1cc(Nc2cnc(C#N)cn2)n[nH]1]
Example 12

TABLE 1-continued
 Example 13
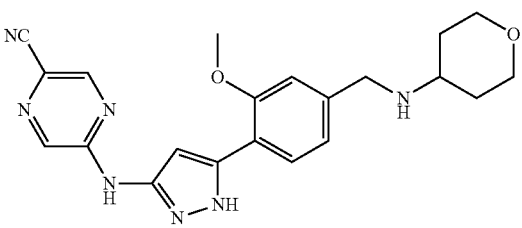 [SMILES: COc1cc(CNC2CCOCC2)ccc1-c1cc(Nc2cnc(C#N)cn2)n[nH]1] Example 14
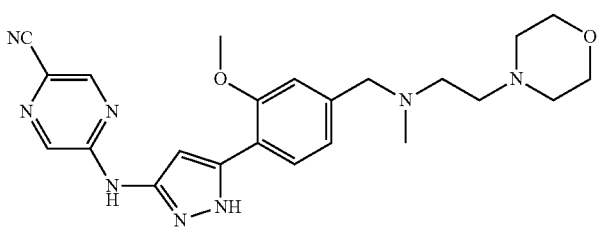 [SMILES: COc1cc(CN(C)CCN2CCOCC2)ccc1-c1cc(Nc2cnc(C#N)cn2)n[nH]1] Example 15
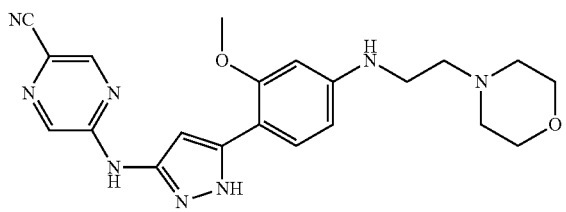 [SMILES: COc1cc(NCCN2CCOCC2)ccc1-c1cc(Nc2cnc(C#N)cn2)n[nH]1] Example 16
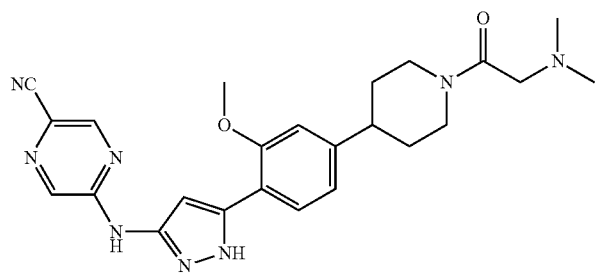 [SMILES: COc1cc(C2CCN(C(=O)CN(C)C)CC2)ccc1-c1cc(Nc2cnc(C#N)cn2)n[nH]1] Example 17
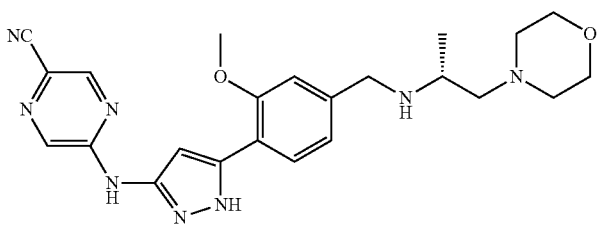 [SMILES: COc1cc(CN[C@H](C)CN2CCOCC2)ccc1-c1cc(Nc2cnc(C#N)cn2)n[nH]1] Example 18
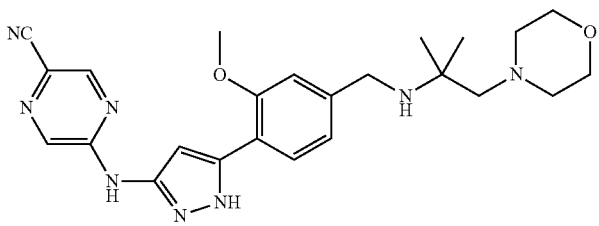 [SMILES: COc1cc(CNC(C)(C)CN2CCOCC2)ccc1-c1cc(Nc2cnc(C#N)cn2)n[nH]1] Example 19

TABLE 1-continued
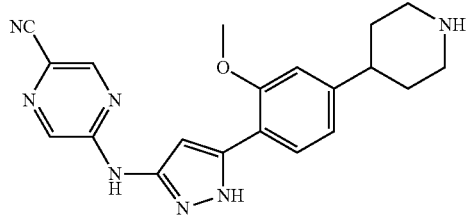 [SMILES: COc1cc(C2CCNCC2)ccc1-c1cc(Nc2cnc(C#N)cn2)n[nH]1] Example 20
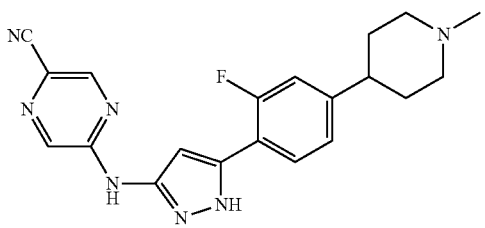 [SMILES: CN1CCC(c2ccc(-c3cc(Nc4cnc(C#N)cn4)n[nH]3)c(F)c2)CC1] Example 21
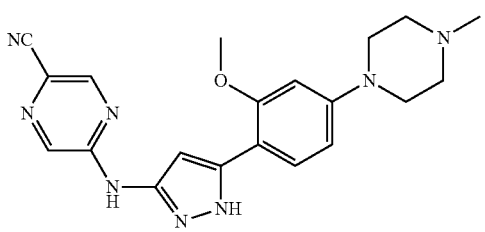 [SMILES: COc1cc(N2CCN(C)CC2)ccc1-c1cc(Nc2cnc(C#N)cn2)n[nH]1] Example 22
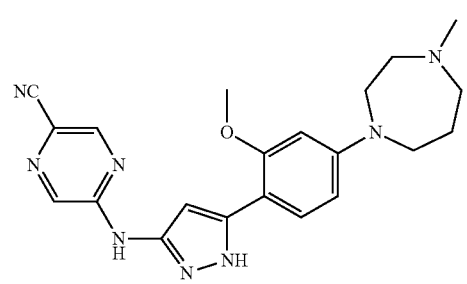 [SMILES: COc1cc(N2CCCN(C)CC2)ccc1-c1cc(Nc2cnc(C#N)cn2)n[nH]1] Example 23
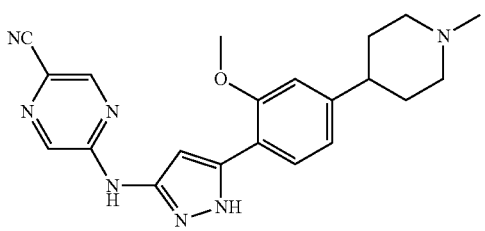 [SMILES: COc1cc(C2CCN(C)CC2)ccc1-c1cc(Nc2cnc(C#N)cn2)n[nH]1] Example 24
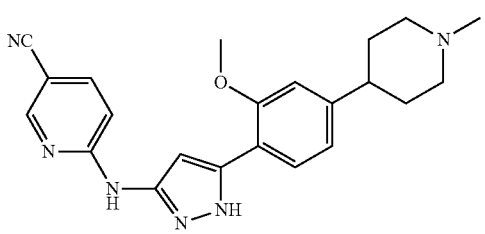 [SMILES: COc1cc(C2CCN(C)CC2)ccc1-c1cc(Nc2ccc(C#N)cn2)n[nH]1] Example 25

TABLE 1-continued
| | |
|---|---|
| 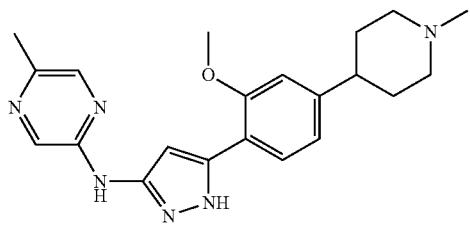 [SMILES: COc1cc(C2CCN(C)CC2)ccc1-c1cc(Nc2cnc(C)cn2)n[nH]1] | Example 26 |
| 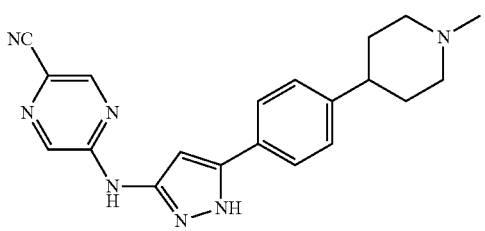 [SMILES: CN1CCC(c2ccc(-c3cc(Nc4cnc(C#N)cn4)n[nH]3)cc2)CC1] | Example 27 |
|  | Example 28 |
| 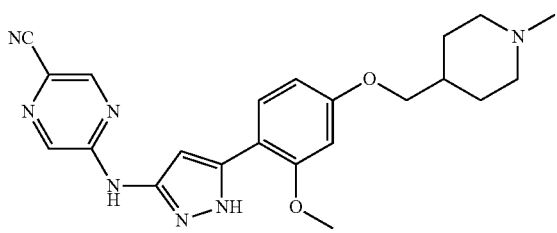 [SMILES: COc1cc(OCC2CCN(C)CC2)ccc1-c1cc(Nc2cnc(C#N)cn2)n[nH]1] | Example 29 |
| 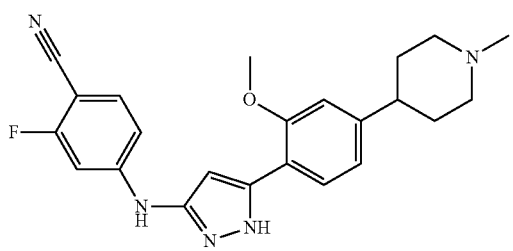 [SMILES: COc1cc(C2CCN(C)CC2)ccc1-c1cc(Nc2ccc(C#N)c(F)c2)n[nH]1] | Example 30 |
| 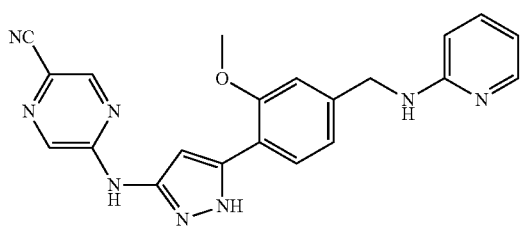 [SMILES: COc1cc(CNc2ccccn2)ccc1-c1cc(Nc2cnc(C#N)cn2)n[nH]1] | Example 31 |
| 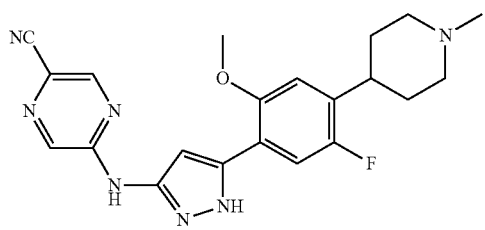 [SMILES: COc1cc(C2CCN(C)CC2)c(F)cc1-c1cc(Nc2cnc(C#N)cn2)n[nH]1] | Example 32 |

TABLE 1-continued
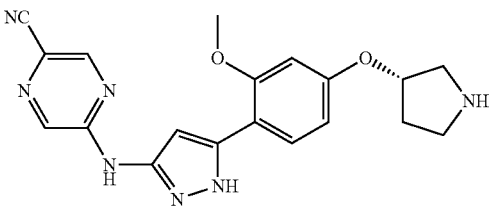 [SMILES: COc1cc(O[C@H]2CCNC2)ccc1-c1cc(Nc2cnc(C#N)cn2)n[nH]1]
Example 33
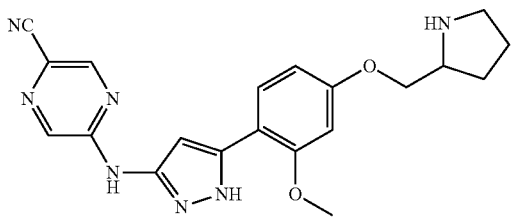 [SMILES: COc1cc(OCC2CCCN2)ccc1-c1cc(Nc2cnc(C#N)cn2)n[nH]1]
Example 34
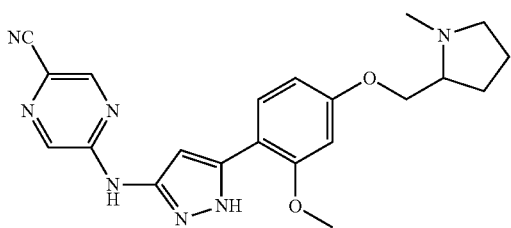 [SMILES: COc1cc(OCC2CCCN2C)ccc1-c1cc(Nc2cnc(C#N)cn2)n[nH]1]
Example 35
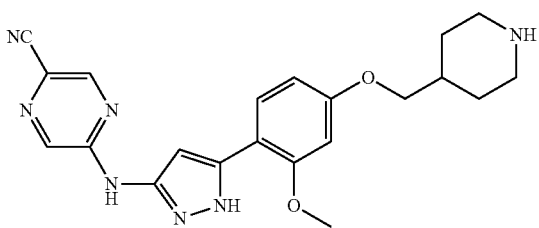 [SMILES: COc1cc(OCC2CCNCC2)ccc1-c1cc(Nc2cnc(C#N)cn2)n[nH]1]
Example 36
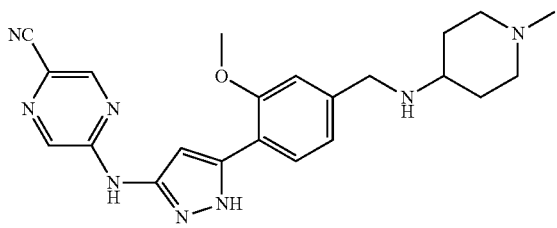 [SMILES: COc1cc(CNC2CCN(C)CC2)ccc1-c1cc(Nc2cnc(C#N)cn2)n[nH]1]
Example 37
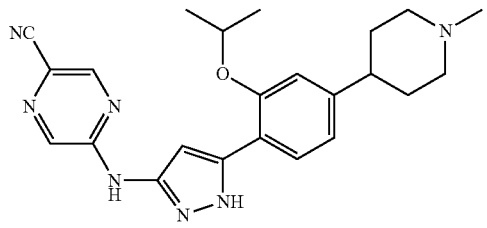 [SMILES: CC(C)Oc1cc(C2CCN(C)CC2)ccc1-c1cc(Nc2cnc(C#N)cn2)n[nH]1]
Example 38
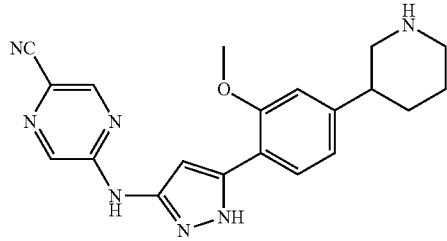 [SMILES: COc1cc(C2CCCNC2)ccc1-c1cc(Nc2cnc(C#N)cn2)n[nH]1]
Example 39

TABLE 1-continued
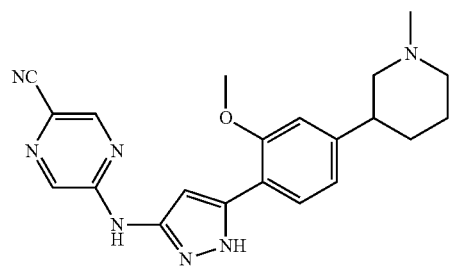 [SMILES: COc1cc(C2CCCN(C)C2)ccc1-c1cc(Nc2cnc(C#N)cn2)n[nH]1] Example 40
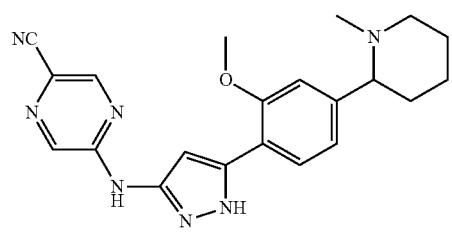 [SMILES: COc1cc(C2CCCCN2C)ccc1-c1cc(Nc2cnc(C#N)cn2)n[nH]1] Example 41
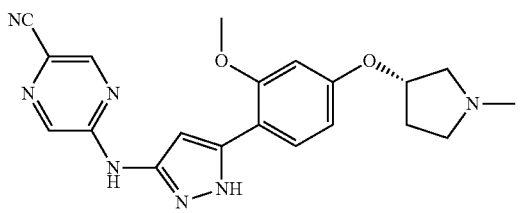 [SMILES: COc1cc(O[C@H]2CCN(C)C2)ccc1-c1cc(Nc2cnc(C#N)cn2)n[nH]1] Example 42
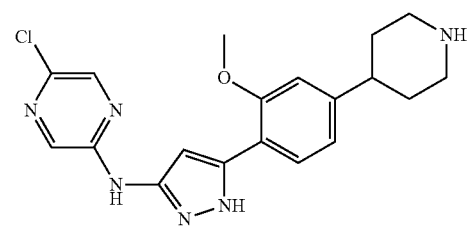 [SMILES: COc1cc(C2CCNCC2)ccc1-c1cc(Nc2cnc(Cl)cn2)n[nH]1] Example 43
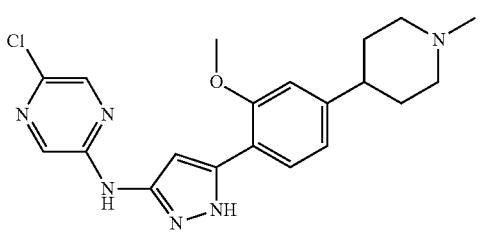 [SMILES: COc1cc(C2CCN(C)CC2)ccc1-c1cc(Nc2cnc(Cl)cn2)n[nH]1] Example 44
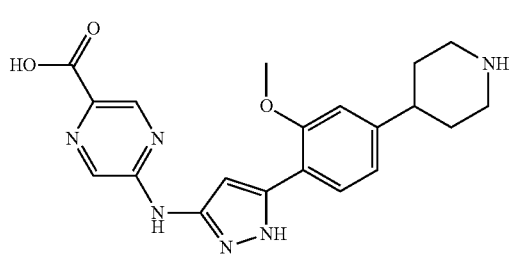 [SMILES: COc1cc(C2CCNCC2)ccc1-c1cc(Nc2cnc(C(=O)O)cn2)n[nH]1] Example 45

TABLE 1-continued
| | |
|---|---|
| 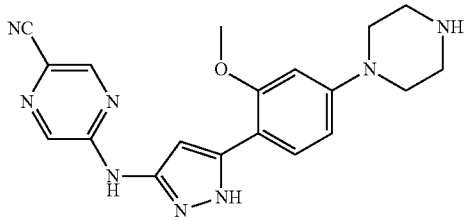 [SMILES: COc1cc(N2CCNCC2)ccc1-c1cc(Nc2cnc(C#N)cn2)n[nH]1] | Example 46 |
| 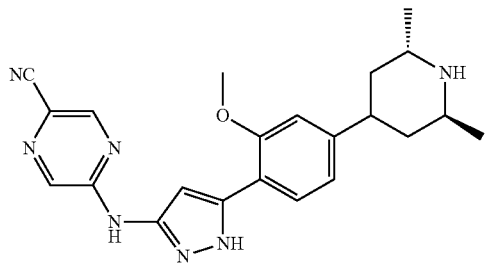 [SMILES: COc1cc(C2C[C@H](C)N[C@@H](C)C2)ccc1-c1cc(Nc2cnc(C#N)cn2)n[nH]1] | Example 47 |
| 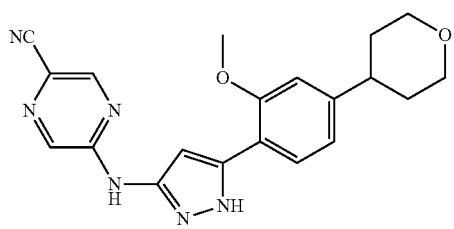 [SMILES: COc1cc(C2CCOCC2)ccc1-c1cc(Nc2cnc(C#N)cn2)n[nH]1] | Example 48 |
| 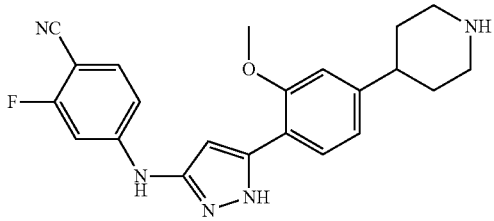 [SMILES: COc1cc(C2CCNCC2)ccc1-c1cc(Nc2ccc(C#N)c(F)c2)n[nH]1] | Example 49 |
| 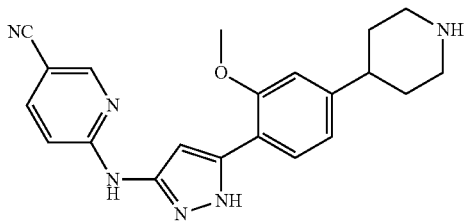 | Example 50 |
| 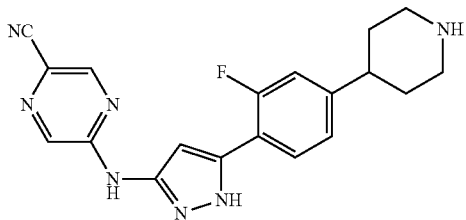 [SMILES: N#Cc1cnc(Nc2cc(-c3ccc(C4CCNCC4)cc3F)[nH]n2)cn1] | Example 51 |

TABLE 1-continued
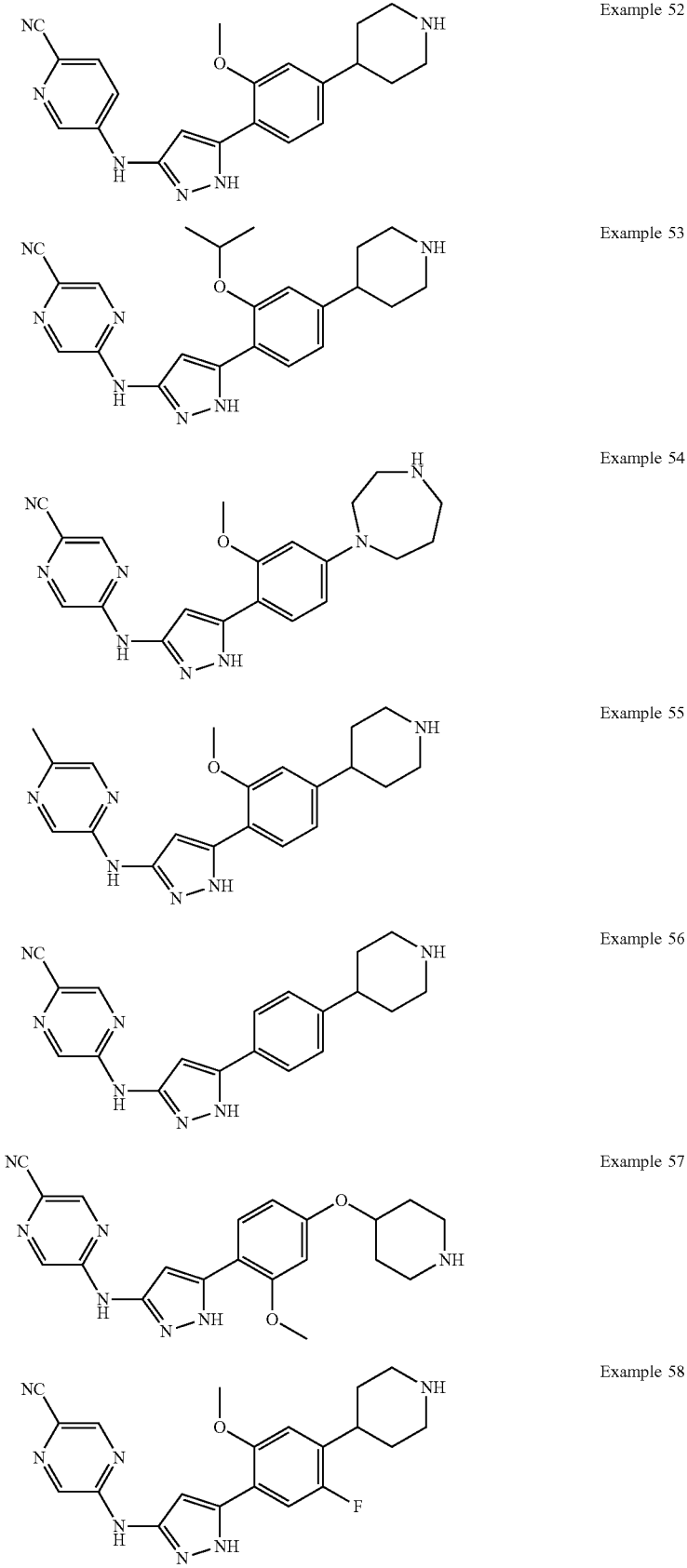
| | |
|---|---|
| | Example 52 |
| | Example 53 |
| | Example 54 |
| | Example 55 |
| | Example 56 |
| | Example 57 |
| | Example 58 |

TABLE 1-continued
Example 59
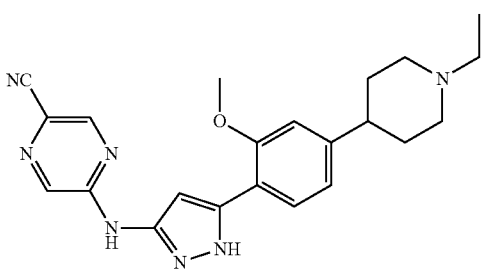 [SMILES: CCN1CCC(c2ccc(-c3cc(Nc4cnc(C#N)cn4)n[nH]3)c(OC)c2)CC1]
Example 60
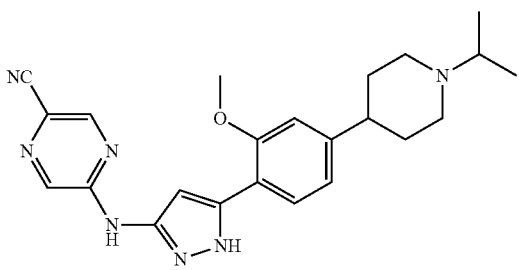 [SMILES: COc1cc(C2CCN(C(C)C)CC2)ccc1-c1cc(Nc2cnc(C#N)cn2)n[nH]1]
Example 61
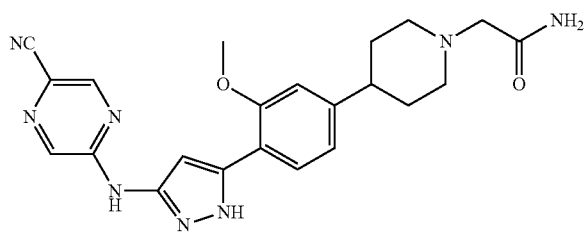 [SMILES: COc1cc(C2CCN(CC(N)=O)CC2)ccc1-c1cc(Nc2cnc(C#N)cn2)n[nH]1]
Example 62
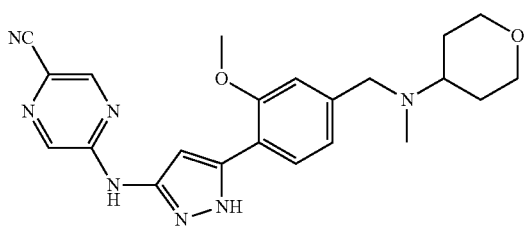 [SMILES: COc1cc(CN(C)C2CCOCC2)ccc1-c1cc(Nc2cnc(C#N)cn2)n[nH]1]
Example 63
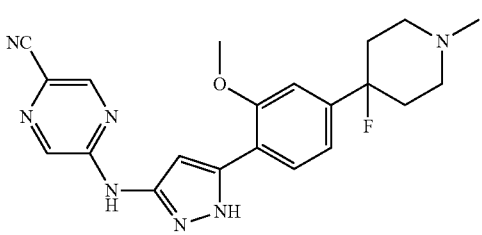 [SMILES: COc1cc(C2(F)CCN(C)CC2)ccc1-c1cc(Nc2cnc(C#N)cn2)n[nH]1]
Example 64

TABLE 1-continued
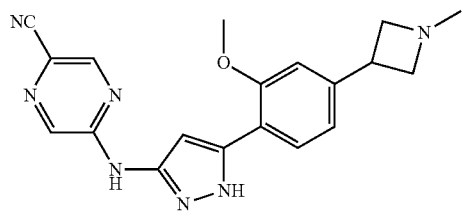 [SMILES: COc1cc(C2CN(C)C2)ccc1-c1cc(Nc2cnc(C#N)cn2)n[nH]1]
Example 65
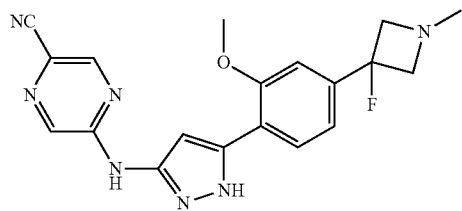 [SMILES: COc1cc(C2(F)CN(C)C2)ccc1-c1cc(Nc2cnc(C#N)cn2)n[nH]1]
Example 66
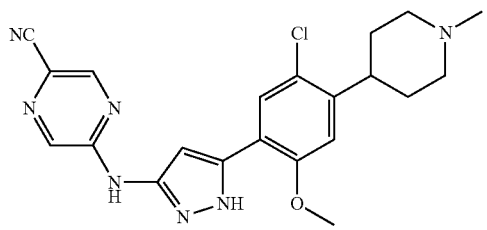 [SMILES: COc1cc(C2CCN(C)CC2)c(Cl)cc1-c1cc(Nc2cnc(C#N)cn2)n[nH]1]
Example 67
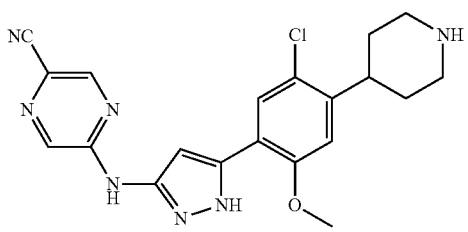 [SMILES: COc1cc(C2CCNCC2)c(Cl)cc1-c1cc(Nc2cnc(C#N)cn2)n[nH]1]
Example 68
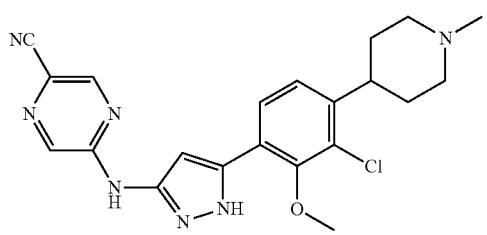 [SMILES: COc1c(-c2cc(Nc3cnc(C#N)cn3)n[nH]2)ccc(C2CCN(C)CC2)c1Cl]
Example 69
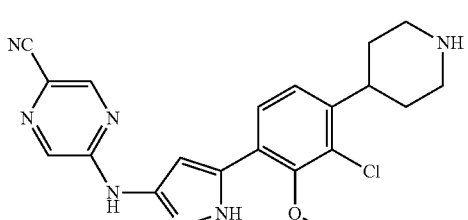
Example 70
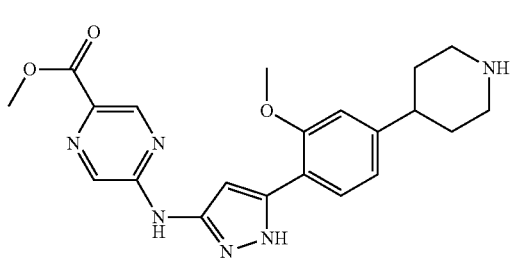 [SMILES: COC(=O)c1cnc(Nc2cc(-c3ccc(C4CCNCC4)cc3OC)[nH]n2)cn1]
Example 71

TABLE 1-continued
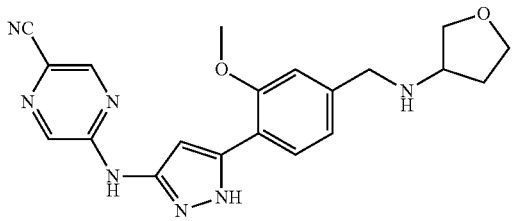 [SMILES: COc1cc(CNC2CCOC2)ccc1-c1cc(Nc2cnc(C#N)cn2)n[nH]1] Example 72
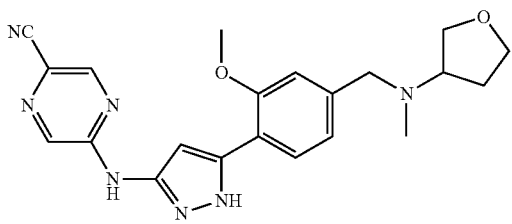 [SMILES: COc1cc(CN(C)C2CCOC2)ccc1-c1cc(Nc2cnc(C#N)cn2)n[nH]1] Example 73
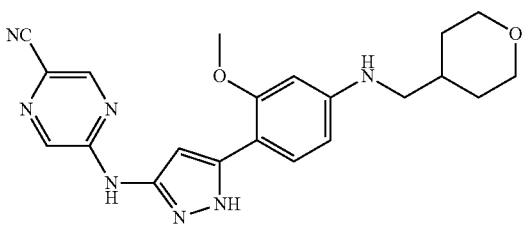 [SMILES: COc1cc(NCC2CCOCC2)ccc1-c1cc(Nc2cnc(C#N)cn2)n[nH]1] Example 74
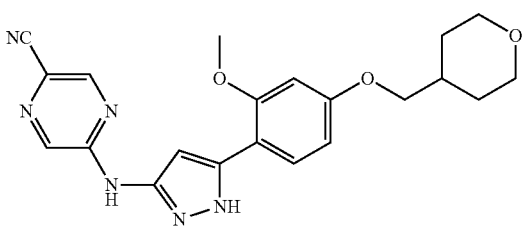 [SMILES: COc1cc(OCC2CCOCC2)ccc1-c1cc(Nc2cnc(C#N)cn2)n[nH]1] Example 75
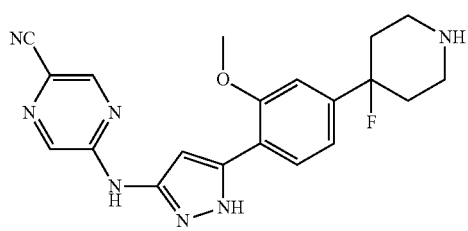 [SMILES: COc1cc(C2(F)CCNCC2)ccc1-c1cc(Nc2cnc(C#N)cn2)n[nH]1] Example 76
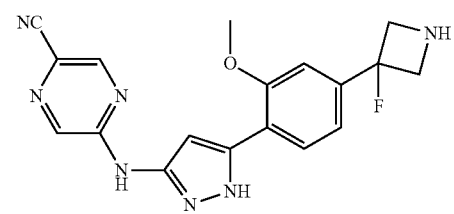 [SMILES: COc1cc(C2(F)CNC2)ccc1-c1cc(Nc2cnc(C#N)cn2)n[nH]1] Example 77
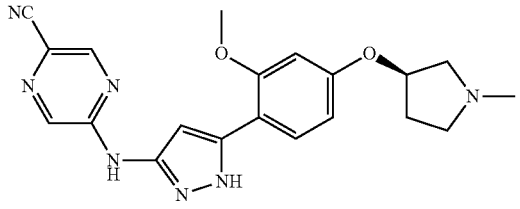 [SMILES: COc1cc(O[C@@H]2CCN(C)C2)ccc1-c1cc(Nc2cnc(C#N)cn2)n[nH]1] Example 78

TABLE 1-continued
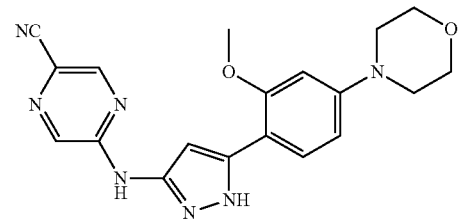
Example 79
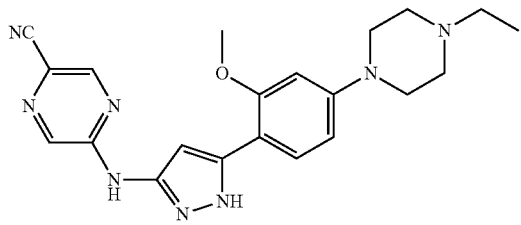 [SMILES: CCN1CCN(c2ccc(-c3cc(Nc4cnc(C#N)cn4)n[nH]3)c(OC)c2)CC1]
Example 80
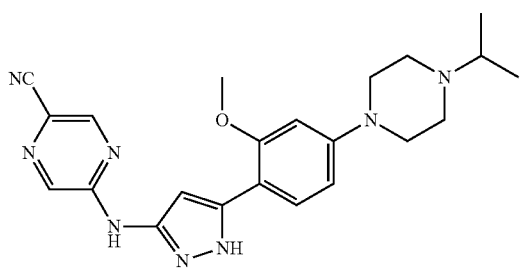
Example 81
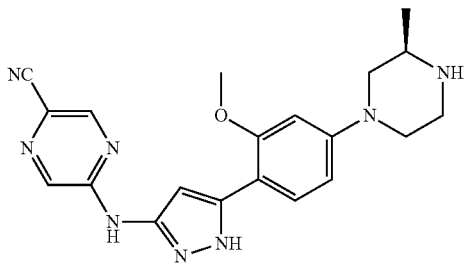 [SMILES: COc1cc(N2CCN[C@H](C)C2)ccc1-c1cc(Nc2cnc(C#N)cn2)n[nH]1]
Example 82
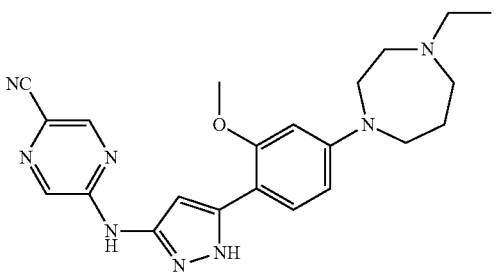 [SMILES: CCN1CCCN(c2ccc(-c3cc(Nc4cnc(C#N)cn4)n[nH]3)c(OC)c2)CC1]
Example 83
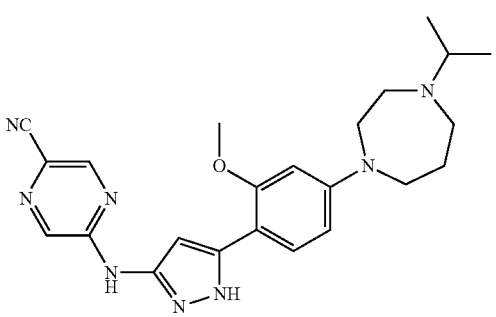 [SMILES: COc1cc(N2CCCN(C(C)C)CC2)ccc1-c1cc(Nc2cnc(C#N)cn2)n[nH]1]
Example 84

TABLE 1-continued
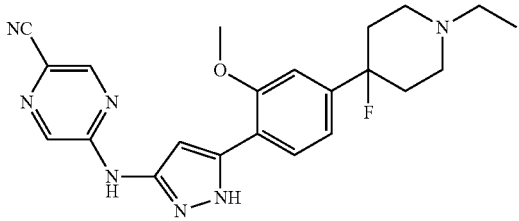 [SMILES: CCN1CCC(F)(c2ccc(-c3cc(Nc4cnc(C#N)cn4)n[nH]3)c(OC)c2)CC1] Example 85
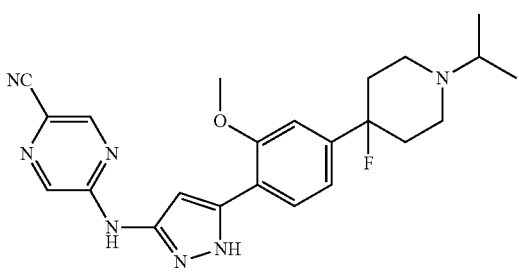 [SMILES: COc1cc(C2(F)CCN(C(C)C)CC2)ccc1-c1cc(Nc2cnc(C#N)cn2)n[nH]1] Example 86
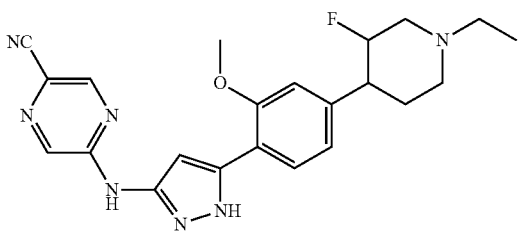 [SMILES: CCN1CCC(c2ccc(-c3cc(Nc4cnc(C#N)cn4)n[nH]3)c(OC)c2)C(F)C1] Example 87
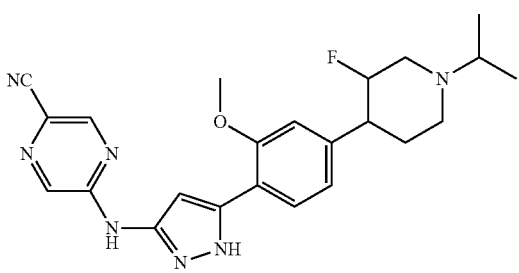 [SMILES: COc1cc(C2CCN(C(C)C)CC2F)ccc1-c1cc(Nc2cnc(C#N)cn2)n[nH]1] Example 88
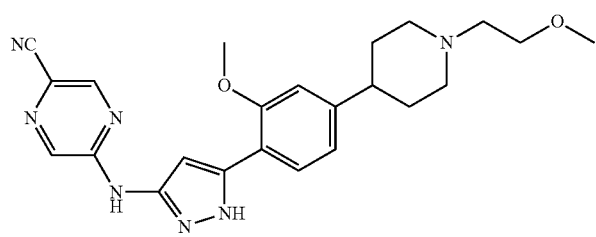 [SMILES: COCCN1CCC(c2ccc(-c3cc(Nc4cnc(C#N)cn4)n[nH]3)c(OC)c2)CC1] Example 89
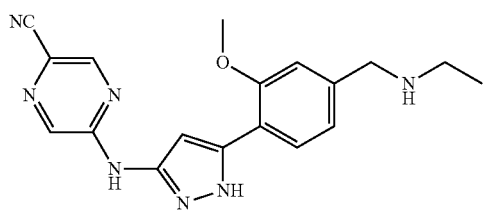 [SMILES: CCNCc1ccc(-c2cc(Nc3cnc(C#N)cn3)n[nH]2)c(OC)c1] Example 90

TABLE 1-continued
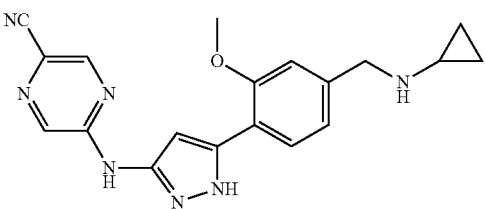 [SMILES: COc1cc(CNC2CC2)ccc1-c1cc(Nc2cnc(C#N)cn2)n[nH]1] Example 91
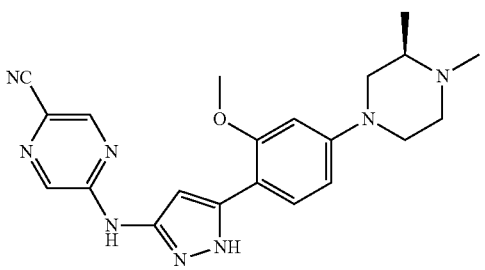 [SMILES: COc1cc(N2CCN(C)[C@H](C)C2)ccc1-c1cc(Nc2cnc(C#N)cn2)n[nH]1] Example 92
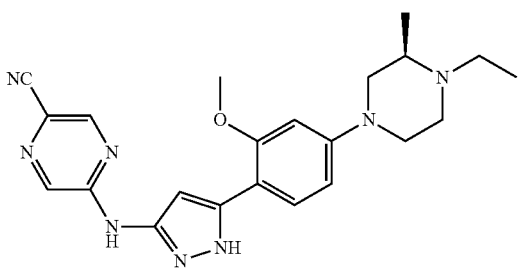 [SMILES: CCN1CCN(c2ccc(-c3cc(Nc4cnc(C#N)cn4)n[nH]3)c(OC)c2)C[C@H]1C] Example 93
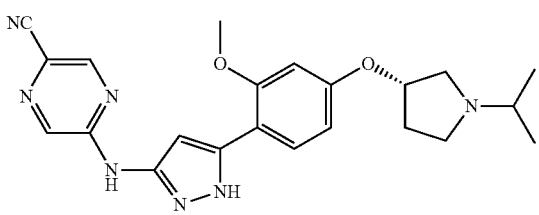 [SMILES: COc1cc(O[C@H]2CCN(C(C)C)C2)ccc1-c1cc(Nc2cnc(C#N)cn2)n[nH]1] Example 94
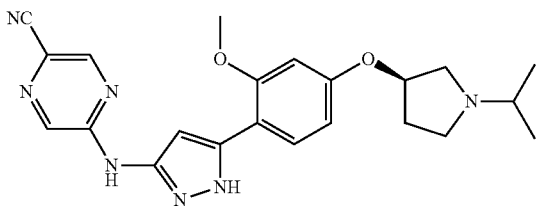 [SMILES: COc1cc(O[C@@H]2CCN(C(C)C)C2)ccc1-c1cc(Nc2cnc(C#N)cn2)n[nH]1] Example 95
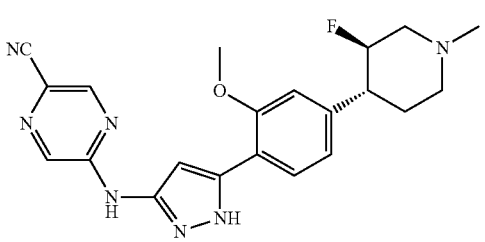 [SMILES: COc1cc([C@H]2CCN(C)C[C@@H]2F)ccc1-c1cc(Nc2cnc(C#N)cn2)n[nH]1] Example 96

TABLE 1-continued
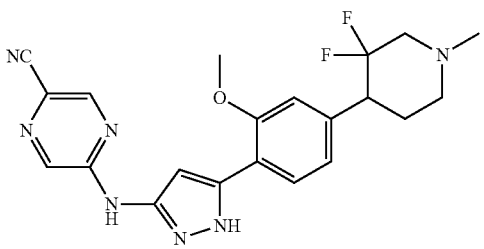 [SMILES: COc1cc(C2CCN(C)CC2(F)F)ccc1-c1cc(Nc2cnc(C#N)cn2)n[nH]1] Example 97
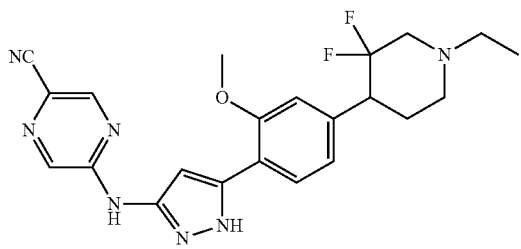 [SMILES: CCN1CCC(c2ccc(-c3cc(Nc4cnc(C#N)cn4)n[nH]3)c(OC)c2)C(F)(F)C1] Example 98
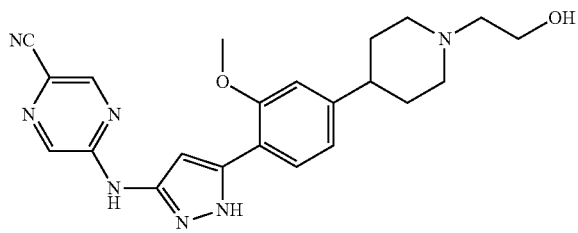 [SMILES: COc1cc(C2CCN(CCO)CC2)ccc1-c1cc(Nc2cnc(C#N)cn2)n[nH]1] Example 99
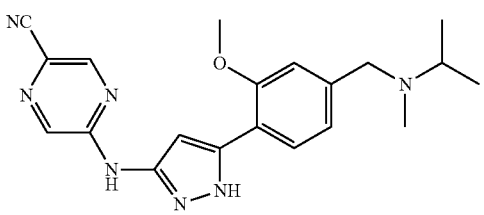 [SMILES: COc1cc(CN(C)C(C)C)ccc1-c1cc(Nc2cnc(C#N)cn2)n[nH]1] Example 100
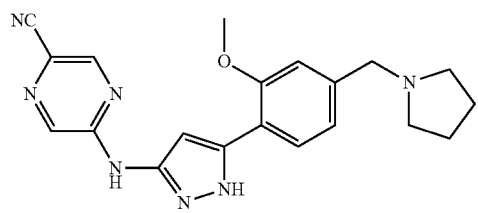 [SMILES: COc1cc(CN2CCCC2)ccc1-c1cc(Nc2cnc(C#N)cn2)n[nH]1] Example 101
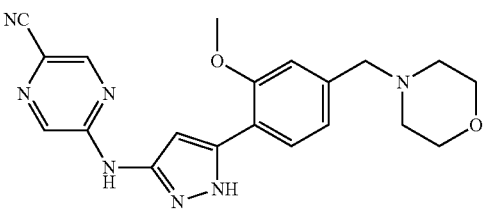 [SMILES: COc1cc(CN2CCOCC2)ccc1-c1cc(Nc2cnc(C#N)cn2)n[nH]1] Example 102
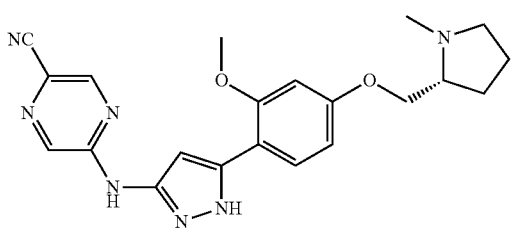 [SMILES: COc1cc(OC[C@H]2CCCN2C)ccc1-c1cc(Nc2cnc(C#N)cn2)n[nH]1] Example 103

TABLE 1-continued
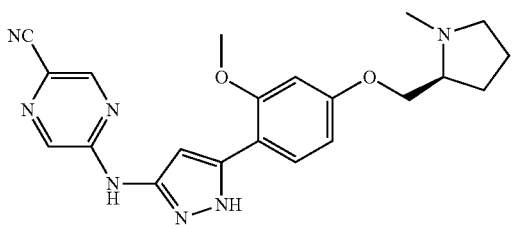 [SMILES: COc1cc(OC[C@@H]2CCCN2C)ccc1-c1cc(Nc2cnc(C#N)cn2)n[nH]1]
Example 104
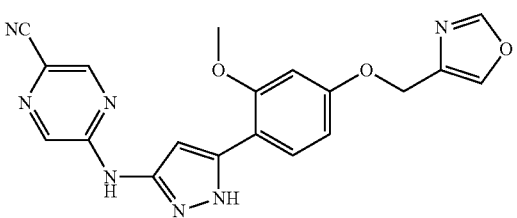 [SMILES: COc1cc(OCc2cocn2)ccc1-c1cc(Nc2cnc(C#N)cn2)n[nH]1]
Example 105
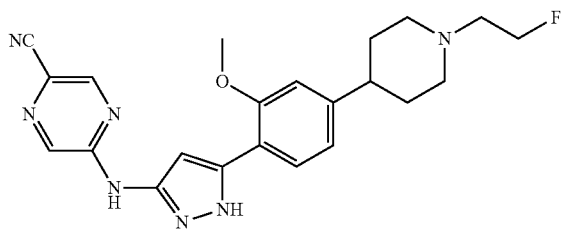 [SMILES: COc1cc(C2CCN(CCF)CC2)ccc1-c1cc(Nc2cnc(C#N)cn2)n[nH]1]
Example 106
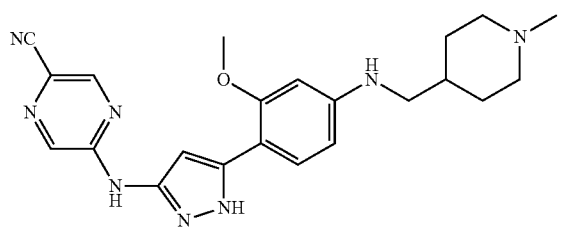 [SMILES: COc1cc(NCC2CCN(C)CC2)ccc1-c1cc(Nc2cnc(C#N)cn2)n[nH]1]
Example 107
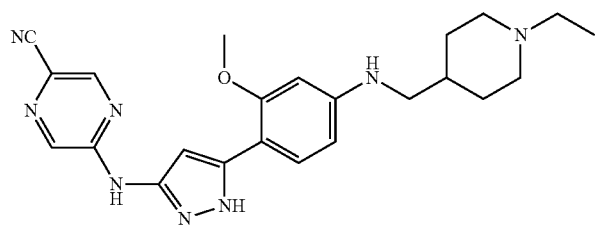 [SMILES: CCN1CCC(CNc2ccc(-c3cc(Nc4cnc(C#N)cn4)n[nH]3)c(OC)c2)CC1]
Example 108
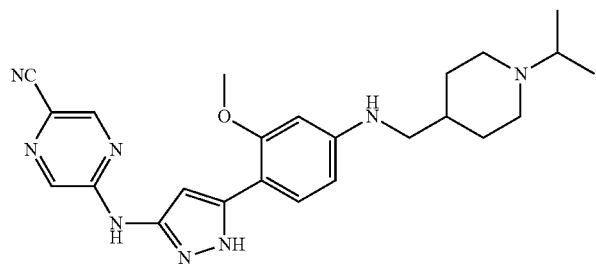
Example 109
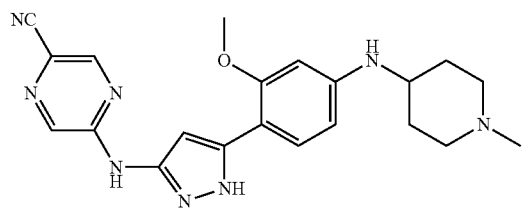 [SMILES: COc1cc(NC2CCN(C)CC2)ccc1-c1cc(Nc2cnc(C#N)cn2)n[nH]1]
Example 110

TABLE 1-continued
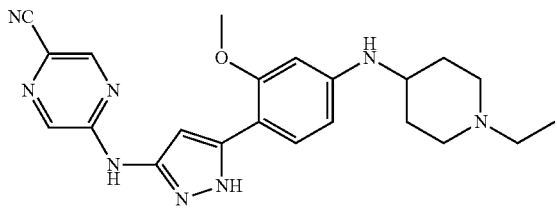
Example 111
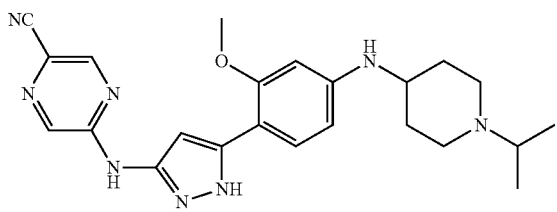 [SMILES: CCN1CCC(Nc2ccc(-c3cc(Nc4cnc(C#N)cn4)n[nH]3)c(OC)c2)CC1]
Example 112
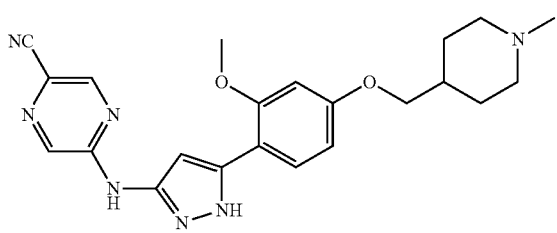 [SMILES: COc1cc(OCC2CCN(C)CC2)ccc1-c1cc(Nc2cnc(C#N)cn2)n[nH]1]
Example 113
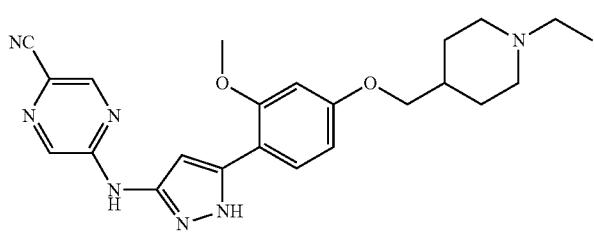 [SMILES: CCN1CCC(COc2ccc(-c3cc(Nc4cnc(C#N)cn4)n[nH]3)c(OC)c2)CC1]
Example 114
Example 115
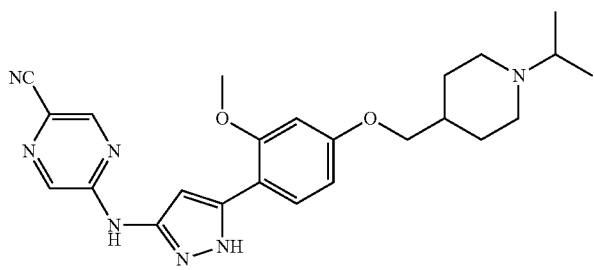 [SMILES: COc1cc(OCC2CCN(C(C)C)CC2)ccc1-c1cc(Nc2cnc(C#N)cn2)n[nH]1]
Example 116
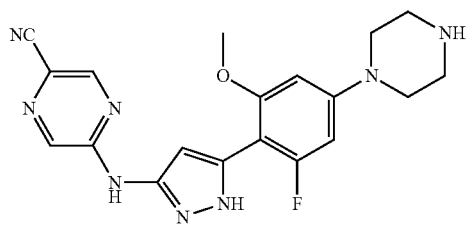 [SMILES: COc1cc(N2CCNCC2)cc(F)c1-c1cc(Nc2cnc(C#N)cn2)n[nH]1]

TABLE 1-continued
| | |
|---|---|
| 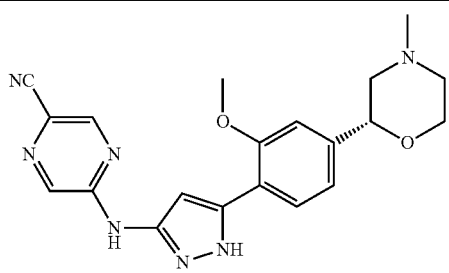 | Example 117 |
| 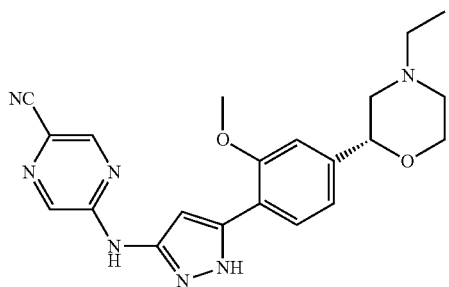 [SMILES: CCN1CCO[C@H](c2ccc(-c3cc(Nc4cnc(C#N)cn4)n[nH]3)c(OC)c2)C1] | Example 118 |
| 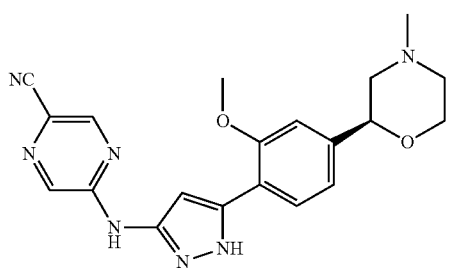 [SMILES: COc1cc([C@H]2CN(C)CCO2)ccc1-c1cc(Nc2cnc(C#N)cn2)n[nH]1] | Example 119 |
| 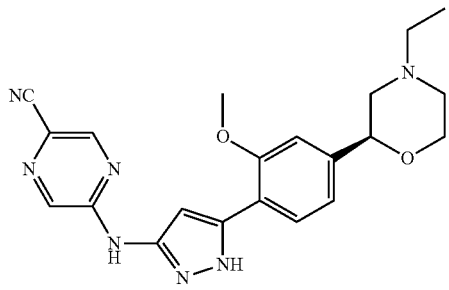 [SMILES: CCN1CCO[C@@H](c2ccc(-c3cc(Nc4cnc(C#N)cn4)n[nH]3)c(OC)c2)C1] | Example 120 |
| 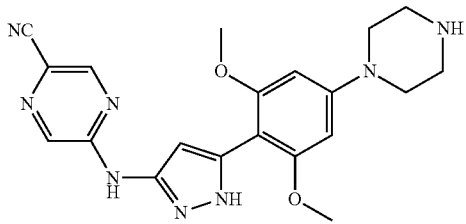 [SMILES: COc1cc(N2CCNCC2)cc(OC)c1-c1cc(Nc2cnc(C#N)cn2)n[nH]1] | Example 121 |
| 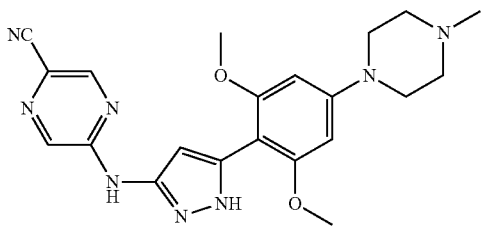 [SMILES: COc1cc(N2CCN(C)CC2)cc(OC)c1-c1cc(Nc2cnc(C#N)cn2)n[nH]1] | Example 122 |

TABLE 1-continued
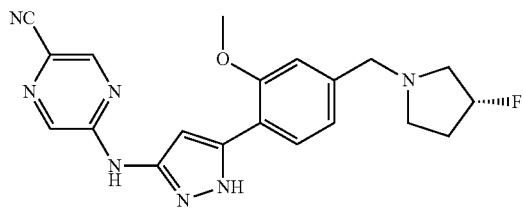 [SMILES: COc1cc(CN2CC[C@@H](F)C2)ccc1-c1cc(Nc2cnc(C#N)cn2)n[nH]1]
Example 123
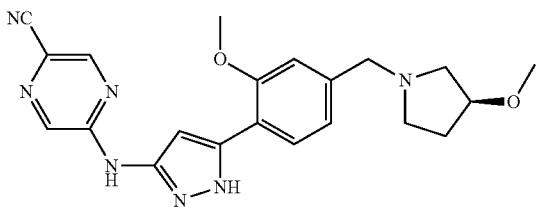 [SMILES: COc1cc(CN2CC[C@H](OC)C2)ccc1-c1cc(Nc2cnc(C#N)cn2)n[nH]1]
Example 124
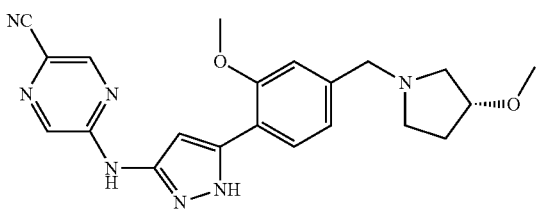 [SMILES: COc1cc(CN2CC[C@@H](OC)C2)ccc1-c1cc(Nc2cnc(C#N)cn2)n[nH]1]
Example 125
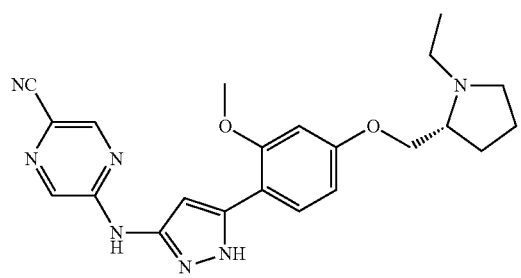 [SMILES: CCN1CCC[C@@H]1COc1ccc(-c2cc(Nc3cnc(C#N)cn3)n[nH]2)c(OC)c1]
Example 126
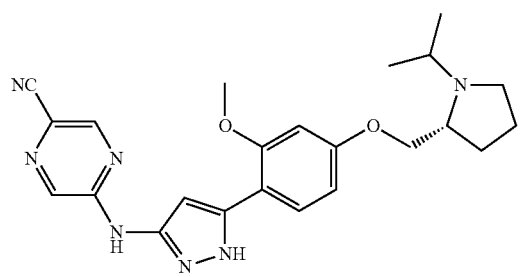 [SMILES: COc1cc(OC[C@H]2CCCN2C(C)C)ccc1-c1cc(Nc2cnc(C#N)cn2)n[nH]1]
Example 127***
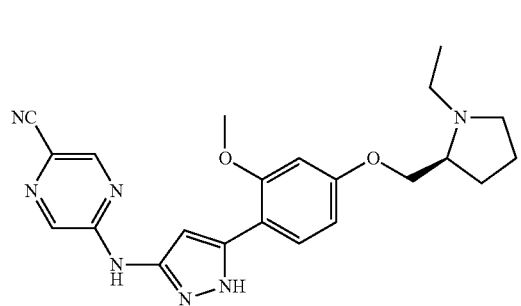 [SMILES: CCN1CCC[C@H]1COc1ccc(-c2cc(Nc3cnc(C#N)cn3)n[nH]2)c(OC)c1]
Example 128

TABLE 1-continued
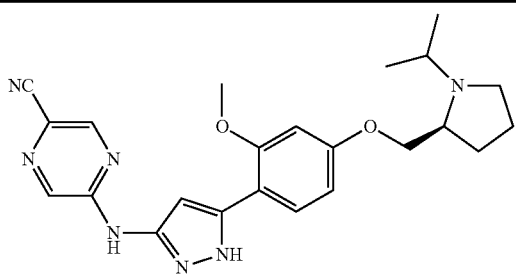 Example 129
 Example 130
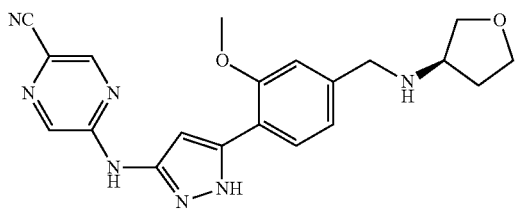 [SMILES: COc1cc(CN[C@@H]2CCOC2)ccc1-c1cc(Nc2cnc(C#N)cn2)n[nH]1] Example 131
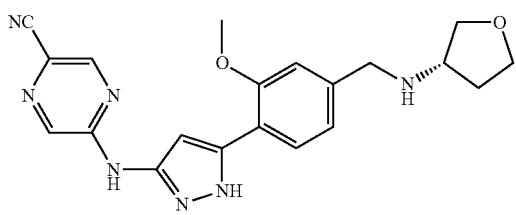 [SMILES: COc1cc(CN[C@H]2CCOC2)ccc1-c1cc(Nc2cnc(C#N)cn2)n[nH]1] Example 132
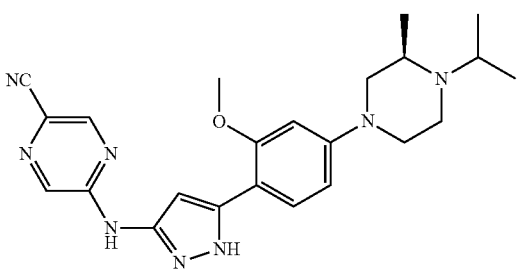 [SMILES: COc1cc(N2CCN(C(C)C)[C@H](C)C2)ccc1-c1cc(Nc2cnc(C#N)cn2)n[nH]1] Example 133
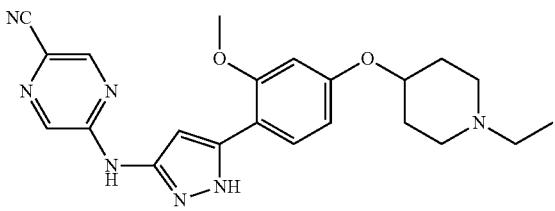 Example 134
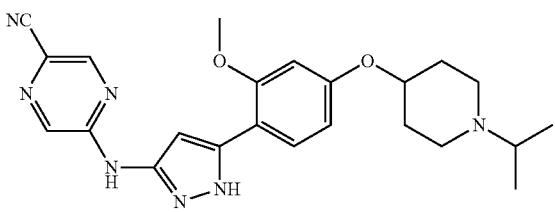 [SMILES: CCN1CCC(Oc2ccc(-c3cc(Nc4cnc(C#N)cn4)n[nH]3)c(OC)c2)CC1] Example 135

TABLE 1-continued
| | |
|---|---|
|  | Example 136 |
| 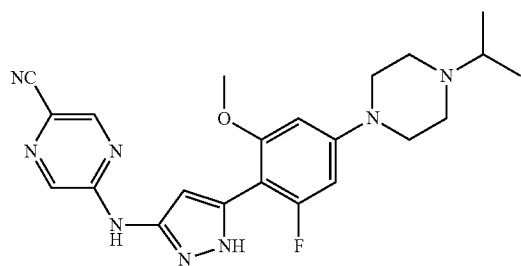 [SMILES: COc1cc(N2CCN(C(C)C)CC2)cc(F)c1-c1cc(Nc2cnc(C#N)cn2)n[nH]1] | Example 137 |
| 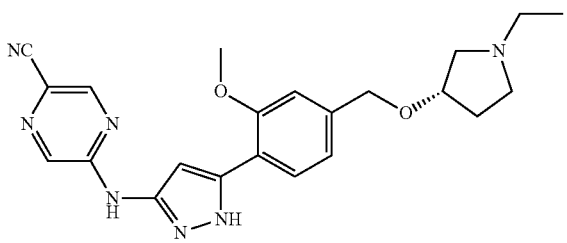 [SMILES: CCN1CC[C@H](OCc2ccc(-c3cc(Nc4cnc(C#N)cn4)n[nH]3)c(OC)c2)C1] | Example 138 |
| 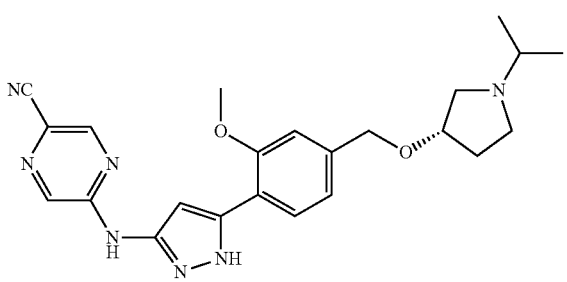 [SMILES: COc1cc(CO[C@H]2CCN(C(C)C)C2)ccc1-c1cc(Nc2cnc(C#N)cn2)n[nH]1] | Example 139 |
| 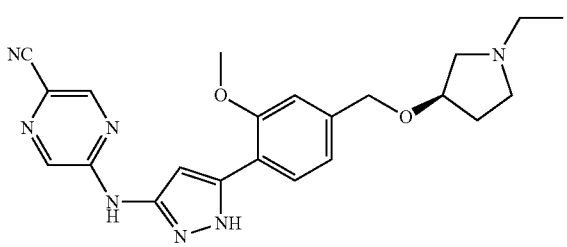 [SMILES: CCN1CC[C@@H](OCc2ccc(-c3cc(Nc4cnc(C#N)cn4)n[nH]3)c(OC)c2)C1] | Example 140 |
| 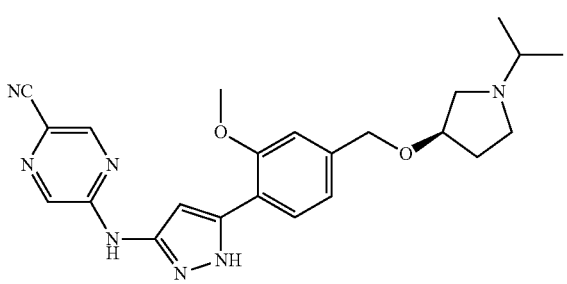 [SMILES: COc1cc(CO[C@@H]2CCN(C(C)C)C2)ccc1-c1cc(Nc2cnc(C#N)cn2)n[nH]1] | Example 141 |

TABLE 1-continued
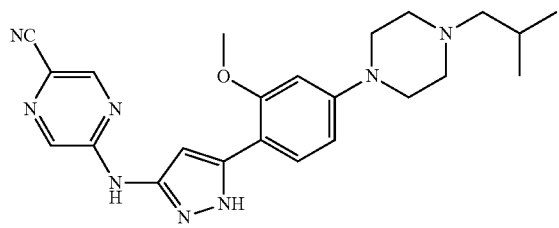 [SMILES: COc1cc(N2CCN(CC(C)C)CC2)ccc1-c1cc(Nc2cnc(C#N)cn2)n[nH]1]
Example 142
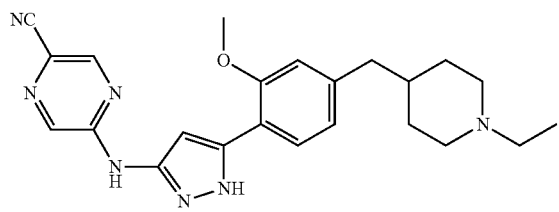 [SMILES: CCN1CCC(Cc2ccc(-c3cc(Nc4cnc(C#N)cn4)n[nH]3)c(OC)c2)CC1]
Example 143
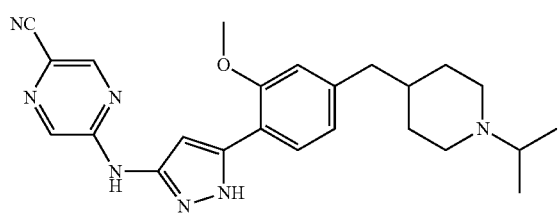
Example 144
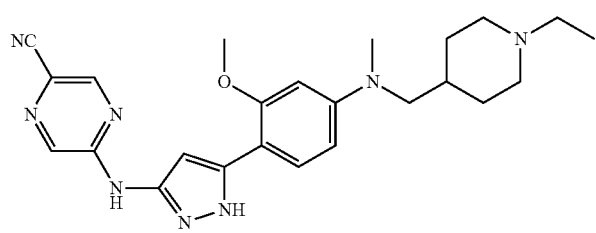 [SMILES: CCN1CCC(CN(C)c2ccc(-c3cc(Nc4cnc(C#N)cn4)n[nH]3)c(OC)c2)CC1]
Example 145
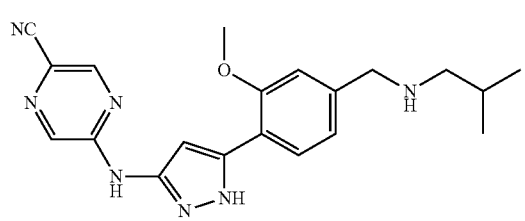 [SMILES: COc1cc(CNCC(C)C)ccc1-c1cc(Nc2cnc(C#N)cn2)n[nH]1]
Example 146
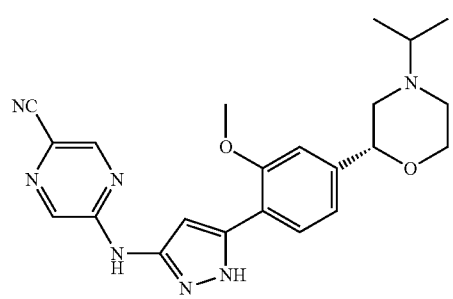 [SMILES: COc1cc([C@@H]2CN(C(C)C)CCO2)ccc1-c1cc(Nc2cnc(C#N)cn2)n[nH]1]
Example 147

TABLE 1-continued
| | |
|---|---|
| 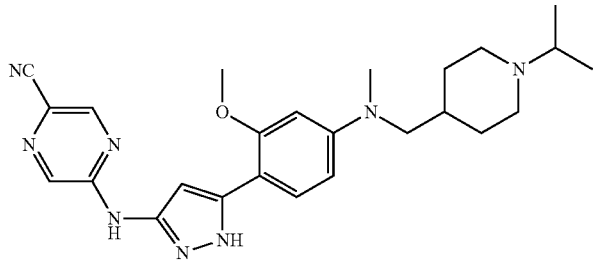 [SMILES: COc1cc(N(C)CC2CCN(C(C)C)CC2)ccc1-c1cc(Nc2cnc(C#N)cn2)n[nH]1] | Example 148 |
| 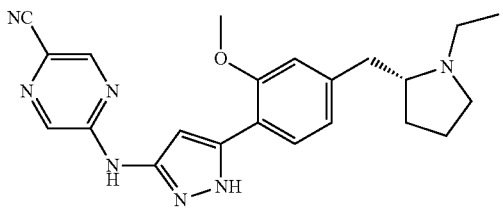 [SMILES: CCN1CCC[C@@H]1Cc1ccc(-c2cc(Nc3cnc(C#N)cn3)n[nH]2)c(OC)c1] | Example 149 |
| 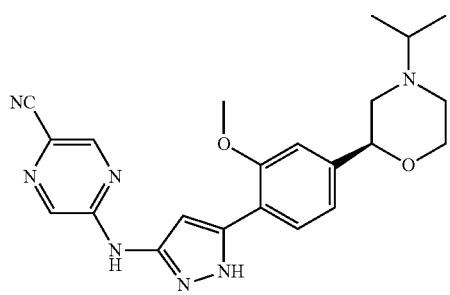 [SMILES: COc1cc([C@H]2CN(C(C)C)CCO2)ccc1-c1cc(Nc2cnc(C#N)cn2)n[nH]1] | Example 150 |
| 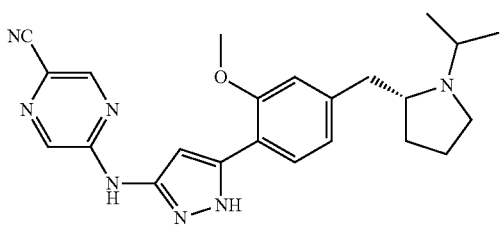 [SMILES: COc1cc(C[C@H]2CCCN2C(C)C)ccc1-c1cc(Nc2cnc(C#N)cn2)n[nH]1] | Example 151 |
| 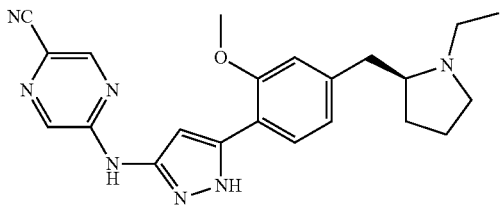 [SMILES: CCN1CCC[C@H]1Cc1ccc(-c2cc(Nc3cnc(C#N)cn3)n[nH]2)c(OC)c1] | Example 152 |
| 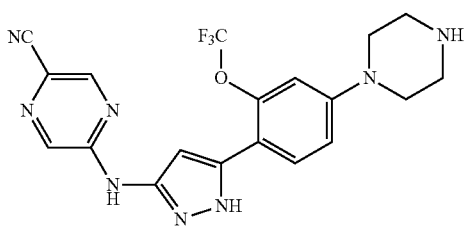 [SMILES: N#Cc1cnc(Nc2cc(-c3ccc(N4CCNCC4)cc3OC(F)(F)F)[nH]n2)cn1] | Example 153 |

TABLE 1-continued
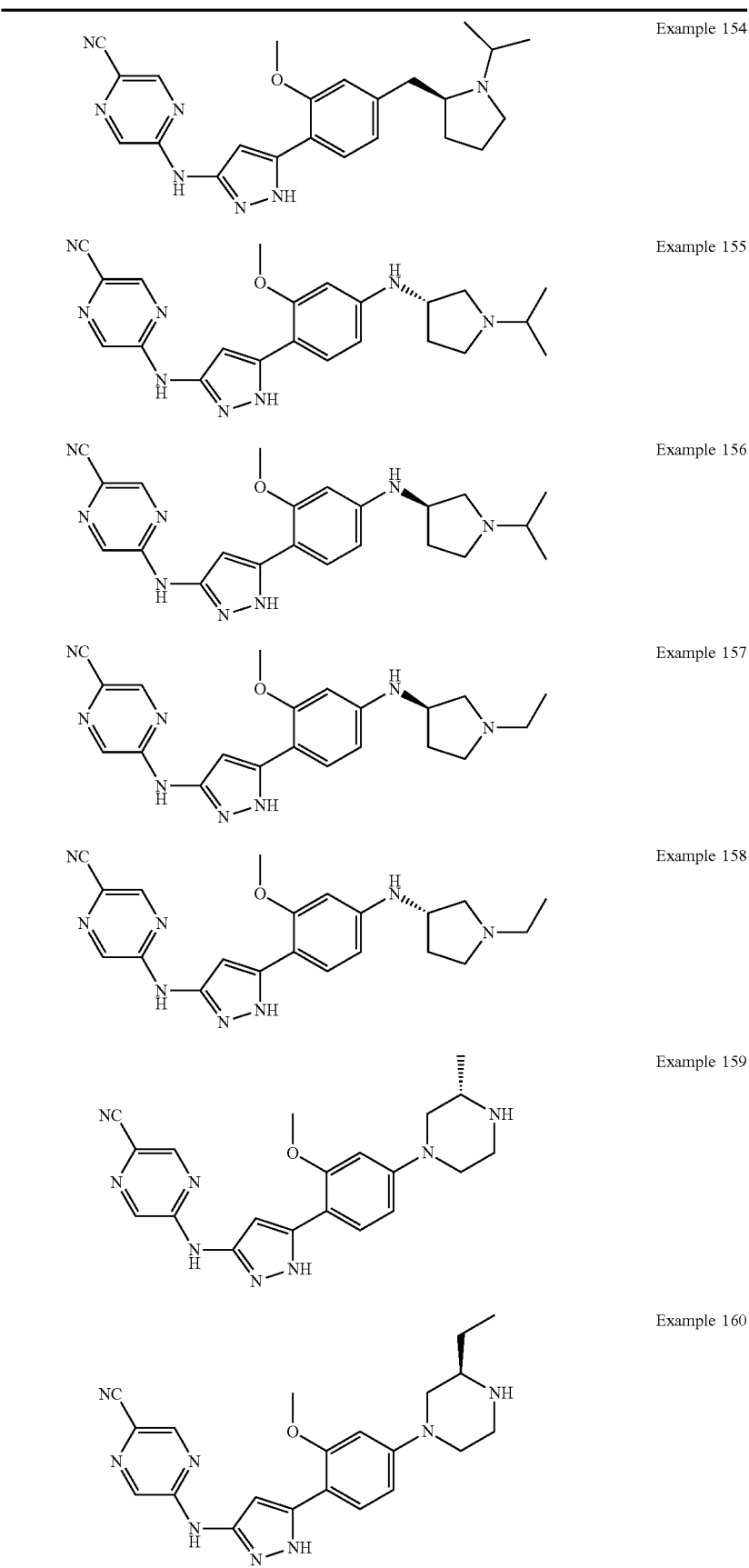
Example 154
Example 155
Example 156
Example 157
Example 158
Example 159
Example 160

TABLE 1-continued
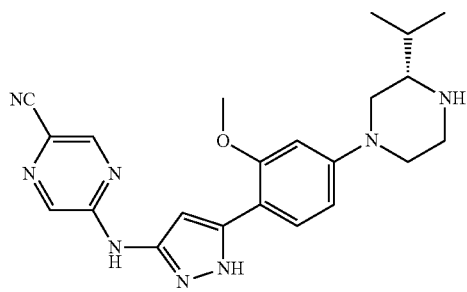 [SMILES: COc1cc(N2CCN[C@@H](C(C)C)C2)ccc1-c1cc(Nc2cnc(C#N)cn2)n[nH]1]
Example 161
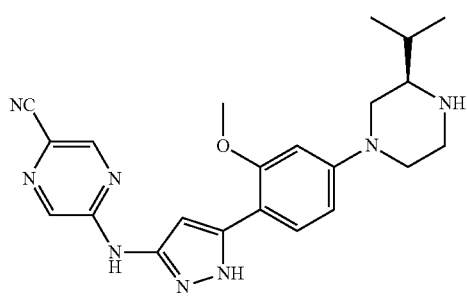 [SMILES: COc1cc(N2CCN[C@H](C(C)C)C2)ccc1-c1cc(Nc2cnc(C#N)cn2)n[nH]1]
Example 162
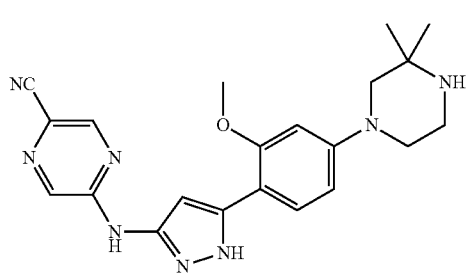 [SMILES: COc1cc(N2CCNC(C)(C)C2)ccc1-c1cc(Nc2cnc(C#N)cn2)n[nH]1]
Example 163
Synthetic Methods
Synthetic methods A to T were used to prepare the compounds of Examples 1 to 163. The reaction schemes for synthetic methods A to T are shown below.
Synthetic Method A
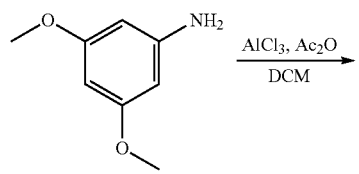
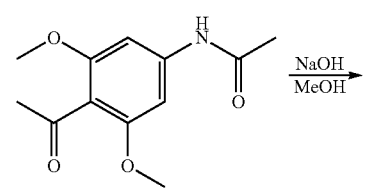
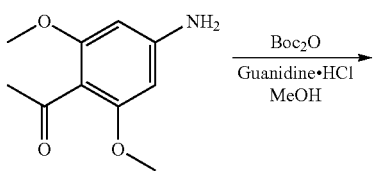
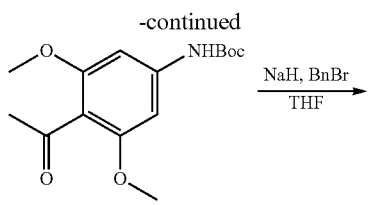
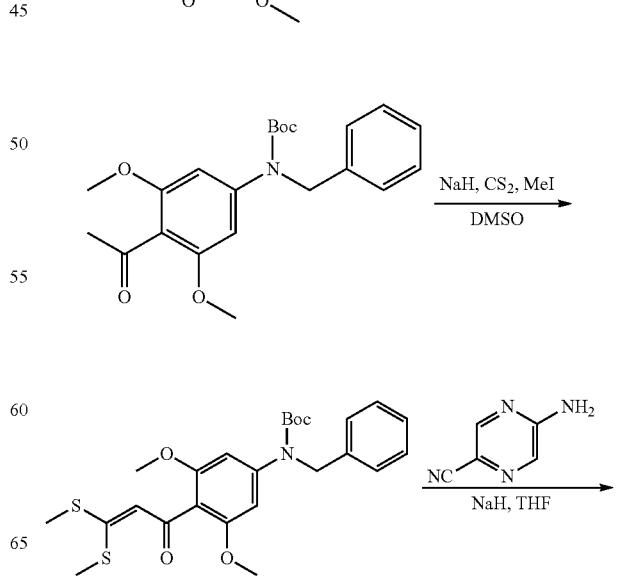

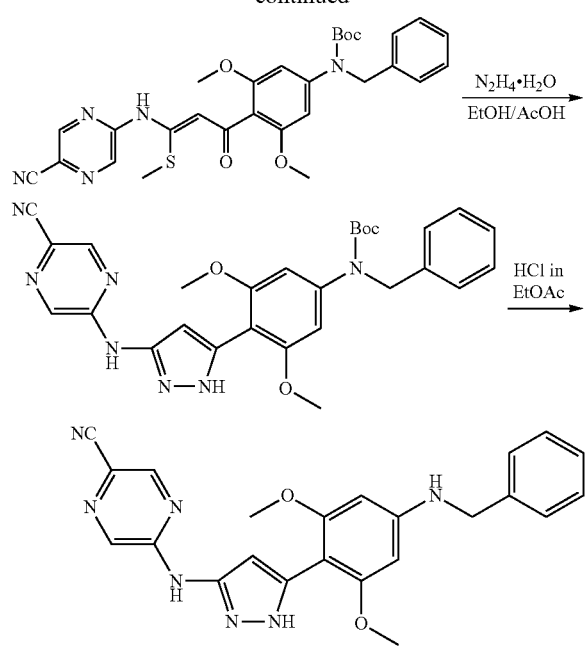
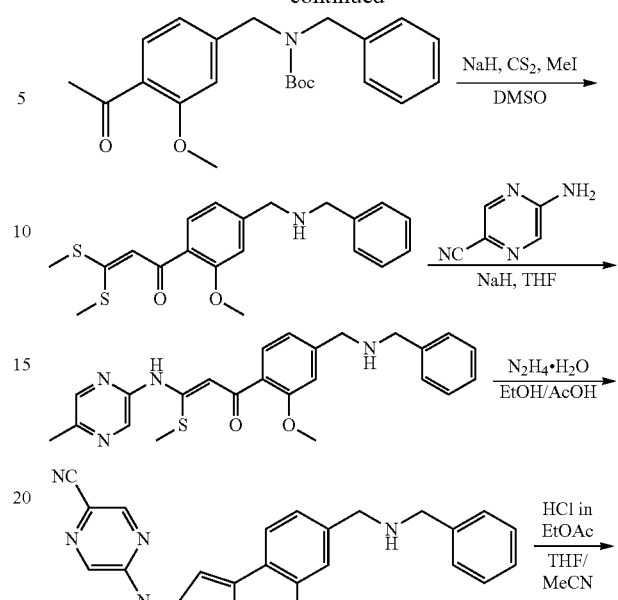
Synthetic Method B
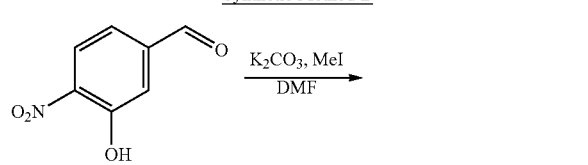
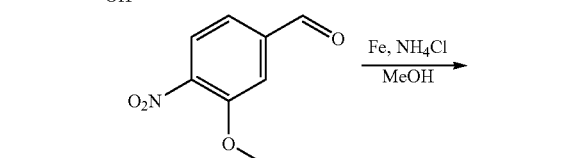
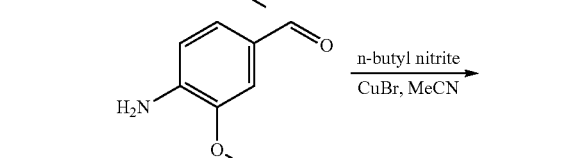
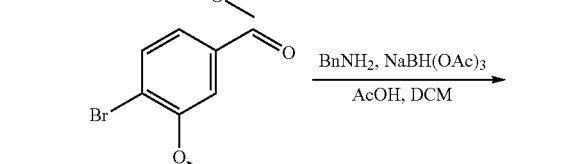
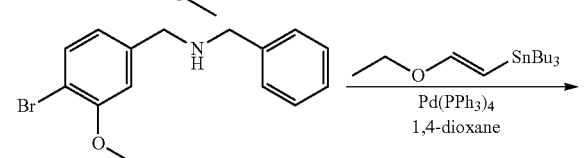
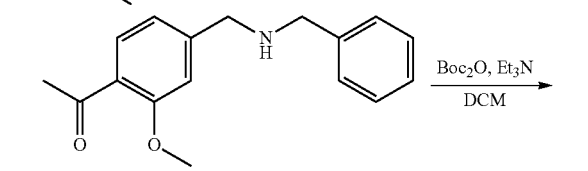
Synthetic Method C
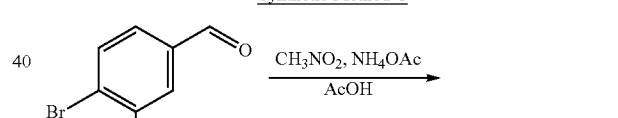
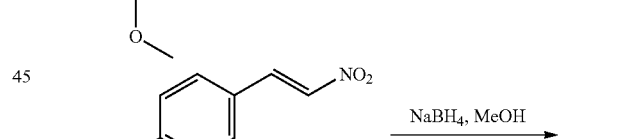
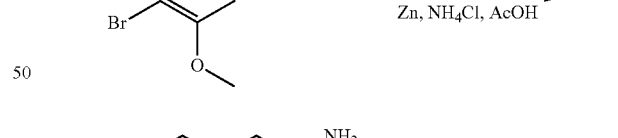
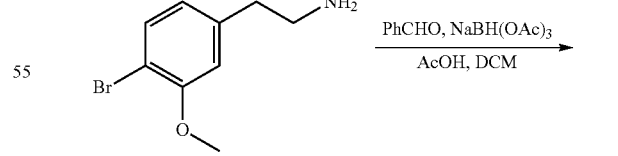

-continued
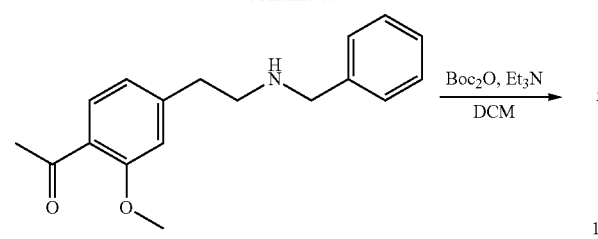
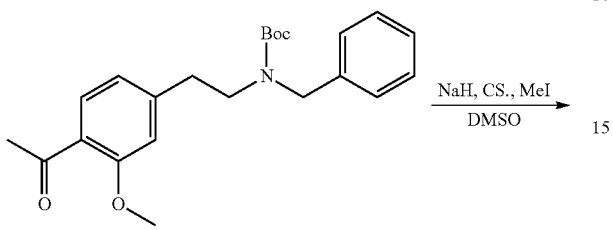
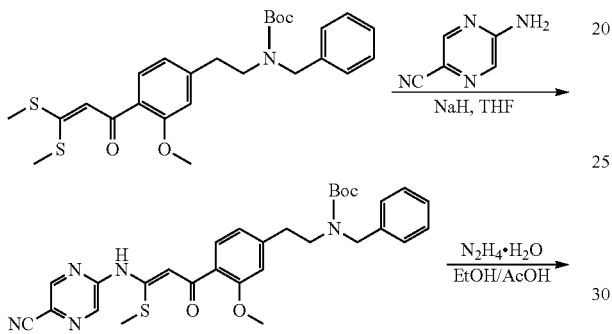
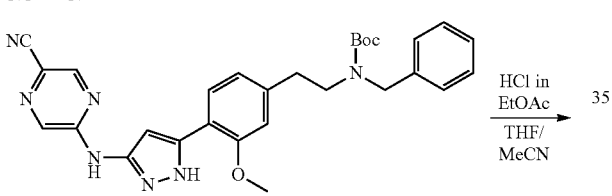
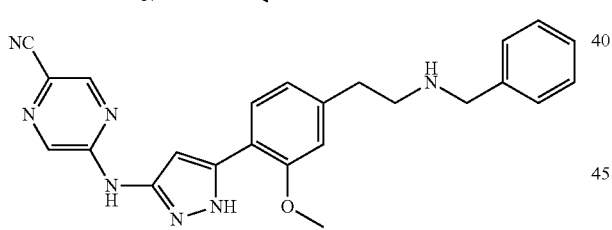
Synthetic Method D
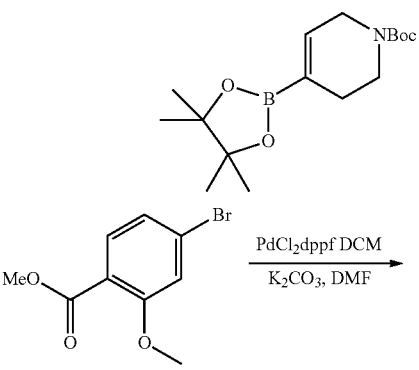
-continued
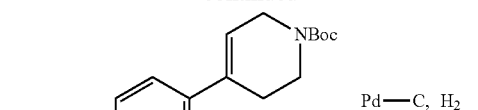
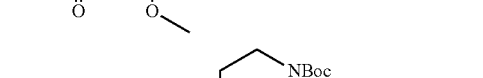
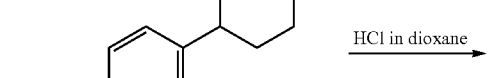
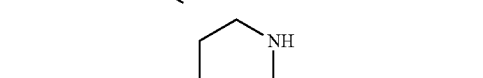
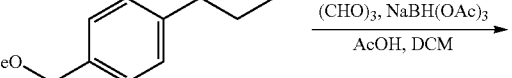
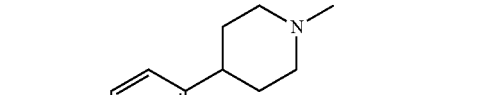
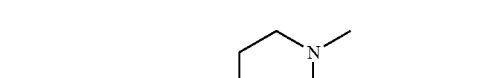
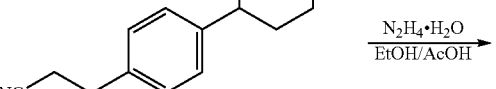
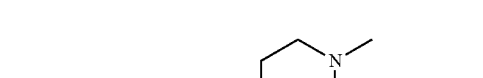
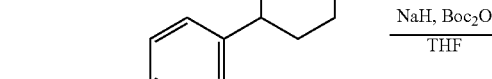
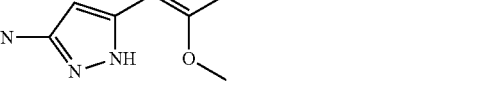
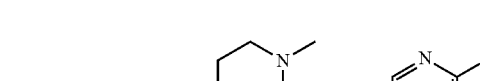
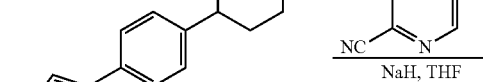

107
-continued
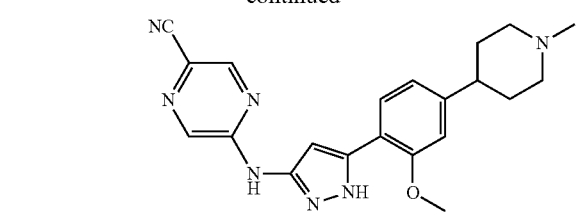
Synthetic Method E
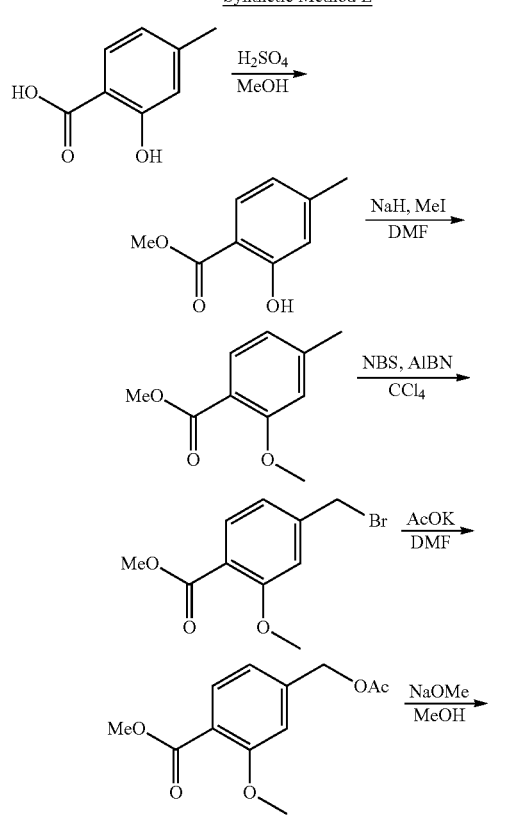
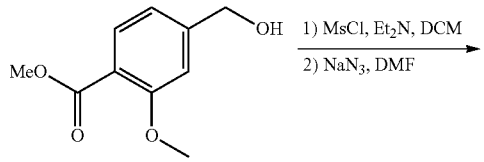
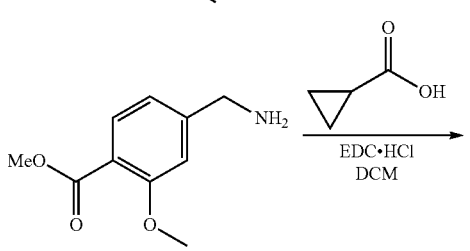
108
-continued
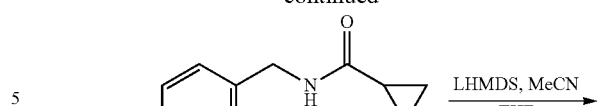
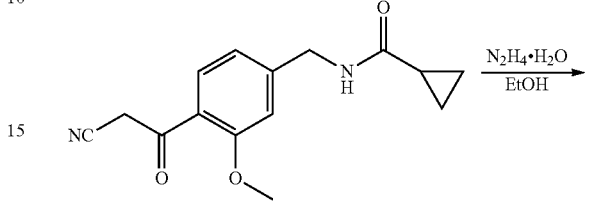
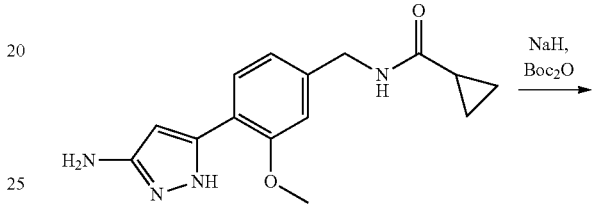
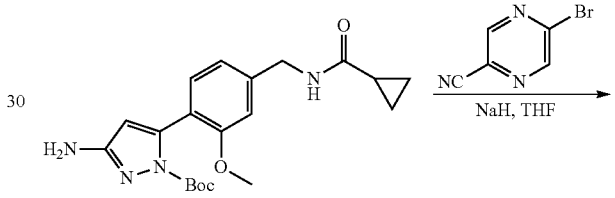
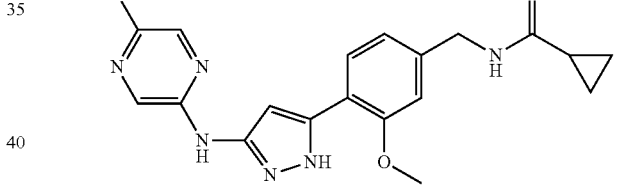
Synthetic Method F
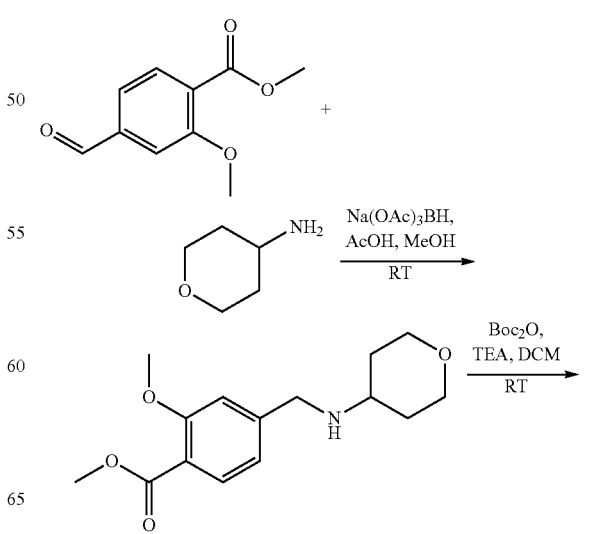

109
-continued
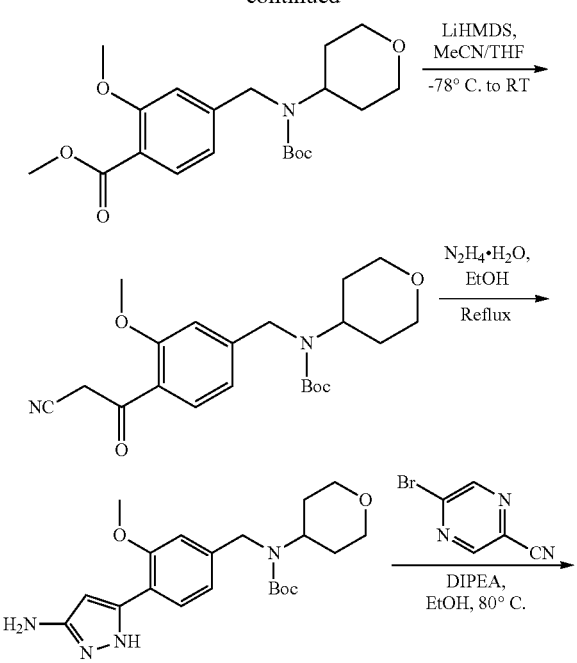
Synthetic Method G
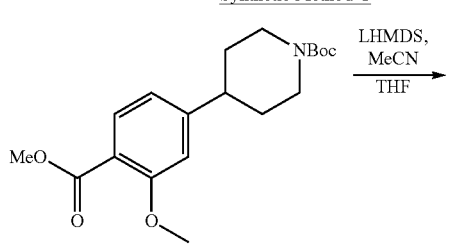
110
-continued
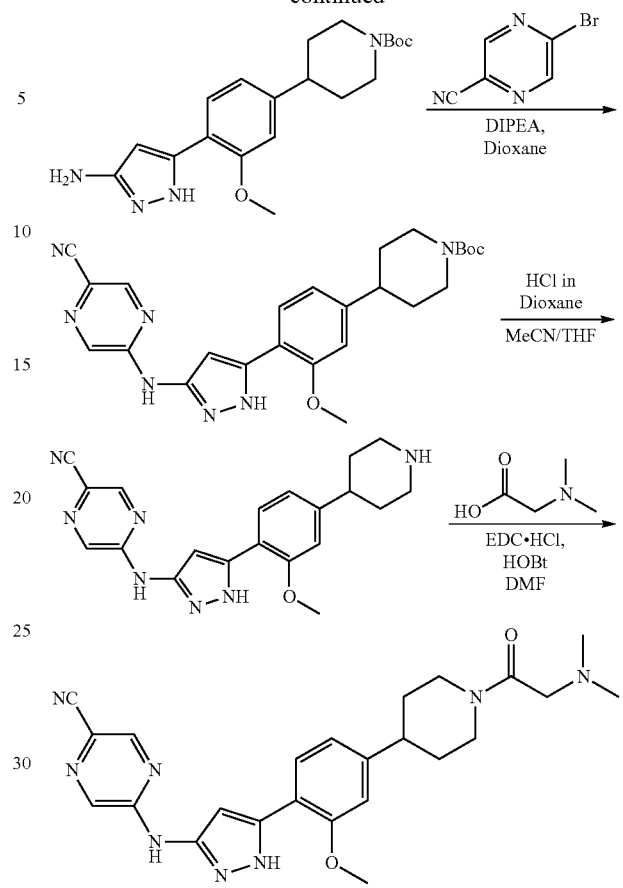
Synthetic Method H
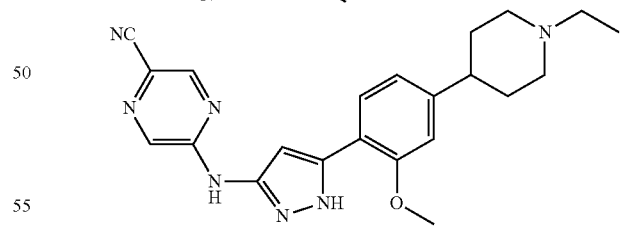
Synthetic Method I
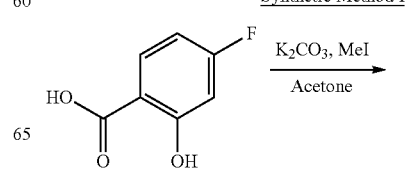

111
-continued
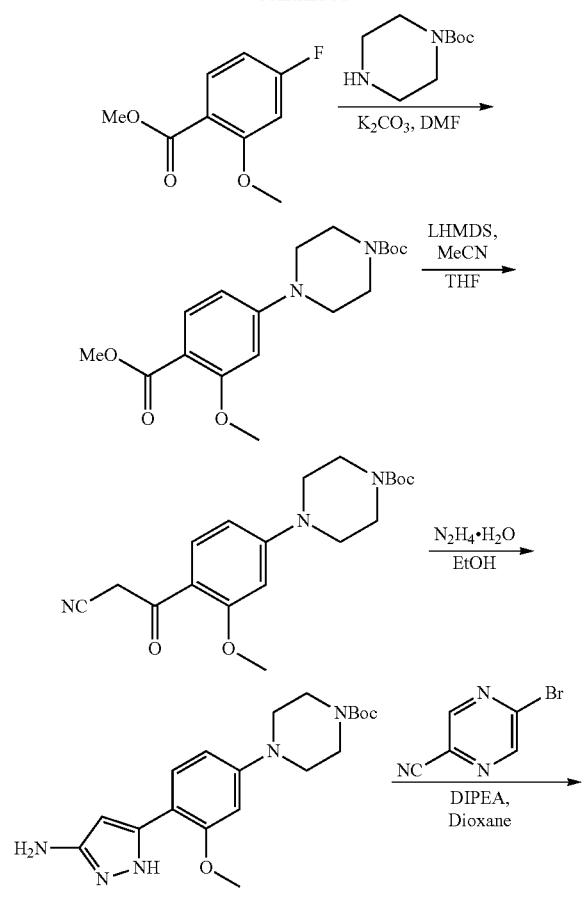
112
Synthetic Method J
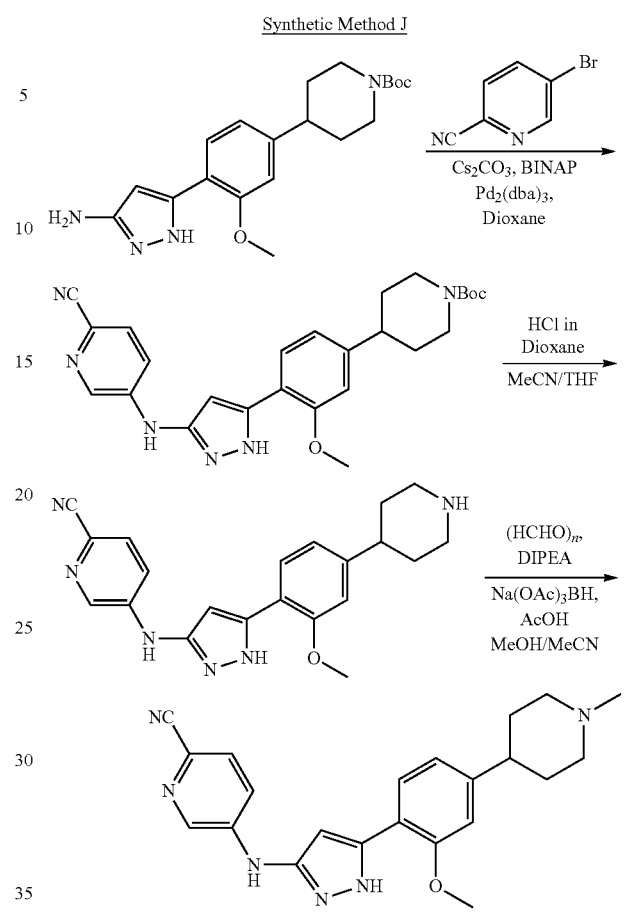
Synthetic Method K
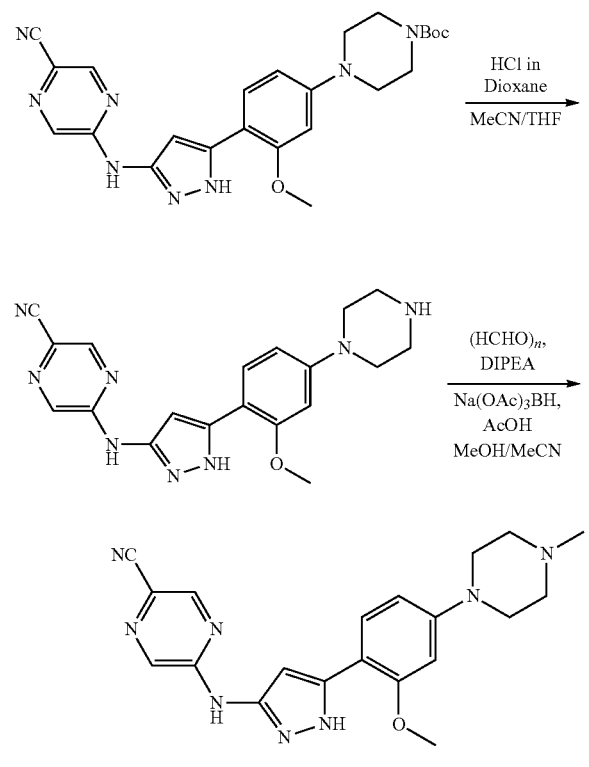

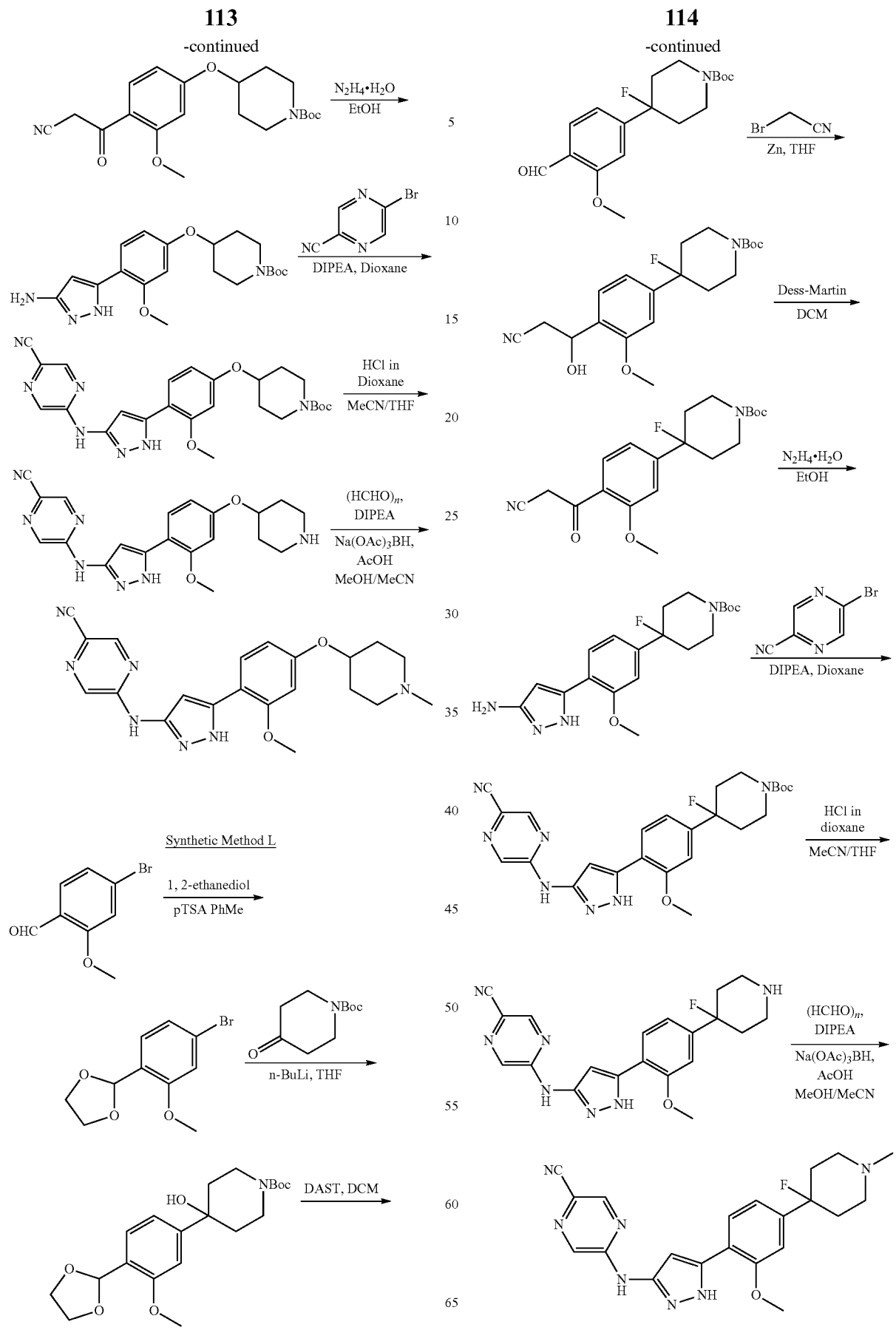

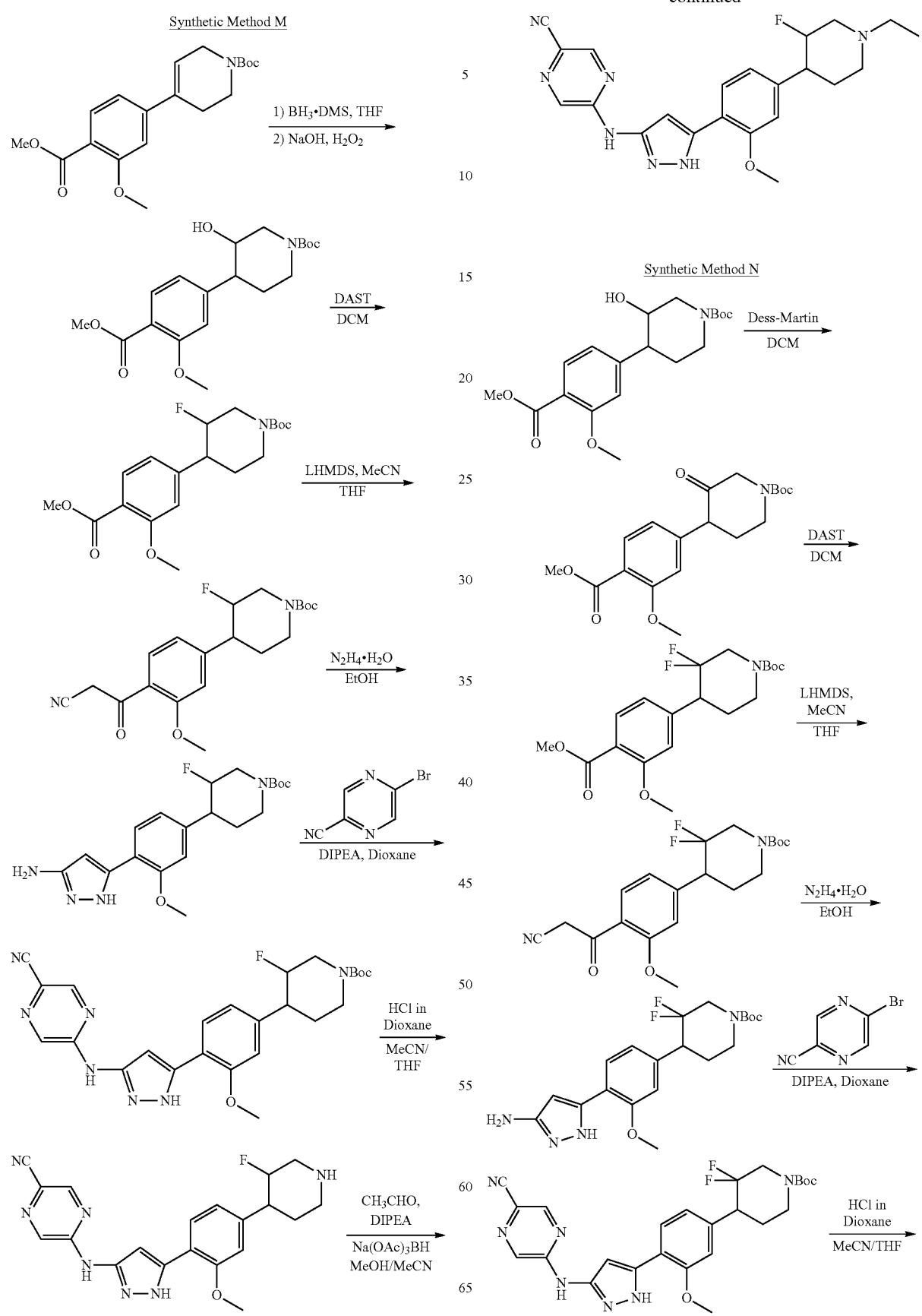

117
-continued
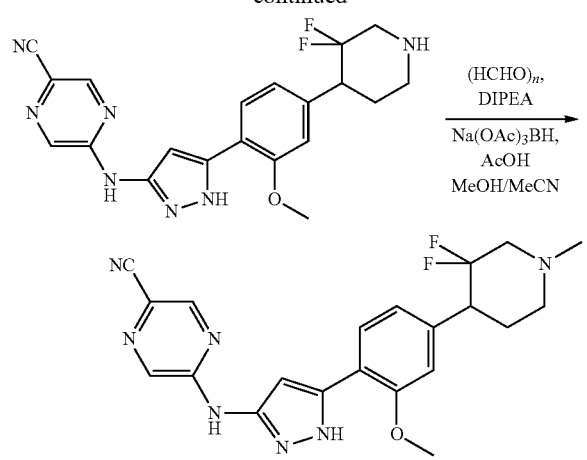
Synthetic Method O
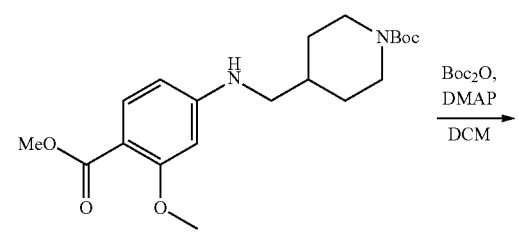
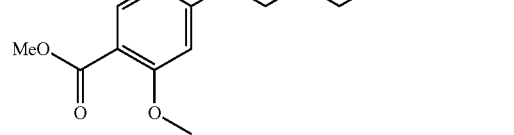
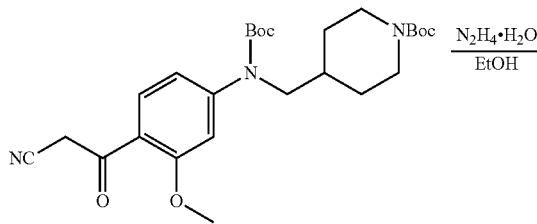
118
-continued
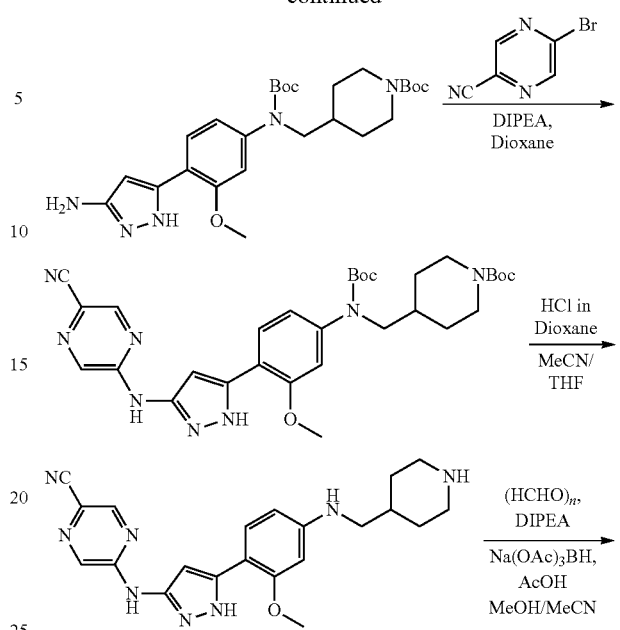
Synthetic Method P
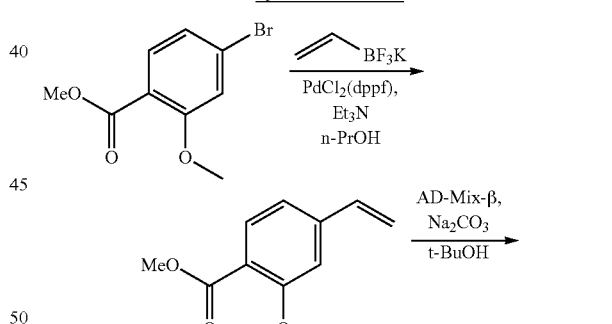
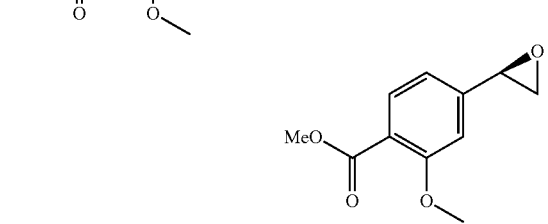

119
-continued
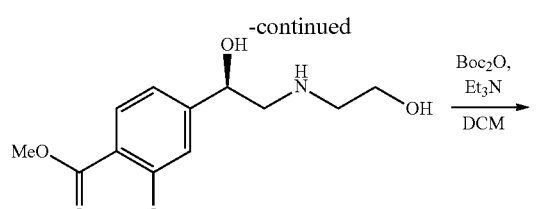
Boc₂O, Et₃N / DCM →
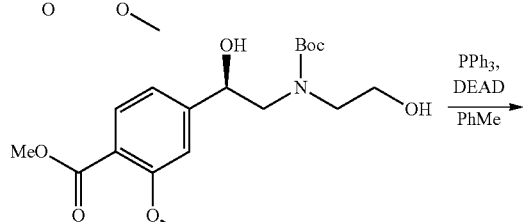
PPh₃, DEAD / PhMe →
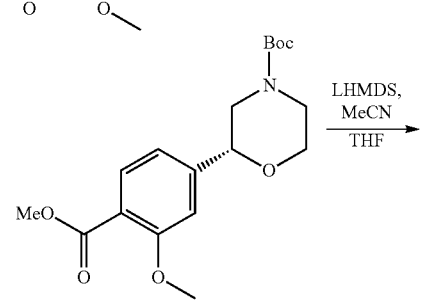
LHMDS, MeCN / THF →
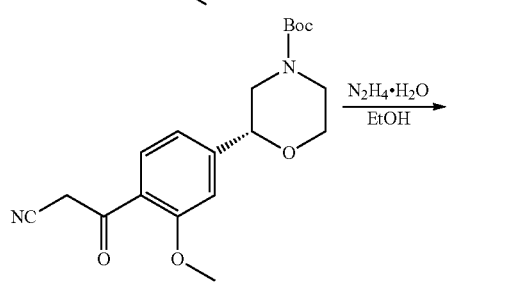
N₂H₄·H₂O / EtOH →
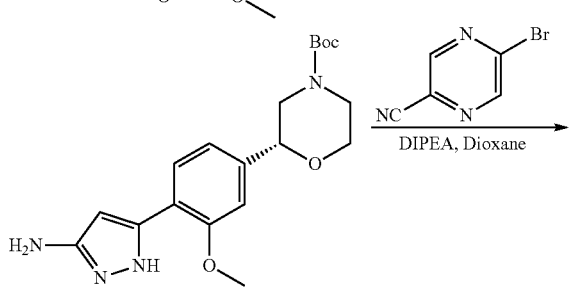
DIPEA, Dioxane →
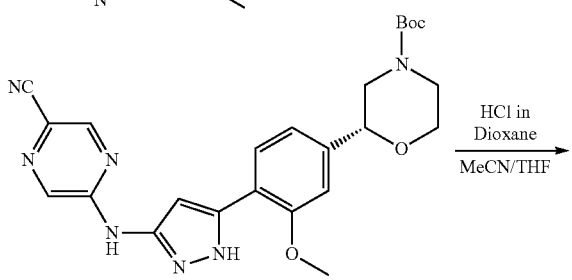
HCl in Dioxane MeCN/THF →
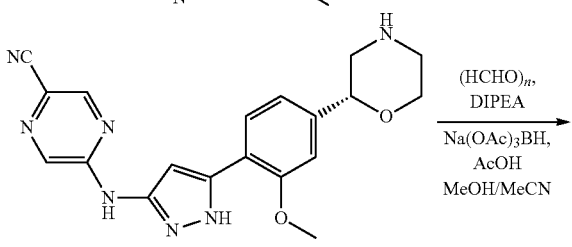
(HCHO)ₙ, DIPEA Na(OAc)₃BH, AcOH MeOH/MeCN →
120
-continued
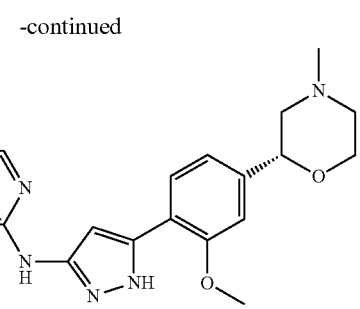
Synthetic Method Q
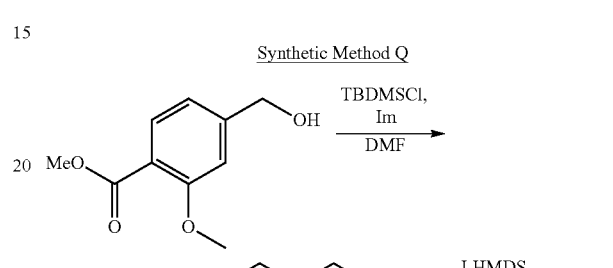
TBDMSCl, Im / DMF →
LHMDS, MeCN / THF →
N₂H₄·H₂O / EtOH →
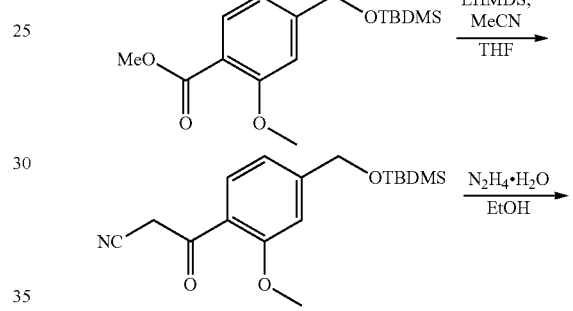
DIPEA, Dioxane →
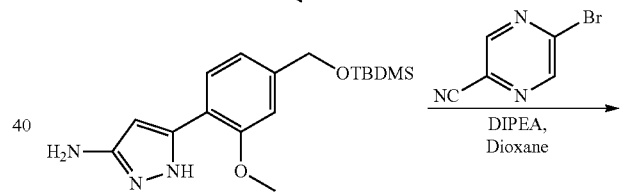
TBAF / THF →
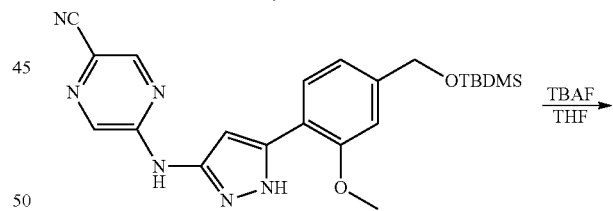
Dess-Martin / DCM →
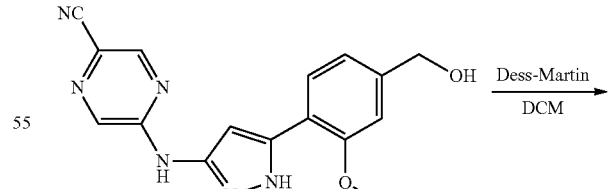
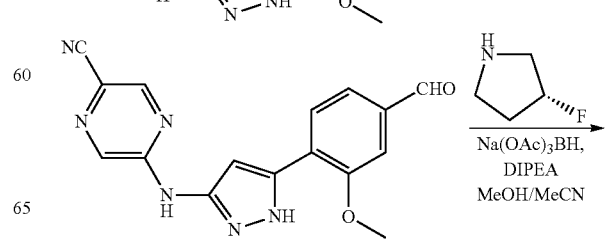
Na(OAc)₃BH, DIPEA MeOH/MeCN →

121
-continued
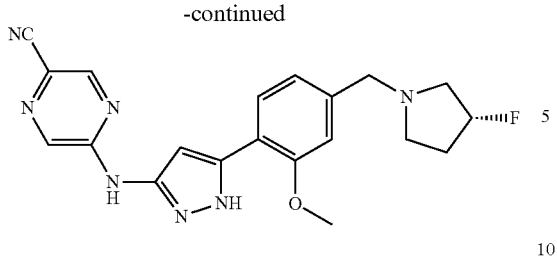
Synthetic Method R
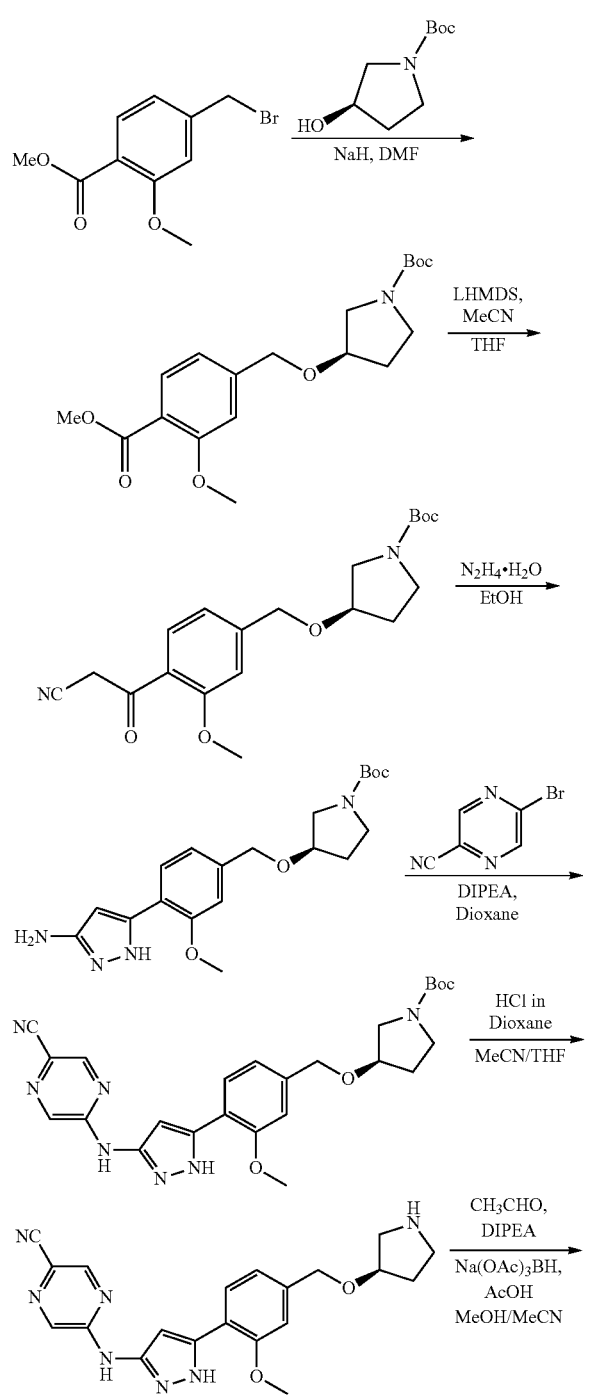
122
-continued
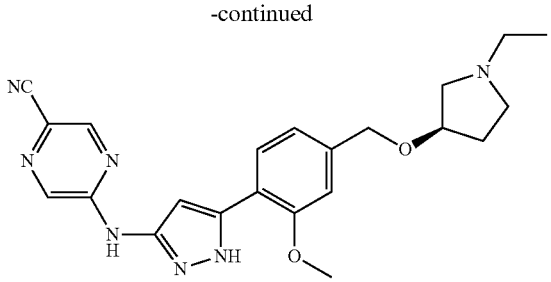
Synthetic Method S
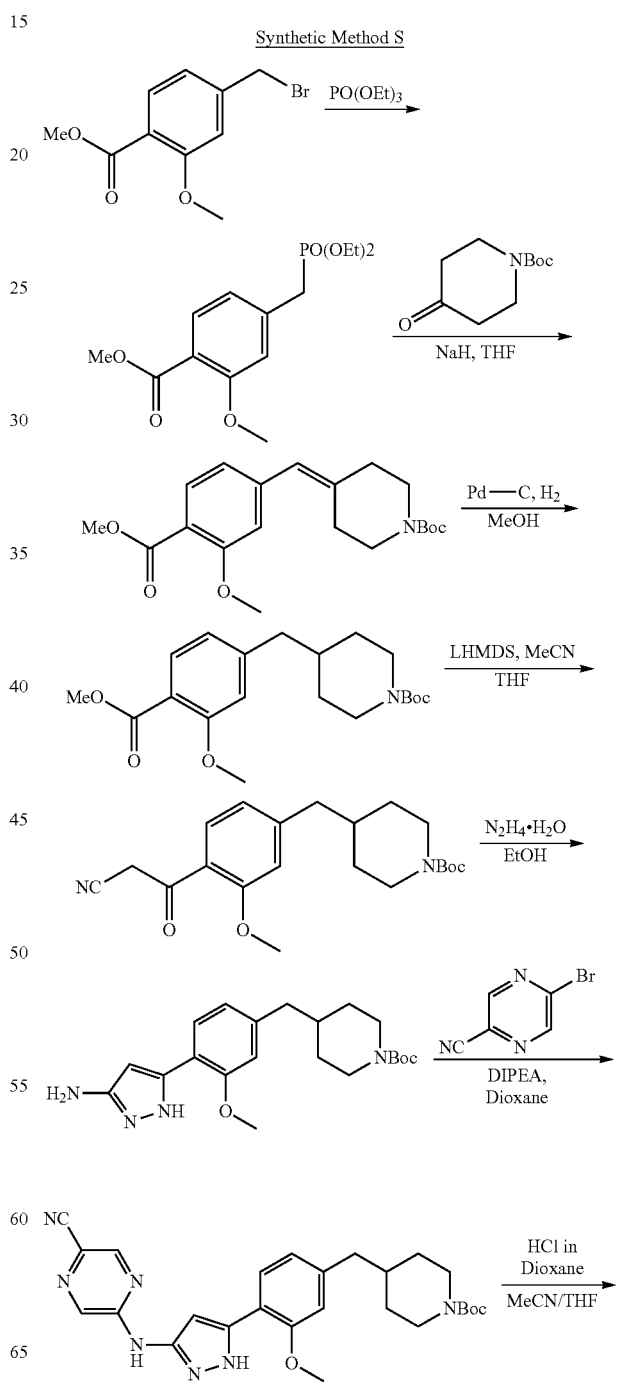

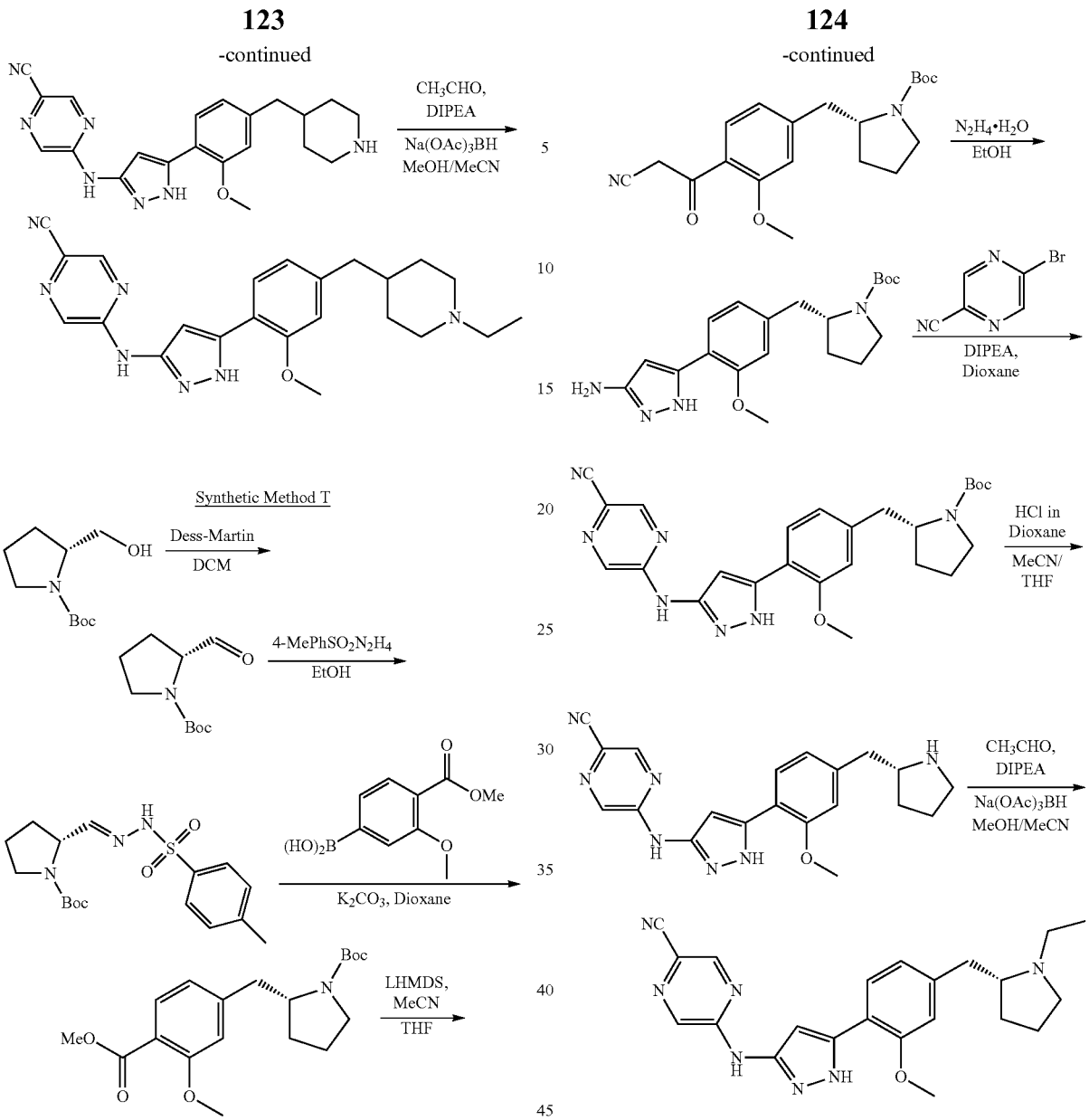

TABLE 2

| Ex. No. | Name | Synthetic Method | ¹H NMR | LC (RT) | MS(MH+) | LCMS Method |
|---|---|---|---|---|---|---|
| 1 | 5-[5-(4-benzylamino-2,6-dimethoxy-phenyl)-1H-pyrazol-3-ylaminoypyrazine-2-carbonitrile | A | (DMSO-$d_6$) δ 11.99 (s, 1H), 10.58 (s, 1H), 8.63 (s, 1H), 7.39 (t, 2H) 7.33 (s, 2H), 7.25 (t, 1H), 6.62 (d, 2H), 5.99 (s, 2H), 4.35 (s, 2H) and 3.38 (s, 6H). | 2.28 | 428 | A |
| 2 | 5-[5-(4-benzylamino-2-methoxy-phenyl)-1H-pyrazol-3-ylamino]-pyrazine-2-carbonitrile | A | (DMSO-$d_6$) δ 12.20 (br s, 1H), 10.68 (s, 1H), 8.67 (s,1H), 8.50 (bs,1H), 7.40-7.07 (m, 7H), 6.70 (s, 1H), 6.37 (s, 1H), 6.27 (d, 1H), 4.34 (s, 2H) and 3.78 (s, 3H). | 2.31 | 398 | A |
| 3 | 5-{5-[4-(benzylamino-methyl)-2-methoxy-phenyl]-1H-pyrazol-3-ylamino}-pyrazine-2-carbonitrile hydrochloride | B | (DMSO-$d_6$) δ 12.70 (s, 1H), 10.80 (s, 1H), 9.56 (s, 2H), 8.67 (s, 1H), 8.53 (s, 1H), 7.85 (d, 1H), 7.56 (t, 2H), 7.45 (q, 3H), 7.18 (d, 1H), 7.01 (s, 1H), 4.20 (d, 4H) and 3.93 (d, 3H). | 1.79 | 412 | A |
| 4 | 5-{5-[4-(2-benzylamino-ethyl)-2-methoxy-phenyl]-1H-pyrazol-3-ylamino}-pyrazine-2-carbonitrile hydrochloride | C | (DMSO-$d_6$) δ 10.79 (s, 1H), 9.44 (s, 2H), 8.67 (s, 1H), 8.53 (br s, 1H), 7.64 (d, 1H), 7.58 (d, 2H), 7.48-7.42 (m, 3H), 7.05 (s, 1H), 6.93 (dd, 2H), 4.18 (s, 2H), 3.91 (s, 3H), 3.20 (d, 2H) and 3.05 (d, 2H). | 1.85 | 426 | A |

TABLE 2-continued

| Ex. No. | Name | Synthetic Method | ¹H NMR | LC (RT) | MS(MH⁺) | LCMS Method |
|---|---|---|---|---|---|---|
| 5 | 5-{5-[4-(benzylamino-methyl)-phenyl]-1H-pyrazol-3-ylamino}-pyrazine-2-carbonitrile hydrochloride | A | (DMSO-$d_6$) δ 10.89 (s, 1H), 9.74 (br s, 2H), 8.67 (s, 1H), 8.50 (br s, 1H), 7.82 (d, 1H), 7.66 (s, 1H), 7.57 (dd, 2H), 7.46-7.40 (m, 3H), 6.99 (br s, 1H) and 4.22 (d, 4H). | 1.79 | 382 | A |
| 6 | 5-[5-(4-{[(S)-1-(4-fluoro-phenyl)-ethylamino]-methyl}-2-methoxy-phenyl)-1H-pyrazol-3-ylamino]-pyrazine-2-carbonitrile hydrochloride | A | (DMSO-$d_6$) δ 10.81 (s, 1H), 10.14 (br s, 1H), 9.78 (d, 1H), 8.67 (s, 1H), 8.52 (br s, 1H), 7.72-7.67 (m, 3H), 7.46 (s, 1H), 7.33 (t, 2H), 7.10 (dd, 1H), 7.00 (s, 1H), 4.44-4.39 (m, 1H), 4.05 (d, 1H), 3.91 (s, 3H), 3.86-3.81 (m, 1H) and 1.65 (d, 3H). | 1.91 | 444 | A |
| 7 | 5-[5-(4-{[(R)-1-(4-fluoro-phenyl)-ethylamino]-methyl}-2-methoxy-phenyl)-1H-pyrazol-3-ylamino]-pyrazine-2-carbonitrile hydrochloride | A | (DMSO-$d_6$) δ 10.80 (s, 1H), 10.10 (br s, 1H), 9.76 (br s, 1H), 8.67 (s, 1H), 8.52 (br s, 1H), 7.72-7.67 (m, 3H), 7.45 (s, 1H), 7.33 (t, 2H), 7.11 (dd, 1H), 6.99 (s, 1H), 4.44-4.39 (m, 1H), 4.08-4.04 (m, 1H), 3.93 (s, 3H), 3.86-3.81 (m, 1H) and 1.65 (d, 3H). | 1.91 | 444 | A |
| 8 | 5-(5-{4-[(4-fluoro-benzylamino)-methyl]-2-methoxy-phenyl}-1H-pyrazol-3-ylamino)-pyrazine-2-carbonitrile hydrochloride | A | (DMSO-$d_6$) δ 12.69 (s, 1H), 10.82 (s, 1H), 9.73 (s, 2H), 8.67 (d, 1H), 8.53 (s, 1H), 7.75 (d, 1H), 7.63 (q, 2H), 7.46 (s, 1H), 7.30 (t, 2H), 7.18 (d, 1H), 7.01 (s, 1H), 4.18 (d, 4H) and 3.94 (s, 3H). | 1.85 | 430 | A |
| 9 | 5-(5-{2-methoxy-4-[(2-morpholin-4-yl-ethylamino)-methyl]-phenyl}-1H-pyrazol-3-ylamino)-pyrazine-2-carbonitrile hydrochloride | A | (DMSO-$d_6$) δ 12.75 (d, 1H), 11.10 (t, 1H), 10.81 (s, 1H), 9.66-9.56 (m, 1H), 8.66 (s, 1H), 8.49 (d, 1H), 7.75 (dd, 1H), 7.50 (s, 1H), 7.21 (s, 1H), 7.15 (s, 1H), 4.25 (s, 2H), 4.05 (s, 3H), 3.82 (d, 2H), 3.56 (d, 2H), 3.50 (s, 4H), 3.16-3.08 (m, 2H) and 1.20 (t, 1H). | 1.70 | 435 | A |
| 10 | (5-{2-methoxy-4-[(2-morpholin-4-yl-ethylamino)-methyl]-phenyl}-1H-pyrazol-3-yl)-pyrazin-2-yl-amine hydrochloride | A | (DMSO-$d_6$) δ 12.39 (br s, 1H), 11.19 (br s, 1H), 9.84 (s, 1H), 9.69 (br s, 2H), 8.56 (s, 1H), 8.14 (s, 1H), 7.92 (d, 1H), 7.76 (d, 1H), 7.50 (s, 1H), 7.22 (d, 1H), 6.89 (s, 1H), 4.25 (t, 2H), 4.03 (t, 2H), 4.01 (s, 3H), 3.83 (s, 2H), 3.62-3.50 (m, 6H) and 3.15 (d, 2H). | 1.52 | 410 | A |
| 11 | 5-{5-[2-methoxy-4-(1-methyl-piperidin-4-yl)-phenyl]-1H-pyrazol-3-ylamino}-pyrazine-2-carbonitrile hydrochloride | D | (DMSO-$d_6$) δ 12.39 (br s, 1H), 10.77 (s, 1H), 10.49 (br s, 1H), 8.67 (s, 1H), 8.54 (s, 1H), 7.65 (d, 1H), 7.01 (s, 1H), 6.92 (d, 2H), 3.93 (s, 3H), 3.49 (d, 2H), 3.12-3.01 (m, 2H), 2.90-2.77 (m, 4H) and 2.08-2.03 (m, 4H). | 1.70 | 390 | A |
| 12 | 5-[5-(4-{[(1-cyclopropane-carbonyl-piperidin-4-ylmethyl)-amino]-methyl}-2-methoxy-phenyl)-1H-pyrazol-3-ylamino]-pyrazine-2-carboxamide hydrochloride | A | (DMSO-$d_6$) δ 12.71 (s, 1H), 10.80 (br s, 1H), 9.27 (br s, 2H), 8.67 (s, 1H), 8.53 (br s, 1H), 7.74 (d, 1H), 7.50 (s, 1H), 7.20 (d, 2H), 7.07 (dd, 1H), 4.33 (m, 2H), 4.35-4.28 (m, 2H), 4.17 (s, 4H), 3.95 (s, 3H), 3.41-3.36 (m, 1H), 3.09-3.06 (m, 1H), 2.83 (d, 2H), 2.03-1.97 (m, 2H), 1.85-1.75 (m, 2H), 1.67-1.07 (m, 3H) and 0.69-0.67 (m, 4H). | 1.72 | 487 | A |
| 13 | N-[[4-[3-[(5-cyanopyrazin-2-yl)amino]-1H-pyrazol-5-yl]-3-methoxy-phenyl]methyl]cyclopropanecarboxamide | E | (DMSO-$d_6$) δ 12.58 (s, 1 H), 10.71 (s, 1H), 8.64 (s, 1H), 8.57 (s, 1H), 8.48 (s, 1H), 7.61 (s, 1H), 7.03 (s, 1H), 6.91 (s, 2H), 4.29 (s, 2H), 3.87 (s, 3H), 1.60 (s, 1H) and 0.68 (br s, 4H). | 4.44 | 320 | B |
| 14 | 5-[[5-[2-methoxy-4-[(tetrahydropyran-4-ylamino)methyl]phenyl]-1H-pyrazol-3-yl]amino]pyrazine-2-carbonitrile hydrochloride | F | (DMSO-$d_6$) δ 10.77 (s, 1H), 9.58 (br s, 2H), 8.64 (s, 1H), 8.51 (s, 1H), 7.72 (d, 1H), 7.58 (s, 1H), 7.22 (d, 1H), 6.98 (s, 1H), 4.17 (s, 2H), 3.94 (s, 3H), 3.94-3.86 (m, 2H), 3.32-3.28 (m, 1H), 3.28-3.24 (m, 1H), 2.04 (t, 2H) and 1.72 (t, 2H). | 3.61 | 406 | B |
| 15 | 5-[[5-[2-methoxy-4-[[methyl(2-morpholinoethyl)amino]methyl]phenyl]-1H-pyrazol-3-yl]amino]pyrazine-2-carbonitrile hydrochloride | F | (DMSO-$d_6$) δ 11.53 (br s, 1 H), 11.35 (br s, 1H), 10.77 (s, 1H), 8.63 (s, 1H), 8.51 (s, 1H), 7.73 (s, 1H), 7.57 (s, 1H), 7.24 (d, 1H), 6.98 (s, 1H), 4.40 (s, 2H), 3.92 (s, 4H), 3.62 (s, 4H), 3.29 (br s, 4H) and 2.47 (s, 3H) | 3.57 | 449 | B |
| 16 | 5-[[5-[2-methoxy-4-(2-morpholinoethylamino)phenyl]-1H-pyrazol-3-yl]amino]pyrazine-2-carbonitrile hydrochloride | A | (DMSO-$d_6$) δ 11.40 (s, 1H), 10.68 (s, 1H), 8.62 (s, 1H), 8.52 (s, 1H), 7.39 (d, 1H), 6.71 (s, 1H), 6.35 (s, 1H), 6.32 (d, 1H), 4.00 (br s, 4H), 3.91 (s, 3H), 3.55 (t, 2H), 3.44 (br s, 2H), 3.24 (t, 2H) and 3.13 (br s, 2H). | 3.56 | 421 | B |
| 17 | 5-[[5-[4-[1-[2-(dimethylamino)acetyl]-4-piperidyl]-2-methoxy-phenyl]-1H-pyrazol-3-yl]amino]pyrazine-2-carbonitrile hydrochloride | G | (DMSO-$d_6$) δ 10.80 (s, 1H), 9.72 (s, 1H), 8.67 (s, 1H), 8.55 (s, 1H), 7.63 (s, 1H), 7.02 (s, 1H), 6.93 (d, 2H), 4.54 (d, 1H), 4.43-4.29 (m, 2H), 3.91 (s, 3H), 3.74 (d, 1H), 3.21-3.15 (m, 1H), 2.89-2.75 (m, 8H), 1.91-1.87 (m, 2H), 1.71-1.68 (m, 1H) and 1.58-1.54 (m, 1H). | 3.90 | 461 | B |
| 18 | 5-[[5-[2-methoxy-4-[[[(1R)-1-methyl-2-morpholino-ethyl]amino]methyl]phenyl]-1H-pyrazol-3-yl]amino]pyrazine-2-carbonitrile hydrochloride | F | (DMSO-$d_6$) δ 11.42 (s, 1H), 10.82 (s, 1H), 10.05 (d, 1H), 9.78 (d, 1H), 8.67 (s, 1H), 8.54 (s, 1H), 7.75 (d, 1H), 7.64 (s, 1H), 7.28 (d, 2H), 7.01 (s, 1H), 4.36-4.24 (m, 2H), 3.97-3.89 (m, 7H), 3.79-3.76 (m, 2H), 3.57 (br s, 2H), 3.45-3.42 (m, 1H), 3.17 (br s, 2H) and 1.53-1.52 (m, 3H). | 3.69 | 449 | B |

TABLE 2-continued

| Ex. No. | Name | Synthetic Method | ¹H NMR | LC (RT) | MS(MH⁺) | LCMS Method |
|---|---|---|---|---|---|---|
| 19 | 5-[[5-[4-[[(1,1-dimethyl-2-morpholino-ethyl)amino]methyl]-2-methoxy-phenyl]-1H-pyrazol-3-yl]amino]pyrazine-2-carbonitrile hydrochloride | F | (DMSO-d$_6$) δ 10.73 (s, 1H), 10.09 (s,1H), 8.63 (s,1H), 8.51 (s, 1H), 7.71 (d, 1H), 7.58 (s, 1H), 7.25 (d, 1H), 6.96 (s 1H), 4.22 (br s, 2H), 3.75 (s, 3H), 3.69 (br m, 2H), 3.32 (br m, 8H), 1.82 (br m, 2H) and 1.61 (s, 6H). | 3.79 | 463 | B |
| 20 | 5-[[5-[2-methoxy-4-(4-piperidyl)phenyl]-1H-pyrazol-3-yl]amino]pyrazine-2-carbonitrile hydrochloride | G | (DMSO-d$_6$) δ 10.78 (s, 1H), 9.13 (d, 1H), 8.95 (d, 1H), 8.67 (d, 1H), 8.55 (s, 1H), 7.65 (d, 1H), 6.99 (s, 1H), 6.92 (s, 2H), 6.87 (s, 1H), 3.92 (s, 3H), 3.36 (d, 2H), 3.03-2.92 (m, 2H), 2.90-2.87 (m, 1H) and 1.99-1.90 (m, 4H). | 3.72 | 376 | B |
| 21 | 5-[[5-[2-fluoro-4-(1-methyl-4-piperidyl)phenyl]-1H-pyrazol-3-yl]amino]pyrazine-2-carbonitrile hydrochloride | H | (DMSO-d$_6$) δ 10.90 (s, 1H), 8.70 (s, 1H), 8.51 (s, 1H), 7.84 (d, 1H), 7.26-7.21 (m, 2H), 6.95 (s, 1H), 3.57-3.51 (m, 2H), 3.10-3.04 (m, 2H), 2.89-2.85 (m, 1H), 2.78 (d, 3H) and 2.06-1.97 (m, 4H). | 3.64 | 378 | B |
| 22 | 5-[[5-[2-methoxy-4-(4-methylpiperazin-1-yl)phenyl]-1H-pyrazol-3-yl]amino]pyrazine-2-carbonitrile hydrochloride | I | (DMSO-d$_6$) δ 12.56 (s, 1H), 11.17 (s, 1H), 10.77 (s, 1H), 8.67 (s, 1H), 8.56 (s, 1H), 7.57 (d, 1H), 6.84 (s, 1H), 6.70-6.66 (m, 2H), 3.98 (d, 2H), 3.91 (s, 3H), 3.49 (d, 2H), 3.24-3.10 (m, 4H) and 2.81 (d, 3H). | 3.53 | 391 | B |
| 23 | 5-[[5-[2-methoxy-4-(4-methyl-1,4-diazepan-1-yl)phenyl]-1H-pyrazol-3-yl]amino]pyrazine-2-carbonitrile hydrochloride | I | (DMSO-d$_6$) δ 12.38 (s, 1H), 10.73 (s, 1H), 10.66 (s, 1H), 8.67 (s, 1H), 8.55 (d, 1H), 7.50 (d, 1H), 6.79 (s, 1H), 6.45 (dd, 1H), 6.40 (s, 1H), 3.94 (s, 1H), 3.91 (s, 3H), 3.77-3.70 (m, 1H), 3.54-3.42 (m, 4H), 3.24-3.07 (m, 2H), 2.82-2.80 (d, 3H), 2.36-2.32 (m, 1H) and 2.20 (m, 1H). | 3.71 | 405 | B |
| 24 | 5-[[5-[2-methoxy-4-(1-methyl-4-piperidyl)phenyl]-1H-pyrazol-3-yl]amino]pyridine-2-carbonitrile hydrochloride | J | (DMSO-d$_6$) δ 10.58 (s, 1H), 9.68 (s, 1H), 8.67 (s, 1H), 8.02-8.00 (m, 1H), 7.81 (d, 1H), 7.69-7.67 (m, 1H), 7.02 (s, 1H), 6.92 (d, 1H), 6.38 (d, 1H), 3.92 (s, 3H), 3.49 (d, 1H), 3.07-3.04 (m, 2H), 2.90-2.84 (m, 1H), 2.78 (d, 3H) and 2.04-1.99 (m, 4H). | 3.64 | 389 | B |
| 25 | 6-[[5-[2-methoxy-4-(1-methyl-4-piperidyl)phenyl]-1H-pyrazol-3-yl]amino]pyridine-3-carbonitrile hydrochloride | J | (DMSO-d$_6$) δ 10.59 (s, 1H), 10.23 (s, 1H), 8.58 (s, 1H), 7.95-7.92 (m, 1H), 7.65 (d, 1H), 7.32-7.28 (m, 1H), 7.01 (s, 1H), 6.92 (d, 1H), 6.80 (s, 1H), 3.92 (s, 3H), 3.49 (d, 1H), 3.11-3.04 (m, 2H), 2.90-2.82 (m, 1H), 2.78 (d, 3H) and 2.08-2.02 (m, 4H). | 3.80 | 389 | B |
| 26 | N-[5-[2-methoxy-4-(1-methyl-4-piperidyl)phenyl]-1H-pyrazol-3-yl] 5-methyl-pyrazin-2-amine hydrochloride | J | (DMSO-d$_6$) δ 10.92 (s, 1H), 10.31 (s, 1H), 8.61 (s, 1H), 8.21 (s, 1H), 7.69 (d, 1H), 7.03 (s, 1H), 6.93 (d, 1H), 6.71 (s, 1H), 3.92 (s, 3H), 3.61-3.49 (br d, 2H), 3.06 (d, 2H), 2.88-2.85 (br d, 1H), 2.76 (d, 3H), 2.42 (s, 3H) and 2.11-2.03 (m, 4H). | 3.55 | 379 | B |
| 27 | 5-[[5-[4-(1-methyl-4-piperidyl)phenyl]-1H-pyrazol-3-yl]amino]pyrazine-2-carbonitrile hydrochloride | H | (DMSO-d$_6$) δ 10.88 (s, 1H), 10.61 (s, 1H), 8.69 (s, 1H), 8.50 (s, 1H), 7.73 (d, 2H), 7.34 (d, 2H), 6.92 (d, 2H), 3.49 (t, 2H), 3.06 (t, 2H), 2.89-2.87 (m, 1H), 2.68 (s, 3H), 2.18-2.07 (m, 2H) and 1.99-1.92 (m, 2H). | 3.62 | 360 | B |
| 28 | 5-[[5-[2-methoxy-4-[(1-methyl-4-piperidyl)oxy]phenyl]-1H-pyrazol-3-yl]amino]pyrazine-2-carbonitrile hydrochloride | K | (DMSO-d$_6$) δ 12.55 (br s, 1H), 10.92 (br s, 1H), 10.77 (br s, 1H), 8.66 (s, 1H), 8.55 (s, 1H), 7.62-7.60 (m, 1H), 6.86 (s, 1H), 6.79-6.71 (m, 2H), 4.65 (br s, 1H), 3.89 (s, 3H), 3.47 (d, 1H), 3.29 (d, 1H), 3.18-3.08 (m, 2H), 2.77-2.74 (m, 3H), 2.34-2.14 (m, 2H), 2.06 (d, 1H) and 1.94 (d, 1H). | 3.75 | 406 | B |
| 29 | 5-[[5-[2-methoxy-4-[(1-methyl-4-piperidyl)methoxy]phenyl]-1H-pyrazol-3-yl]amino]pyrazine-2-carbonitrile hydrochloride | K | (DMSO-d$_6$) δ 10.79 (br s, 1H), 10.58 (br s, 1H), 8.67 (d, 1H), 8.55 (d, 1H), 7.59 (d, 1H), 6.85 (s, 1H), 6.68 (d, 1H), 6.65 (d, 1H), 3.93 (d, 2H), 3.90 (s, 3H), 3.42 (d, 2H), 3.01-2.92 (m, 2H), 2.71 (d, 3H), 1.99-1.91 (m, 3H) and 1.69-1.60 (m, 2H). | 3.80 | 420 | B |
| 30 | 2-fluoro-4-[[5-[2-methoxy-4-(1-methyl-4-piperidyl)phenyl]-1H-pyrazol-3-yl]amino]benzonitrile hydrochloride | J | (DMSO-d$_6$) δ 12.45 (s, 1H), 10.35 (s, 1H), 9.70 (s, 1H), 7.69-7.59 (m, 3H), 7.14 (d, 1H), 7.05 (s, 1H), 6.92 (d, 1H), 6.37 (s, 1H), 3.92 (s, 3H), 3.53 (d, 2H), 3.11-3.02 (m, 2H), 2.86-2.82 (m, 1H), 2.68 (d, 3H) and 2.08-1.92 (m, 4H). | 3.95 | 406 | B |
| 31 | 5-[[5-[2-methoxy-4-[(2-pyridylamino)methyl]phenyl]-1H-pyrazol-3-yl]amino]pyrazine-2-carbonitrile | F | (DMSO-d$_6$) δ 14.30 (br s, 1H), 10.82(s, 1H), 9.51 (br s, 1H), 8.67 (s, 1H), 8.55 (s, 1H), 7.96-7.92 (m, 2H), 7.69 (d, 1H), 7.35 (s, 1H), 7.19 (d, 1H), 7.11 (d, 1H), 6.96 (s, 1H), 6.89 (t, 1H), 4.72 (d, 2H) and 3.93 (s, 3H). | 3.72 | 399 | B |
| 32 | 5-[[5-[5-fluoro-2-methoxy-4-(1-methyl-4-piperidyl)phenyl]-1H-pyrazol-3-yl]amino]pyrazine-2-carbonitrile hydrochloride | J | (DMSO-d$_6$) δ 10.81 (s, 1H), 10.69 (s, 1H), 8.67 (s, 1H), 8.53 (s, 1H), 7.59-7.55 (m, 1H), 7.01 (s, 1H), 6.98 (d, 1H), 3.92 (s, 3H), 3.49 (d, 2H), 3.15-3.07 (m, 3H), 2.77 (d, 3H), 2.21-2.12 (m, 2H) and 1.99-1.96 (m, 3H). | 3.74 | 408 | B |
| 33 | 5-[[5-[2-methoxy-4-[(3S)-pyrrolidin-3-yl]oxy-phenyl]-1H-pyrazol-3-yl]amino]pyrazine-2-carbonitrile hydrochloride | K | (DMSO-d$_6$) δ 10.76 (s, 1H), 9.60 (s, 1H), 9.46 (s, 1H), 8.67 (d, 1H), 8.54 (s, 1H), 7.63 (d, 1H), 6.87 (s, 1H), 6.69 (t, 2H), 5.30 (q, 1H), 3.90 (s, 3H), 3.50 (q, 1H), 3.36-3.27 (m, 3H) and 2.24-2.18 (m, | 3.68 | 378 | B |

TABLE 2-continued

| Ex. No. | Name | Synthetic Method | ¹H NMR | LC (RT) | MS(MH⁺) | LCMS Method |
|---|---|---|---|---|---|---|
| 34 | 5-[[5-[2-methoxy-4-(pyrrolidin-2-ylmethoxy)phenyl]-1H-pyrazol-3-yl]amino]pyrazine-2-carbonitrile hydrochloride | K | (DMSO-d₆) δ 10.76 (s, 1H), 9.67 (s, 1H), 9.08 (s, 1H), 8.67 (s, 1H), 8.54 (s, 1H), 7.64 (d, 1H), 6.88 (s, 1H), 6.74 (s, 1H), 6.70 (d, 1H), 4.39-4.31 (m, 1H), 4.25-4.20 (m, 1H), 3.91 (s, 3H), 3.93-3.90 (m, 1H), 3.66 (t, 1H), 3.22 (s, 3H) and 2.33-2.23 (m, 2H). | 3.90 | 392 | B |
| 35 | 5-[[5-[2-methoxy-4-[(1-methylpyrrolidin-2-yl)methoxy]phenyl]-1H-pyrazol-3-yl]amino]pyrazine-2-carbonitrile hydrochloride | K | (DMSO-d₆) δ 10.80 (s, 1H), 10.67 (s, 1H), 8.67 (d, 1H), 8.54 (s, 1H), 7.64 (d, 1H), 6.98 (s, 1H), 6.88 (s, 1H), 6.79 (d, 1H), 6.71 (q, 1H), 4.42 (d, 2H), 3.91 (s, 3H), 3.85-3.81 (m, 1H), 3.62-3.59 (m, 1H) 3.15 (t, 1H), 2.97 (d, 3H), 2.34-2.24 (m, 1H), 2.08-2.05 (m, 1H), 2.02-1.99 (m, 1H) and 1.88-1.79 (m, 1H). | 3.71 | 406 | B |
| 36 | 5-[[5-[2-methoxy-4-(4-piperidylmethoxy)phenyl]-1H-pyrazol-3-yl]amino]pyrazine-2-carbonitrile hydrochloride | K | (DMSO-d₆) δ 13.00-12.00 (br s, 1H), 10.77 (br s, 1H), 9.08 (d, 1H), 8.67 (s, 1H), 8.54 (s, 1H), 7.59 (d, 1H), 6.85 (s, 1H), 6.67-6.63 (m, 2H), 3.93 (d, 2H), 3.89 (s, 3H), 3.29 (d, 2H), 2.95-2.86 (m, 2H), 2.08 (s, 1H), 1.93 (d, 2H) and 1.56-1.48 (m, 2H). | 3.86 | 406 | B |
| 37 | 5-[[5-[2-methoxy-4-[[(1-methyl-4-piperidyl)amino]methyl]phenyl]-1H-pyrazol-3-yl]amino]pyrazine-2-carbonitrile hydrochloride | F | (DMSO-d₆) δ 10.85 (s, 1H), 10.77 (s, 1H), 9.91 (s, 1H), 8.68 (s, 1H), 8.54 (s, 1H), 7.74 (d, 1H), 7.62 (s, 1H), 7.26 (d, 1H), 7.01 (s, 1H), 4.22 (d, 2H), 3.96 (s, 3H), 3.50 (d, 2H), 3.25 (br s, 1H), 3.15 (d, 1H), 3.00 (q, 2H), 2.69 (d, 3H), 2.36 (t, 2H) and 2.08 (q, 2H). | 3.01 | 419 | B |
| 38 | 5-[[5-[2-isopropoxy-4-(1-methyl-4-piperidyl)phenyl]-1H-pyrazol-3-yl]amino]pyrazine-2-carbonitrile hydrochloride | H | (DMSO-d₆) δ 12.63 (s, 1H), 10.78 (s, 1H), 10.45 (s, 1H), 8.66 (s, 1H), 8.56 (s, 1H), 7.67 (d, 1H), 7.06 (s, 1H), 7.01 (s, 1H), 6.89 (d, 1H), 4.76-4.73 (m, 1H), 3.49 (d, 2H), 3.06 (br s, 2H), 2.90 (d, 1H), 2.78 (d, 3H), 2.01 (br d, 4H) and 1.37 (d, 6H). | 3.94 | 418 | B |
| 39 | 5-[[5-[2-methoxy-4-(3-piperidyl)phenyl]-1H-pyrazol-3-yl]amino]pyrazine-2-carbonitrile hydrochloride | H | (DMSO-d₆) δ 10.82 (s, 1H), 9.39 (s, 1H), 9.17 (s, 1H), 8.67 (d, 1H), 8.54 (s, 1H), 7.64 (t, 1H), 7.08 (d, 1H), 6.95 (d, 2H), 3.92 (s, 3H), 3.44-3.39 (m, 2H), 3.07 (t, 2H), 2.90 (s, 1H) and 1.89-1.76 (m, 4H). | 3.72 | 376 | B |
| 40 | 5-[[5-[2-methoxy-4-(1-methyl-3-piperidyl)phenyl]-1H-pyrazol-3-yl]amino]pyrazine-2-carbonitrile hydrochloride | H | (DMSO-d₆) δ 10.86 (s, 1H), 10.82 (s, 1H), 8.67 (d, 1H), 8.54 (s, 1H), 7.67 (d, 1H), 7.05 (s, 1H), 6.95 (d, 2H), 3.93 (s, 3H), 3.47-3.37 (m, 2H), 3.24-3.14 (m, 2H), 2.99-2.93 (m, 1H), 2.75 (d, 3H), 1.94 (d, 3H) and 1.66 (d, 1H). | 3.75 | 390 | B |
| 41 | 5-[[5-[2-methoxy-4-(1-methyl-2-piperidyl)phenyl]-1H-pyrazol-3-yl]amino]pyrazine-2-carbonitrile hydrochloride | H | (DMSO-d₆) δ 10.82 (s, 1H), 9.70 (d, 1H), 9.29 (d, 1H), 8.67 (d, 1H), 8.54 (s, 1H), 7.74 (d, 1H), 7.56 (s, 1H), 7.21 (d, 1H), 6.99 (s, 1H), 4.28-4.25 (m, 1H), 3.97 (s, 3H), 3.35 (d, 2H), 3.06-3.01 (m, 1H), 1.94-1.77 (m, 5H) and 1.66-1.64 (m, 1H). | 3.83 | 376 | B |
| 42 | 5-[[5-[2-methoxy-4-[(3S)-1-methylpyrrolidin-3-yl]oxy-phenyl]1H-pyrazol-3-yl]amino]pyrazine-2-carbonitrile hydrochloride | K | (DMSO-d₆) δ 10.77 (s, 1H), 8.67 (s, 1H), 8.55 (s, 1H), 7.63 (s, 1H), 6.87 (s, 1H), 6.70 (q, 2H), 5.25 (d, 1H) 3.90 (s, 3H), 3.65-3.38 (m, 2H), 3.44-3.38 (m, 1H), 3.24-3.12 (m, 2H), 2.88 (q, 3H) and 2.36-2.14 (m, 2H). | 3.70 | 392 | B |
| 43 | 5-chloro-N-[5-[2-methoxy-4-(4-piperidyl)phenyl]-1H-pyrazol-3-yl]pyrazin-2-amine hydrochloride | J | (DMSO-d₆) δ 10.03 (s, 1H), 9.22 (d, 1H), 9.05 (d, 1H), 8.48 (s, 1H), 8.26 (s, 1H), 7.64 (d, 1H), 6.99 (s, 1H), 6.90 (d, 1H), 6.73 (s, 1H), 3.91 (s, 3H), 3.36 (d, 2H), 2.98 (d, 1H), 2.93-2.88 (m, 2H) and 1.95-1.89 (m, 4H). | 3.98 | 385 | B |
| 44 | 5-chloro-N-[5-[2-methoxy-4-(1-methyl-4-piperidyl)phenyl]-1H-pyrazol-3-yl]pyrazin-2-amine hydrochloride | J | (DMSO-d₆) δ 10.70 (s, 1H), 10.04 (s, 1H), 8.48 (s, 1H), 8.27 (s, 1H), 7.65 (d, 1H), 7.04 (d, 1H), 6.91 (d, 1H), 6.74 (s, 1H), 3.91 (s, 3H), 3.49 (d, 2H), 2.89 (d, 1H), 3.10-3.04 (m, 2H), 2.89 (d, 1H), 2.77 (d, 3H) and 2.11-2.03 (m, 4H). | 3.95 | 399 | B |
| 45 | 5-[[5-[2-methoxy-4-(4-piperidyl)phenyl]-1H-pyrazol-3-yl]amino]pyrazine-2-carboxylic acid hydrochloride | J | (DMSO-d₆) δ 9.30 (d, 1H), 9.12 (br d, 1H), 8.98(d, 1H), 8.89 (br d, 1H), 7.96 (d, 1H), 6.97 (s, 1H), 6.91 (d, 1H), 5.60 (s, 1H), 3.89 (s, 3H), 3.37 (d, 2H), 3.04-2.96 (m, 2H), 2.91-2.87 (br m, 1H) and 1.99-1.90 (m, 4H). | 3.60 | 395 | B |
| 46 | 5-[[5-(2-methoxy-4-piperazin-1-yl-phenyl)-1H-pyrazol-3-yl]amino]pyrazine-2-carbonitrile hydrochloride | I | (DMSO-d₆) δ 12.56 (s, 1H), 10.75 (s, 1H), 9.22 (s, 1H), 8.67 (s, 1H), 8.54 (s, 1H), 7.55 (d, 1H), 6.84 (s, 1H), 6.68-6.64 (m, 2H), 3.91 (s, 3H), 3.50-3.47 (m, 4H) and 3.23 (br s, 4H). | 3.54 | 377 | B |
| 47 | 5-[[5-[4-[(2S,6S)-2,6-dimethyl-4-piperidyl]-2-methoxy-phenyl]-1H-pyrazol-3-yl]amino]pyrazine-2-carbonitrile hydrochloride | J | (DMSO-d₆) δ 10.78 (s, 1H), 9.04 (s, 1H), 9.04 (s, 1H), 8.67 (s, 1H), 8.53 (s, 1H), 7.65 (d, 1H), 7.01 (s, 1H), 6.92 (s, 1H), 6.90 (s, 1H), 3.92 (s, 3H), 3.82-3.78 (m, 1H), 3.47-3.43 (m, 1H), 3.17-3.12 (m, 1H), 2.08-1.99 (m, 2H), 1.80 (d, 1H), 1.69-1.59 (m, 1H), 1.44 (d, 3H) and 1.30 (d, 3H). | 3.90 | 404 | B |

TABLE 2-continued

| Ex. No. | Name | Synthetic Method | ¹H NMR | LC (RT) | MS(MH⁺) | LCMS Method |
|---|---|---|---|---|---|---|
| 48 | 5-[[5-(2-methoxy-4-tetrahydropyran-4-yl-phenyl)-1H-pyrazol-3-yl]amino]pyrazine-2-carbonitrile hydrochloride | J | (DMSO-d$_6$) δ 10.77 (s, 1H), 8.67 (s, 1H), 8.55 (s, 1H), 7.60 (d, 1H), 7.03 (d, 1H), 6.94 (dd, 2H), 3.98-3.95 (m, 2H), 3.92 (s, 3H), 3.48-3.42 (m, 2H), 2.84-2.80 (m, 1H) and 1.76-1.70 (m, 4H). | 4.85 | 377 | B |
| 49 | 2-fluoro-4-[[5-[2-methoxy-4-(4-piperidyl)phenyl]-1H-pyrazol-3-yl]amino]benzonitrile hydrochloride | J | (DMSO-d$_6$) δ 12.42 (br s, 1H), 9.76 (s, 1H), 9.15 (br s, 1H), 8.98 (br s, 1H), 7.69-7.60 (m, 3H), 7.16 (d, 1H), 7.04 (s, 1H), 6.90 (d, 1H), 6.34 (s, 1H), 3.91 (s, 3H), 3.41-3.35 (m, 2H), 3.00 (t, 2H), 2.91-2.85 (m, 1H) and 2.01-1.88 (m, 4H). | 4.02 | 392 | B |
| 50 | 6-[[5-[2-methoxy-4-(4-piperidyl)phenyl]-1H-pyrazol-3-yl]amino]pyridine-3-carbonitrile hydrochloride | J | (DMSO-d$_6$) δ 10.19 (s, 1H), 8.94 (s, 1H), 8.76 (d, 1H), 8.57 (s, 1H), 7.93 (d, 1H), 7.64 (d, 1H), 7.32 (s, 1H), 6.98 (s, 1H), 6.90 (d, 1H), 6.80 (s, 1H), 3.91 (s, 3H), 3.38 (d, 2H), 3.00-2.95 (m, 2H), 2.95-2.89 (m, 1H) and 1.99-1.84 (m, 4H). | 3.73 | 375 | B |
| 51 | 5-[[5-[2-fluoro-4-(4-piperidyl)phenyl]-1H-pyrazol-3-yl]amino]pyrazine-2-carbonitrile hydrochloride | J | (DMSO-d$_6$) δ 10.91 (s, 1H), 9.10 (s, 1H), 8.69 (s, 1H), 8.51 (s, 1H), 7.85 (d, 1H), 7.23-7.21 (m, 2H), 6.95 (s, 1H), 3.36 (d, 2H), 3.02-2.97 (m, 2H), 2.94-2.90 (m, 1H) and 1.99-1.88 (m, 4H). | 3.72 | 364 | B |
| 52 | 5-[[5-[2-methoxy-4-(4-piperidyl)phenyl]-1H-pyrazol-3-yl]amino]pyridine-2-carbonitrile hydrochloride | J | (DMSO-d$_6$) δ 10.51 (s, 1H), 9.69 (s, 1H), 9.06 (d, 1H), 8.87 (d, 1H), 8.67 (d, 1H), 8.03-8.00 (m, 1H), 7.81 (d, 1H), 7.68 (d, 1H), 6.99 (s, 1H), 6.90 (s, 1H), 6.37 (s, 1H), 3.92 (s, 3H), 3.37 (d, 2H), 3.03-2.87 (m, 3H) and 1.98-1.89 (m, 4H). | 3.65 | 375 | B |
| 53 | 5-[[5-[2-isopropoxy-4-(4-piperidyl)phenyl]-1H-pyrazol-3-yl]amino]pyrazine-2-carbonitrile hydrochloride | H | (DMSO-d$_6$) δ 10.80 (s, 1H), 9.11 (d, 1H), 8.97 (d, 1H), 8.66 (d, 1H), 8.57 (s, 1H), 7.67 (d, 1H), 7.06 (s, 1H), 6.99 (s, 1H), 6.88 (d, 1H), 4.77-4.71 (m, 1H), 3.36 (d, 2H), 2.98 (d, 2H), 2.90-2.84 (m, 1H), 1.99-1.86 (m, 4H) and 1.37 (d, 6H). | 4.00 | 404 | B |
| 54 | 5-[[5-[4-(1,4-diazepan-1-yl)-2-methoxy-phenyl]-1H-pyrazol-3-yl]amino]pyrazine-2-carbonitrile hydrochloride | I | (DMSO-d$_6$) δ 10.80 (s, 1H), 9.30 (s, 1H), 8.67 (d, 1H), 7.51 (d, 1H), 6.79 (d, 1H), 6.48 (d, 1H), 6.41 (s, 1H), 3.91 (s, 3H), 3.81 (d, 2H), 3.65-3.57 (m, 2H), 3.23 (s, 2H), 3.10 (s, 2H) and 2.14 (d, 2H). | 3.70 | 391 | B |
| 55 | N-[5-[2-methoxy-4-(4-piperidyl)phenyl]-1H-pyrazol-3-yl]-5-methyl-pyrazin-2-amine hydrochloride | J | (DMSO-d$_6$) δ 10.26 (s, 1H), 9.18 (s, 1H), 9.03 (d, 1H), 8.60 (s, 1H), 8.20 (s, 1H), 7.68 (d, 1H), 7.01 (s, 1H), 6.92 (d, 1H), 6.71 (s, 1H), 3.92 (s, 3H), 3.37 (d, 2H), 2.99 (d, 2H), 2.91-2.88 (m, 1H), 2.42 (s, 3H) and 1.97-1.89 (br m, 4H). | 3.62 | 365 | B |
| 56 | 5-[[5-[4-(4-piperidyl)phenyl]-1H-pyrazol-3-yl]amino]pyrazine-2-carbonitrile hydrochloride | H | (DMSO-d$_6$) δ 10.87 (s, 1H), 9.06 (s, 1H), 8.68 (s, 1H), 8.50 (s, 1H), 7.72 (d, 2H), 7.32 (d, 2H), 6.92 (s, 1H), 3.41-3.34 (m, 2H), 3.04-2.96 (m, 2H), 2.91-2.85 (m, 1H) and 1.92 (br s, 4H). | 3.63 | 346 | B |
| 57 | 5-[[5-[2-methoxy-4-(4-piperidyloxy)phenyl]-1H-pyrazol-3-yl]amino]pyrazine-2-carbonitrile hydrochloride | K | (DMSO-d$_6$) δ 12.54 (br s, 1H), 10.76 (br s, 1H), 8.98 (s, 2H), 8.58 (s, 1H), 7.57 (s, 1H), 6.73-6.70 (m, 3H), 4.75-4.71 (m, 1H), 3.83 (s, 3H), 3.21 (s, 2H), 3.07 (s, 2H), 2.10 (s, 2H) and 1.84 (s, 2H). | 3.77 | 392 | B |
| 58 | 5-[[5-[5-fluoro-2-methoxy-4-(4-piperidyl)phenyl]-1H-pyrazol-3-yl]amino]pyrazine-2-carbonitrile hydrochloride | J | (DMSO-d$_6$) δ 10.82 (s, 1H), 9.21 (d, 1H), 8.99-8.96 (m, 1H), 8.67 (d, 1H), 8.54 (s, 1H), 7.57 (d, 1H), 7.01 (s, 1H), 6.97 (d, 1H), 3.92 (s, 3H), 3.36 (d, 2H), 3.18-3.12 (m, 1H), 3.07-2.99 (m, 2H), 2.09-1.99 (m, 2H) and 1.92 (d, 2H). | 3.83 | 394 | B |
| 59 | 5-[[5-[4-[(isopropylamino)methyl]-2-methoxy-phenyl]-1H-pyrazol-3-yl]amino]pyrazine-2-carbonitrile hydrochloride | F | (DMSO-d$_6$) δ 10.83 (s, 1H), 9.45 (s, 2H), 8.67 (d, 1H), 8.54 (s, 1H), 7.74 (d, 1H), 7.62 (d, 1H), 7.25 (dd, 1H), 7.00 (s, 1H), 4.15 (t, 2H), 3.96 (s, 3H), 3.31-3.24 (m, 1H) and 1.34 (d, 6H). | 3.66 | 364 | B |
| 60 | 5-[[5-[4-(1-ethyl-4-piperidyl)-2-methoxy-phenyl]-1H-pyrazol-3-yl]amino]pyrazine-2-carbonitrile hydrochloride | H | (DMSO-d$_6$) δ 10.79 (s, 1H), 10.67 (s, 1H), 8.67 (s, 1H), 8.55 (s, 1H), 7.66 (d, 1H), 7.03 (s, 1H), 6.92 (s, 1H), 3.92 (s, 3H), 3.55 (d, 2H), 3.13-3.10 (m, 2H), 3.03-2.95 (m, 2H), 2.91-2.85 (m, 1H), 2.18-2.09 (m, 2H), 2.02 (d, 2H) and 1.30 (t, 3H). | 3.70 | 404 | B |
| 61 | 5-[[5-[4-(1-isopropyl-4-piperidyl)-2-methoxy-phenyl]-1H-pyrazol-3-yl]amino]pyrazine-2-carbonitrile hydrochloride | J | (DMSO-d$_6$) δ 10.80 (s, 1H), 10.65 (s, 1H), 8.67 (d, 1H), 8.55 (s, 1H), 7.66 (d, 1H), 7.031 (s, 1H), 6.93 (d, 2H), 3.92 (s, 3H), 3.45-3.42 (m, 3H), 3.10-3.02 (m, 2H), 2.93-2.87 (m, 1H), 2.34-2.22 (m, 2H), 2.02-1.99 (m, 2H) and 1.33-1.31 (m, 6H). | 3.74 | 418 | B |
| 62 | 2-[4-[4-[3-[(5-cyanopyrazin-2-yl)amino]-1H-pyrazol-5-yl]-3-methoxy-phenyl]-1-piperidyl]acetamide hydrochloride | J | (DMSO-d$_6$) δ 12.61 (br s, 1H), 10.79 (s, 1H), 9.83 (s, 1H), 8.67 (s, 1H), 8.55 (s, 1H), 8.10 (s, 1H), 7.73 (s, 1H), 7.66 (d, 1H), 7.01 (s, 1H), 6.92 (s, 2H), 3.95 (s, 2H), 3.93 (s, 3H), 3.59-3.57 (m, 2H), 3.25-3.17 (m, 2H), 2.89-2.83 (m, 1H), 2.15 (t, 2H) and 2.09-2.03 (m, 2H). | 3.65 (d, | 433 | B |
| 63 | 5-[[5-[2-methoxy-4-[[methyl(tetrahydropyran-4-yl)amino]methyl]phenyl]-1H-pyrazol-3-yl]amino]pyrazine-2-carbonitrile hydrochloride | F | (DMSO-d$_6$) δ 12.68 (s, 1H), 11.09 (s, 1H), 10.82 (s, 1H), 8.67 (d, 1H), 8.54 (s, 1H), 7.76 (d, 1H), 7.64 (s, 1H), 7.26 (d, 1H), 7.02 (s, 1H), 4.52-4.48 (m, 1H), 4.20-4.15 (m, 1H), 4.00 (d, 2H), 3.97 (s, 3H), 3.50-3.43 (m, 1H), 3.32 (q, 2H), 2.58 (d, 3H), 2.17 (d, 1H), 2.08 (d, 1H) and 1.91-1.81 (m, 2H). | 3.54 | 420 | B |

TABLE 2-continued

| Ex. No. | Name | Synthetic Method | $^1$H NMR | LC (RT) | MS(MH$^+$) | LCMS Method |
|---|---|---|---|---|---|---|
| 64 | 5-[[5-[4-(4-fluoro-1-methyl-4-piperidyl)-2-methoxy-phenyl]-1H-pyrazol-3-yl]amino]pyrazine-2-carbonitrile hydrochloride | L | (DMSO-d$_6$) δ 11.13 (br s, 1H), 10.81 (s, 1H), 8.68 (s, 1H), 8.54 (s, 1H), 7.76 (d, 1H), 7.17 (s, 1H), 7.06 (d, 1H), 6.99 (s, 1H), 3.95 (s, 3H), 3.49 (d, 2H), 3.29-3.26 (m, 2H), 2.85 (d, 3H), 2.68-2.59 (m, 2H) and 2.28-2.22 (m, 2H). | 3.79 | 408 | B |
| 65 | 5-[[5-[2-methoxy-4-(1-methylazetidin-3-yl)phenyl]-1H-pyrazol-3-yl]amino]pyrazine-2-carbonitrile hydrochloride | H | (DMSO-d$_6$) δ 12.86 (br s, 1H), 10.79 (br s, 2H), 8.67 (s, 1H), 8.53 (s, 1H), 7.69 (d, 1H), 7.17 (s, 1H), 7.11 (d, 1H), 6.97 (s, 1H), 4.47-4.01 (m, 5H), 3.91 (s, 3H), 2.94 (s, 1H) and 2.87 (d, 2H). | 3.53 | 362 | B |
| 66 | 5-[[5-[4-(3-fluoro-1-methyl-azetidin-3-yl)-2-methoxy-phenyl]-1H-pyrazol-3-yl]amino]pyrazine-2-carbonitrile hydrochloride | L | (DMSO-d$_6$) δ 11.53 (br s, 1H), 10.83 (s, 1H), 8.68 (s, 1H), 8.54 (s, 1H), 7.82 (t, 1H), 7.45 (s, 1H), 7.29-7.23 (m, 2H), 7.03 (s, 1H), 4.92-4.83 (m, 1H), 4.75-4.68 (m, 2H), 4.63-4.55 (m, 1H), 3.99 (s, 3H) and 2.95 (d, 3H). | 3.64 | 380 | B |
| 67 | 5-[[5-[5-chloro-2-methoxy-4-(1-methyl-4-piperidyl)phenyl]-1H-pyrazol-3-yl]amino]pyrazine-2-carbonitrile hydrochloride | H | (DMSO-d$_6$) δ 11.00 (s, 1H), 10.83 (s, 1H), 8.68 (s, 1H), 8.53 (s, 1H), 7.80 (s, 1H), 7.03 (s, 2H), 3.94 (s, 3H), 3.50 (d, 2H), 3.25-3.11 (m, 3H), 2.77 (d, 3H), 2.21-2.12 (m, 2H) and 1.97 (d, 2H). | 3.97 | 424 | B |
| 68 | 5-[[5-[5-chloro-2-methoxy-4-(4-piperidyl)phenyl]-1H-pyrazol-3-yl]amino]pyrazine-2-carbonitrile hydrochloride | H | (DMSO-d$_6$) δ 10.85 (s, 1H), 9.18 (s, 1H), 9.09 (d, 1H), 8.68 (d, 1H), 8.53 (s, 1H), 7.79 (s, 1H), 7.02 (s, 2H), 3.94 (s, 3H), 3.43-3.36 (m, 2H), 3.30-3.25 (m, 1H), 3.11-3.02 (m, 2H), 2.09-1.99 (m, 2H) and 1.94-1.91 (m, 2H). | 4.04 | 410 | B |
| 69 | 5-[[5-[3-chloro-2-methoxy-4-(1-methyl-4-piperidyl)phenyl]-1H-pyrazol-3-yl]amino]pyrazine-2-carbonitrile hydrochloride | H | (DMSO-d$_6$) δ 10.88 (s, 1H), 10.66 (s, 1H), 8.69 (s, 1H), 8.54 (s, 1H), 7.74 (d, 1H), 7.21 (d, 1H), 7.04 (s, 1H), 3.70 (s, 3H), 3.51 (d, 2H), 3.30-3.24 (m, 1H), 3.20-3.12 (m, 2H), 2.77 (d, 3H) and 2.09-1.96 (m, 4H). | 3.83 | 424 | B |
| 70 | 5-[[5-[3-chloro-2-methoxy-4-(4-piperidyl)phenyl]-1H-pyrazol-3-yl]amino]pyrazine-2-carbonitrile hydrochloride | H | (DMSO-d$_6$) δ 10.90 (s, 1H), 9.14 (s, 2H), 8.69 (d, 1H), 8.54 (s, 1H), 7.74 (d, 1H), 7.21 (d, 1H), 7.04 (s, 1H), 3.69 (s, 3H), 3.39-3.30 (m, 3H), 3.11-3.02 (m, 2H) and 2.01-1.91 (m, 4H). | 3.90 | 410 | B |
| 71 | methyl 5-[[5-[2-methoxy-4-(4-piperidyl)phenyl]-1H-pyrazol-3-yl]amino]pyrazine-2-carboxylate hydrochloride | J | (DMSO-d$_6$) δ 9.31 (s, 1H), 9.04 (br s, 1H), 9.00 (s, 1H), 8.81 (br s, 1H), 7.96 (d, 1H), 6.97 (s, 1H), 6.91 (d, 1H), 5.60 (s, 1H), 3.93 (s, 3H), 3.89 (s, 3H), 3.38 (d, 2H), 3.00 (d, 2H), 2.94-2.85 (br m, 1H), 2.03-1.97 (m, 2H) and 1.89-1.83 (m, 2H). | 3.90 | 409 | B |
| 72 | 5-[[5-[2-methoxy-4-[(tetrahydrofuran-3-ylamino)methyl]phenyl]-1H-pyrazol-3-yl]amino]pyrazine-2-carbonitrile hydrochloride | F | (DMSO-d$_6$) δ 10.83 (s, 1H), 9.79 (s, 2H), 8.67 (d, 1H), 8.54 (s, 1H), 7.74 (d, 1H), 7.57 (d, 1H), 7.24 (dd, 1H), 7.01 (s, 1H), 4.23-4.15 (m, 2H), 4.01-3.91 (m, 5H), 3.84-3.81 (m, 2H), 3.70-3.65 (m, 1H) and 2.25-2.13 (m, 2H). | | | |
| 73 | 5-[[5-[2-methoxy-4-[[methyl(tetrahydrofuran-3-yl)amino]methyl]phenyl]-1H-pyrazol-3-yl]amino]pyrazine-2-carbonitrile hydrochloride | F | (DMSO-d$_6$) δ 11.50 (br s, 1H), 10.83 (s, 1H), 8.67 (d, 1H), 8.54 (s, 1H), 7.76 (d, 1H), 7.63 (s, 1H), 7.26 (d, 1H), 7.02 (s, 1H), 4.48-4.15 (m, 6H), 4.01-3.99 (m, 2H), 3.96 (s, 3H), 3.78-3.73 (m, 1H), 3.66-3.60 (m, 1H), 2.56 (d, 3H), 2.44-2.30 (m, 1H) and 2.25-2.21 (m, 1H). | 3.57 | 406 | B |
| 74 | 5-[[5-[2-methoxy-4-(tetrahydropyran-4-ylmethylamino)phenyl]-1H-pyrazol-3-yl]amino]pyrazine-2-carbonitrile hydrochloride | I | (DMSO-d$_6$) δ 10.86 (s, 1H), 8.68 (s, 1H), 8.55 (s, 1H), 7.50 (d, 1H), 6.80 (s, 1H), 6.59 (s, 1H), 6.52 (d, 1H), 3.86 (br s, 5H), 3.28 (t, 2H), 3.05 (d, 2H), 1.87-1.84 (m, 1H), 1.71 (d, 2H) and 1.27-1.23 (m, 2H). | 4.67 | 406 | B |
| 75 | 5-[[5-[2-methoxy-4-(tetrahydropyran-4-ylmethoxy)phenyl]-1H-pyrazol-3-yl]amino]pyrazine-2-carbonitrile | K | (DMSO-d$_6$) δ 12.65 (br s, 1H), 10.75 (s, 1H), 8.67 (d, 1H), 8.53 (s, 1H), 7.57 (d, 1H), 6.85 (s, 1H), 6.68 (d, 1H), 6.64 (dd, 1H), 3.91-3.88 (m, 7H), 3.37-3.31 (m, 2H), 2.03-2.01 (m, 1H), 1.71 (d, 2H) and 1.40-1.30 (m, 2H). | 4.97 | 407 | B |
| 76 | 5-[[5-[4-(4-fluoro-4-piperidyl)-2-methoxy-phenyl]-1H-pyrazol-3-yl]amino]pyrazine-2-carbonitrile hydrochloride | L | (DMSO-d$_6$) δ 10.82 (s, 1H), 9.29 (br s, 1H), 9.19 (br s, 1H), 8.68 (s, 1H), 8.54 (s, 1H), 7.76 (d, 1H), 7.15 (s, 1H), 7.06 (d, 1H), 6.99 (s, 1H), 3.95 (s, 3H), 3.38-3.36 (m, 2H), 3.19-3.10 (m, 2H), 2.60-2.57 (m, 1H), 2.50-2.45 (m, 1H) and 2.19-2.13 (m, 2H). | 3.85 | 394 | B |
| 77 | 5-[[5-[4-(3-fluoroazetidin-3-yl)-2-methoxy-phenyl]-1H-pyrazol-3-yl]amino]pyrazine-2-carbonitrile hydrochloride | L | (DMSO-d$_6$) δ 10.85 (s, 1H), 10.05 (br s, 1H), 8.68 (s, 1H), 8.54 (s, 1H), 7.81-7.80 (d, 1H), 7.45-7.42 (d, 1H), 7.33-7.20 (m, 2H), 7.03 (s, 1H), 4.65-4.52 (m, 4H) and 4.00 (s, 3H). | 3.69 | 366 | B |
| 78 | 5-[[5-[2-methoxy-4-[(3R)-1-methylpyrrolidin-3-yl]oxy-phenyl]-1H-pyrazol-3-yl]amino]pyrazine-2-carbonitrile hydrochloride | K | (DMSO-d$_6$) δ 11.51 (s, 1H), 11.05 (s, 1H), 10.81 (s, 1H), 8.67 (d, 1H), 8.55 (s, 1H), 7.63 (d, 1H), 6.87 (s, 1H), 6.72 (s, 1H), 6.68 (d, 1H), 5.25 (d, 1H), 3.90 (s, 3H), 3.42 (s, 1H), 3.22-3.19 (m, 2H), 2.88-2.85 (d, 3H), 2.33-2.24 (m, 2H) and 2.12 (m, 1H). | 3.69 | 392 | B |

TABLE 2-continued

| Ex. No. | Name | Synthetic Method | $^1$H NMR | LC (RT) | MS(MH$^+$) | LCMS Method |
|---|---|---|---|---|---|---|
| 79 | 5-[[5-(2-methoxy-4-morpholino-phenyl)-1H-pyrazol-3-yl]amino]pyrazine-2-carbonitrile | I | (DMSO-d$_6$) δ 12.40 (s, 1H), 10.69 (s, 1H), 8.66 (d, 1H), 8.55 (s, 1H), 7.51 (d, 1H), 6.82 (d, 1H), 6.62 (d, 1H), 6.59 (d, 1H), 3.90 (s, 3H), 3.77-3.74 (m, 4H) and 3.22-3.17 (m, 4H). | 4.66 | 378 | B |
| 80 | 5-[[5-[4-(4-ethylpiperazin-1-yl)-2-methoxy-phenyl]-1H-pyrazol-3-yl]amino]pyrazine-2-carbonitrile hydrochloride | I | (DMSO-d$_6$) δ 12.49 (s, 1H), 10.98 (s, 1H), 10.75 (s, 1H), 8.67 (d, 1H), 8.55 (s, 1H), 7.57 (d, 1H), 6.84 (s, 1H), 6.69 (d, 1H), 6.66 (d, 1H), 3.98 (d, 2H), 3.91 (s, 3H), 3.56 (d, 2H), 3.26-3.14 (m, 4H), 3.08 (q, 2H) and 1.30 (t, 3H). | 3.56 | 405 | B |
| 81 | 5-[[5-[4-(4-isopropylpiperazin-1-yl)-2-methoxy-phenyl]-1H-pyrazol-3-yl]amino]pyrazine-2-carbonitrile hydrochloride | I | (DMSO-d$_6$) δ 11.03 (s, 1H), 10.78 (s, 1H), 8.67 (d, 1H), 8.55 (s, 1H), 7.56 (d, 1H), 6.84 (s, 1H), 6.69 (d, 1H), 6.66 (d, 1H), 3.98 (d, 2H), 3.91 (s, 3H), 3.55 (d, 1H), 3.49 (d, 2H), 3.30 (t, 2H), 3.12 (q, 2H) and 1.33 (d, 6H). | 3.66 | 419 | B |
| 82 | 5-[[5-[2-methoxy-4-[(3R)-3-methylpiperazin-1-yl]phenyl]-1H-pyrazol-3-yl]amino]pyrazine-2-carbonitrile hydrochloride | I | (DMSO-d$_6$) δ 10.83 (s, 1H), 9.71 (s, 1H), 9.50 (s, 1H), 8.67 (s, 1H), 8.56 (s, 1H), 7.54 (s, 1H), 6.84 (s, 1H), 6.69 (s, 1H), 6.65 (s, 1H), 3.90 (s, 5H), 3.33 (s, 2H), 3.16-3.10 (m, 2H), 2.92-2.87 (m, 1H) and 1.34 (d, 3H). | 3.72 | 391 | B |
| 83 | 5-[[5-[4-(4-ethyl-1,4-diazepan-1-yl)-2-methoxy-phenyl]-1H-pyrazol-3-yl]amino]pyrazine-2-carbonitrile hydrochloride | I | (DMSO-d$_6$) δ 12.44 (s, 1H), 10.81 (s, 1H), 10.75 (s, 1H), 8.67 (d, 1H), 8.56 (s, 1H), 7.51 (d, 1H), 6.78 (s, 1H), 6.46 (dd, 1H), 6.41 (d, 1H), 3.98 (d, 2H), 3.91 (s, 3H), 3.83-3.77 (m, 1H), 3.57-3.52 (m, 4H), 3.19-3.10 (m, 2H), 3.05-3.01 (m, 1H), 2.42-2.34 (m, 1H), 2.22-2.17 (m, 1H) and 1.28 (t, 3H). | 3.85 | 419 | B |
| 84 | 5-[[5-[4-(4-isopropyl-1,4-diazepan-1-yl)-2-methoxy-phenyl]-1H-pyrazol-3-yl]amino]pyrazine-2-carbonitrile hydrochloride | I | (DMSO-d$_6$) δ 12.50 (s, 1H), 10.74 (s, 1H), 10.55 (s, 1H), 8.67 (d, 1H), 8.56 (s, 1H), 7.51 (d, 1H), 6.78 (s, 1H), 6.46 (dd, 1H), 6.41 (d, 1H), 3.98-3.82 (m, 5H), 3.58-3.55 (m, 3H), 3.45 (d, 2H), 3.16 (q, 1H), 2.98 (q, 1H), 2.41-2.38 (m, 1H), 2.23-2.19 (m, 1H) and 1.27 (d, 6H). | 3.90 | 433 | B |
| 85 | 5-[[5-[4-(1-ethyl-4-fluoro-4-piperidyl)-2-methoxy-phenyl]-1H-pyrazol-3-yl]amino]pyrazine-2-carbonitrile hydrochloride | L | (DMSO-d$_6$) δ 11.22 (s, 1H), 10.82 (s, 1H), 8.69 (s, 1H), 8.54 (s, 1H), 7.76 (d, 1H), 7.18 (s, 1H), 7.07 (d, 1H), 6.99 (s, 1H), 3.95 (s, 3H), 3.57-3.54 (m, 2H), 3.22-3.15 (m, 4H), 2.79-2.65 (m, 2H), 2.26-2.21 (m, 2H) and 1.33 (t, 3H). | 3.91 | 422 | B |
| 86 | 5-[[5-[4-(4-fluoro-1-isopropyl-4-piperidyl)-2-methoxy-phenyl]-1H-pyrazol-3-yl]amino]pyrazine-2-carbonitrile hydrochloride | L | (DMSO-d$_6$) δ 11.22 (br s, 1H), 10.81 (s, 1H), 8.68 (s, 1H), 8.54 (s, 1H), 7.76 (d, 1H), 7.21 (s, 1H), 7.09 (d, 1H), 6.98 (s, 1H), 3.95 (s, 3H), 3.57 (m, 1H), 3.47 (d, 2H), 3.24-3.16 (m, 2H), 2.96-2.89 (m, 1H), 2.85-2.79 (m, 1H), 2.26-2.20 (m, 2H) and 1.36 (d, 6H). | 4.05 | 436 | B |
| 87 | 5-[[5-[4-(1-ethyl-3-fluoro-4-piperidyl)-2-methoxy-phenyl]-1H-pyrazol-3-yl]amino]pyrazine-2-carbonitrile hydrochloride | M | (DMSO-d$_6$) δ 11.49 (br s, 1H), 10.82 (s, 1H), 8.68 (d, 1H), 8.54 (s, 1H), 7.69 (d, 1H), 7.08 (s, 1H), 6.99 (d, 1H), 6.95 (s, 1H), 5.38-5.25 (m, 1H), 3.92 (s, 3H), 3.86 (d, 1H), 3.55 (d, 1H), 3.24-3.21 (m, 2H), 3.15-3.03 (m, 3H), 2.29-2.26 (m, 1H), 2.11-2.08 (m, 1H) and 1.34 (t, 3H). | 3.78 | 422 | B |
| 88 | 5-[[5-[4-(3-fluoro-1-isopropyl-4-piperidyl)-2-methoxy-phenyl]-1H-pyrazol-3-yl]amino]pyrazine-2-carbonitrile hydrochloride | M | (DMSO-d$_6$) δ 11.45 (br s, 1H), 10.80 (s, 1H), 8.68 (s, 1H), 8.55 (s, 1H), 7.69 (d, 1H), 7.10 (s, 1H), 6.99 (d, 1H), 6.95 (s, 1H), 5.54-5.36 (m, 1H), 3.92 (s, 3H), 3.75-3.72 (m, 1H), 3.62-3.61 (m, 1H), 3.44-3.41 (m, 1H), 3.17-3.11 (m, 3H), 2.42-2.34 (m, 2H), 2.10 (m, 1H) and 1.35 (d, 6H). | 3.82 | 436 | B |
| 89 | 5-[[5-[2-methoxy-4-[1-(2-methoxyethyl)-4-piperidyl]phenyl]-1H-pyrazol-3-yl]amino]pyrazine-2-carbonitrile hydrochloride | H | (DMSO-d$_6$) δ 10.85 (s, 1H), 10.80 (s, 1H), 8.67 (s, 1H), 8.56 (s, 1H), 7.66 (s, 1H), 7.02 (s, 1H), 6.92 (d, 2H), 3.91 (s, 3H), 3.78 (br s, 2H), 3.58 (s, 2H), 3.32 (br s, 5H), 3.10 (d, 2H), 2.85 (br s, 1H), 2.18-2.12 (m, 2H) and 1.99 (d, 2H). | 3.85 | 434 | B |
| 90 | 5-[[5-[4-(ethylaminomethyl)-2-methoxy-phenyl]-1H-pyrazol-3-yl]amino]pyrazine-2-carbonitrile hydrochloride | F | (DMSO-d$_6$) δ 10.83 (s, 1H), 9.55 (s, 1H), 8.67 (s, 1H), 8.54 (s, 1H), 7.73 (d, 1H), 7.56 (s, 1H), 7.21 (d, 1H), 6.99 (s, 1H), 4.13 (s, 2H), 3.95 (s, 3H), 3.01-2.95 (m, 2H) and 1.27 (t, 3H). | 3.67 | 350 | B |
| 91 | 5-[[5-[4-[(cyclopropylamino)methyl]-2-methoxy-phenyl]-1H-pyrazol-3-yl]amino]pyrazine-2-carbonitrile hydrochloride | F | (DMSO-d$_6$) δ 10.85 (s, 1H), 9.56 (s, 1H), 8.67 (s, 1H), 8.54 (s, 1H), 7.72 (d, 1H), 7.55 (s, 1H), 7.22 (d, 1H), 7.01 (s, 1H), 4.23 (s, 2H), 3.95 (s, 3H), 2.65 (br s, 1H), 0.96 (d, 2H) and 0.73 (d, 2H). | 3.73 | 362 | B |
| 92 | 5-[[5-[4-[(3R)-3,4-dimethylpiperazin-1-yl]-2-methoxy-phenyl]-1H-pyrazol-3-yl]amino]pyrazine-2-carbonitrile hydrochloride | I | (DMSO-d$_6$) δ 11.44 (s, 1H), 10.89 (s, 1H), 9.69 (s, 1H), 8.67 (s, 1H), 8.56 (s, 1H), 7.57 (s, 1H), 6.84 (s, 1H), 6.71-6.68 (m, 2H), 4.03-3.99 (m, 2H), 3.91 (s, 3H), 3.31-3.00 (m, 5H), 2.79 (s, 3H) and 1.21 (d, 3H). | 3.69 | 405 | B |

TABLE 2-continued

| Ex. No. | Name | Synthetic Method | ¹H NMR | LC (RT) | MS(MH⁺) | LCMS Method |
|---|---|---|---|---|---|---|
| 93 | 5-[[5-[4-[(3R)-4-ethyl-3-methyl-piperazin-1-yl]-2-methoxy-phenyl]-1H-pyrazol-3-yl]amino]pyrazine-2-carbonitrile hydrochloride | I | (DMSO-d$_6$) δ 11.18 (s, 1H), 10.78 (s, 1H), 8.67 (s, 1H), 8.56 (s, 1H), 7.54 (s, 1H), 6.84 (s, 1H), 6.69 (s, 1H), 6.66 (s, 1H), 4.01-3.94 (m, 2H), 3.91 (s, 3H), 3.76 (s, 1H), 3.55-3.52 (m, 2H), 3.39-3.26 (m, 2H), 3.15-3.04 (m, 3H), 1.41 (d, 3H) and 1.34-1.23 (m, 3H). | 3.69 | 419 | B |
| 94 | 5-[[5-[4-[(3S)-1-isopropylpyrrolidin-3-yl]oxy-2-methoxy-phenyl]-1H-pyrazol-3-yl]amino]pyrazine-2-carbonitrile hydrochloride | K | (DMSO-d$_6$) δ 11.89 (s, 1H), 11.32 (s, 1H), 10.81 (s, 1H), 8.66 (s, 1H), 8.56 (s, 1H), 7.63 (d, 1H), 6.87 (s, 1H), 6.74-6.67 (m, 2H), 5.24 (s, 1H), 3.90 (s, 3H), 3.60-3.45 (m, 4H), 3.23-3.16 (m, 1H), 2.21-2.12 (m, 2H) and 1.32-1.30 (d, 6H). | 3.81 | 420 | B |
| 95 | 5-[[5-[4-[(3R)-1-isopropylpyrrolidin-3-yl]oxy-2-methoxy-phenyl]-1H-pyrazol-3-yl]amino]pyrazine-2-carbonitrile hydrochloride | K | (DMSO-d$_6$) δ 11.70 (s, 1H), 11.04 (s, 1H), 10.83 (s, 1H), 8.67 (s, 1H), 8.55 (s, 1H), 7.63 (d, 1H), 6.87 (s, 1H), 6.73 (s, 1H), 6.70 (s, 1H), 5.23 (s, 1H), 3.90 (s, 3H), 3.55-3.23 (m, 5H), 2.21-1.98 (m, 2H) and 1.30 (d, 6H). | 3.80 | 420 | B |
| 96 | 5-[[5-[4-[(3R,S),4(R,S))-3-fluoro-1-methyl-4-piperidyl]-2-methoxy-phenyl]-1H-pyrazol-3-yl]amino]pyrazine-2-carbonitrile hydrochloride | M | (DMSO-d$_6$) δ 11.55 (br s, 1H), 10.80 (s, 1H), 8.68 (d, 1H), 8.55 (s, 1H), 7.69 (d, 1H), 7.08 (d, 1H), 6.98 (d, 1H), 6.95 (s, 1H), 5.31-5.18 (m, 1H), 3.92 (s, 3H), 3.82 (d, 1H), 3.49 (s, 1H), 3.21-2.94 (m, 3H), 2.87 (d, 3H), 2.23-2.20 (m, 1H) and 2.11-2.08 (m, 1H). | 3.74 | 408 | B |
| 97 | 5-[[5-[4-(3,3-difluoro-1-methyl-4-piperidyl)-2-methoxy-phenyl]-1H-pyrazol-3-yl]amino]pyrazine-2-carbonitrile hydrochloride | N | (DMSO-d$_6$) δ 11.28 (br s, 1H), 10.82 (s, 1H), 8.67 (d, 1H), 8.54 (s, 1H), 7.71 (d, 1H), 7.01 (s, 1H), 6.99 (d, 2H), 4.08 (t, 1H), 3.92 (s, 3H), 3.77-3.69 (m, 1H), 3.54-3.49 (m, 2H), 3.25 (m, 1H), 2.89 (d, 3H), 2.45-2.34 (m, 1H) and 2.21-2.19 (m, 1H). | 3.79 | 426 | B |
| 98 | 5-[[5-[4-(1-ethyl-3,3-difluoro-4-piperidyl)-2-methoxy-phenyl]-1H-pyrazol-3-yl]amino]pyrazine-2-carbonitrile hydrochloride | N | (DMSO-d$_6$) δ 11.09 (br s, 1H), 10.84 (s, 1H), 8.68 (s, 1H), 8.54 (s, 1H), 7.71 (d, 1H), 7.00 (s, 1H), 6.99 (d, 2H), 4.06 (t, 1H), 3.92 (s, 3H), 3.71-3.43 (m, 4H), 3.27-3.25 (m, 2H), 2.44-2.38 (m, 1H), 2.22-2.18 (m, 1H) and 1.32 (t, 3H). | 3.84 | 440 | B |
| 99 | 5-[[5-[4-[1-(2-hydroxyethyl)-4-piperidyl]-2-methoxy-phenyl]-1H-pyrazol-3-yl]amino]pyrazine-2-carbonitrile hydrochloride | H | (DMSO-d$_6$) δ 10.82 (s, 1H), 10.32 (s, 1H), 8.67 (s, 1H), 8.55 (s, 1H), 7.65 (d, 1H), 7.02 (s, 1H), 6.93 (s, 1H), 6.91 (s, 1H), 3.92 (s, 3H), 3.83-3.81 (m, 2H), 3.64-3.61 (m, 2H), 3.19-3.06 (m, 4H), 2.90-2.84 (m, 1H), 2.19-2.10 (m, 2H) and 2.02-1.99 (m, 2H). | 3.70 | 420 | B |
| 100 | 5-[[5-[4-[[isopropyl(methyl)amino]methyl]-2-methoxy-phenyl]-1H-pyrazol-3-yl]amino]pyrazine-2-carbonitrile hydrochloride | F | (DMSO-d$_6$) δ 10.84 (s, 1H), 10.72 (s, 1H), 8.68 (d, 1H), 8.55 (s, 1H), 7.73 (s, 1H), 7.66 (s, 1H), 7.28 (d, 1H), 7.01 (s, 1H), 4.36 (m, 1H), 4.21-4.19 (m, 1H), 3.95 (s, 3H), 3.56 (s, 1H), 2.54 (d, 3H) and 1.34 (d, 6H). | 3.64 | 378 | B |
| 101 | 5-[[5-[2-methoxy-4-(pyrrolidin-1-ylmethyl)phenyl]-1H-pyrazol-3-yl]amino]pyrazine-2-carbonitrile hydrochloride | F | (DMSO-d$_6$) δ 11.26 (s, 1H), 10.84 (s, 1H), 8.68 (d, 1H), 8.53 (s, 1H), 7.74 (d, 1H), 7.58 (s, 1H), 7.23 (d, 1H), 7.01 (s, 1H), 4.36 (d, 2H), 3.96 (s, 3H), 3.36-3.34 (m, 2H), 3.07-3.01 (m, 2H), 2.06-1.95 (m, 2H) and 1.92-1.89 (m, 2H). | 3.63 | 376 | B |
| 102 | 5-[[5-[2-methoxy-4-(morpholinomethyl)phenyl]-1H-pyrazol-3-yl]amino]pyrazine-2-carbonitrile hydrochloride | F | (DMSO-d$_6$) δ 11.79 (s, 1H), 10.84 (s, 1H), 8.68 (s, 1H), 8.54 (s, 1H), 7.75 (d, 1H), 7.65 (s, 1H), 7.23 (d, 1H), 7.01 (s, 1H), 4.35 (d, 2H), 3.97 (s, 3H), 3.92-3.85 (m, 4H), 3.23 (d, 2H) and 3.11-3.08 (m, 2H). | 3.54 | 392 | B |
| 103 | 5-[[5-[2-methoxy-4-[[(2R)-1-methylpyrrolidin-2-yl]methoxy]phenyl]-1H-pyrazol-3-yl]amino]pyrazine-2-carbonitrile hydrochloride | K | (DMSO-d$_6$) δ 12.68 (s, 1H), 10.78 (br s, 2H), 8.67 (s, 1H), 8.54 (s, 1H), 7.64 (d, 1H), 6.89 (s, 1H), 6.79 (s, 1H), 6.71 (dd, 1H), 4.39 (dd, 1H), 4.27 (dd, 1H), 3.86 (s, 3H), 3.85-3.79 (m, 1H), 3.60-3.59 (m, 1H), 3.14-3.10 (m, 1H), 2.96 (s, 3H), 2.33-2.23 (m, 1H), 2.08-1.91 (m, 2H) and 1.88-1.81 (m, 1H). | 3.67 | 406 | B |
| 104 | 5-[[5-[2-methoxy-4-[[(2S)-1-methylpyrrolidin-2-yl]methoxy]phenyl]-1H-pyrazol-3-yl]amino]pyrazine-2-carbonitrile hydrochloride | K | (DMSO-d$_6$) δ 10.91 (s, 1H), 10.80 (s, 1H), 8.67 (d, 1H), 8.54 (s, 1H), 7.64 (d, 1H), 6.88 (s, 1H), 6.79 (d, 1H), 6.71 (dd, 1H), 4.46-4.38 (m, 2H), 3.91 (s, 3H), 3.83-3.79 (m, 1H), 3.60-3.57 (m, 1H), 3.14-3.09 (m, 1H), 2.95 (s, 3H), 2.30-2.25 (m, 1H), 2.08-1.94 (m, 2H) and 1.87-1.81 (m, 1H). | 3.74 | 406 | B |
| 105 | 5-[[5-[2-methoxy-4-(oxazol-4-ylmethoxy)phenyl]-1H-pyrazol-3-yl]amino]pyrazine-2-carbonitrile | K | (DMSO-d$_6$) δ 12.49 (br s, 1H), 10.71 (s, 1H), 8.66 (s, 1H), 8.54 (s, 1H), 8.43 (s, 1H), 8.27 (s, 1H), 7.58 (d, 1H), 6.85 (s, 1H), 6.79 (s, 1H), 6.75 (d, 1H), 5.09 (s, 2H) and 3.90 (s, 3H). | 4.54 | 390 | B |
| 106 | 5-[[5-[4-[1-(2-fluoroethyl)-4-piperidyl]-2-methoxy-phenyl]-1H-pyrazol-3-yl]amino]pyrazine-2-carbonitrile hydrochloride | H | (DMSO-d$_6$) δ 11.14 (s, 1H), 10.83-10.81 (d, 1H), 8.68 (s, 1H), 8.54 (s, 1H), 7.67 (d, 1H), 7.02 (s, 1H), 6.93 (s, 1H), 6.91 (s, 1H), 4.96 (d, 2H), 3.92 (s, 3H), 3.60-3.49 (m, 4H), 3.17-3.15 (m, 2H), 2.88-2.84 (m, 1H) and 2.18-2.02 (m, 4H). | 3.78 | 422 | B |

TABLE 2-continued

| Ex. No. | Name | Synthetic Method | ¹H NMR | LC (RT) | MS(MH⁺) | LCMS Method |
|---|---|---|---|---|---|---|
| 107 | 5-[[5-[2-methoxy-4-[(1-methyl-4-piperidyl)methylamino]phenyl]-1H-pyrazol-3-yl]amino]pyrazine-2-carbonitrile hydrochloride | O | (DMSO-d₆) δ 10.83 (s, 1H), 10.56 (br s, 1H), 8.67 (d, 1H), 8.60 (s, 1H), 7.46 (d, 1H), 6.77 (s, 1H), 6.46 (s, 1H), 6.41 (d, 1H), 3.85 (s, 3H), 3.39 (d, 2H), 3.04 (d, 2H), 2.94-2.86 (m, 2H), 2.68 (dd, 3H), 1.98-1.94 (m, 3H) and 1.56-1.48 (m, 2H). | 3.75 | 419 | B |
| 108 | 5-[[5-[4-[(1-ethyl-4-piperidyl)methylamino]-2-methoxy-phenyl]-1H-pyrazol-3-yl]amino]pyrazine-2-carbonitrile hydrochloride | O | (DMSO-d₆) δ 12.49 (s, 1H), 10.85 (s, 1H), 10.46 (br s, 1H), 8.67 (s, 1H), 8.56 (s, 1H), 7.46 (d, 1H), 6.77 (s, 1H), 6.48 (s, 1H), 6.42 (d, 1H), 3.86 (s, 3H), 3.46 (d, 2H), 3.17-3.14 (m, 2H), 3.05-3.01 (m, 2H), 2.87-2.79 (m, 2H), 1.99-1.96 (m, 2H), 1.89-1.84 (m, 1H), 1.61-1.52 (m, 2H) and 1.26 (t, 3H). | 3.80 | 433 | B |
| 109 | 5-[[5-[4-[(1-isopropyl-4-piperidyl)methylamino]-2-methoxy-phenyl]-1H-pyrazol-3-yl]amino]pyrazine-2-carbonitrile hydrochloride | O | (DMSO-d₆) δ 12.59 (s, 1H), 10.89 (s, 1H), 10.38 (br s, 1H), 8.68 (s, 1H), 8.56 (s, 1H), 7.49 (d, 1H), 6.79 (s, 1H), 6.52 (s, 1H), 6.46 (d, 1H), 3.86 (s, 3H), 3.37-3.34 (m, 3H), 3.05 (d, 2H), 2.90-2.87 (m, 2H), 1.99-1.91 (m, 3H), 1.72-1.66 (m, 2H) and 1.27 (d, 6H). | 3.78 | 447 | B |
| 110 | 5-[[5-[2-methoxy-4-[(1-methyl-4-piperidyl)amino]phenyl]-1H-pyrazol-3-yl]amino]pyrazine-2-carbonitrile hydrochloride | O | (DMSO-d₆) δ 12.38 (s, 1H), 10.87 (s, 1H), 10.75 (s, 1H), 8.66 (s, 1H), 8.56 (s, 1H), 7.43 (d, 1H), 6.75 (s, 1H), 6.41 (s, 1H), 6.37 (d, 1H), 3.84 (s, 3H), 3.57 (t, 1H), 3.44 (d, 2H), 3.10-3.02 (m, 2H), 2.72 (d, 3H), 2.12 (d, 2H), 1.89 (d, 2H) and 1.83-1.77 (m, 2H). | 3.66 | 405 | B |
| 111 | 5-[[5-[4-[(1-ethyl-4-piperidyl)amino]-2-methoxy-phenyl]1H-pyrazol-3-yl]amino]pyrazine-2-carbonitrile hydrochloride | O | (DMSO-d₆) δ 12.56(s, 1H), 10.78 (s, 1H), 10.63 (s, 1H), 8.67 (s, 1H), 8.56 (s, 1H), 7.46 (d, 1H), 6.77 (s, 1H), 6.47 (s, 1H), 6.42 (d, 1H), 3.85 (s, 3H), 3.58 (t, 1H), 3.50 (d, 2H), 3.11-2.95 (m, 4H), 2.13 (d, 2H), 1.91-1.81 (m, 2H) and 1.29-1.26 (m, 3H). | 3.67 | 419 | B |
| 112 | 5-[[5-[4-[(1-isopropyl-4-piperidyl)amino]-2-methoxy-phenyl]1H-pyrazol-3-yl]amino]pyrazine-2-carbonitrile hydrochloride | O | (DMSO-d₆) δ 12.38 (s, 1H), 10.73 (s, 1H), 10.16 (s, 1H), 8.66 (s, 1H), 8.55 (s, 1H), 7.42 (d, 1H), 6.75 (s, 1H), 6.40 (s, 1H), 6.36 (d, 1H), 3.85 (s, 3H), 3.60 (d, 1H) 3.46-3.35 (m, 1H), 3.40-3.37 (m, 2H), 3.24 (m, 1H), 2.14-2.11 (m, 2H), 1.93-1.81 (m, 2H) and 1.29 (d, 6H). | 3.72 | 433 | B |
| 113 | 5-[[5-[2-methoxy-4-[(1-methyl-4-piperidyl)oxymethyl]phenyl]-1H-pyrazol-3-yl]amino]pyrazine-2-carbonitrile hydrochloride | K | (DMSO-d₆) δ 10.96 (br s, 1H), 10.86 (s, 1H), 8.67 (s, 1H), 8.55 (s, 1H), 7.68 (dd, 1H), 7.12-6.96 (m, 3H), 4.56 (d, 2H), 3.92 (d, 3H), 3.58-3.55 (m, 1H), 3.39 (d, 1H), 3.23 (d, 1H), 3.01 (d, 1H), 2.72-2.67 (m, 3H), 2.17 (d, 1H), 2.03 (br s, 2H) and 1.82-1.75 (m, 1H). | 3.94 | 420 | B |
| 114 | 5-[[5-[4-[(1-ethyl-4-piperidyl)oxymethyl]-2-methoxy-phenyl]-1H-pyrazol-3-yl]amino]pyrazine-2-carbonitrile hydrochloride | K | (DMSO-d₆) δ 10.81 (br s, 1H), 10.53(s, 1H), 8.68 (s, 1H), 8.54 (s, 1H), 7.67 (dd, 1H), 7.12 (d, 1H), 7.04 (dd, 1H), 6.96 (s, 1H), 4.57 (d, 2H), 3.92 (s, 3H), 3.62-3.57 (m, 1H), 3.46 (d, 1H), 3.30 (d, 1H), 3.12-3.02 (m, 3H), 2.89 (q, 1H), 2.18 (d, 1H), 2.04 (br s, 2H), 1.85-1.76 (m, 1H) and 1.27-1.22 (m, 3H). | 3.90 | 434 | B |
| 115 | 5-[[5-[4-[(1-isopropyl-4-piperidyl)oxymethyl]-2-methoxy-phenyl]-1H-pyrazol-3-yl]amino]pyrazine-2-carbonitrile hydrochloride | K | (DMSO-d₆) δ 10.81 (s, 1H), 10.46(d, 1H), 8.68(s, 1H), 8.54 (s, 1H), 7.67 (dd, 1H), 7.12 (d, 1H), 7.03 (dd, 1H), 6.96 (s, 1H), 4.57 (d, 2H), 3.92 (s, 3H), 3.61 (m, 1H), 3.43-3.34 (m, 2H), 3.22 (d, 1H), 3.07-2.93 (m, 2H), 2.19-2.04 (m, 3H), 1.91-1.88 (m, 1H) and 1.29-1.24 (m, 6H). | 3.95 | 448 | B |
| 116 | 5-[[5-(2-fluoro-6-methoxy-4-piperazin-1-yl-phenyl)-1H-pyrazol-3-yl]amino]pyrazine-2-carbonitrile hydrochloride | I | (DMSO-d₆) δ 12.52 (s, 1H), 10.82 (s, 1H), 9.50 (s, 1H), 8.59 (s, 1H), 8.49 (s, 1H), 6.78 (s, 1H), 6.58 (d, 1H), 6.51 (s, 1H), 3.88 (s, 3H), 3.55 (br s, 4H) and 3.19 (br s, 4H). | 3.73 | 395 | B |
| 117 | 5-[[5-[2-methoxy-4-[(2R)-4-methylmorpholin-2-yl]phenyl]-1H-pyrazol-3-yl]amino]pyrazine-2-carbonitrile hydrochloride | P | (DMSO-d₆) δ 11.44 (s, 1H), 10.81 (s, 1H), 8.67 (d, 1H), 8.53 (s, 1H), 7.73 (d, 1H), 7.13 (s, 1H), 7.05 (dd, 1H), 6.99 (s, 1H), 4.91 (d, 1H), 4.20 (dd, 1H), 4.06-4.02 (m, 1H), 3.94 (s, 3H), 3.67 (d, 1H), 3.45 (d, 1H), 3.16-3.11 (m, 2H) and 2.80 (d, 3H). | 3.69 | 392 | B |
| 118 | 5-[[5-[2-methoxy-4-[(2R)-4-ethylmorpholin-2-yl]phenyl]-1H-pyrazol-3-yl]amino]pyrazine-2-carbonitrile hydrochloride | P | (DMSO-d₆) δ 11.41 (s, 1H), 10.81 (s, 1H), 8.67 (d, 1H), 8.53 (s, 1H), 7.73 (d, 1H), 7.15 (s, 1H), 7.07 (d, 1H), 6.98 (s, 1H), 4.96 (d, 1H), 4.20 (dd, 1H), 4.09 (m, 1H), 3.94 (s, 3H), 3.68 (d, 1H), 3.50 (d, 1H), 3.19-3.05 (m, 4H) and 1.31 (t, 3H). | 3.69 | 406 | B |
| 119 | 5-[[5-[2-methoxy-4-[(2S)-4-methylmorpholin-2-yl]phenyl]-1H-pyrazol-3-yl]amino]pyrazine-2-carbonitrile hydrochloride | P | (DMSO-d₆) δ 11.57 (s, 1H), 10.81 (s, 1H), 8.67 (d, 1H), 8.53 (s, 1H), 7.73 (d, 1H), 7.13 (d, 1H), 7.05 (d, 1H), 6.98 (s, 1H), 4.20 (dd, 1H), 4.04 (t, 1H), 3.94 (s, 3H), 3.66 (d, 1H), 3.45 (d, 1H), 3.19-3.08 (m, 2H) and 2.80 (d, 3H). | 3.65 | 392 | B |

TABLE 2-continued

| Ex. No. | Name | Synthetic Method | ¹H NMR | LC (RT) | MS(MH⁺) | LCMS Method |
|---|---|---|---|---|---|---|
| 120 | 5-[[5-[2-methoxy-4-[(2S)-4-ethylmorpholin-2-yl]phenyl]-1H-pyrazol-3-yl]amino]pyrazine-2-carbonitrile hydrochloride | P | (DMSO-d₆) δ 10.93 (s, 1H), 10.79 (s, 1H), 8.67 (s, 1H), 8.53 (s, 1H), 7.72 (d, 1H), 7.18 (s, 1H), 7.10 (d, 1H), 6.98 (s, 1H), 5.04 (d, 1H), 4.22-4.12 (m, 2H), 3.95 (s, 3H), 3.62-3.47 (m, 5H), 3.25-3.08 (m, 3H) and 1.34 (d, 3H). | 3.68 | 406 | B |
| 121 | 5-[[5-(2,6-dimethoxy-4-piperazin-1-yl-phenyl)-1H-pyrazol-3-yl]amino]pyrazine-2-carbonitrile hydrochloride | I | (DMSO-d₆) δ 12.29 (s, 1H), 10.72 (s, 1H), 9.32 (s, 2H), 8.65 (s, 1H), 8.58 (s, 1H), 6.71 (s, 1H), 6.32 (s, 2H), 3.81 (s, 6H), 3.53-3.51 (m, 4H) and 3.22-3.17 (m, 4H). | 3.61 | 407 | B |
| 122 | 5-[[5-[2,6-dimethoxy-4-(4-methylpiperazin-1-yl)phenyl]-1H-pyrazol-3-yl]amino]pyrazine-2-carbonitrile hydrochloride | I | (DMSO-d₆) δ 12.28 (s, 1H), 11.25 (s, 1H), 10.75 (s, 1H), 8.65 (s, 1H), 8.58 (s, 1H), 6.71 (s, 1H), 6.33 (s, 2H), 4.02 (d, 2H), 3.82 (s, 6H), 3.49 (d, 2H), 3.25-3.09 (m, 4H) and 2.81 (d, 3H). | 3.57 | 421 | B |
| 123 | 5-[[5-[4-[[(3R)-3-fluoropyrrolidin-1-yl]methyl]-2-methoxy-phenyl]-1H-pyrazol-3-yl]amino]pyrazine-2-carbonitrile hydrochloride | Q | (DMSO-d₆) δ 11.85 (s, 1H), 11.51 (s, 1H), 10.84 (s, 1H), 8.68 (s, 1H), 8.54 (s, 1H), 7.75 (t, 1H), 7.59 (d, 1H), 7.27 (dd, 1H), 7.02 (s, 1H), 5.53-5.39 (m, 1H), 4.54-4.40 (m, 2H), 3.96 (s, 3H), 3.62-3.53 (m, 2H), 3.41-3.39 (m, 1H), 3.30-3.29 (m, 1H) and 2.33-2.22 (m, 2H). | 3.56 | 394 | B |
| 124 | 5-[[5-[2-methoxy-4-[[(3S)-3-methoxypyrrolidin-1-yl]methyl]phenyl]-1H-pyrazol-3-yl]amino]pyrazine-2-carbonitrile hydrochloride | Q | (DMSO-d₆) δ 11.63 (s, 1H), 11.07 (s, 1H), 10.83 (s, 1H), 8.68 (d, 1H), 8.54 (s, 1H), 7.76-7.73 (t, 1H), 7.57 (d, 1H), 7.24 (t, 1H), 7.01 (s, 1H), 4.40-4.36 (m, 2H), 4.15-4.09 (m, 1H), 3.96 (s, 3H), 3.63-3.57 (m, 1H), 3.45-3.36 (m, 2H), 3.27 (d, 3H), 3.29-3.24 (m, 2H), 2.34-2.30 (m, 1H), 2.13-2.11 (m, 1H) and 2.05-1.99 (m, 1H). | 3.77 | 406 | B |
| 125 | 5-[[5-[2-methoxy-4-[[(3R)-3-methoxypyrrolidin-1-yl]methyl]phenyl]-1H-pyrazol-3-yl]amino]pyrazine-2-carbonitrile hydrochloride | Q | (DMSO-d₆) δ 11.56 (s, 1H), 11.01 (s, 1H), 10.83 (s, 1H), 8.68 (s, 1H), 8.53 (s, 1H), 7.76-7.73 (t, 1H), 7.56 (d, 1H), 7.24 (t, 1H), 7.02 (s, 1H), 4.40-4.37 (m, 2H), 4.15-4.11 (m, 1H), 3.95 (s, 3H), 3.63-3.60 (m, 1H), 3.58-3.46 (m, 1H), 3.44-3.41 (d, 3H), 2.39-2.17 (m, 1H) and 2.13-2.01 (m, 2H). | 3.72 | 406 | B |
| 126 | 5-[[5-[4-[[(2R)-1-ethylpyrrolidin-2-yl]methoxy]-2-methoxy-phenyl]-1H-pyrazol-3-yl]amino]pyrazine-2-carbonitrile hydrochloride | K | (DMSO-d₆) δ 10.80 (s, 1H), 10.63 (br s, 1H), 8.67 (d, 1H), 8.54 (s, 1H), 7.65-7.63 (d, 1H), 6.88 (s, 1H), 6.77 (d, 1H), 6.71-6.68 (dd, 1H), 4.49-4.36 (m, 2H), 3.91 (s, 3H), 3.20-3.10 (m, 2H), 2.28-2.21 (m, 2H), 2.08-1.93 (m, 2H), 1.88-1.82 (m, 1H) and 1.31 (t, 3H). | 3.78 | 420 | B |
| 127 | 5-[[5-[4-[[(2R)-1-isopropylpyrrolidin-2-yl]methoxy]-2-methoxy-phenyl]1H-pyrazol-3-yl]amino]pyrazine-2-carbonitrile hydrochloride | K | (DMSO-d₆) δ 10.77 (s, 1H), 10.52 (br s, 2H), 8.67 (s, 1H), 8.54 (s, 1H), 7.64 (d, 1H), 6.87 (s, 1H), 6.75 (s, 1H), 6.68 (d, 1H), 4.47 (t, 1H), 4.34 (d, 1H), 4.05 (br s, 1H), 3.91 (s, 3H), 3.77 (s, 1H), 3.43-3.40 (m, 1H), 3.28-3.26 (m, 1H), 2.23-2.18 (m, 1H), 1.99-1.87 (m, 3H), 1.36 (d, 3H) and 1.29 (d, 3H). | 3.86 | 434 | B |
| 128 | 5-[[5-[4-[[(2S)-1-ethylpyrrolidin-2-yl]methoxy]-2-methoxy-phenyl]-1H-pyrazol-3-yl]amino]pyrazine-2-carbonitrile hydrochloride | K | (DMSO-d₆) δ 10.82 (s, 2H), 8.67 (s, 1H), 8.55 (s, 1H), 7.64 (d, 1H), 6.88 (s, 1H), 6.77 (d, 1H), 6.70 (dd, 1H), 4.51 (dd, 1H), 4.38 (dd, 1H), 3.91 (s, 3H), 3.87-3.82 (m, 1H), 3.62-3.52 (m, 2H), 3.19-3.11 (m, 2H), 2.28-2.23 (m, 1H), 2.05-1.95 (m, 2H), 1.86-1.81 (m, 1H) and 1.32-1.29 (t, 3H). | 3.76 | 420 | B |
| 129 | 5-[[5-[4-[[(2S)-1-isopropylpyrrolidin-2-yl]methoxy]-2-methoxy-phenyl]1H-pyrazol-3-yl]amino]pyrazine-2-carbonitrile hydrochloride | K | (DMSO-d₆) δ 10.78 (s, 1H), 10.60 (s, 1H), 8.67 (s, 1H), 8.54 (s, 1H), 7.64 (s, 1H), 6.87 (s, 1H), 6.75 (s, 1H), 6.68 (d, 1H), 4.51-4.46 (m, 1H), 4.36-4.34 (m, 1H), 4.04 (s, 1H), 3.91 (s, 3H), 3.77 (s, 1H), 3.45-3.37 (m, 1H), 3.27-3.25 (m, 1H), 2.23-2.18 (m, 2H), 1.98 (m, 2H), 1.91-1.85 (m, 1H), 1.36 (d, 3H) and 1.29 (d, 3H). | 3.88 | 434 | B |
| 130 | 5-[[5-[4-[(cyclopropylmethylamino)methyl]-2-methoxy-phenyl]-1H-pyrazol-3-yl]amino]pyrazine-2-carbonitrile hydrochloride | F | (DMSO-d₆) δ 10.84 (s, 1H), 9.50 (s, 2H), 8.67 (d, 1H), 8.53 (s, 1H), 7.74 (d, 1H), 7.53 (d, 1H), 7.20 (dd, 1H), 7.01 (s, 1H), 4.17 (t, 2H), 3.95 (s, 3H), 2.81 (q, 2H), 1.17-1.13 (m, 1H), 0.61-0.56 (m, 2H) and 0.40-0.37 (m, 2H). | 3.81 | 376 | B |
| 131 | 5-[[5-[2-methoxy-4-[[[(3R)-tetrahydrofuran-3-yl]amino]methyl]phenyl]-1H-pyrazol-3-yl]amino]pyrazine-2-carbonitrile hydrochloride | F | (DMSO-d₆) δ 10.83 (s, 1H), 9.72 (s, 2H), 8.67 (d, 1H), 8.53 (s, 1H), 7.74 (d, 1H), 7.56 (s, 1H), 7.23 (d, 1H), 7.01 (s, 1H), 4.19 (m, 2H), 4.00-3.91 (m, 5H), 3.82-3.81 (m, 2H), 3.70-3.65 (m, 1H) and 2.24-2.13 (m, 2H). | 3.64 | 392 | B |
| 132 | 5-[[5-[2-methoxy-4-[[[(3S)-tetrahydrofuran-3-yl]amino]methyl]phenyl]-1H-pyrazol-3-yl]amino]pyrazine-2-carbonitrile hydrochloride | F | (DMSO-d₆) δ 10.85 (s, 1H), 9.84 (br s, 2H), 8.67 (d, 1H), 8.54 (s, 1H), 7.74 (d, 1H), 7.59 (d, 1H), 7.24 (d, 1H), 7.01 (s, 1H), 4.19-4.18 (m, 2H), 3.99-3.91 (m, 5H), 3.84-3.81 (m, 2H), 3.70-3.64 (m, 1H) and 2.24-2.15 (m, 2H). | 3.64 | 392 | B |

TABLE 2-continued

| Ex. No. | Name | Synthetic Method | ¹H NMR | LC (RT) | MS(MH⁺) | LCMS Method |
|---|---|---|---|---|---|---|
| 133 | 5-[[5-[4-[(3R)-4-isopropyl-3-methyl-piperazin-1-yl]-2-methoxy-phenyl]-1H-pyrazol-3-yl]amino]pyrazine-2-carbonitrile hydrochloride | I | (DMSO-$d_6$) δ 10.91 (s, 1H), 10.76 (s, 1H), 8.67 (d, 1H), 8.55 (s, 1H), 7.56 (d, 1H), 6.84 (s, 1H), 6.70-6.66 (m, 2H), 4.04-3.85 (m, 3H), 3.92 (s, 3H), 3.50-3.27 (m, 3H), 3.19-3.04 (m, 2H), 1.41 (t, 6H) and 1.18 (d, 3H). | 3.77 | 433 | B |
| 134 | 5-[[5-[4-[(1-ethyl-4-piperidyl)oxy]-2-methoxy-phenyl]-1H-pyrazol-3-yl]amino]pyrazine-2-carbonitrile hydrochloride | K | (DMSO-$d_6$) δ 10.77 (s, 1H), 10.67 (br s, 1H), 8.67 (d, 1H), 8.54 (s, 1H), 7.61 (dd, 1H), 6.86 (s, 1H), 6.79-6.71 (m, 2H), 4.88 (br s, 1H), 3.89 (s, 3H), 3.54 (d, 1H), 3.37 (d, 1H), 3.17-3.02 (m, 4H), 2.27-2.16 (m, 2H), 2.09-2.05 (m, 2H), 1.98-1.95 (m, 1H) and 1.28 (t, 3H). | 3.84 | 420 | B |
| 135 | 5-[[5-[4-[(1-isopropyl-4-piperidyl)oxy]-2-methoxy-phenyl]-1H-pyrazol-3-yl]amino]pyrazine-2-carbonitrile hydrochloride | K | (DMSO-$d_6$) δ 10.76 (s, 1H), 10.03 (br s, 1H), 8.67 (d, 1H), 8.53 (s, 1H), 7.62-7.59 (m, 1H), 6.86 (s, 1H), 6.79-6.71 (m, 2H), 4.88 (br s, 1H), 4.74-4.68 (m, 1H), 3.90 (s, 3H), 3.53-3.43 (d, 2H), 3.31 (d, 1H), 3.19-3.08 (m, 2H), 2.29-2.18 (m, 2H), 2.11 (d, 1H), 2.01-1.92 (m, 1H) and 1.29 (d, 6H). | 3.91 | 434 | B |
| 136 | 5-[[5-[4-(4-ethylpiperazin-1-yl)-2-fluoro-6-methoxy-phenyl]-1H-pyrazol-3-yl]amino]pyrazine-2-carbonitrile hydrochloride | I | (DMSO-$d_6$) δ 11.13 (s, 1H), 10.78 (s, 1H), 8.67 (d, 1H), 8.55 (s, 1H), 6.77 (s, 1H), 6.61 (dd, 1H), 6.54 (s, 1H), 4.04 (d, 2H), 3.90 (s, 3H), 3.54 (d, 2H), 3.28 (t, 2H), 3.20-3.13 (m, 2H), 3.10-3.02 (m, 2H) and 1.30 (t, 3H). | 3.66 | 423 | B |
| 137 | 5-[[5-[4-(4-isopropylpiperazin-1-yl)-2-fluoro-6-methoxy-phenyl]-1H-pyrazol-3-yl]amino]pyrazine-2-carbonitrile hydrochloride | I | (DMSO-$d_6$) δ 10.98 (s, 1H), 10.79 (s, 1H), 8.67 (d, 1H), 8.54 (s, 1H), 6.78 (s, 1H), 6.61 (dd, 1H), 6.54 (s, 1H), 4.04 (d, 2H), 3.90 (s, 3H), 3.54-3.46 (m, 3H), 3.33 (t, 2H), 3.15-3.07 (m, 2H), 3.10-3.02 (m, 2H) and 1.33 (d, 6H). | 3.77 | 437 | B |
| 138 | 5-[[5-[4-[[(3S)-1-ethylpyrrolidin-3-yl]oxymethyl]-2-methoxy-phenyl]-1H-pyrazol-3-yl]amino]pyrazine-2-carbonitrile hydrochloride | R | (DMSO-$d_6$) δ 11.32 (s, 1H), 10.82 (s, 1H), 8.67 (d, 1H), 8.57 (s, 1H), 7.68 (dd, 1H), 7.19 (d, 1H), 7.05 (t, 1H), 6.97 (s, 1H), 4.55-4.53 (m, 2H), 4.38-4.30 (m, 1H), 3.93 (d, 3H), 3.65-3.60 (m, 1H), 3.57-3.43 (m, 1H), 3.18-3.13 (m, 4H), 2.31-2.23 (m, 1H), 2.05-2.01 (m, 1H) and 1.28-1.24 (m, 3H). | 3.84 | 420 | B |
| 139 | 5-[[5-[4-[[(3S)-1-isopropylpyrrolidin-3-yl]oxymethyl]-2-methoxy-phenyl]-1H-pyrazol-3-yl]amino]pyrazine-2-carbonitrile hydrochloride | R | (DMSO-$d_6$) δ 11.15 (s, 1H), 10.81 (s, 1H), 10.52 (s, 1H), 8.68 (s, 1H), 8.53 (s, 1H), 7.68 (dd, 1H), 7.15 (d, 1H), 7.07-7.02 (m, 1H), 6.97 (s, 1H), 4.60-4.52 (m, 2H), 4.34-4.30 (m, 1H), 3.93 (d, 3H), 3.67-3.37 (m, 3H), 3.25-3.14 (m, 2H), 2.30-2.18 (m, 1H), 2.08-1.95 (m, 1H) and 1.30-1.28 (m, 6H). | 3.89 | 434 | B |
| 140 | 5-[[5-[4-[[(3R)-1-ethylpyrrolidin-3-yl]oxymethyl]-2-methoxy-phenyl]-1H-pyrazol-3-yl]amino]pyrazine-2-carbonitrile hydrochloride | R | (DMSO-$d_6$) δ 12.91 (s, 1H), 10.82 (s, 1H), 8.68 (s, 1H), 8.54 (s, 1H), 7.68 (d, 1H), 7.16 (d, 1H), 7.05 (t, 1H), 6.97 (s, 1H), 4.58-4.53 (m, 2H), 4.35-4.31 (m, 1H), 3.93 (d, 3H), 3.70-3.67 (m, 1H), 3.59-3.54 (m, 1H), 3.20-3.09 (m, 4H), 2.34-2.31 (m, 1H), 2.07-2.02 (m, 1H) and 1.27-1.24 (m, 3H). | 3.84 | 420 | B |
| 141 | 5-[[5-[4-[[(3R)-1-isopropylpyrrolidin-3-yl]oxymethyl]-2-methoxy-phenyl]-1H-pyrazol-3-yl]amino]pyrazine-2-carbonitrile | R | (DMSO-$d_6$) δ 11.39 (d, 1H), 10.83 (s, 1H), 10.78 (s, 1H), 8.67 (d, 1H), 8.54 (s, 1H), 7.68 (d, 1H), 7.16 (d, 1H), 7.07-7.02 (m, 1H), 6.96 (s, 1H), 4.56-4.51 (m, 2H), 4.33-4.30 (m, 1H), 3.92 (d, 3H), 3.68-3.35 (m, 3H), 3.27-3.14 (m, 2H), 2.29-2.17 (m, 1H), 2.07-1.96 (m, 1H) and 1.31-1.28 (m, 6H). | 3.89 | 434 | B |
| 142 | 5-[[5-[4-(4-isobutylpiperazin-1-yl)-2-methoxy-phenyl]-1H-pyrazol-3-yl]amino]pyrazine-2-carbonitrile hydrochloride | I | (DMSO-$d_6$) δ 10.87 (s, 1H), 10.79 (s, 1H), 8.67 (d, 1H), 8.56 (s, 1H), 7.56 (d, 1H), 6.84 (s, 1H), 6.69 (s, 1H), 6.66 (d, 1H), 3.91 (br s, 5H), 3.56-3.42 (m, 4H), 3.15-3.08 (m, 2H), 2.99 (t, 2H), 2.19-2.12 (m, 1H) and 1.03 (d, 6H). | 3.88 | 433 | B |
| 143 | 5-[[5-[4-[(1-ethyl-4-piperidyl)methyl]-2-methoxy-phenyl]-1H-pyrazol-3-yl]amino]pyrazine-2-carbonitrile hydrochloride | S | (DMSO-$d_6$) δ 10.81 (s, 1H), 10.29 (s, 1H), 8.67 (d, 1H), 8.55 (s, 1H), 7.61 (d, 1H), 7.00-6.99 (m, 1H), 6.93 (s, 1H), 6.90-6.89 (m, 1H), 3.90 (s, 3H), 3.42-3.39 (m, 2H), 3.04-2.98 (m, 2H), 2.83-2.72 (m, 2H), 2.58-2.56 (d, 2H), 1.82-1.81 (m, 1H), 1.78-1.75 (m, 2H), 1.60-1.51 (m, 2H) and 1.25-1.21 (m, 3H). | 3.95 | 418 | B |
| 144 | 5-[[5-[4-[(1-isopropyl-4-piperidyl)methyl]-2-methoxy-phenyl]-1H-pyrazol-3-yl]amino]pyrazine-2-carbonitrile hydrochloride | S | (DMSO-$d_6$) δ 10.79 (s, 1H), 10.16 (s, 1H), 8.67 (s, 1H), 8.54 (s, 1H), 7.61 (d, 1H), 6.98 (s, 1H), 6.93 (s, 1H), 6.88-6.86 (m, 1H), 3.91 (s, 3H), 3.39-3.34 (m, 1H), 3.31-3.28 (m, 2H), 2.91-2.83 (m, 2H), 2.57 (d, 2H), 1.86-1.84 (m, 1H), 1.78-1.75 (m, 2H), 1.69-1.63 (m, 2H) and 1.25-1.24 (m, 6H). | 4.02 | 432 | B |
| 145 | 5-[[5-[4-[(1-ethyl-4-piperidyl)methyl-methyl-amino]-2-methoxy-phenyl]-1H-pyrazol-3-yl]amino]pyrazine-2-carbonitrile hydrochloride | O | (DMSO-$d_6$) δ 10.77 (s, 1H), 10.31 (s, 1H), 8.67 (s, 1H), 8.56 (s, 1H), 7.49 (d, 1H), 6.77 (s, 1H), 6.40 (d, 2H), 3.90 (s, 3H), 3.44 (d, 2H), 3.33 (d, 2H), 3.02-2.97 (m, 5H), 2.80 (q, 2H), 1.98 (br s, 1H), 1.82 (d, 2H), 1.63-1.54 (q, 2H) and 1.23 (t, 3H). | 4.02 | 447 | B |

TABLE 2-continued

| Ex. No. | Name | Synthetic Method | ¹H NMR | LC (RT) | MS(MH⁺) | LCMS Method |
|---|---|---|---|---|---|---|
| 146 | 5-[[5-[4-[(isobutylamino)methyl]-2-methoxy-phenyl]-1H-pyrazol-3-yl]amino]pyrazine-2-carbonitrile hydrochloride | F | (DMSO-d$_6$) δ 10.84 (s, 1H), 9.41 (s, 2H), 8.67 (d, 1H), 8.54 (s, 1H), 7.74 (d, 1H), 7.59 (s, 1H), 7.23 (d, 1H), 7.00 (s, 1H), 4.15 (t, 2H), 3.95 (s, 3H), 2.71 (q, 2H), 2.11-2.04 (m, 1H) and 0.95 (d, 6H). | 3.90 | 378 | B |
| 147 | 5-[[5-[4-[(2R)-4-isopropylmorpholin-2-yl]-2-methoxy-phenyl]-1H-pyrazol-3-yl]amino]pyrazine-2-carbonitrile hydrochloride | P | (DMSO-d$_6$) δ 11.36 (s, 1H), 10.80 (s, 1H), 8.67 (d, 1H), 8.53 (s, 1H), 7.73 (s, 1H), 7.17 (s, 1H), 7.09 (d, 1H), 6.98 (s, 1H), 5.05 (d, 1H), 4.22-4.14 (m, 2H), 3.95 (s, 3H), 3.60-3.39 (m, 3H), 3.17-3.02 (m, 2H) and 1.34 (d, 6H). | 3.76 | 420 | B |
| 148 | 5-[[5-[4-[(1-isopropyl-4-piperidyl)methyl-methyl-amino]-2-methoxy-phenyl]-1H-pyrazol-3-yl]amino]pyrazine-2-carbonitrile hydrochloride | O | (DMSO-d$_6$) δ 10.76 (s, 1H), 10.17 (s, 1H), 8.67 (s, 1H), 8.56 (s, 1H), 7.49 (d, 1H), 6.77 (s, 1H), 6.40 (d, 2H), 3.91 (s, 3H), 3.39-3.32 (m, 5H), 3.02 (s, 3H), 2.92-2.84 (m, 2H), 2.02-1.98 (m, 1H), 1.83-1.80 (m, 2H), 1.73-1.67 (m, 2H) and 1.24 (d, 6H). | 4.04 | 461 | B |
| 149 | 5-[[5-[4-[[(2R)-1-ethylpyrrolidin-2-yl]methyl]-2-methoxy-phenyl]-1H-pyrazol-3-yl]amino]pyrazine-2-carbonitrile hydrochloride | T | (DMSO-d$_6$) δ 10.79 (s, 1H), 10.72 (s, 1H), 8.67 (d, 1H), 8.54 (s, 1H), 7.65 (d, 1H), 7.17 (d, 1H), 7.01 (dd, 1H), 6.95 (s, 1H), 3.93 (s, 3H), 3.63-3.58 (m, 2H), 3.39-3.30 (m, 2H), 3.09-3.04 (m, 1H), 3.02-2.93 (m, 2H), 2.01-1.90 (m, 3H), 1.78-1.72 (m, 1H) and 1.27 (t, 3H). | 3.78 | 404 | B |
| 150 | 5-[[5-[4-[(2S)-4-isopropylmorpholin-2-yl]-2-methoxy-phenyl]-1H-pyrazol-3-yl]amino]pyrazine-2-carbonitrile hydrochloride | P | (DMSO-d$_6$) δ 12.74 (br s, 1H), 10.99 (s, 1H), 10.80 (s, 1H), 8.68 (d, 1H), 8.52 (s, 1H), 7.72 (d, 1H), 7.17 (s, 1H), 7.09 (d, 1H), 6.98 (s, 1H), 5.00 (d, 1H), 4.22 (dd, 1H), 4.12 (td, 1H), 3.95 (s, 3H), 3.58 (d, 1H), 3.50 (q, 1H), 3.43 (d, 1H), 3.18-3.03 (m, 2H) and 1.33 (d, 6H). | 3.75 | 420 | B |
| 151 | 5-[[5-[4-[[(2R)-1-isopropylpyrrolidin-2-yl]methyl]-2-methoxy-phenyl]-1H-pyrazol-3-yl]amino]pyrazine-2-carbonitrile hydrochloride | T | (DMSO-d$_6$) δ 10.79 (s, 1H), 10.58 (s, 1H), 8.67 (s, 1H), 8.53 (s, 1H), 7.65 (d, 1H), 7.16 (s, 1H), 7.01 (d, 1H), 6.95 (s, 1H), 3.93 (s, 3H), 3.78 (br s, 1H), 3.55 (br s, 1H), 3.39-3.31 (m, 2H), 3.20 (br s, 1H), 3.02-2.99 (m, 1H), 1.94 (br s, 3H), 1.75 (br s, 1H), 1.35 (d, 3H) and 1.24 (d, 3H). | 3.84 | 418 | B |
| 152 | 5-[[5-[4-[[(2S)-1-ethylpyrrolidin-2-yl]methyl]-2-methoxy-phenyl]-1H-pyrazol-3-yl]amino]pyrazine-2-carbonitrile hydrochloride | T | (DMSO-d$_6$) δ 10.79 (s, 1H), 10.68 (s, 1H), 8.67 (d, 1H), 8.54 (s, 1H), 7.65 (d, 1H), 7.17 (s, 1H), 7.01 (d, 1H), 6.95 (s, 1H), 3.93 (s, 3H), 3.63-3.57 (m, 2H), 3.39-3.31 (m, 2H), 3.09-2.93 (m, 3H), 1.99-1.91 (m, 3H), 1.78-1.72 (m, 1H) and 1.28 (t, 3H). | 3.76 | 404 | B |
| 153 | 5-[[5-(2-methoxy-4-piperazin-1-yl-phenyl)-1H-pyrazol-3-yl]amino]pyrazine-2-carbonitrile hydrochloride | I | (DMSO-d$_6$) δ 12.98 (s, 1H), 10.84 (s, 1H), 9.32 (s, 2H), 8.66 (d, 1H), 8.53 (s, 1H), 7.74 (d, 1H), 7.16-7.13 (m, 1H), 7.03 (s, 1H), 6.83 (s, 1H), 3.57-3.51 (m, 4H) and 3.22-3.17 (m, 4H). | 3.92 | 431 | B |
| 154 | 5-[[5-[4-[[(2S)-1-isopropylpyrrolidin-2-yl]methyl]-2-methoxy-phenyl]-1H-pyrazol-3-yl]amino]pyrazine-2-carbonitrile hydrochloride | T | (DMSO-d$_6$) δ 10.78 (s, 1H), 10.56 (s, 1H), 8.67 (s, 1H), 8.54 (s, 1H), 7.65 (d, 1H), 7.17 (s, 1H), 7.02 (d, 1H), 6.95 (s, 1H), 3.94 (s, 3H), 3.79 (br s, 1H), 3.36-3.30 (m, 2H), 3.22-3.17 (m, 1H), 3.02-2.97 (m, 1H), 1.96-1.86 (m, 3H), 1.80-1.75 (m, 1H), 1.35 (d, 3H) and 1.25 (d, 3H). | 3.81 | 418 | B |
| 155 | 5-[[5-[4-[[(3S)-1-isopropylpyrrolidin-3-yl]amino]-2-methoxy-phenyl]-1H-pyrazol-3-yl]amino]pyrazine-2-carbonitrile hydrochloride | O | (DMSO-d$_6$) δ 11.33 (d, 1H), 10.76 (s, 1H), 8.66 (s, 1H), 8.56 (s, 1H), 7.44 (d, 1H), 6.75 (s, 1H), 6.34 (s, 1H), 6.30 (d, 1H), 4.30-4.20 (m, 1H), 3.85 (d, 3H), 3.60-3.59 (m, 1H), 3.50-3.40 (m, 1H), 3.32-3.25 (m, 1H), 3.17-2.91 (m, 1H), 2.46-2.42 (m, 1H), 2.27-2.22 (m, 1H), 1.99-1.89 (m, 1H) and 1.31 (d, 6H). | 3.73 | 419 | B |
| 156 | 5-[[5-[4-[[(3R)-1-isopropylpyrrolidin-3-yl]amino]-2-methoxy-phenyl]-1H-pyrazol-3-yl]amino]pyrazine-2-carbonitrile hydrochloride | O | (DMSO-d$_6$) δ 11.15 (br s, 1H), 11.00 (br s, 1H), 10.72 (s, 1H), 8.66 (d, 1H), 8.56 (br s, 1H), 7.44 (d, 1H), 6.75 (s, 1H), 6.33 (s, 1H), 6.29 (dd, 1H), 4.32-4.17 (m, 1H), 3.86 (s, 3H), 3.65-3.37 (m, 3H), 3.35-3.23 (m, 1H), 3.21-3.11 (m, 1H), 2.97-2.88 (m, 1H), 2.30-2.20 (m, 1H) and 1.31 (d, 6H). | 3.78 | 419 | B |
| 157 | 5-[[5-[4-[[(3R)-1-ethylpyrrolidin-3-yl]amino]-2-methoxy-phenyl]-1H-pyrazol-3-yl]amino]pyrazine-2-carbonitrile hydrochloride | O | ND | 3.71 | 405 | B |
| 158 | 5-[[5-[4-[[(3S)-1-ethylpyrrolidin-3-yl]amino]-2-methoxy-phenyl]-1H-pyrazol-3-yl]amino]pyrazine-2-carbonitrile hydrochloride | O | (DMSO-d$_6$) δ 11.08 (br s, 1H), 10.98 (br s, 1H), 10.72 (s, 1H), 8.66 (s, 1H), 8.56 (s, 1H), 7.44 (d, 1H), 6.75 (s, 1H), 6.33 (s, 1H), 6.29 (d, 1H), 4.38-4.17 (m, 2H), 3.94-3.86 (m, 1H), 3.85 (s, 3H), 3.61-3.52 (m, 1H), 3.42-3.33 (m, 1H), 3.28-3.15 (m, 2H), 3.14-3.03 (m, 1H), 2.92-2.85 (m, 1H), 2.32-2.20 (m, 1H), 2.03-1.87 (m, 2H) and 1.26 (t, 3H). | 3.66 | 405 | B |
| 159 | 5-[[5-[2-methoxy-4-[(3S)-3-methylpiperazin-1-yl]phenyl]-1H-pyrazol-3-yl]amino]pyrazine-2-carbonitrile hydrochloride | I | ND | 3.68 | 391 | B |

TABLE 2-continued

| Ex. No. | Name | Synthetic Method | ¹H NMR | LC (RT) | MS(MH⁺) | LCMS Method |
|---|---|---|---|---|---|---|
| 160 | 5-[[5-[4-[(3R)-3-ethylpiperazin-1-yl]-2-methoxy-phenyl]-1H-pyrazol-3-yl]amino]pyrazine-2-carbonitrile hydrochloride | I | ND | 3.83 | 405 | B |
| 161 | 5-[[5-[4-[(3S)-3-isopropylpiperazin-1-yl]-2-methoxy-phenyl]-1H-pyrazol-3-yl]amino]pyrazine-2-carbonitrile hydrochloride | I | ND | 3.97 | 419 | B |
| 162 | 5-[[5-[4-[(3R)-3-isopropylpiperazin-1-yl]-2-methoxy-phenyl]-1H-pyrazol-3-yl]amino]pyrazine-2-carbonitrile hydrochloride | I | ND | 3.94 | 419 | B |
| 163 | 5-[[5-[4-(3,3-dimethylpiperazin-1-yl)-2-methoxy-phenyl]-1H-pyrazol-3-yl]amino]pyrazine-2-carbonitrile hydrochloride | I | ND | 3.85 | 405 | B |

ND = Not determined

Synthetic Route A

Illustrated with Reference to Example 1

Example 1

5-[5-(4-Benzylamino-2,6-dimethoxy-phenyl)-1H-pyrazol-3-ylamino]-pyrazine-2-carbonitrile)

1A. N-(4-Acetyl-3,5-dimethoxy-phenyl)-acetamide

AlCl₃ (36.0 g, 27.5 mmol) was added in portions to a stirred solution of 3,5-dimethoxy-phenylamine (12.0 g, 78.4 mmol) and Ac₂O (20.0 g, 19.6 mmol) in DCM (120 mL) at 0° C. The mixture was stirred for 15 minutes then allowed to warm to room temperature and stirring continued for a further one hour. The reaction mixture was poured onto ice and the resulting precipitate collected by filtration. The collected solid was dried under reduced pressure to give the title compound (5.0 g, 27%) as a white solid.

1B. 1-(4-Amino-2,6-dimethoxy-phenyl)-ethanone

A mixture of N-(4-acetyl-3,5-dimethoxy-phenyl)-acetamide (5.0 g, 21.1 mmol) in MeOH (50 mL) and 5N aq. NaOH (50 mL) was heated to reflux for 4 hours. The mixture was allowed to cool to room temperature and concentrated under reduced pressure. The residue was partitioned between water (100 mL) and EtOAc (50 mL) then the separated aqueous phase was extracted with EtOAc (3×50 mL). The combined organic extracts were dried (Na₂SO₄) and evaporated under reduced pressure to give the title compound (3.8 g, 92%).

1C. (4-Acetyl-3,5-dimethoxy-phenyl)-carbamic acid tert-butyl ester

Boc₂O (6.37 g, 29.2 mmol) was added to a stirred solution of 1-(4-amino-2,6-dimethoxy-phenyl)-ethanone (6.37 g, 29.2 mmol) and guanidine hydrochloride (1.85 g, 19.5 mmol) in EtOH (38 mL). The mixture was heated to reflux for 12 hours and then allowed to cool to room temperature. DCM (200 mL) was added then the mixture washed with water (2×50 mL), dried (Na₂SO₄) and evaporated under reduced pressure. The residue was purified by column chromatography on neutral silica gel (60-120 mesh) using 0-10% EtOAc/hexanes as the eluent to give the title compound (3.5 g, 61%).

1D. (4-Acetyl-3,5-dimethoxy-phenyl)-benzyl-carbamic acid tert-butyl ester

NaH (60% in mineral oil, 0.57 g, 14.2 mmol) was added in portions to a stirred solution of (4-acetyl-3,5-dimethoxy-phenyl)-carbamic acid tert-butyl ester (3.5 g, 11.9 mmol) in THF (18 mL) at 0° C. and the resulting mixture stirred for 30 minutes. Benzyl bromide (3.04 g, 17.8 mmol) was added dropwise over 10 minutes then the mixture was heated to 70° C. for 3 hours. The solution was allowed to cool to room temperature then water (40 mL) was carefully added and the mixture extracted with EtOAc (4×50 mL). The combined organic extracts were dried (Na₂SO₄) and evaporated under reduced pressure to leave a residue that was purified by column chromatography on neutral silica gel (60-120 mesh size) using 0-5% EtOAc/hexanes as the eluent to give the title compound (3.0 g, 66%).

1E. Benzyl-[4-(3,3-bis-methylsulfanyl-acryloyl)-3,5-dimethoxy-phenyl]-carbamic acid tert-butyl ester A solution of (4-acetyl-3,5-dimethoxy-phenyl)-benzyl-carbamic acid tert-butyl ester (3.0 g, 7.8 mmol) in DMSO (15 mL) was added slowly to a stirred slurry of NaH (0.78 g, 19.5 mmol) in DMSO (15 mL) maintaining the internal temperature at 10-15° C. After stirring at 10° C. for 10 minutes, carbon disulfide (1.18 g, 15.6 mmol) was added and stirring continued for a further 10 minutes. Methyl iodide (2.19 g, 15.6 mmol) was added at 10° C. then the mixture was allowed to warm to room temperature and stirring continued for 10 minutes. The reaction mixture was carefully poured onto ice then extracted with EtOAc (4×50 mL). The combined organic extracts were washed with brine (100 mL), dried (Na₂SO₄) and evaporated under reduced pressure to leave a residue that was purified by column chromatography on neutral silica gel (60-120 mesh size) using 0-17% EtOAc/hexanes as the eluent to give the title compound (1.7 g, 45%).

1F. Benzyl-{4-[(Z)-3-(5-cyano-pyrazin-2-ylamino)-3-methylsulfanyl-acryloyl]-3,5-dimethoxy-phenyl}-carbamic acid tert-butyl ester A solution of 2-amino-5-cyanopyrazine (1.25 g, 5.2 mmol) in THF (10 mL) was added slowly to a stirred slurry of NaH (60% in mineral oil) (0.21 g, 5.2 mmol) in THF (17 mL) at 0° C. The mixture was stirred for 30 minutes at 0° C. then a solution of benzyl-[4-(3,3-bis-methylsulfanyl-acryloyl)-3,5-dimethoxy-phenyl]-carbamic acid tert-butyl ester (1.7 g, 3.48 mmol) in THF (7 mL) was added dropwise and the reaction mixture was heated to 80° C. for 12 hours. The solution was allowed to cool to room temperature then water (40 mL) was carefully added and the mixture extracted with EtOAc (3×25 mL). The combined organic extracts were dried ($Na_2SO_4$) and evaporated under reduced pressure to leave a residue that was purified by column chromatography on neutral silica gel (60-120 mesh size) using 0-70% EtOAc/hexanes as the eluent to give the title compound (0.9 g, 46%).

1G. Benzyl-{4-[5-(5-cyano-Pyrazin-2-ylamino)-2H-pyrazol-3-yl]-3,5-dimethoxy-phenyl}-carbamic acid tert-butyl ester A stirred solution of hydrazine monohydrate (0.077 g, 2.40 mmol), benzyl-{4-[(Z)-3-(5-cyano-pyrazin-2-ylamino)-3-methylsulfanyl-acryloyl]-3,5-dimethoxy-phenyl}-carbamic acid tert-butyl ester (0.90 g, 1.6 mmol) and acetic acid (2 drops) in EtOH (0.7 mL) was heated to 60° C. for 15 minutes. The mixture was allowed to cool to room temperature and the precipitated solid collected by filtration. The solid was washed with $Et_2O$ (2×5 mL) and dried under reduced pressure to give the title compound (0.10 g, 12%).

1H. 5-[5-(4-Benzylamino-2,6-dimethoxy-phenyl)-1H-pyrazol-3-ylamino]-pyrazine-2-carbonitrile Trifluoroacetic acid (1 mL) was added dropwise to a stirred solution of benzyl-{4-[5-(5-cyano-pyrazin-2-ylamino)-2H-pyrazol-3-yl]-3,5-dimethoxy-phenyl}-carbamic acid tert-butyl ester (0.10 g, 0.19 mmol) in DCM (2 mL) at room temperature. The mixture was stirred at room temperature for 3 hours then heated to 40° C. for a further 2 hours. The solvents were evaporated under reduced pressure to leave a residue which was purified by preparative HPLC to give the title compound (0.025 g, 34%) as an off-white solid.

Synthetic Route B

Illustrated with Reference to Example 3

Example 3

5-{5-[4-(Benzylamino-methyl)-2-methoxy-phenyl]-1H-pyrazol-3-ylamino}-pyrazine-2-carbonitrile hydrochloride)

3A. 3-Methoxy-4-nitro-benzaldehyde

A mixture of 2-hydroxy-4-nitro-benzaldehyde (8.0 g, 47.9 mmol), methyl iodide (10.2 g, 71.9 mmol) and potassium carbonate (6.61 g, 47.9 mmol) in DMF (80 mL) was stirred at 60° C. for 3 hours. The cooled reaction mixture was diluted with EtOAc (100 mL), washed with water (200 mL), dried ($Na_2SO_4$) and evaporated under reduced pressure to give the title compound (6.5 g, 75%) which was used without further purification.

3B. 4-Amino-3-methoxy-benzaldehyde

A stirred mixture of 3-methoxy-4-nitro-benzaldehyde (6.5 g, 35.9 mmol), iron powder (4.51 g, 80.8 mmol) and $NH_4Cl$ (3.87 g, 71.8 mmol) in MeOH (50 mL) and water (50 mL) was heated to reflux for 3 hours. The cooled reaction mixture was filtered through a pad of celite and diluted with EtOAc (100 ml). The separated organic phase was washed with water (2×50 mL), dried ($Na_2SO_4$) and evaporated under reduced pressure to give the title compound (4.5 g, 83%) which was used without further purification.

3C. 4-Bromo-3-methoxy-benzaldehyde

A mixture of 4-amino-3-methoxy-benzaldehyde (4.5 g, 29.8 mmol), n-butyl nitrite (4.6 g, 35.8 mmol) and copper bromide (6.83 g, 47.7 mmol) in MeCN (45 mL) was stirred at room temperature for 12 hours. The reaction mixture was diluted with EtOAc (100 mL), washed with water (200 mL), dried ($Na_2SO_4$) and evaporated under reduced pressure to leave a residue which was purified by column chromatography on neutral silica gel (60-120 mesh) using 0-70% EtOAc/hexanes as the eluent to give the title compound (4.2 g, 66%).

3D. Benzyl-(4-bromo-3-methoxy-benzyl)-amine $NaBH(OAc)_3$ (6.24 g, 29.4 mmol) was added in portions to a stirred solution of 4-bromo-3-methoxy-benzaldehyde (4.2 g, 19.6 mmol), benzylamine (2.51 g, 23.6 mmol) and acetic acid (2.35 g, 39.3 mmol) in DCM (42 mL) at room temperature. The resulting solution was stirred for 12 hours then diluted with EtOAc (40 mL), washed with water (40 mL), dried ($Na_2SO_4$) and evaporated under reduced pressure to leave a residue which was purified by column chromatography on neutral silica gel (60-120 mesh) using 0-2% MeOH/DCM as the eluent to give the title compound (3.8 g, 64%).

3E. 1-[4-(Benzylamino-methyl)-2-methoxy-phenyl]-ethanone

A stirred solution of benzyl-(4-bromo-3-methoxy-benzyl)-amine (3.8 g, 12.5 mmol) and tributyl(1-ethoxyvinyl)tin (5.39 g, 15.0 mmol) in 1,4-dioxane (40 mL) was degassed with nitrogen for 15 minutes. Tetrakis(triphenylphosphine)palladium(O) (0.72 g, 0.62 mmol) was added to the mixture and the resulting solution heated to 130° C. for 16 hours. The mixture was allowed to cool to room temperature then diluted with EtOAc (60 mL), washed with water (40 mL), dried ($Na_2SO_4$) and evaporated under reduced pressure to leave a residue which was purified by column chromatography on neutral silica gel (60-120 mesh) using 0-2% MeOH/DCM as the eluent to give the title compound (1.5 g, 45%).

3F. (4-Acetyl-3-methoxy-benzyl)-benzyl-carbamic acid tert-butyl ester $Boc_2O$ (1.45 g, 6.69 mmol) was added to a stirred solution of 1-[4-(benzylamino-methyl)-2-methoxy-phenyl]-ethanone (1.5 g, 5.57 mmol) and $Et_3N$ (1.69 g, 16.7 mmol) in DCM (5 mL) and the resulting mixture stirred at room temperature for 3 hours. The mixture was diluted with DCM (20 mL), washed with water (2×20 mL), dried ($Na_2SO_4$) and evaporated under reduced pressure to leave a residue which was purified by column chromatography on neutral silica gel (60-120 mesh) using 0-2% MeOH/DCM as the eluent to give the title compound (1.5 g, 73%).

3G. Benzyl-[4-(3,3-bis-methylsulfanyl-acryloyl)-3-methoxy-benzyl]-carbamic acid tert-butyl ester A solution of (4-acetyl-3-methoxy-benzyl)-benzyl-carbamic acid tert-butyl ester (1.5 g, 4.1 mmol) in DMSO (15 mL) was added slowly to a stirred slurry of NaH (60% in mineral oil, 0.41 g, 10.2 mmol) in DMSO (20 mL) maintaining the internal temperature at 10-15° C. After stirring at 10° C. for 10 minutes, carbon disulfide (0.62 g, 8.1 mmol) was added and stirring continued for a further 10 minutes. Methyl iodide (1.15 g, 8.1 mmol) was added at 10° C. then the mixture was allowed to warm to room temperature and stirring continued for 10 minutes. The reaction mixture was carefully poured onto ice then extracted with EtOAc (4×50 mL). The combined organic extracts were washed with brine (50 mL), dried ($Na_2SO_4$) and evaporated under reduced pressure to leave a residue that was purified by column chromatography on neutral silica gel (60-120 mesh) using 0-30% EtOAc/hexanes as the eluent to give the title compound (0.75 g, 39%).

3H. Benzyl-{4-[(Z)-3-(5-cyano-Pyrazin-2-ylamino)-3-methylsulfanyl-acryloyl]-3-methoxy-benzyl}-carbamic acid tert-butyl ester A solution of 2-amino-5-cyanopyrazine (0.29 g, 2.4 mmol) in THF (8 mL) was added slowly to a stirred slurry of NaH (60% in mineral oil, 0.095 g, 2.4 mmol) in THF (8 mL) at 0° C. The mixture was stirred for 30 minutes at 0° C. then a solution of benzyl-[4-(3,3-bis-methylsulfanyl-acryloyl)-3-methoxy-benzyl]-carbamic acid tert-butyl ester (0.75 g, 1.58 mmol) in THF (7 mL) was added dropwise and the reaction mixture was then heated to 80° C. for 12 hours. The solution was allowed to cool to room temperature then water (40 mL) was carefully added and the mixture extracted with EtOAc (3×25 mL). The combined organic extracts were dried ($Na_2SO_4$) and evaporated under reduced pressure to leave a residue that was purified by column chromatography on neutral silica gel (60-120 mesh) using 0-80% EtOAc/hexanes as the eluent to give the title compound (0.28 g, 32%).

3I. Benzyl-{4-[5-(5-cyano-pyrazin-2-ylamino)-2H-pyrazol-3-yl]-3-methoxy-benzyl}-carbamic acid tert-butyl ester A stirred solution of hydrazine monohydrate (0.024 g, 0.77 mmol), benzyl-{4-[(Z)-3-(5-cyano-pyrazin-2-ylamino)-3-methylsulfanyl-acryloyl]-3-methoxy-benzyl}-carbamic acid tert-butyl ester (0.28 g, 0.51 mmol) and acetic acid (2 drops) in EtOH (0.7 mL) was heated to 60° C. for 15 minutes. The solution was allowed to cool to room temperature then water (10 mL) was added and the mixture extracted with EtOAc (3×25 mL). The combined organic extracts were dried ($Na_2SO_4$) and evaporated under reduced pressure to leave a residue that was purified by column chromatography on neutral silica gel (60-120 mesh) using 0-10% MeOH/DCM as the eluent to give the title compound (0.035 g, 13%).

3J. 5-{5-[4-(Benzylamino-methyl)-2-methoxy-phenyl]-1H-pyrazol-3-ylamino}-pyrazine-2-carbonitrile hydrochloride A 4N solution of HCl in $Et_2O$ (1 mL) was added dropwise to a stirred solution of benzyl-{4-[5-(5-cyano-pyrazin-2-ylamino)-2H-pyrazol-3-yl]-3-methoxy-benzyl}-carbamic acid tert-butyl ester (0.035 g, 0.06 mmol) in DCM (2 mL) at room temperature. The mixture was stirred for 18 hours at room temperature and then the solvents were evaporated under reduced pressure to leave a solid which was washed with $Et_2O$ (2×5 mL) and dried to give the title compound (0.012 g, 43%) as a white solid.

Synthetic Route C

Illustrated with Reference to Example 4

Example 4

5-{5-[4-(2-Benzylamino-ethyl)-2-methoxy-phenyl]-1H-pyrazol-3-ylamino}-pyrazine-2-carbonitrile hydrochloride)

4A. 1-Bromo-2-methoxy-4-((E)-2-nitro-vinyl)-benzene

A stirred solution of 4-bromo-3-methoxy-benzaldehyde (5.0 g, 23.3 mmol), ammonium acetate (2.4 g, 30.2 mmol) and nitromethane (6.3 mL, 116 mmol) in glacial acetic acid (20 mL) was heated to 80° C. for 12 hours. The mixture was allowed to cool to room temperature then poured into water (100 mL). The resulting solid was collected by filtration and then dissolved in DCM (80 mL). The solution was washed with brine (20 mL), dried ($Na_2SO_4$) and evaporated under reduced pressure to leave a residue which was purified by column chromatography on neutral silica gel using DCM as the eluent to give the title compound (4.2 g, 40%).

4B. 2-(4-Bromo-3-methoxy-phenyl)-ethylamine

Sodium borohydride (2.9 g, 77.5 mmol) was added in portions to a stirred solution of 1-bromo-2-methoxy-4-((E)-2-nitro-vinyl)-benzene (4.0 g, 15.5 mmol) in MeOH (50 mL) at 0° C. The resulting solution was allowed to warm to room temperature and stirring continued for one hour. Water (2 mL) was carefully added followed by the careful addition of 50% aqueous acetic acid solution (5 mL) whilst maintaining the temperature below 30° C. Zinc powder (5.1 g, 77.5 mmol) and saturated aqueous $NH_4Cl$ solution (20 mL) were added and the resulting mixture heated to 50° C. for one hour. The cooled mixture was diluted with DCM (50 mL) and filtered through a cotton wool plug. Water (40 mL) was added to the filtrate and the separated aqueous phase was extracted with DCM (2×50 mL). The combined organic extracts were washed with brine (20 ml), dried ($Na_2SO_4$) and evaporated under reduced pressure to leave a residue that was purified by column chromatography on neutral silica gel (60-120 mesh) using 8-10% MeOH/DCM as the eluent to give the title compound (2.0 g, 56%).

4C. Benzyl-[2-(4-bromo-3-methoxy-phenyl)-ethyl]-amine

Benzaldehyde (0.83 g, 7.9 mmol) was added dropwise to a stirred solution of 2-(4-bromo-3-methoxy-phenyl)-ethylamine (2.0 g, 8.7 mmol) and glacial acetic acid (0.94 mL, 15.8 mmol) in EtOH (40 mL) at room temperature. The mixture was stirred for one hour then $NaBH(OAc)_3$ (3.35 g, 15.8 mmol) was added in portions and the resulting mixture stirred for a further 4 hours. Saturated aq. $NaHCO_3$ (50 mL) was added and the mixture extracted with DCM (3×30 mL). The combined organic extracts were washed with brine (20 ml), dried ($Na_2SO_4$) and evaporated under reduced pressure to leave a residue that was purified by column chromatography on neutral silica gel (60-120 mesh) using 2-3.5% MeOH/DCM as the eluent to give the title compound (1.5 g, 59%).

4D. 1-[4-(2-Benzylamino-ethyl)-2-methoxy-phenyl]-ethanone

A stirred solution of benzyl-[2-(4-bromo-3-methoxy-phenyl)-ethyl]-amine (1.5 g, 4.68 mmol) and tributyl(1-ethoxyvinyl)tin (2.1 g, 5.6 mmol) in 1,4-dioxane (20 mL) was degassed with nitrogen for 15 minutes. Tetrakis(triphenylphosphine)palladium(O) (0.27 g, 0.23 mmol) was added to the mixture and the resulting solution heated to 100° C. for 12 hours. The solution was allowed to cool to room temperature and 1N aq. HCl solution (6 mL) was added and the mixture stirred for a further 2 hours. Saturated aq. NaHCO$_3$ solution was carefully added to attain pH10 and the mixture extracted with EtOAc (3×30 mL). The combined organic extracts were dried (Na$_2$SO$_4$) and evaporated under reduced pressure. The residue was dissolved in DCM (10 mL) and 3N HCl in dioxane (2 mL) added. The solution was stirred for 30 minutes then the solvents were removed under reduced pressure. The resulting solid was triturated with Et$_2$O (4×50 mL) and dried to give the title compound (1.4 g, 93%) as its hydrochloride salt.

4E. [2-(4-Acetyl-3-methoxy-phenyl)-ethyl]-benzyl-carbamic acid tert-butyl ester Boc$_2$O (1.51 g, 6.58 mmol) was added to a stirred solution of 1-[4-(2-benzylamino-ethyl)-2-methoxy-phenyl]-ethanone (1.40 g, 4.38 mmol) and Et$_3$N (1.23 mL, 8.76 mmol) in DCM (30 mL) and the resulting mixture stirred at room temperature for 6 hours. The mixture was partitioned between DCM (30 mL) and water (50 mL) then the separated aqueous phase was extracted with DCM (3×30 mL). The combined organic extracts were washed with brine (20 mL), dried (Na$_2$SO$_4$) and evaporated under reduced pressure to leave a residue that was purified by column chromatography on neutral silica gel (60-120 mesh) using 10-20% EtOAc/hexanes as the eluent to give the title compound (1.2 g, 71%).

4F. Benzyl-{2-[4-(3,3-bis-methylsulfanyl-acryloyl)-3-methoxy-phenyl]-ethyl}-carbamic acid tert-butyl ester A solution of [2-(4-acetyl-3-methoxy-phenyl)-ethyl]-benzyl-carbamic acid tert-butyl ester (1.0 g, 2.60 mmol) in DMSO (3 mL) was added slowly to a stirred slurry of NaH (60% in mineral oil, 0.26 g, 6.5 mmol) in DMSO (6 mL) maintaining the internal temperature at 10-15° C. After stirring at 10° C. for 30 minutes, carbon disulfide (0.32 mL, 5.20 mmol) was added and stirring continued for a further 20 minutes. Methyl iodide (0.35 mL, 5.72 mmol) was added at 10° C. then the mixture was allowed to warm to room temperature and stirring continued for 30 minutes. Water (50 mL) was carefully added and the mixture extracted with EtOAc (3×30 mL). The combined organic extracts were washed with brine (20 mL), dried (Na$_2$SO$_4$) and evaporated under reduced pressure to leave a residue that was purified by column chromatography on neutral silica gel (60-120 mesh size) using 0-30% EtOAc/hexanes as the eluent to give the title compound (0.60 g, 47%).

4G. Benzyl-(2-{4-[(Z)-3-(5-cyano-pyrazin-2-ylamino)-3-methylsulfanyl-acryloyl]-3-methoxy-phenyl}-ethyl)-carbamic acid tert-butyl ester A solution of 2-amino-5-cyanopyrazine (0.12 g, 0.92 mmol) was added in portions to a stirred slurry of NaH (60% in mineral oil) (0.040 g, 0.92 mmol) in THF (3 mL) at room temperature. The mixture was stirred for 30 minutes then benzyl-{2-[4-(3,3-bis-methylsulfanyl-acryloyl)-3-methoxy-phenyl]-ethyl}-carbamic acid tert-butyl ester (0.30 g, 0.62 mmol) was added and the reaction mixture was then heated to 65° C. for 12 hours. The solution was allowed to cool to room temperature then water (10 mL) was carefully added and the mixture extracted with EtOAc (3×20 mL). The combined organic extracts were washed with brine (10 mL), dried (Na$_2$SO$_4$) and evaporated under reduced pressure to leave a residue that was purified by column chromatography on neutral silica gel (60-120 mesh) using 15-30% EtOAc/hexanes as the eluent to give the title compound (0.17 g, 49%).

4H. Benzyl-(2-{4-[5-(5-cyano-pyrazin-2-ylamino)-2H-pyrazol-3-yl]-3-methoxy-phenyl}-ethyl)-carbamic acid tert-butyl ester A stirred solution of hydrazine monohydrate (0.03 mL, 0.60 mmol), benzyl-(2-{4-[(Z)-3-(5-cyano-pyrazin-2-ylamino)-3-methylsulfanyl-acryloyl]-3-methoxy-phenyl}-ethyl)-carbamic acid tert-butyl ester (0.17 g, 0.30 mmol) and acetic acid (0.05 mL, 0.9 mmol) in EtOH (2 mL) was heated to 65° C. for 3 hours. The solution was allowed to cool to room temperature then water (20 mL) was added and the mixture extracted with EtOAc (3×20 mL). The combined organic extracts were washed with brine (10 mL), dried (Na$_2$SO$_4$) and evaporated under reduced pressure to leave a residue that was purified by column chromatography on neutral silica gel (60-120 mesh) using 1.5% MeOH/DCM as the eluent to give the title compound (0.095 g, 60%).

4I. 5-{5-[4-(2-Benzylamino-ethyl)-2-methoxy-phenyl]-1H-pyrazol-3-ylamino}-pyrazine-2-carbonitrile hydrochloride 3N HCl in dioxane (0.5 mL) was added dropwise to a stirred solution of benzyl-(2-{4-[5-(5-cyano-pyrazin-2-ylamino)-2H-pyrazol-3-yl]-3-methoxy-phenyl}-ethyl)-carbamic acid tert-butyl ester (0.090 g, 0.17 mmol) in MeCN (2 mL) and THF (2 mL) at room temperature. The mixture was stirred for 30 minutes at room temperature then the mixture heated to 50° C. for 3 hours. The mixture was allowed to cool to room temperature and the precipitated solid was collected by filtration. The collected solid was washed with THF/MeCN (1:1, 1.5 mL) and Et$_2$O (10 mL) and dried to give the title compound (0.055 g, 70%) as a white solid.

Synthetic Route D

Illustrated with Reference to Example 11

Example 11

5-{5-[2-Methoxy-4-(1-methyl-piperidin-4-yl)-phenyl]-1H-pyrazol-3-ylamino}-pyrazine-2-carbonitrile hydrochloride)

11 A. 4-(3-Methoxy-4-methoxycarbonyl-phenyl)-3,6-dihydro-2H-pyridine-1-carboxylic acid tert-butyl ester A solution of 4-bromo-2-methoxy-benzoic acid methyl ester (4.0 g, 16.5 mmol), 1-Boc-piperidine-4-boronic acid pinacol ester (5.1 g, 16.5 mmol) and K$_2$CO$_3$ (6.6 g, 49.5 mmol) in DMF (25 mL) was degassed with nitrogen for 15 minutes. PdCl$_2$(dppf).DCM (1.0 g, 0.6 mmol) was added at room temperature then the mixture was heated to 90° C. and stirring continued for 5 hours. Water (100 mL) was added and the mixture extracted with EtOAc (2×50 mL) then the combined organic extracts were washed with brine (50 mL), dried (Na$_2$SO$_4$) and evaporated under reduced pressure. The residue was purified by column chromatography on neutral silica gel using 10-15% EtOAc/hexanes as the eluent to give the title compound (5.0 g, 87%).

11B. 4-(3-Methoxy-4-methoxycarbonyl-phenyl)-piperidine-1-carboxylic acid tert-butyl ester A mixture of 4-(3-methoxy-4-methoxycarbonyl-phenyl)-3,6-dihydro-2H-pyridine-1-carboxylic acid tert-butyl ester (5.0 g, 14.4 mmol) and 10% Pd/C (0.5 g) was stirred under a hydrogen atmosphere at room temperature for 6 hours. The mixture was filtered through a pad of celite and the solvents evaporated under reduced pressure to give the title compound (4.5 g, 90%) which was used without further purification.

11C. 2-Methoxy-4-piperidin-4-yl-benzoic acid methyl ester

3N HCl in dioxane (15 mL) was added to a stirred solution of 4-(3-methoxy-4-methoxycarbonyl-phenyl)-piperidine-1-carboxylic acid tert-butyl ester (4.5 g, 12.8 mmol) in DCM (50 mL) at 0° C. The mixture was allowed to warm to room temperature and stirring continued for 5 hours then the solvents were removed under reduced pressure. The residue was triturated with Et$_2$O (2×10 mL) then partitioned between DCM (50 mL) and saturated NaHCO$_3$ solution (50 mL). The separated aqueous phase was extracted with DCM (2×50 mL) then the combined organic extracts were dried (Na$_2$SO$_4$) and evaporated under reduced pressure to give the title compound (2.5 g, 78%) which was used without further purification.

11D. 2-Methoxy-4-(1-methyl-piperidin-4-yl)-benzoic acid methyl ester

Formalin (37% formaldehyde in water) (5.0 mL, 50 mmol) was added to a stirred solution of 2-methoxy-4-piperidin-4-yl-benzoic acid methyl ester (0.3 g, 1.1 mmol) in MeOH (15 mL) and the mixture stirred for 30 minutes. The solution was cooled to 0° C. and NaBH(AcO)$_3$ (3.20 g, 15 mmol) was added and the resulting solution stirred for 3 hours at room temperature. Saturated NaHCO$_3$ solution (100 mL) was added and the mixture extracted with DCM (3×75 mL). The combined organic extracts were washed with brine (30 mL), dried (Na$_2$SO$_4$) and evaporated under reduced pressure to give the title compound (2.5 g, 95%) which was used without further purification.

11E. 3-[2-Methoxy-4-(1-methyl-piperidin-4-yl)-phenyl]-3-oxo-propionitrile

LHMDS (1M in hexane) (24 mL, 24 mmol) was added dropwise to MeCN (1.78 mmol, 34.2 mmol) in dry toluene (50 mL) at −78° C. under a nitrogen atmosphere and the resulting yellow solution stirred for 30 minutes at −78° C. A solution of 2-methoxy-4-(1-methyl-piperidin-4-yl)-benzoic acid methyl ester (1.8 g, 6.84 mmol) in dry toluene (50 mL) was added dropwise maintaining the temperature at −78° C., then the mixture was allowed to warm to room temperature and stirring continued for 30 minutes. The mixture was cooled to 0° C. and water (150 mL) was carefully added then the separated aqueous phase was extracted with EtOAc (2×50 mL). The combined organic extracts were washed with brine (25 mL), dried (Na$_2$SO$_4$) and evaporated under reduced pressure to leave a residue that was purified by column chromatography on neutral silica gel (60-120 mesh) using 2-3% MeOH/DCM as the eluent to give the title compound (1.40 g, 75%).

11F. 5-[2-Methoxy-4-(1-methyl-piperidin-4-yl)-phenyl]-1H-pyrazol-3-ylamine

A stirred solution of hydrazine monohydrate (0.22 g, 4.44 mmol) and 3-[2-methoxy-4-(1-methyl-piperidin-4-yl)-phenyl]-3-oxo-propionitrile (1.0 g, 3.67 mmol) in EtOH (2 mL) was heated to 85° C. for 10 hours. The solution was allowed to cool to room temperature and evaporated under reduced pressure to leave a residue that was purified by column chromatography on neutral silica gel (60-120 mesh size) using 10% MeOH/DCM as the eluent to give the title compound (0.60 g, 57%).

11G. 3-Amino-5-[2-methoxy-4-(1-methyl-piperidin-4-yl)-phenyl]-pyrazole-1-carboxylic acid tert-butyl ester NaH (60% in mineral oil) (0.031 g, 0.77 mmol) was added in portions to a stirred solution of 5-[2-methoxy-4-(1-methyl-piperidin-4-yl)-phenyl]-1H-pyrazol-3-ylamine (0.20 g, 0.69 mmol) in a mixture of THF (15 mL) and DMF (5 mL) at 0° C. The mixture was stirred for 30 minutes then Boc$_2$O (0.17 g, 0.77 mmol) was added and then the mixture allowed to warm to room temperature and stirring continued for one hour. The mixture was poured into water (50 mL) and extracted with EtOAc (3×30 mL). The combined organic extracts were washed with brine (25 mL), dried (Na$_2$SO$_4$) and evaporated under reduced pressure to leave a solid that was washed with Et$_2$O (8 mL) to give the title compound (0.23 g, 84%).

11H. 5-{5-[2-Methoxy-4-(1-methyl-piperidin-4-yl)-phenyl]-1H-pyrazol-3-ylamino}-pyrazine-2-carbonitrile hydrochloride NaH (60% in mineral oil) (0.016 g, 0.38 mmol) was added in portions to a stirred solution of 3-amino-5-[2-methoxy-4-(1-methyl-piperidin-4-yl)-phenyl]-pyrazole-1-carboxylic acid tert-butyl ester (0.75 g, 0.19 mmol) in THF (3 mL) at 0° C. The mixture was stirred for 10 minutes then 5-bromopyrazine-2-carbonitrile (0.036 g, 0.19 mmol) was added and then the mixture allowed to warm to room temperature and stirring continued for one hour. The mixture was poured into water (50 mL) and extracted with EtOAc (3×30 mL). The combined organic extracts were washed with brine (25 mL), dried (Na$_2$SO$_4$) and evaporated under reduced pressure to leave a solid that was purified by preparative HPLC to give the title compound (0.03 g, 40%) as its free base. This material was dissolved in MeCN (1 mL) and THF (1 mL) then 3N HCl in dioxane (0.2 mL) was added. The mixture was stirred at room temperature for 30 minutes then the solvents were removed under reduced pressure to leave a solid which was washed with Et$_2$O (5 mL) and dried to give the title compound (0.032 g, 98%) as a white solid.

Synthetic Route E

Illustrated with Reference to Example 13

Example 13

N-[[4-[3-[(5-cyanopyrazin-2-yl)amino]-1H-pyrazol-5-yl]-3-methoxy-phenyl]methyl]cyclopropanecarboxamide)

13A. Methyl 2-hydroxy-4-methyl-benzoate

Concentrated $H_2SO_4$ (200 mL) was added dropwise over 30 minutes to a stirred solution of 2-hydroxy-4-methyl-benzoic acid (100 g, 657 mmol) in MeOH (500 mL) at room temperature. The mixture was heated to reflux for 5 hours then allowed to cool to room temperature and carefully poured into ice cold saturated $NaHCO_3$ solution (300 mL). The mixture was extracted with DCM (4×500 mL) and the combined organic extracts dried ($Na_2SO_4$) and evaporated under reduced pressure to give the title compound (100 g, 94%) which was used without further purification.

13B. Methyl 2-methoxy-4-methyl-benzoate

A solution of methyl 2-hydroxy-4-methyl-benzoate (100 g, 602 mmol) in DMF (170 mL) was added dropwise over 30 minutes to a stirred slurry of NaH (33.8 g, 1.41 mol) in dry DMF (330 mL) at 0° C. under a nitrogen atmosphere. The resulting mixture was stirred at 0° C. for a further 30 minutes then iodomethane (255 g, 1.81 mol) was added dropwise over 20 minutes. The mixture was heated to 70° C. for 3 hours then allowed to cool and carefully poured into ice-cold 1N HCl solution (1500 mL). The mixture was extracted with DCM (2×1000 mL) and the combined organic extracts dried ($Na_2SO_4$) and evaporated under reduced pressure. The residue was purified by column chromatography on neutral silica gel using 15% EtOAc/hexanes as the eluent to give the title compound (102 g, 94%).

13C. Methyl 4-(bromomethyl)-2-methoxy-benzoate

A stirred solution of methyl 2-methoxy-4-methyl-benzoate (100 g, 555 mmol) and N-bromosuccinimide (108.6 g, 610 mmol) in carbon tetrachloride (1300 mL) was degassed with nitrogen for 15 minutes. α,α'-Azoisobutyronitrile (18.2 g, 111 mmol) was added in one portion and the resulting mixture heated to 70° C. for 15 hours then allowed to cool to room temperature. The mixture was poured into water (600 mL) and then the separated aqueous phase extracted with DCM (2×800 mL). The combined organic extracts were dried ($Na_2SO_4$) and evaporated under reduced pressure to give the title compound (144 g) which was used without further purification.

13D. Methyl 4-(acetoxymethyl)-2-methoxy-benzoate

A stirred mixture of methyl 4-(bromomethyl)-2-methoxy-benzoate (144 g, 558 mmol) and potassium acetate (285 g, 2.9 mol) in dry DMF (1440 mL) was heated to 80° C. for one hour then the cooled mixture was poured into ice-water (5000 mL). The mixture was extracted with DCM (2×1000 mL) and the combined organic extracts were dried ($Na_2SO_4$) and evaporated under reduced pressure. The residue was purified by column chromatography on neutral silica gel using 15% EtOAc/hexanes as the eluent to give the title compound (63.0 g, 48% over two steps).

13E. Methyl 4-(hydroxymethyl)-2-methoxy-benzoate

A solution of methyl 4-(acetoxymethyl)-2-methoxy-benzoate (63.0 g, 265 mmol) in MeOH (500 mL) was added dropwise to a stirred solution of sodium methoxide (2.86 g, 52.9 mmol) in MeOH (280 mL) at room temperature. The mixture was stirred for two hours then poured into 2N HCl solution (1000 mL) and extracted with DCM (3×1000 mL). The combined organic extracts were dried ($Na_2SO_4$) to afford the title compound (49.0 g, 94%) which was used without further purification.

13F. Methyl 2-methoxy-4-(methylsulfonyloxymethyl)benzoate

Methanesulfonyl chloride (2.1 mL, 26.8 mmol) was added dropwise to a stirred solution of methyl 4-(hydroxymethyl)-2-methoxy-benzoate (5.0 g, 25.5 mmol) and triethylamine (7.1 mL, 51.0 mmol) in DCM (120 mL) at 0° C. under a nitrogen atmosphere. The resulting mixture was stirred at 0° C. for two hours then partitioned between DCM (100 mL) and 1N HCl (100 mL). The separated organic phase was washed with brine (50 mL), dried ($Na_2SO_4$) and evaporated under reduced pressure to give the title compound (7.6 g, 100%) which was used without further purification.

13G. Methyl 4-(azidomethyl)-2-methoxy-benzoate

A solution of sodium azide (9.0 g, 138 mmol) and methyl 2-methoxy-4-(methylsulfonyloxymethyl)benzoate (7.6 g, 27.7 mmol) in dry DMF (60 mL) was heated to 70° C. for 3 hours. The cooled reaction mixture was poured into cold water (500 mL) and the resulting mixture extracted with EtOAc (3×100 mL). The combined organic extracts were washed with brine (50 mL), dried ($Na_2SO_4$) and evaporated under reduced pressure to give the title compound (7.8 g, 100%) which was used without further purification.

13H. Methyl 4-(aminomethyl)-2-methoxy-benzoate

A mixture of methyl 4-(azidomethyl)-2-methoxy-benzoate (7.8 g, 27.7 mmol) and 10% Pd on carbon (0.78 g) in MeOH (80 mL) was stirred at room temperature under a hydrogen atmosphere for 3 hours. The mixture was filtered through celite and the filtrate evaporated under reduced pressure to leave a residue which was purified by column chromatography on neutral silica gel using 6-7% MeOH/chloroform to give the title compound (3.1 g, 45% over two steps).

13I. Methyl 4-[(cyclopropanecarbonylamino)methyl]-2-methoxy-benzoate

1-Ethyl-3-(3-dimethylaminopropyl)carbodiimide hydrochloride (1.75 g, 11.3 mmol) and hydroxybenzotriazole (0.14 g, 1.0 mmol) were added to a stirred solution of methyl 4-(aminomethyl)-2-methoxy-benzoate (2.0 g, 10.3 mmol) and cyclopropane carboxylic acid (0.82 mL, 10.3 mmol) in DCM (85 mL) at room temperature under a nitrogen atmosphere. The mixture was stirred at room temperature for 3 hours then diluted with DCM (150 mL) and washed with saturated $NaHCO_3$ solution (3×75 mL), brine (50 mL), dried ($Na_2SO_4$) and evaporated under reduced pressure. The residue was purified by column chromatography on neutral silica gel using 55% EtOAc/hexane as the eluent to give the title compound (2.2 g, 82%).

13J. N-[[4-(2-cyanoacetyl)-3-methoxy-phenyl]methyl]cyclopropanecarboxamide

A solution of LiHMDS (1.0M in hexane, 29.4 mL, 29.4 mmol) was added dropwise over 20 minutes to a stirred solution of acetonitrile (1.72 g, 42.0 mmol) in dry THF (58 mL) at −78° C. under a nitrogen atmosphere. Stirring was continued for 30 minutes then a solution of methyl 4-[(cyclopropanecarbonylamino)methyl]-2-methoxy-benzoate (2.2 g, 8.4 mmol) in THF (50 mL) was added dropwise over 20 minutes maintaining the temperature at −78° C. The mixture was allowed to warm to room temperature and stirring continued for 2 hours. The mixture was poured into cold saturated ammonium chloride solution (100 mL) and extracted with EtOAc (3×150 mL). The combined organic extracts were washed with brine (50 mL), dried ($Na_2SO_4$) and evaporated under reduced pressure to give the title compound (2.0 g, 88%) as a white solid.

13K. N-[[4-(3-amino-1H-pyrazol-5-yl)-3-methoxy-phenyl]methyl]cyclopropane carboxamide A stirred mixture of N-[[4-(2-cyanoacetyl)-3-methoxy-phenyl]methyl]cyclopropanecarboxamide (0.5 g, 1.8 mmol) and hydrazine hydrate (98% in water, 0.11 g, 2.20 mmol) in EtOH (10 mL) was heated to reflux for 18 hours. The solvents were evaporated under reduced pressure to leave a solid which was recrystallized from EtOH to give the title compound (0.35 g, 67%) as a white solid.

13L. tert-Butyl 3-amino-5-[4-[(cyclopropanecarbonylamino)methyl]-2-methoxy-phenyl]pyrazole-1-carboxylate A solution of N-[[4-(3-amino-1H-pyrazol-5-yl)-3-methoxy-phenyl]methyl]cyclopropane carboxamide (0.5 g, 1.70 mmol) in a mixture of dry DMF (12 mL) and dry THF (18 mL) was added dropwise to a stirred suspension of sodium hydride (0.07 g, 1.70 mmol) in dry THF (12 mL) at 0° C. under a nitrogen atmosphere. The mixture was stirred for 30 minutes at 0° C. then a solution of $Boc_2O$ (0.37 g, 1.70 mmol) in dry THF (10 mL) was added dropwise maintaining the temperature at 0° C. The reaction mixture was allowed to warm to room temperature and stirring continued for 1.5 hours. The solution was poured into ice-water (100 mL) and extracted with EtOAc (3×100 mL). The combined organic extracts were washed with brine (50 mL), dried ($Na_2SO_4$) and evaporated under reduced pressure to leave a residue which was purified by column chromatography on neutral silica gel using 2% MeOH/DCM as the eluent to give the title compound (0.37 g, 55%) as an off-white solid.

13M. N-[[4-[3-[(5-cyanopyrazin-2-yl)amino]-1H-pyrazol-5-yl]-3-methoxy-phenyl]methyl]cyclopropanecarboxamide A solution of tert-butyl 3-amino-5-[4-[(cyclopropanecarbonylamino)methyl]-2-methoxy-phenyl]pyrazole-1-carboxylate (185 mg, 4.80 mmol) in a mixture of dry THF (2 mL) and dry DMF (1 mL) was added dropwise to a stirred suspension of sodium hydride (38 mg, 9.6 mmol) in THF (2 mL) at 0° C. under a nitrogen atmosphere. The mixture was stirred for 10 minutes then a solution of 5-bromopyrazine-2-carbonitrile (88 mg, 4.80 mmol) in dry THF (1 mL) was added dropwise maintaining the temperature at 0° C. The mixture was allowed to slowly warm to room temperature and stirring continued for 2 hours. After pouring into ice-water (20 mL) the mixture was extracted with EtOAc (5×25 mL) then the combined organic extracts were washed with brine (20 mL), dried ($Na_2SO_4$) and evaporated under reduced pressure. The residue was dissolved in 4N HCl in EtOAc (10 mL) and stirred for 30 mins then the solvents were evaporated under reduced pressure to leave a residue which was purified by preparative HPLC to give the title compound (41 mg, 31%) as an off-white solid.

Synthetic Route F

Illustrated with Reference to Example 14

Example 14

5-[[5-[2-Methoxy-4-[(tetrahydropyran-4-ylamino)methyl]phenyl]-1H-pyrazol-3-yl]amino]pyrazine-2-carbonitrile hydrochloride)

14A. Methyl 4-formyl-2-methoxy-benzoate

Dess-Martin periodinane (81.2 g, 191 mmol) was added in portions to a stirred solution of methyl 4-(hydroxymethyl)-2-methoxy-benzoate (25.0 g, 128 mmol) in DCM (375 mL) under a nitrogen atmosphere. The solution was stirred for one hour then filtered through a pad of celite washing with DCM (100 mL). The filtrate was evaporated under reduced pressure to leave a residue which was purified by column chromatography on neutral silica gel using 10% EtOAc/hexane as the eluent to give the title compound (23.5 g, 95%).

14B. Methyl 2-methoxy-4-[(tetrahydropyran-4-ylamino)methyl]benzoate

Sodium methoxide (0.83 g, 15.4 mmol) was added to a stirred solution of tetrahydro-2H-pyran-4-amine hydrochloride (2.12 g, 15.4 mmol) in MeOH (35 mL) at room temperature under a nitrogen atmosphere and the mixture stirred for 30 minutes. The solution was passed through a Millipore filter and the resulting clear solution added to a stirred solution of methyl 4-formyl-2-methoxy-benzoate (3.0 g, 15.4 mmol) in MeOH (35 mL). Glacial acetic acid (1.8 mL, 30.8 mmol) was added and the mixture stirred for one hour then the solution was cooled to 0° C. and sodium triacetoxyborohydride (9.79 g, 4.62 mmol) was added in portions over 15 minutes. The mixture was allowed to warm to room temperature and stirring continued for 18 hours before partitioning between saturated $NaHCO_3$ solution (200 mL) and EtOAC (200 mL). The separated aqueous phase was extracted with EtOAc (2×200 mL) then the combined organic extracts were washed with brine (75 mL), dried ($Na_2SO_4$) and evaporated under reduced pressure. The residue was purified by column chromatography on neutral silica gel using 2% MeOH/DCM as the eluent to give the title compound (3.1 g, 72%).

14C. Methyl 4-[[tert-butoxycarbonyl(tetrahydropyran-4-yl)amino]methyl]-2-methoxy-benzoate $Boc_2O$ (1.83 g, 8.40 mmol) was added to a stirred solution of methyl 2-methoxy-4-[(tetrahydropyran-4-ylamino)methyl]benzoate (2.40 g, 7.60 mmol) and $Et_3N$ (2.15 g, 8.40 mmol) in DCM (60 mL) and the resulting mixture stirred at room temperature for 18 hours. The mixture was diluted DCM (200 mL), washed with 5% citric acid solution, water (2×50 mL), brine (20 mL), dried ($Na_2SO_4$) and evaporated under reduced pressure to give the title compound (3.1 g, 95%) which was used without further purification.

14D. tert-Butyl N-[[4-(2-cyanoacetyl)-3-methoxy-phenyl]methyl]-N-tetrahydropyran-4-yl-carbamate A solution of LiHMDS (1.0M in hexane, 23.1 mL, 23.1 mmol) was added dropwise over 20 minutes to a stirred solution of acetonitrile (1.35 g, 33.0 mmol) in dry THF (70 mL) at −78° C. under a nitrogen atmosphere. Stirring was continued for 30 minutes then a solution of methyl 4-[[tert-butoxycarbonyl(tetrahydropyran-4-yl)amino]methyl]-2-methoxy-benzoate (2.5 g, 6.6 mmol) in THF (140 mL) was added dropwise over 20 minutes maintaining the temperature at −78° C. The mixture was stirred at −78° C. for 30 minutes then allowed to warm to room temperature and stirring continued for one hour. The mixture was poured into cold saturated ammonium chloride solution (100 mL) and extracted with EtOAc (3×150 mL). The combined organic extracts were washed with brine (50 mL), dried ($Na_2SO_4$) and evaporated under reduced pressure to give the title compound (2.9 g, 100%) as a white solid.

14E. tert-Butyl N-[[4-(3-amino-1H-pyrazol-5-yl)-3-methoxy-phenyl]methyl]-N-tetrahydropyran-4-yl-carbamate A solution of tert-butyl N-[[4-(2-cyanoacetyl)-3-methoxy-phenyl]methyl]-N-tetrahydropyran-4-yl-carbamate (2.90 g, 7.5 mmol) and hydrazine hydrate (99% in water, 2.9 g, 9.0 mmol) in ethanol (60 mL) was heated to reflux for 18 hours. The mixture was allowed to cool to room temperature and the solvents evaporated under reduced pressure to leave a residue which was purified by column chromatography on neutral silica gel using 2-3% MeOH/$CHCl_3$ as the eluent to give the title compound (1.5 g, 50%).

14F. tert-Butyl N-[[4-[3-[(5-cyanopyrazin-2-yl)amino]-1H-pyrazol-5-yl]-3-methoxy-phenyl]methyl]-N-tetrahydropyran-4-yl-carbamate A stirred solution of tert-butyl N-[[4-(3-amino-1H-pyrazol-5-yl)-3-methoxy-phenyl]methyl]-N-tetrahydropyran-4-yl-carbamate (0.5 g, 1.2 mmol), diisopropylethylamine (0.63 mL, 3.6 mmol) and 5-bromopyrazine-2-carbonitrile (0.66 g, 3.6 mmol) in dry 1,4-dioxane (12 mL) was heated to 80° C. for 24 hours. After cooling to room temperature the reaction mixture was poured into ice-water (50 mL) and extracted with EtOAc (3×50 mL). The combined organic extracts were washed with brine (30 mL), dried ($Na_2SO_4$) and evaporated under reduced pressure to leave a residue which was purified by column chromatography on neutral silica gel using 1% MeOH/$CHCl_3$ as the eluent to give the title compound (0.39 g, 64%).

14G. 5-[[5-[2-Methoxy-4-[(tetrahydropyran-4-ylamino)methyl]phenyl]-1H-pyrazol-3-yl]amino]pyrazine-2-carbonitrile hydrochloride 4N HCl in dioxane (0.4 mL) was added to a stirred solution of tert-butyl N-[[4-[3-[(5-cyanopyrazin-2-yl)amino]-1H-pyrazol-5-yl]-3-methoxy-phenyl]methyl]-N-tetrahydropyran-4-yl-carbamate (0.09 g, 0.18 mmol) in dry dioxane (10 mL) and the resulting mixture stirred at room temperature for 4 hours. The solvents were evaporated under reduced pressure to leave a solid that was triturated with $Et_2O$ (3×10 mL) and dried to give the title compound (52 mg, 72%) as an off-white solid.

Synthetic Route G

Illustrated with Reference to Example 17

Example 17

5-[[5-[4-[1-[2-(Dimethylamino)acetyl]-4-piperidyl]-2-methoxy-phenyl]-1H-pyrazol-3-yl]amino]pyrazine-2-carbonitrile hydrochloride)

17A. tert-Butyl 4-[4-(2-cyanoacetyl)-3-methoxy-phenyl]-piperidine-1-carboxylate A solution of LiHMDS (1.0M in hexane, 90.0 mL, 90.0 mmol) was added dropwise over 20 minutes to a stirred solution of acetonitrile (5.3 g, 129 mmol) in dry THF (250 mL) at −78° C. under a nitrogen atmosphere. Stirring was continued for 30 minutes then a solution of methyl tert-butyl 4-(3-methoxy-4-methoxycarbonyl-phenyl)piperidine-1-carboxylate (Example 11B) (9.0 g, 25.8 mmol) in THF (250 mL) was added dropwise over 20 minutes maintaining the temperature at −78° C. The mixture was stirred at −78° C. for 30 minutes then allowed to warm to room temperature and stirring continued for one hour. The mixture was poured into cold saturated ammonium chloride solution (300 mL) and extracted with EtOAc (5×200 mL). The combined organic extracts were washed with brine (100 mL), dried ($Na_2SO_4$) and evaporated under reduced pressure to leave a residue which was purified by column chromatography on neutral silica gel using 40% EtOAc/hexane as the eluent to give the title compound (7.0 g, 76%) as a white solid.

17B. tert-Butyl 4-[4-(3-amino-1H-pyrazol-5-yl)-3-methoxy-phenyl]piperidine-1-carboxylate A solution of tert-butyl 4-[4-(2-cyanoacetyl)-3-methoxy-phenyl]piperidine-1-carboxylate (7.0 g, 19.5 mmol) and hydrazine hydrate (99% in water, 1.17 g, 23.4 mmol) in ethanol (150 mL) was heated to reflux for 18 hours. The mixture was allowed to cool to room temperature and the solvents evaporated under reduced pressure to leave a residue which was purified by column chromatography on neutral silica gel using 2% MeOH/$CHCl_3$ as the eluent to give the title compound (5.1 g, 70%).

17C. tert-Butyl 4-[4-[3-[(5-cyanopyrazin-2-yl)amino]-1H-pyrazol-5-yl]-3-methoxy-phenyl]piperidine-1-carboxylate A stirred solution of tert-butyl 4-[4-(3-amino-1H-pyrazol-5-yl)-3-methoxy-phenyl]piperidine-1-carboxylate (0.6 g, 1.6 mmol), diisopropylethylamine (0.84 mL, 4.8 mmol) and 5-bromopyrazine-2-carbonitrile (0.88 g, 4.8 mmol) in dry 1,4-dioxane (12 mL) was heated to 80° C. for 24 hours. After cooling to room temperature the reaction mixture was poured into ice-water (50 mL) and extracted with EtOAc (3×50 mL). The combined organic extracts were washed with brine (30 mL), dried ($Na_2SO_4$) and evaporated under reduced pressure to leave a residue which was purified by

17D. 5-[[5-[2-Methoxy-4-(4-piperidyl)phenyl]-1H-pyrazol-3-yl]amino]pyrazine-2-carbonitrile 4N HCl in dioxane (25 mL) was added to a stirred solution of tert-butyl 4-[4-[3-[(5-cyanopyrazin-2-yl)amino]-1H-pyrazol-5-yl]-3-methoxy-phenyl]piperidine-1-carboxylate (0.56 g, 0.98 mmol) in a mixture of dry dioxane (25 mL) and dry THF (25 mL) and the resulting mixture stirred at room temperature for 2 hours. The solvents were evaporated under reduced pressure to leave a solid that was triturated with EtOAc (3×10 mL) and dried to give the title compound (0.54 mg, 100%) as an off-white solid.

17E. 5-[[5-[4-[1-[2-(Dimethylamino)acetyl]-4-piperidyl]-2-methoxy-phenyl]-1H-pyrazol-3-yl]amino]pyrazine-2-carbonitrile hydrochloride 1-Ethyl-3-(3-dimethylaminopropyl)carbodiimide hydrochloride (0.20 g, 1.02 mmol) and hydroxybenzotriazole (12 mg, 0.09 mmol) were added to a stirred solution of 5-[[5-[2-methoxy-4-(4-piperidyl)phenyl]-1H-pyrazol-3-yl]amino]pyrazine-2-carbonitrile (0.35 g, 0.93 mmol) and N,N'-dimethylglycine (96 mg, 0.93 mmol) in DMF (4 mL) at room temperature under a nitrogen atmosphere. The mixture was stirred at room temperature for 5 hours then diluted with DCM (150 mL) and washed with saturated NaHCO$_3$ solution (3×75 mL), brine (50 mL), dried (Na$_2$SO$_4$) and evaporated under reduced pressure. The residue was purified by column chromatography on neutral silica gel using 7% MeOH/DCM as the eluent. The resulting solid was dissolved in a mixture of MeOH (4 mL) and MeCN (8 mL) and a solution of 4N HCl in dioxane (0.2 mL) was added and the resulting mixture stirred for 30 minutes. The solvents were evaporated under reduced pressure to leave a solid that was triturated with EtOAc (3×10 mL) and dried to give the title compound (0.24 g, 54%) as an off-white solid.

Synthetic Route H

Illustrated with Reference to Example 60

Example 60

5-[[5-[4-(1-ethyl-4-piperidyl)-2-methoxy-phenyl]-1H-pyrazol-3-yl]amino]pyrazine-2-carbonitrile hydrochloride)

Diisopropylethylamine (0.25 mL, 1.46 mmol) was added to a stirred suspension of 5-[[5-[2-methoxy-4-(4-piperidyl)phenyl]-1H-pyrazol-3-yl]amino]pyrazine-2-carbonitrile hydrochloride (prepared using Synthetic Route G) (0.3 g, 0.73 mmol) in a mixture of MeOH (10 mL) and MeCN (20 mL) and the mixture stirred for 20 minutes at room temperature under a nitrogen atmosphere. Acetaldehyde (0.1 g, 2.19 mmol) was added and the mixture stirred for a further 20 minutes then the mixture was cooled to 0° C. and NaBH(OAc)$_3$ (0.50 g, 2.34 mmol) was added in portions over 10 minutes. The mixture was allowed to warm to room temperature and stirred for a further hour then poured into ice-water (30 mL) and solid NaHCO$_3$ was added to adjust the pH of the solution to 8. The mixture was extracted with EtOAc (4×50 mL) and the combined organic extracts were washed with brine (20 mL), dried (Na$_2$SO$_4$) and evaporated under reduced pressure. The residue was purified by column chromatography on neutral silica gel using 9% MeOH/DCM as the eluent. The resulting solid was dissolved in a mixture of THF (4 mL) and MeCN (4 mL) and a solution of 4N HCl in dioxane (1 mL) was added and the resulting mixture stirred for one hour. The solvents were evaporated under reduced pressure to leave a solid that was triturated with EtOAc (3×10 mL) and dried to give the title compound (71 mg, 29%) as an off-white solid.

Synthetic Route I

Illustrated with Reference to Example 22

Example 22

5-[[5-[2-methoxy-4-(4-methylpiperazin-1-yl)phenyl]-1H-pyrazol-3-yl]amino]pyrazine-2-carbonitrile hydrochloride)

22A. Methyl 4-fluoro-2-methoxy-benzoate

Potassium carbonate (15.5 g, 112 mmol) was added to a stirred solution of 4-fluoro-2-hydroxy-benzoic acid (5.0 g, 32.1 mmol) in acetone (100 mL) and the mixture heated to 40° C. under a nitrogen atmosphere for 20 minutes. Methyl iodide (15.8 g, 112 mmol) was added dropwise and then the mixture heated to reflux for 20 hours then allowed to cool to room temperature. The mixture was filtered through celite and the filtrate concentrated under reduced pressure to give the title compound (5.9 g, 100%) which was used without further purification.

22B. tert-Butyl 4-(3-methoxy-4-methoxycarbonyl-phenyl)piperazine-1-carboxylate Potassium carbonate (1.49 g, 10.8 mmol) was added to a stirred solution of methyl 4-fluoro-2-methoxy-benzoate (1.0 g, 5.4 mmol) in DMSO (10 mL) and the mixture stirred at room temperature under a nitrogen atmosphere for 20 minutes. N-Boc piperazine (2.01 g, 10.8 mmol) was added and then the mixture heated to 80° C. for 18 hours. The cooled mixture was poured into ice-water (100 mL) and extracted with EtOAc (5×150 mL). The combined organic extracts were washed with brine (100 mL), dried (Na$_2$SO$_4$) and evaporated under reduced pressure to leave a residue which was purified by column chromatography on neutral silica gel using 45% EtOAc/hexane as the eluent to give the title compound (4.6 g, 41%) as a white solid.

22C. tert-Butyl 4-[4-(2-cyanoacetyl)-3-methoxy-phenyl]piperazine-1-carboxylate A solution of LiHMDS (1.0M in hexane, 46.0 mL, 46.0 mmol) was added dropwise over 40 minutes to a stirred solution of acetonitrile (2.69 g, 65.5 mmol) in dry THF (100 mL) at −78° C. under a nitrogen atmosphere. Stirring was continued for 30 minutes then a solution of tert-butyl 4-(3-methoxy-4-methoxycarbonyl-phenyl)piperazine-1-carboxylate (4.6 g, 13.1 mmol) in THF (100 mL) was added dropwise over 20 minutes maintaining the temperature at −78° C. The mixture was stirred at −78° C. for 30 minutes then allowed to warm to room temperature and stirring continued for one hour. The mixture was poured into cold saturated ammonium chloride solution (150 mL) and extracted with EtOAc (5×100 mL). The combined organic extracts were washed with brine (50 mL), dried (Na$_2$SO$_4$)

and evaporated under reduced pressure to leave the title compound (5.3 g, 100%) which was used without further purification.

22D. tert-Butyl 4-[4-(3-amino-1H-pyrazol-5-yl)-3-methoxy-phenyl]piperazine-1-carboxylate A solution of tert-butyl 4-[4-(2-cyanoacetyl)-3-methoxy-phenyl]piperazine-1-carboxylate (5.3 g, 14.8 mmol) and hydrazine hydrate (99% in water, 2.96 g, 59.2 mmol) in ethanol (120 mL) was heated to reflux for 18 hours. The mixture was allowed to cool to room temperature and the solvents evaporated under reduced pressure to leave a residue which was purified by column chromatography on neutral silica gel using 2% MeOH/CHCl$_3$ as the eluent to give the title compound (2.0 g, 36%).

22E. tert-Butyl 4-[4-[3-[(5-cyanopyrazin-2-yl)amino]-1H-pyrazol-5-yl]-3-methoxy-phenyl]piperazine-1-carboxylate A stirred solution of tert-butyl 4-[4-(3-amino-1H-pyrazol-5-yl)-3-methoxy-phenyl]piperazine-1-carboxylate (0.5 g, 1.3 mmol), diisopropylethylamine (0.70 mL, 3.9 mmol) and 5-bromopyrazine-2-carbonitrile (0.71 g, 3.9 mmol) in dry 1,4-dioxane (5 mL) was heated to 80° C. for 4 hours. After cooling to room temperature the reaction mixture was poured into ice-water (50 mL) and extracted with EtOAc (3×100 mL). The combined organic extracts were washed with brine (30 mL), dried (Na$_2$SO$_4$) and evaporated under reduced pressure to leave a residue which was purified by column chromatography on neutral silica gel using 1.5% MeOH/DCM as the eluent to give the title compound (0.32 g, 50%).

22F. 5-[[5-(2-Methoxy-4-piperazin-1-yl-phenyl)-1H-pyrazol-3-yl]amino]pyrazine-2-carbonitrile hydrochloride 4N HCl in dioxane (4 mL) was added to a stirred solution of tert-butyl 4-[4-[3-[(5-cyanopyrazin-2-yl)amino]-1H-pyrazol-5-yl]-3-methoxy-phenyl]piperazine-1-carboxylate (0.56 g, 0.98 mmol) in a mixture of dry MeCN (10 mL) and dry THF (10 mL) and the resulting mixture stirred at room temperature for 4 hours. The solvents were evaporated under reduced pressure to leave a solid that was triturated with n-pentane (3×10 mL) and Et$_2$O (3×10 mL) and dried to give the title compound (0.24 mg, 100%) as an off-white solid.

22G. 5-[[5-[2-Methoxy-4-(4-methylpiperazin-1-yl)phenyl]-1H-pyrazol-3-yl]amino]pyrazine-2-carbonitrile hydrochloride Diisopropylethylamine (0.12 mL, 0.68 mmol) was added to a stirred suspension of 5-[[5-(2-methoxy-4-piperazin-1-yl-phenyl)-1H-pyrazol-3-yl]amino]pyrazine-2-carbonitrile hydrochloride (0.14 g, 0.34 mmol) in a mixture of MeOH (2 mL) and MeCN (4 mL) and the mixture stirred for 20 minutes at room temperature under a nitrogen atmosphere. Formalin (37-41% w/v in water; 31 mg, 0.10 mmol) was added followed by the addition of glacial acetic acid (0.04 mL, 0.68 mmol) and the mixture stirred for a further 20 minutes then the mixture was cooled to 0° C. and NaBH(OAc)$_3$ (0.22 g, 1.02 mmol) was added in portions over 10 minutes. The mixture was allowed to warm to room temperature and stirred for a further hour then poured into ice-water (30 mL) and solid NaHCO$_3$ was added to adjust the pH of the solution to 8. The mixture was extracted with EtOAc (4×30 mL) and the combined organic extracts were washed with brine (20 mL), dried (Na$_2$SO$_4$) and evaporated under reduced pressure. The residue was triturated with EtOAc (3×5 mL) and dried to leave an off-white solid. The solid was dissolved in a mixture of THF (3 mL) and MeCN (3 mL) then a solution of 4N HCl in dioxane (0.5 mL) was added and the resulting mixture stirred for one hour. The solvents were evaporated under reduced pressure to leave a solid that was triturated with n-pentane (3×10 mL) and dried to give the title compound (35 mg, 24%) as an off-white solid.

Synthetic Route J

Illustrated with Reference to Example 24

Example 24

5-[[5-[2-methoxy-4-(1-methyl-4-piperidyl)phenyl]-1H-pyrazol-3-yl]amino]pyridine-2-carbonitrile hydrochloride)

24A. tert-Butyl 4-[4-[3-[(6-cyano-3-pyridyl)amino]-1H-pyrazol-5-yl]-3-methoxy-phenyl]piperidine-1-carboxylate A stirred suspension of tert-butyl 4-[4-(3-amino-1H-pyrazol-5-yl)-3-methoxy-phenyl]piperidine-1-carboxylate (Example 17B) (1.0 g, 2.7 mmol), 5-bromo-2-cyanopyridine (0.59 g, 3.2 mmol), cesium carbonate (1.75 g, 5.4 mmol) and (±)-BINAP (0.125 g, 0.2 mmol) in dry dioxane (10 mL) was degassed with nitrogen for 30 minutes at room temperature. Tris(dibenzylideneacetone)dipalladium(O) (0.183 g, 0.2 mmol) was added and the resulting mixture heated to 100° C. for 5 hours. After cooling to room temperature the reaction mixture was poured into ice-water (20 mL) and extracted with EtOAc (3×50 mL). The combined organic extracts were washed with brine (20 mL), dried (Na$_2$SO$_4$) and evaporated under reduced pressure to leave a residue which was purified by column chromatography on neutral silica gel using 3% MeOH/CHCl$_3$ as the eluent to give the title compound (0.40 g, 31%).

24B. 5-[[5-[2-Methoxy-4-(4-piperidyl)phenyl]-1H-pyrazol-3-yl]amino]pyridine-2-carbonitrile hydrochloride 4N HCl in dioxane (10 mL) was added to a stirred solution of tert-butyl 4-[4-[3-[(6-cyano-3-pyridyl)amino]-1H-pyrazol-5-yl]-3-methoxy-phenyl]piperidine-1-carboxylate (0.40 g, 0.89 mmol) in a mixture of dry MeCN (10 mL) and dry THF (10 mL) and the resulting mixture stirred at room temperature for one hour. The solvents were evaporated under reduced pressure to leave a solid that was triturated with Et$_2$O (3×10 mL) and dried to give the title compound (0.38 mg, 100%) as an off-white solid.

24C. 5-[[5-[2-methoxy-4-(1-methyl-4-piperidyl)phenyl]-1H-pyrazol-3-yl]amino]pyridine-2-carbonitrile hydrochloride Diisopropylethylamine (0.23 mL, 1.30 mmol) was added to a stirred suspension of 5-[[5-[2-methoxy-4-(4-piperidyl)phenyl]-1H-pyrazol-3-yl]amino]pyridine-2-carbonitrile hydrochloride (0.27 g, 0.65 mmol) in a mixture of MeOH (4 mL) and MeCN (16 mL) and the mixture stirred for 20 minutes at room temperature under a nitrogen atmosphere. Formalin (37-41% w/v in water; 0.1 mL, 1.3 mmol) was added followed by the addition of glacial acetic acid (0.08 mL, 1.30 mmol) and the mixture stirred for a further 20 minutes then the mixture was cooled to 0° C. and NaBH(OAc)$_3$ (0.44 g, 2.08 mmol) was added in portions over 10 minutes. The mixture was allowed to warm to room temperature and stirred for a further hour then poured into ice-water (30 mL) and solid NaHCO$_3$ was added to adjust the pH of the solution to 8. The mixture was extracted with EtOAc (3×50 mL) and the combined organic extracts were washed with brine (20 mL), dried (Na$_2$SO$_4$) and evaporated under reduced pressure. The residue was purified by column chromatography on neutral silica gel using 9% MeOH/CHCl$_3$ as the eluent to leave an off-white solid. The solid was dissolved in a mixture of THF (10 mL) and MeCN (10 mL) then a solution of 4N HCl in dioxane (0.2 mL) was added and the resulting mixture stirred for one hour. The solvents were evaporated under reduced pressure to leave a solid that was triturated with Et$_2$O (3×10 mL) and dried to give the title compound (140 mg, 51%) as an off-white solid.

Synthetic Route K

Illustrated with Reference to Example 28

Example 28

5-[[5-[2-methoxy-4-[(1-methyl-4-piperidyl)oxy]phenyl]-1H-pyrazol-3-yl]amino]pyrazine-2-carbonitrile hydrochloride)

28A. 4-Hydroxy-2-methoxy-benzoic acid

Sodium dihydrogen phosphate (63.1 g, 526 mmol) and sodium chlorite (41.6 g, 460 mmol) were added to a stirred solution of 4-hydroxy-2-methoxy-benzaldehyde (20.0 g, 132 mmol) in a mixture of DMSO (400 mL) and water (300 mL) at 0° C. The mixture was allowed to warm to room temperature and stirring continued for 6 hours. The mixture was diluted with water (1000 mL) and solid NaHCO$_3$ was added to adjust the pH of the solution to 8. The solution was washed with EtOAc (1000 mL), the pH adjusted to 4 by the addition of 1N HCl solution and extracted with EtOAc (6×500 mL). The combined organic extracts were washed with brine (300 mL), dried (Na$_2$SO$_4$) and evaporated under reduced pressure to give the title compound (22.0 g, 100%) which was used without further purification.

28B. Methyl 4-hydroxy-2-methoxy-benzoate

Concentrated H$_2$SO$_4$ (52 mL) was added dropwise over 20 minutes to a stirred solution of 4-hydroxy-2-methoxy-benzoic acid (22.0 g, 131 mmol) in MeOH (520 mL) at room temperature. The mixture was heated to reflux for 2 hours then allowed to cool to room temperature and poured into ice-water (300 mL). The mixture was extracted with EtOAc (2×1000 mL) and the combined organic extracts dried (Na$_2$SO$_4$) and evaporated under reduced pressure. The residue was purified by column chromatography on neutral silica gel using 25% EtOAc/hexane as the eluent to give the title compound (12.0 g, 50%).

28C. tert-Butyl 4-(3-methoxy-4-methoxycarbonyl-phenoxy)piperidine-1-carboxylate

Diisopropyl azodicarboxylate (5.6 g, 27.5 mmol) was added to a stirred solution of methyl 4-hydroxy-2-methoxy-benzoate (2.0 g, 11.0 mmol), tert-butyl 4-hydroxypiperidine-1-carboxylate (6.6 g, 33 mmol) and triphenylphosphine (7.2 g, 27.5 mmol) in THF (100 mL) at 0-10° C. under a nitrogen atmosphere. The resulting mixture was sonicated at 40° C. for 2 hours then poured into ice-water (100 mL). The mixture was extracted with EtOAc (2×250 mL) and the combined organic extracts washed with brine (50 mL), dried (Na$_2$SO$_4$) and evaporated under reduced pressure. The residue was purified by column chromatography on neutral silica gel using 10% EtOAc/hexane as the eluent to give the title compound (4.80 g, 100%).

28D. tert-Butyl 4-[4-(2-cyanoacetyl)-3-methoxy-phenoxy]piperidine-1-carboxylate

A solution of LiHMDS (1.0 M in hexane, 92.0 mL, 92.0 mmol) was added dropwise over 40 minutes to a stirred solution of acetonitrile (5.4 g, 131 mmol) in dry THF (250 mL) at −78° C. under a nitrogen atmosphere. Stirring was continued for 30 minutes then a solution of tert-butyl 4-(3-methoxy-4-methoxycarbonyl-phenoxy)piperidine-1-carboxylate (4.8 g, 13.1 mmol) in THF (250 mL) was added dropwise over 20 minutes maintaining the temperature at −78° C. The mixture was stirred at −78° C. for 30 minutes then allowed to warm to room temperature and stirring continued for one hour. The mixture was poured into cold saturated ammonium chloride solution (150 mL) and extracted with EtOAc (3×200 mL). The combined organic extracts were washed with brine (50 mL), dried (Na$_2$SO$_4$) and evaporated under reduced pressure to leave the title compound (5.0 g, 100%) which was used without further purification.

28E. tert-Butyl 4-[4-(3-amino-1H-pyrazol-5-yl)-3-methoxy-phenoxy]piperidine-1-carboxylate A solution of tert-butyl 4-[4-(2-cyanoacetyl)-3-methoxy-phenoxy]piperidine-1-carboxylate (1.0 g, 2.7 mmol) and hydrazine hydrate (99% in water, 0.54 g, 10.0 mmol) in ethanol (20 mL) was heated to reflux for 16 hours. The mixture was allowed to cool to room temperature and the solvents evaporated under reduced pressure to leave a residue which was purified by column chromatography on neutral silica gel using 90% EtOAc/hexane as the eluent to give the title compound (0.2 g, 19%).

28F. tert-Butyl 4-[4-[3-[(5-cyanopyrazin-2-yl)amino]-1H-pyrazol-5-yl]-3-methoxy-phenoxy]piperidine-1-carboxylate A stirred solution of tert-butyl 4-[4-(3-amino-1H-pyrazol-5-yl)-3-methoxy-phenoxy]piperidine-1-carboxylate (1.0 g, 2.6 mmol), diisopropylethylamine (1.4 mL, 7.8 mmol) and 5-bromopyrazine-2-carbonitrile (1.43 g, 7.8 mmol) in dry 1,4-dioxane (10 mL) was heated to 80° C. for 24 hours. After cooling to room temperature the reaction mixture was poured into ice-water (50 mL) and extracted with EtOAc (3×50 mL). The combined organic extracts were washed with brine (30 mL), dried (Na$_2$SO$_4$) and evaporated under reduced pressure to leave a residue which was purified by column chromatography on neutral silica gel using 45% EtOAc/hexane as the eluent to give the title compound (0.21 g, 17%).

28G. 5-[[5-[2-Methoxy-4-(4-piperidyloxy)phenyl]-1H-pyrazol-3-yl]amino]pyrazine-2-carbonitrile hydrochloride 4N HCl in dioxane (6 mL) was added to a stirred solution of tert-butyl 4-[4-[3-[(5-cyanopyrazin-2-yl)amino]-1H- pyrazol-5-yl]-3-methoxy-phenoxy]piperidine-1-carboxylate (0.21 g, 0.50 mmol) in a mixture of dry MeCN (5 mL) and dry THF (5 mL) and the resulting mixture stirred at room temperature for 2 hours. The solvents were evaporated under reduced pressure to leave a solid that was triturated with EtOAc (3×2 mL) and MeOH (3×2 mL) and dried to give the title compound (0.20 g, 100%) as an off-white solid.

28H. 5-[[5-[2-Methoxy-4-[(1-methyl-4-piperidyl)oxy]phenyl]-1H-pyrazol-3-yl]amino]pyrazine-2-carbonitrile Diisopropylethylamine (0.16 mL, 0.94 mmol) was added to a stirred suspension of 5-[[5-[2-methoxy-4-(4-piperidyloxy)phenyl]-1H-pyrazol-3-yl]amino]pyrazine-2-carbonitrile hydrochloride (0.20 g, 0.47 mmol) in a mixture of MeOH (4 mL) and MeCN (8 mL) and the mixture stirred for 20 minutes at room temperature under a nitrogen atmosphere. Formalin (37-41% w/v in water; 0.08 mL, 0.94 mmol) was added followed by the addition of glacial acetic acid (0.05 mL, 1.50 mmol) and the mixture stirred for a further 20 minutes then the mixture was cooled to 0° C. and NaBH(OAc)$_3$ (0.32 g, 1.50 mmol) was added in portions over 10 minutes. The mixture was allowed to warm to room temperature and stirred for a further hour then poured into ice-water (30 mL) and solid NaHCO$_3$ was added to adjust the pH of the solution to 8. The mixture was extracted with EtOAc (4×50 mL) and the combined organic extracts were washed with brine (20 mL), dried (Na$_2$SO$_4$) and evaporated under reduced pressure. The residue was purified by column chromatography on neutral silica gel using 7% MeOH/CHCl$_3$ as the eluent to leave an off-white solid. The solid was dissolved in a mixture of THF (5 mL) and MeCN (5 mL) then a solution of 4N HCl in dioxane (0.5 mL) was added and the resulting mixture stirred for one hour. The solvents were evaporated under reduced pressure to leave a solid that was triturated with Et$_2$O (3×5 mL) and dried to give the title compound (68 mg, 69%) as an off-white solid.

Synthetic Route L

Illustrated with Reference to Example 64

Example 64

5-[[5-[4-(4-Fluoro-1-methyl-4-piperidyl)-2-methoxy-phenyl]-1H-pyrazol-3-yl]amino]pyrazine-2-carbonitrile hydrochloride)

64A. 2-(4-Bromo-2-methoxy-phenyl)-1,3-dioxolane

A mixture of 4-bromo-2-methoxy-benzaldehyde (25.0 g, 117 mmol), ethanediol (9.7 mL, 175 mmol) and p-toluenesulfonic acid (67 mg, 0.35 mmol) in toluene (250 mL) was heated to reflux under Dean-Stark conditions for 5 hours. The cooled solution was poured into saturated NaHCO$_3$ solution (100 mL) and the separated aqueous phase was extracted with EtOAc (3×100 mL). The combined organic extracts were washed with brine (50 mL), dried (Na$_2$SO$_4$) and evaporated under reduced pressure to leave a residue that was purified by column chromatography on neutral silica gel using 5% EtOAc/hexane as the eluent to give the title compound (6.8 g, 23%).

64B. tert-Butyl 4-[4-(1,3-dioxolan-2-yl)-3-methoxy-phenyl]-4-hydroxy-piperidine-1-carboxylate A solution of n-BuLi (1.6 M in hexane, 21.5 mL, 34.3 mmol) was added dropwise to a stirred solution of 2-(4-bromo-2-methoxy-phenyl)-1,3-dioxolane (6.8 g, 26.4 mmol) in dry THF (90 mL) at −78° C. under a nitrogen atmosphere. The mixture was stirred for 30 minutes then a solution of tert-butyl 4-oxopiperidine-1-carboxylate (5.26 g, 26.4 mmol) in THF (45 mL) was added dropwise maintaining the temperature at −78° C. The reaction mixture was allowed to slowly warm to room temperature and stirring continued for 12 hours. The mixture was poured into cold saturated ammonium chloride solution (100 mL) and extracted with EtOAc (3×100 mL). The combined organic extracts were washed with brine (50 mL), dried (Na$_2$SO$_4$) and evaporated under reduced pressure to leave a residue that was purified by column chromatography on neutral silica gel using 45% EtOAc/hexane as the eluent to give the title compound (2.9 g, 29%).

64C. tert-Butyl 4-fluoro-4-(4-formyl-3-methoxy-phenyl)-piperidine-1-carboxylate Diethylaminosulfur trifluoride (1.1 mL, 8.4 mmol) was added dropwise to a stirred solution of tert-butyl 4-[4-(1,3-dioxolan-2-yl)-3-methoxy-phenyl]-4-hydroxy-piperidine-1-carboxylate (2.9 g, 7.6 mmol) in DCM (10 mL) at −78° C. under a nitrogen atmosphere. The reaction mixture was allowed to warm to room temperature and stirring continued for 5 hours. The mixture was poured into saturated sodium carbonate solution (50 mL) and the separated aqueous phase extracted with DCM (3×50 mL). The combined organic extracts were washed with 1N citric acid solution (30 mL), dried (Na$_2$SO$_4$) and evaporated under reduced pressure to leave a residue that was purified by column chromatography on neutral silica gel using 10% EtOAc/hexane as the eluent to give the title compound (1.8 g, 70%).

64D. tert-Butyl 4-[4-(2-cyano-1-hydroxy-ethyl)-3-methoxy-phenyl]-4-fluoro-piperidine-1-carboxylate A solution of 2-bromoacetonitrile (1.1 g, 9.0 mmol) in dry THF (10 mL) was added to a stirred suspension of tert-butyl 4-fluoro-4-(4-formyl-3-methoxy-phenyl)-piperidine-1-carboxylate (1.8 g, 5.3 mmol) and zinc dust (0.69 g, 10.6 mmol) in dry THF (10 mL). The mixture was stirred for 30 minutes then poured into saturated ammonium chloride solution (100 mL) and extracted with EtOAc (3×50 mL). The combined organic extracts were washed with brine (50 mL), dried (Na$_2$SO$_4$) and evaporated under reduced pressure to leave a residue that was purified by column chromatography on neutral silica gel using 20% EtOAc/hexane as the eluent to give the title compound (1.7 g, 84%).

64E. tert-Butyl 4-[4-(2-cyanoacetyl)-3-methoxy-phenyl]-4-fluoro-piperidine-1-carboxylate Dess-Martin periodinane (2.29 g, 5.4 mmol) was added in portions to a stirred solution of tert-butyl 4-[4-(2-cyano-1-hydroxy-ethyl)-3-methoxy-phenyl]-4-fluoro-piperidine-1-carboxylate (1.7 g, 4.5 mmol) in DCM (50 mL) under a nitrogen atmosphere. The solution was stirred for 30 minutes then filtered through a pad of celite washing with DCM (50 mL). The filtrate was evaporated under reduced pressure to leave a residue which was purified by column chromatography on neutral silica gel using 15% EtOAc/hexane as the eluent to give the title compound (1.6 g, 95%).

64F. tert-Butyl 4-[4-(3-amino-1H-pyrazol-5-yl)-3-methoxy-phenyl]-4-fluoro-piperidine-1-carboxylate A solution of tert-butyl 4-[4-(2-cyanoacetyl)-3-methoxy-phenyl]-4-fluoro-piperidine-1-carboxylate (1.6 g, 4.3 mmol)

and hydrazine hydrate (99% in water, 0.33 g, 6.5 mmol) in ethanol (15 mL) was heated to reflux for 18 hours. The mixture was allowed to cool to room temperature and the solvents evaporated under reduced pressure to leave a residue which was purified by column chromatography on neutral silica gel using 75% EtOAc/hexane as the eluent to give the title compound (0.73 g, 44%).

64G. tert-Butyl 4-[4-[3-[(5-cyanopyrazin-2-yl) amino]-1H-pyrazol-5-yl]-3-methoxy-phenyl]-4-fluoro-piperidine-1-carboxylate A stirred solution of tert-butyl 4-[4-(3-amino-1H-pyrazol-5-yl)-3-methoxy-phenyl]-4-fluoro-piperidine-1-carboxylate (0.73 g, 1.9 mmol), diisopropylethylamine (1.0 mL, 5.7 mmol) and 5-bromopyrazine-2-carbonitrile (1.04 g, 5.7 mmol) in dry 1,4-dioxane (8 mL) was heated to 80° C. for 24 hours. After cooling to room temperature the reaction mixture was poured into ice-water (50 mL) and extracted with EtOAc (3×50 mL). The combined organic extracts were washed with brine (30 mL), dried ($Na_2SO_4$) and evaporated under reduced pressure to leave a residue which was purified by column chromatography on neutral silica gel using 4% MeOH/$CHCl_3$ as the eluent to give the title compound (0.52 g, 56%).

64H. 5-[[5-[4-(4-Fluoro-4-piperidyl)-2-methoxy-phenyl]-1H-pyrazol-3-yl]amino]pyrazine-2-carbonitrile hydrochloride 4N HCl in dioxane (4 mL) was added to a stirred solution of tert-butyl 4-[4-[3-[(5-cyanopyrazin-2-yl)amino]-1H-pyrazol-5-yl]-3-methoxy-phenyl]-4-fluoro-piperidine-1-carboxylate (0.37 g, 0.75 mmol) in a mixture of dry MeCN (6 mL) and dry THF (10 mL) and the resulting mixture stirred at room temperature for 30 minutes. The solvents were evaporated under reduced pressure to leave a solid that was triturated with EtOAc (3×2 mL) and dried to give the title compound (0.30 g, 92%) as an off-white solid.

64I. 5-[[5-[4-(4-Fluoro-1-methyl-4-piperidyl)-2-methoxy-phenyl]-1H-pyrazol-3-yl]amino]pyrazine-2-carbonitrile hydrochloride Diisopropylethylamine (0.08 mL, 0.46 mmol) was added to a stirred suspension of 5-[[5-[4-(4-fluoro-4-piperidyl)-2-methoxy-phenyl]-1H-pyrazol-3-yl]amino]pyrazine-2-carbonitrile hydrochloride (0.10 g, 0.23 mmol) in a mixture of MeOH (2 mL) and MeCN (8 mL) and the mixture stirred for 20 minutes at room temperature under a nitrogen atmosphere. Formalin (37-41% w/v in water; 0.014 g, 0.46 mmol) was added and the mixture stirred for a further 20 minutes then the mixture was cooled to 0° C. and NaBH(OAc)$_3$ (0.16 g, 0.74 mmol) was added in portions over 10 minutes. The mixture was allowed to warm to room temperature and stirred for a further hour then poured into ice-water (30 mL). The mixture was extracted with EtOAc (4×25 mL) and the combined organic extracts were washed with brine (20 mL), dried ($Na_2SO_4$) and evaporated under reduced pressure. The residue was purified by column chromatography on neutral silica gel using 8% MeOH/$CHCl_3$ as the eluent to leave an off-white solid. The solid was dissolved in a mixture of THF (5 mL) and MeCN (5 mL) and a solution of 4N HCl in dioxane (0.5 mL) was added and the resulting mixture stirred for one hour. The solvents were evaporated under reduced pressure to leave a solid that was triturated with $Et_2O$ (3×5 mL) and dried to give the title compound (80 mg, 45%) as an off-white solid.

Synthetic Route M

Illustrated with Reference to Example 87

Example 87

5-[[5-[4-(1-ethyl-3-fluoro-4-piperidyl)-2-methoxy-phenyl]-1H-pyrazol-3-yl]amino]pyrazine-2-carbonitrile hydrochloride)

87A. tert-Butyl 3-hydroxy-4-(3-methoxy-4-methoxycarbonyl-phenyl)piperidine-1-carboxylate Borane.DMS (3.3 mL, 34.5 mmol) was added to a stirred solution of tert-butyl 4-(3-methoxy-4-methoxycarbonyl-phenyl)-3,6-dihydro-2H-pyridine-1-carboxylate (Example 11A) (10 g, 28.8 mmol) in dry THF (100 mL) at 0° C. under a nitrogen atmosphere. The mixture was allowed to warm to room temperature and stirring continued for 6 hours before adding 3N sodium hydroxide solution (10.6 mL, 3.17 mmol) and hydrogen peroxide solution (30% in water, 11.8 mL, 104 mmol) at 0° C. The mixture was stirred at 50° C. for 15 hours then the cooled mixture poured into ice-water (100 mL). The mixture was extracted with EtOAc (3×150 mL) and the combined organic extracts were washed with brine (20 mL), dried ($Na_2SO_4$) and evaporated under reduced pressure. The residue was purified by column chromatography on neutral silica gel using 20% EtOAc/hexane as the eluent to give the title compound (7.8 g, 74%).

87B. tert-Butyl 3-fluoro-4-(3-methoxy-4-methoxy-carbonyl-phenyl)piperidine-1-carboxylate Diethylaminosulfur trifluoride (1.8 mL, 13.6 mmol) was added dropwise over 10 minutes to a stirred solution of tert-butyl 3-hydroxy-4-(3-methoxy-4-methoxycarbonyl-phenyl)piperidine-1-carboxylate (2.5 g, 6.8 mmol) in DCM (25 mL) at −78° C. under a nitrogen atmosphere. The reaction mixture was allowed to warm to room temperature and stirring continued for 2 hours. The mixture was poured into saturated sodium bicarbonate solution (100 mL) and the separated aqueous phase extracted with EtOAc (4×100 mL). The combined organic extracts were washed with 1N citric acid solution (30 mL), dried ($Na_2SO_4$) and evaporated under reduced pressure to leave a residue that was purified by column chromatography on neutral silica gel using 16% EtOAc/hexane as the eluent to give the title compound (1.8 g, 72%).

87C. tert-Butyl 4-[4-(2-cyanoacetyl)-3-methoxy-phenyl]-3-fluoro-piperidine-1-carboxylate A solution of LiHMDS (1.0 M in hexane, 18.9 mL, 18.9 mmol) was added dropwise over 30 minutes to a stirred solution of acetonitrile (1.1 g, 27.0 mmol) in dry THF (75 mL) at −78° C. under a nitrogen atmosphere. Stirring was continued for 30 minutes then a solution of tert-butyl 3-fluoro-4-(3-methoxy-4-methoxycarbonyl-phenyl)piperidine-1-carboxylate (2.0 g, 5.4 mmol) in THF (75 mL) was added dropwise over 20 minutes maintaining the temperature at −78° C. The mixture was stirred at −78° C. for 30 minutes then allowed to warm to room temperature and stirring continued for two hours. The mixture was poured into cold saturated ammonium chloride solution (100 mL)

and extracted with EtOAc (5×200 mL). The combined organic extracts were washed with brine (50 mL), dried (Na$_2$SO$_4$) and evaporated under reduced pressure to leave the title compound (2.3 g, 100%) which was used without further purification.

87D. tert-Butyl 4-[4-(3-amino-1H-pyrazol-5-yl)-3-methoxy-phenyl]-3-fluoro-piperidine-1-carboxylate A solution of tert-butyl 4-[4-(2-cyanoacetyl)-3-methoxy-phenyl]-3-fluoro-piperidine-1-carboxylate (0.6 g, 1.6 mmol) and hydrazine hydrate (99% in water, 0.12 g, 2.4 mmol) in ethanol (12 mL) was heated to reflux for 18 hours. The mixture was allowed to cool to room temperature and the solvents evaporated under reduced pressure to leave a residue which was purified by column chromatography on neutral silica gel using 80% EtOAc/hexane as the eluent to give the title compound (0.34 g, 54%).

87E. tert-Butyl 4-[4-[3-[(5-cyanopyrazin-2-yl)amino]-1H-pyrazol-5-yl]-3-methoxy-phenyl]-3-fluoro-piperidine-1-carboxylate A stirred solution of tert-butyl 4-[4-(3-amino-1H-pyrazol-5-yl)-3-methoxy-phenyl]-3-fluoro-piperidine-1-carboxylate (0.8 g, 2.1 mmol), diisopropylethylamine (1.1 mL, 6.3 mmol) and 5-bromopyrazine-2-carbonitrile (1.2 g, 6.3 mmol) in dry 1,4-dioxane (11 mL) was heated to 80° C. for 48 hours. After cooling to room temperature the reaction mixture was poured into ice-water (50 mL) and extracted with EtOAc (4×60 mL). The combined organic extracts were washed with brine (30 mL), dried (Na$_2$SO$_4$) and evaporated under reduced pressure to leave a residue which was purified by column chromatography on neutral silica gel using 70% EtOAc/hexane as the eluent to give the title compound (0.70 g, 69%).

87F. 5-[[5-[4-(3-fluoro-4-piperidyl)-2-methoxy-phenyl]-1H-pyrazol-3-yl]amino]pyrazine-2-carbonitrile hydrochloride 4N HCl in dioxane (4 mL) was added to a stirred solution of tert-butyl 4-[4-[3-[(5-cyanopyrazin-2-yl)amino]-1H-pyrazol-5-yl]-3-methoxy-phenyl]-3-fluoro-piperidine-1-carboxylate (0.70 g, 1.4 mmol) in a mixture of dry MeCN (16 mL) and dry THF (16 mL) and the resulting mixture stirred at room temperature for 3 hours. The solvents were evaporated under reduced pressure to leave a solid that was triturated with EtOAc (3×2 mL) and dried to give the title compound (0.30 g, 92%) as an off-white solid.

87G. 5-[[5-[4-(1-ethyl-3-fluoro-4-piperidyl)-2-methoxy-phenyl]-1H-pyrazol-3-yl]amino]pyrazine-2-carbonitrile hydrochloride Diisopropylethylamine (0.16 mL, 0.94 mmol) was added to a stirred suspension of 5-[[5-[4-(3-fluoro-4-piperidyl)-2-methoxy-phenyl]-1H-pyrazol-3-yl]amino]pyrazine-2-carbonitrile (0.20 g, 0.47 mmol) in a mixture of MeOH (2 mL) and MeCN (8 mL) and the mixture stirred for 20 minutes at room temperature under a nitrogen atmosphere. Acetaldehyde (0.05 mL, 0.94 mmol) was added and the mixture stirred for a further 20 minutes then the mixture was cooled to 0° C. and NaBH(OAc)$_3$ (0.32 g, 1.5 mmol) was added in portions over 10 minutes. The mixture was allowed to warm to room temperature and stirred for a further 30 minutes then poured into ice-water (30 mL) and solid NaHCO$_3$ was added to adjust the pH of the solution to 8. The mixture was extracted with EtOAc (4×50 mL) and the combined organic extracts were washed with brine (20 mL), dried (Na$_2$SO$_4$) and evaporated under reduced pressure. The residue was purified by column chromatography on neutral silica gel using 2% MeOH/CHCl$_3$ as the eluent. The resulting solid was dissolved in a mixture of THF (10 mL) and MeCN (10 mL) and a solution of 4N HCl in dioxane (1 mL) was added and the resulting mixture stirred for one hour. The solvents were evaporated under reduced pressure to leave a solid that was triturated with Et$_2$O (3×10 mL) and dried to give the title compound (75 mg, 35%) as a pale yellow solid.

Synthetic Route N

Illustrated with Reference to Example 97

Example 97

5-[[5-[4-(3,3-Difluoro-1-methyl-4-piperidyl)-2-methoxy-phenyl]-1H-pyrazol-3-yl]amino]pyrazine-2-carbonitrile hydrochloride)

97A. tert-Butyl 4-(3-methoxy-4-methoxycarbonyl-phenyl)-3-oxo-piperidine-1-carboxylate Dess-Martin periodinane (29.1 g, 68.5 mmol) was added in portions to a stirred solution of tert-butyl 3-hydroxy-4-(3-methoxy-4-methoxycarbonyl-phenyl)piperidine-1-carboxylate (Example 87A) (5.0 g, 13.7 mmol) in DCM (100 mL) under a nitrogen atmosphere. The solution was stirred for 30 minutes then filtered through a pad of celite washing with DCM (50 mL) and then solid NaHCO$_3$ was added to the filtrate to adjust the pH of the solution to 8. The mixture was extracted with EtOAc (3×100 mL) and the combined organic extracts were washed with brine (20 mL), dried (Na$_2$SO$_4$) and evaporated under reduced pressure to leave the title compound (4.9 g, 99%) which was used without further purification.

97B. tert-Butyl 3,3-difluoro-4-(3-methoxy-4-methoxycarbonyl-phenyl)piperidine-1-carboxylate Diethylaminosulfur trifluoride (5.4 mL, 40.5 mmol) was added dropwise over 10 minutes to a stirred solution of tert-butyl 4-(3-methoxy-4-methoxycarbonyl-phenyl)-3-oxo-piperidine-1-carboxylate (4.9 g, 13.5 mmol) in DCM (100 mL) at −78° C. under a nitrogen atmosphere. The reaction mixture was allowed to warm to room temperature and stirring continued for one hour. The mixture was poured into saturated sodium bicarbonate solution (100 mL) and the separated aqueous phase extracted with EtOAc (4×60 mL). The combined organic extracts were washed with 1N citric acid solution (30 mL), dried (Na$_2$SO$_4$) and evaporated under reduced pressure to leave a residue that was purified by column chromatography on neutral silica gel using 10% EtOAc/hexane as the eluent to give the title compound (2.6 g, 50%).

97C. tert-Butyl 4-[4-(2-cyanoacetyl)-3-methoxy-phenyl]-3,3-difluoro-piperidine-1-carboxylate A solution of LiHMDS (1.0 M in hexane, 22.8 mL, 22.8 mmol) was added dropwise over 30 minutes to a stirred solution of acetonitrile (1.33 g, 3.25 mmol) in dry THF (25 mL) at −78° C. under a nitrogen atmosphere. Stirring was continued for 30 minutes then a solution of tert-butyl 3,3-difluoro-4-(3-methoxy-4-methoxycarbonyl-phenyl)piperidine-1-carboxylate (2.5 g, 6.5 mmol) in THF (25 mL) was added dropwise over 20 minutes maintaining the temperature at −78° C. The mixture was stirred at −78° C. for 30 minutes then allowed to warm to room temperature and stirring continued for one hour. The mixture was poured into cold saturated ammonium chloride solution (100 mL) and extracted with EtOAc (3×50 mL). The combined organic extracts were washed with brine (50 mL), dried ($Na_2SO_4$) and evaporated under reduced pressure to leave the title compound (2.5 g, 98%) which was used without further purification.

97D. tert-Butyl 4-[4-(3-amino-1H-pyrazol-5-yl)-3-methoxy-phenyl]-3,3-difluoro-piperidine-1-carboxylate A solution of tert-butyl 4-[4-(2-cyanoacetyl)-3-methoxy-phenyl]-3,3-difluoro-piperidine-1-carboxylate (2.5 g, 6.3 mmol) and hydrazine hydrate (99% in water, 1.58 g, 31.5 mmol) in ethanol (50 mL) was heated to reflux for 15 hours. The mixture was allowed to cool to room temperature and the solvents evaporated under reduced pressure to leave a residue which was purified by column chromatography on neutral silica gel using 50% EtOAc/hexane as the eluent to give the title compound (1.8 g, 70%).

97E. tert-Butyl 4-[4-[3-[(5-cyanopyrazin-2-yl)amino]-1H-pyrazol-5-yl]-3-methoxy-phenyl]-3,3-difluoro-piperidine-1-carboxylate A stirred solution of tert-butyl 4-[4-(3-amino-1H-pyrazol-5-yl)-3-methoxy-phenyl]-3,3-difluoro-piperidine-1-carboxylate (0.5 g, 1.2 mmol), diisopropylethylamine (0.63 mL, 3.6 mmol) and 5-bromopyrazine-2-carbonitrile (0.66 g, 3.6 mmol) in dry 1,4-dioxane (10 mL) was heated to 80° C. for 24 hours. After cooling to room temperature the reaction mixture was poured into ice-water (50 mL) and extracted with EtOAc (3×50 mL). The combined organic extracts were washed with brine (30 mL), dried ($Na_2SO_4$) and evaporated under reduced pressure to leave a residue which was purified by column chromatography on neutral silica gel using 2% MeOH/DCM as the eluent to give the title compound (0.43 g, 69%).

97F. 5-[[5-[4-(3,3-difluoro-4-piperidyl)-2-methoxy-phenyl]-1H-pyrazol-3-yl]amino]pyrazine-2-carbonitrile hydrochloride 4N HCl in dioxane (4 mL) was added to a stirred solution of tert-butyl 4-[4-[3-[(5-cyanopyrazin-2-yl)amino]-1H-pyrazol-5-yl]-3-methoxy-phenyl]-3,3-difluoro-piperidine-1-carboxylate (0.70 g, 1.4 mmol) in a mixture of dry MeCN (16 mL) and dry THF (16 mL) and the resulting mixture stirred at room temperature for 1 hour. The solvents were evaporated under reduced pressure to leave a solid that was triturated with $Et_2O$ (3×5 mL) and dried to give the title compound (0.30 g, 92%) as an off-white solid.

97G. 5-[[5-[4-(3,3-Difluoro-1-methyl-4-piperidyl)-2-methoxy-phenyl]-1H-pyrazol-3-yl]amino]pyrazine-2-carbonitrile hydrochloride Diisopropylethylamine (0.12 mL, 0.66 mmol) was added to a stirred suspension of 5-[[5-[4-(3,3-difluoro-4-piperidyl)-2-methoxy-phenyl]-1H-pyrazol-3-yl]amino]pyrazine-2-carbonitrile hydrochloride (0.15 g, 0.33 mmol) in a mixture of MeOH (1.5 mL) and MeCN (6.5 mL) and the mixture stirred for 20 minutes at room temperature under a nitrogen atmosphere. Formalin (37-41% w/v in water; 0.05 mL, 1.06 mmol) was added and the mixture stirred for a further 20 minutes then the mixture was cooled to 0° C. and $NaBH(OAc)_3$ (0.22 g, 1.06 mmol) was added in portions over 10 minutes. The mixture was allowed to warm to room temperature and stirred for a further 20 minutes then poured into ice-water (30 mL). The mixture was extracted with EtOAc (3×25 mL) and the combined organic extracts were washed with brine (20 mL), dried ($Na_2SO_4$) and evaporated under reduced pressure. The residue was purified by column chromatography on neutral silica gel using 2% MeOH/DCM as the eluent to leave an off-white solid. The solid was dissolved in a mixture of THF (3 mL) and MeCN (3 mL) and a solution of 4N HCl in dioxane (1 mL) was added and the resulting mixture stirred for one hour. The solvents were evaporated under reduced pressure to leave a solid that was triturated with $Et_2O$ (3×5 mL) and dried to give the title compound (120 mg, 77%) as an off-white solid.

Synthetic Route O

Illustrated with Reference to Example 107

Example 107

5-[[5-[2-Methoxy-4-[(1-methyl-4-piperidyl)methyl-amino]phenyl]-1H-pyrazol-3-yl]amino]pyrazine-2-carbonitrile hydrochloride)

107A. tert-Butyl 4-[(3-methoxy-4-methoxycarbonyl-anilino)methyl]piperidine-1-carboxylate Nitrogen was bubbled through a stirred suspension of methyl 4-bromo-2-methoxybenzoate (4.0 g, 16.3 mmol), tert-butyl 4-(aminomethyl)piperidine-1-carboxylate (3.5 g, 16.3 mmol), cesium carbonate (10.6 g, 32.6 mmol) and xantphos (3.76 g, 6.5 mmol) in 1,4-dioxane (80 mL) for 20 minutes. $Pd_2(dba)_3$ (2.39 g, 2.6 mmol) was added and the resulting mixture heated to 80° C. for 6 hours. The cooled reaction mixture was poured into water (100 mL) and extracted with EtOAc (2×100 mL). The combined organic extracts were washed with brine (30 mL), dried ($Na_2SO_4$) and evaporated under reduced pressure to leave a residue which was purified by column chromatography on neutral silica gel using 30% EtOAc/hexanes as the eluent to give the title compound (4.5 g, 73%).

107B. tert-Butyl 4-[(N-tert-butoxycarbonyl-3-methoxy-4-methoxycarbonyl-anilino)methyl]piperidine-1-carboxylate A stirred solution of tert-butyl 4-[(3-methoxy-4-methoxycarbonyl-anilino)methyl]piperidine-1-carboxylate (1.15 g, 3.0 mmol), $Boc_2O$ (9.8 g, 4.5 mmol), diisopropylethylamine (2.6 mL, 1.5 mmol) and 4-dimethylaminopyridine (0.04 g, 0.3 mmol) in THF (5 mL) was heated to 75° C. for 18 hours. The cooled reaction mixture was poured into water (50 mL) and extracted with EtOAc (3×50 mL). The combined organic extracts were washed with brine (20 mL), dried ($Na_2SO_4$) and evaporated under reduced pressure to leave a residue which was purified by column chromatography on neutral silica gel using 20% EtOAc/hexanes as the eluent to give the title compound (2.6 g, 45%).

107C. tert-Butyl 4-[[N-tert-butoxycarbonyl-4-(2-cyanoacetyl)-3-methoxy-anilino]methyl]piperidine-1-carboxylate A solution of LiHMDS (1.0 M in hexane, 37.8 mL, 37.8 mmol) was added dropwise over 30 minutes to a stirred solution of acetonitrile (2.2 g, 5.40 mmol) in dry THF (100 mL) at −78° C. under a nitrogen atmosphere. Stirring was continued for 30 minutes then a solution of tert-butyl 4-[(N-tert-butoxycarbonyl-3-methoxy-4-methoxycarbonyl-anilino)methyl]piperidine-1-carboxylate (2.6 g, 5.4 mmol) in THF (100 mL) was added dropwise over 30 minutes maintaining the temperature at −78° C. The mixture was stirred at −78° C. for 30 minutes then allowed to warm to room temperature and stirring continued for 2 hours. The mixture was poured into cold saturated ammonium chloride solution (100 mL) and extracted with EtOAc (3×100 mL). The combined organic extracts were washed with brine (50 mL), dried ($Na_2SO_4$) and evaporated under reduced pressure to leave the title compound (2.7 g, 98%) which was used without further purification.

107D. tert-Butyl 4-[[4-(3-amino-1H-pyrazol-5-yl)-N-tert-butoxycarbonyl-3-methoxy-anilino]methyl]piperidine-1-carboxylate A solution of tert-butyl 4-[[N-tert-butoxycarbonyl-4-(2-cyanoacetyl)-3-methoxy-anilino]methyl]piperidine-1-carboxylate (1.0 g, 2.1 mmol) and hydrazine hydrate (99% in water, 0.42 g, 8.4 mmol) in ethanol (10 mL) was heated to reflux for 18 hours. The mixture was allowed to cool to room temperature and the solvents evaporated under reduced pressure to leave a residue which was purified by column chromatography on neutral silica gel using 1.5% MeOH/$CHCl_3$ as the eluent to give the title compound (0.33 g, 32%).

107E. tert-Butyl 4-[[N-tert-butoxycarbonyl-4-[3-[(5-cyanopyrazin-2-yl)amino]-1H-pyrazol-5-yl]-3-methoxy-anilino]methyl]piperidine-1-carboxylate A stirred solution of tert-butyl 4-[[4-(3-amino-1H-pyrazol-5-yl)-N-tert-butoxycarbonyl-3-methoxy-anilino]methyl]piperidine-1-carboxylate (0.7 g, 1.4 mmol), diisopropylethylamine (0.73 mL, 4.2 mmol) and 5-bromopyrazine-2-carbonitrile (0.77 g, 4.2 mmol) in dry 1,4-dioxane (10 mL) was heated to 80° C. for 48 hours. After cooling to room temperature the reaction mixture was poured into ice-water (50 mL) and extracted with EtOAc (3×50 mL). The combined organic extracts were washed with brine (30 mL), dried ($Na_2SO_4$) and evaporated under reduced pressure to leave a residue which was purified by column chromatography on neutral silica gel using 1% MeOH/DCM as the eluent to give the title compound (0.47 g, 57%).

107F. 5-[[5-[2-Methoxy-4-(4-piperidylmethylamino)phenyl]-1H-pyrazol-3-yl]amino]pyrazine-2-carbonitrile hydrochloride 4N HCl in dioxane (5 mL) was added to a stirred suspension of tert-butyl 4-[[N-tert-butoxycarbonyl-4-[3-[(5-cyanopyrazin-2-yl)amino]-1H-pyrazol-5-yl]-3-methoxy-anilino]methyl]piperidine-1-carboxylate (0.50 g, 0.83 mmol) in a mixture of dry MeCN (4 mL) and dry THF (4 mL) and the resulting mixture stirred at room temperature for 4 hours. The solvents were evaporated under reduced pressure to leave a solid that was triturated with $Et_2O$ (3×5 mL) and dried to give the title compound (0.44 g, 98%) as an off-white solid.

107G. 5-[[5-[2-Methoxy-4-[(1-methyl-4-piperidyl)methylamino]phenyl]-1H-pyrazol-3-yl]amino]pyrazine-2-carbonitrile hydrochloride Diisopropylethylamine (0.12 mL, 0.68 mmol) was added to a stirred suspension of 5-[[5-[2-methoxy-4-(4-piperidylmethylamino)phenyl]-1H-pyrazol-3-yl]amino]pyrazine-2-carbonitrile hydrochloride (0.15 g, 0.34 mmol) in a mixture of MeOH (3 mL) and MeCN (6 mL) and the mixture stirred for 20 minutes at room temperature under a nitrogen atmosphere. Formalin (37-41% w/v in water; 0.06 mL, 6.8 mmol) and glacial acetic acid (0.04 mL, 6.8 mmol) were added and the mixture stirred for a further 20 minutes then the mixture was cooled to 0° C. and $NaBH(OAc)_3$ (0.23 g, 1.09 mmol) was added in portions over 10 minutes. The mixture was allowed to warm to room temperature and stirred for a further 45 minutes then poured into ice-water (30 mL). The mixture was extracted with EtOAc (4×25 mL) and the combined organic extracts were washed with brine (20 mL), dried ($Na_2SO_4$) and evaporated under reduced pressure. The residue was purified by column chromatography on neutral silica gel using 16% MeOH/DCM as the eluent to leave an off-white solid. The solid was dissolved in a mixture of THF (4 mL) and MeCN (4 mL) and a solution of 4N HCl in dioxane (0.5 mL) was added and the resulting mixture stirred for one hour. The solvents were evaporated under reduced pressure to leave a solid that was triturated with a 1:1 mixture of n-pentane/$Et_2O$ (3×5 mL) and dried to give the title compound (60 mg, 39%) as an off-white solid.

Synthetic Route P

Illustrated with Reference to Example 117

Example 117

5-[[5-[2-Methoxy-4-[(2R)-4-methylmorpholin-2-yl]phenyl]-1H-pyrazol-3-yl]amino]pyrazine-2-carbonitrile hydrochloride)

117A. Methyl 2-methoxy-4-vinyl-benzoate

A stirred solution of methyl 4-bromo-2-methoxybenzoate (25.0 g, 103 mmol), potassium ethenyl(trifluoro)borate (17.8 g, 133 mmol), 1,1'-bis(diphenylphosphino)ferrocene dichloropalladium(II) dichloromethane complex (2.5 g, 3.1 mmol) and trimethylamine (14.3 mL, 103 mmol) in n-proponal (250 mL) was heated to reflux for 3 hours. The cooled reaction mixture was poured into water (100 mL) and extracted with EtOAc (3×100 mL). The combined organic extracts were washed with brine (50 mL), dried ($Na_2SO_4$) and evaporated under reduced pressure to leave a residue which was purified by column chromatography on neutral silica gel using 5% EtOAc/hexanes as the eluent to give the title compound (16.4 g, 83%).

117B. Methyl 4-[(1R)-1,2-dihydroxyethyl]-2-methoxy-benzoate

Methyl 2-methoxy-4-vinyl-benzoate (3.5 g, 18.2 mmol) was added to a stirred solution of AD-mix-β (22.0 g) in t-butanol (70 mL) and water (70 mL) at 0° C. and the resulting mixture allowed to warm to room temperature. The mixture was stirred for 3 hours then sodium sulfite (6.88 g, 54.6 mmol) was added and stirring continued for one hour. The mixture was extracted with EtOAc (3×100 mL) and the combined organic extracts were washed with brine (50 mL), dried ($Na_2SO_4$) and evaporated under reduced pressure to leave a solid. The solid was triturated using n-pentane (3×40 mL) and dried to give the title compound (3.5 g, 85%) as a white solid.

117C. Methyl 2-methoxy-4-[(2R)-oxiran-2-yl]benzoate

Chlorotrimethylsilane (15.7 mL, 124 mmol) was added dropwise to a stirred solution of methyl 4-[(1R)-1,2-dihydroxyethyl]-2-methoxy-benzoate (7.0 g, 31 mmol) and trimethylorthoacetate (15.6 mL, 124 mmol) in DCM (70 mL) at room temperature under a nitrogen atmosphere. The mixture was stirred for 90 minutes then the solvents were evaporated under reduced pressure. The residue was dissolved in MeOH (15 mL) and potassium carbonate (8.56 g, 62 mmol) was added and the resulting mixture stirred at room temperature under a nitrogen atmosphere for 3 hours. The solvents were evaporated under reduced pressure and the residue partitioned between water (100 mL) and EtOAc (100 mL). The separated aqueous phase was extracted with EtOAc (2×100 mL) then the combined organic extracts were washed with brine (30 mL), dried ($Na_2SO_4$) and evaporated under reduced pressure. The residue was purified by column chromatography on neutral silica gel using 23% EtOAc/hexanes as the eluent to give the title compound (5.6 g, 87%).

117D. Methyl 4-[(1R)-1-hydroxy-2-(2-hydroxyethylamino)ethyl]-2-methoxy-benzoate A stirred mixture of methyl 2-methoxy-4-[(2R)-oxiran-2-yl]benzoate (1.0 g, 4.8 mmol) and ethanolamine (2.6 mL, 43.2 mmoL) in THF (6 mL) was heated to 60° C. for 6 hours. The cooled reaction mixture was poured into water (20 mL) and extracted with a mixture of EtOAc and THF (1:1, 3×50 mL). The combined organic extracts were washed with brine (20 mL), dried ($Na_2SO_4$) and evaporated under reduced pressure to leave the title compound (0.9 g, 62%) which was used without further purification.

117E. Methyl 4-[(1R)-2-[tert-butoxycarbonyl(2-hydroxyethyl)amino]-1-hydroxy-ethyl]-2-methoxy-benzoate $Boc_2O$ (3.64 g, 16.7 mmol) was added to a stirred solution of methyl 4-[(1R)-1-hydroxy-2-(2-hydroxyethylamino)ethyl]-2-methoxy-benzoate (4.5 g, 16.7 mmol) and $Et_3N$ (3.5 mL, 25.1 mmol) in DCM (45 mL) and the resulting mixture stirred at room temperature for 3 hours. The reaction mixture was poured into water (50 mL) and the separated aqueous phase was extracted with DCM (3×50 mL). The combined organic extracts were washed with brine (50 mL), dried ($Na_2SO_4$) and evaporated under reduced pressure to leave a residue which was purified by column chromatography on neutral silica gel using 85% EtOAc/hexanes as the eluent to give the title compound (3.45 g, 56%).

117F. tert-Butyl (2R)-2-(3-methoxy-4-methoxycarbonyl-phenyl)morpholine-4-carboxylate Diethylazodicarboxylate (40% solution in toluene, 10.1 mL, 23.3 mmol) was added dropwise to a stirred solution of methyl 4-[(1R)-2-[tert-butoxycarbonyl(2-hydroxyethyl)amino]-1-hydroxy-ethyl]-2-methoxy-benzoate (3.45 g, 9.3 mmol) and triphenylphosphine (3.66 g, 14.0 mmol) in toluene (60 mL) at 0° c. under a nitrogen atmosphere. The mixture was allowed to warm to room temperature and stirring continued for 12 hours then poured into water (100 mL) and extracted with EtOAc (3×25 mL). The combined organic extracts were washed with brine (10 mL), dried ($Na_2SO_4$) and evaporated under reduced pressure to leave a residue which was purified by column chromatography on neutral silica gel using 32% EtOAc/hexanes as the eluent to give the title compound (1.85 g, 56%).

117G. tert-Butyl (2R)-2-[4-(2-cyanoacetyl)-3-methoxy-phenyl]morpholine-4-carboxylate A solution of LiHMDS (1.0M in hexane, 32.4 mL, 32.4 mmol) was added dropwise over 40 minutes to a stirred solution of acetonitrile (3.13 mL, 6.0 mmol) in dry THF (150 mL) at −78° C. under a nitrogen atmosphere. Stirring was continued for 30 minutes then a solution of tert-butyl (2R)-2-(3-methoxy-4-methoxycarbonyl-phenyl)morpholine-4-carboxylate (2.1 g, 6.0 mmol) in THF (150 mL) was added dropwise over 30 minutes maintaining the temperature at −78° C. The mixture was stirred at −78° C. for 30 minutes then allowed to warm to room temperature and stirring continued for 30 minutes. The mixture was poured into cold saturated ammonium chloride solution (100 mL) and extracted with EtOAc (3×50 mL). The combined organic extracts were washed with brine (50 mL), dried ($Na_2SO_4$) and evaporated under reduced pressure to leave the title compound (2.1 g, 98%) which was used without further purification.

117H. tert-Butyl (2R)-2-[4-(3-amino-1H-pyrazol-5-yl)-3-methoxy-phenyl]morpholine-4-carboxylate A solution of tert-butyl (2R)-2-[4-(2-cyanoacetyl)-3-methoxy-phenyl]morpholine-4-carboxylate (2.1 g, 5.8 mmol) and hydrazine hydrate (99% in water, 0.44 g, 8.7 mmol) in ethanol (20 mL) was heated to reflux for 12 hours. The mixture was allowed to cool to room temperature and the solvents evaporated under reduced pressure to leave a residue which was purified by column chromatography on neutral silica gel using 1.8% MeOH/$CHCl_3$ as the eluent to give the title compound (0.78 g, 36%).

117I. tert-Butyl (2R)-2-[4-[3-[(5-cyanopyrazin-2-yl)amino]-1H-pyrazol-5-yl]-3-methoxy-phenyl]morpholine-4-carboxylate A stirred mixture of tert-butyl (2R)-2-[4-(3-amino-1H-pyrazol-5-yl)-3-methoxy-phenyl]morpholine-4-carboxylate (0.78 g, 2.1 mmol), diisopropylethylamine (0.73 mL, 4.2 mmol), potassium iodide (0.18 g, 1.1 mmol) and 5-bromopyrazine-2-carbonitrile (1.04 g, 5.7 mmol) in dry 1,4-dioxane (10 mL) was heated to 80° C. for 18 hours. After cooling to room temperature the reaction mixture was poured into ice-water (50 mL) and extracted with EtOAc (3×50 mL). The combined organic extracts were washed with brine (30 mL), dried ($Na_2SO_4$) and evaporated under reduced pressure to leave a residue which was purified by column chromatography on neutral silica gel using 65% EtOAc/hexanes as the eluent to give the title compound (0.60 g, 61%).

117J. 5-[[5-[2-methoxy-4-[(2R)-morpholin-2-yl]phenyl]-1H-pyrazol-3-yl]amino]pyrazine-2-carbonitrile hydrochloride 4N HCl in dioxane (5 mL) was added to a stirred suspension of tert-butyl (2R)-2-[4-[3-[(5-cyanopyrazin-2-yl)amino]-1H-pyrazol-5-yl]-3-methoxy-phenyl]morpholine-4-carboxylate (0.6 g, 1.3 mmol) in a mixture of dry MeCN (5 mL) and dry THF (5 mL) and the resulting mixture stirred at room temperature for 3 hours. The solvents were evaporated under reduced pressure to leave a solid that was triturated with Et$_2$O (3×5 mL) and dried to give the title compound (0.51 g, 98%) as an off-white solid.

117K. 5-[[5-[2-methoxy-4-[(2R)-4-methylmorpholin-2-yl]phenyl]-1H-pyrazol-3-yl]amino]pyrazine-2-carbonitrile hydrochloride Diisopropylethylamine (0.17 mL, 0.98 mmol) was added to a stirred suspension of 5-[[5-[2-methoxy-4-[(2R)-morpholin-2-yl]phenyl]-1H-pyrazol-3-yl]amino]pyrazine-2-carbonitrile hydrochloride (0.16 g, 0.39 mmol) in a mixture of MeOH (5 mL) and MeCN (5 mL) and the mixture stirred for 20 minutes at room temperature under a nitrogen atmosphere. Formalin (37-41% w/v in water; 0.3 mL, 3.9 mmol) was added and the mixture stirred for a further 20 minutes then the mixture was cooled to 0° C. and NaBH(OAc)$_3$ (0.26 g, 1.25 mmol) was added in portions over 10 minutes. The mixture was allowed to warm to room temperature and stirred for a further 45 minutes then poured into ice-water (30 mL). The mixture was extracted with EtOAc (4×25 mL) and the combined organic extracts were washed with brine (20 mL), dried (Na$_2$SO$_4$) and evaporated under reduced pressure. The residue was triturated with n-pentane (3×10 mL) and dried. The solid was dissolved in a mixture of THF (3 mL) and MeCN (3 mL) and a solution of 4N HCl in dioxane (3 mL) was added and the resulting mixture stirred for 30 minutes. The solvents were evaporated under reduced pressure to leave a solid that was triturated with a 10% EtOAc/n-pentane/Et$_2$O (3×5 mL) and dried to leave the title compound (0.12 g, 73%) as a beige solid.

Synthetic Route Q

Illustrated with Reference to Example 123

Example 123

5-[[5-[4-[[(3R)-3-fluoropyrrolidin-1-yl]methyl]-2-methoxy-phenyl]-1H-pyrazol-3-yl]amino]pyrazine-2-carbonitrile hydrochloride)

123A. Methyl 4-[[tert-butyl(dimethyl)silyl]oxymethyl]-2-methoxy-benzoate

A solution of tert-butyldimethylsilyl chloride (9.99 g, 66.3 mmol) in DMF (20 mL) was added dropwise over a period of 15 minutes to a stirred solution of methyl 4-(hydroxymethyl)-2-methoxy-benzoate (5.0 g, 25.5 mmol) and imidazole (4.17 g, 61.2 mmol) in DMF (50 mL) at 0° C. The mixture was allowed to warm to room temperature and stirring continued for one hour then the mixture was poured into water (200 mL) and extracted with EtOAc (2×150 mL). The combined organic extracts were washed with brine (30 mL), dried (Na$_2$SO$_4$) and evaporated under reduced pressure to leave a residue which was purified by column chromatography on neutral silica gel using 4% EtOAc/hexane as the eluent to give the title compound (4.1 g, 52%).

123B. 3-[4-[[tert-Butyl(dimethyl)silyl]oxymethyl]-2-methoxy-phenyl]-3-oxo-propanenitrile A solution of LiHMDS (1.0M in hexane, 90 mL, 90.0 mmol) was added dropwise over 30 minutes to a stirred solution of acetonitrile (5.4 mL, 103 mmol) in dry THF (220 mL) at −78° C. under a nitrogen atmosphere. Stirring was continued for 30 minutes then a solution of methyl 4-[[tert-butyl(dimethyl)silyl]oxymethyl]-2-methoxy-benzoate (4.0 g, 12.9 mmol) in THF (220 mL) was added dropwise over 30 minutes maintaining the temperature at −78° C. The mixture was stirred at −78° C. for 30 minutes then allowed to warm to room temperature and stirring continued for one hour. The mixture was poured into cold saturated ammonium chloride solution (100 mL) and extracted with EtOAc (3×150 mL). The combined organic extracts were washed with brine (50 mL), dried (Na$_2$SO$_4$) and evaporated under reduced pressure to leave the title compound (4.8 g) which was used without further purification.

123C. 5-[4-[[tert-Butyl(dimethyl)silyl]oxymethyl]-2-methoxy-phenyl]-1H-pyrazol-3-amine A solution of 3-[4-[[tert-butyl(dimethyl)silyl]oxymethyl]-2-methoxy-phenyl]-3-oxo-propanenitrile (4.8 g, 13.3 mmol) and hydrazine hydrate (99% in water, 2.7 g, 53.2 mmol) in ethanol (180 mL) was heated to reflux for 16 hours. The mixture was allowed to cool to room temperature and the solvents evaporated under reduced pressure to leave a residue which was purified by column chromatography on neutral silica gel using 1.5% MeOH/CHCl$_3$ as the eluent to give the title compound (2.0 g, 40%).

123D. 5-[[5-[4-[[tert-Butyl(dimethyl)silyl]oxymethyl]-2-methoxy-phenyl]-1H-pyrazol-3-yl]amino]pyrazine-2-carbonitrile A stirred solution of 5-[4-[[tert-butyl(dimethyl)silyl]oxymethyl]-2-methoxy-phenyl]-1H-pyrazol-3-amine (0.6 g, 1.8 mmol), diisopropylethylamine (0.95 mL, 5.4 mmol) and 5-bromopyrazine-2-carbonitrile (0.99 g, 5.4 mmol) in dry 1,4-dioxane (7.5 mL) was heated to 80° C. for 20 hours. After cooling to room temperature the reaction mixture was poured into ice-water (50 mL) and extracted with EtOAc (2×100 mL). The combined organic extracts were washed with brine (30 mL), dried (Na$_2$SO$_4$) and evaporated under reduced pressure to leave a residue which was purified by column chromatography on neutral silica gel using 1.5% MeOH/DCM as the eluent to give the title compound (0.60 g, 76%).

123E. 5-[[5-[4-(Hydroxymethyl)-2-methoxy-phenyl]-1H-pyrazol-3-yl]amino]pyrazine-2-carbonitrile A solution of tetrabuytlammonium fluoride (1.0M in THF, 4.2 mL, 4.2 mmol) was added to a stirred solution of 5-[[5-[4-[[tert-butyl(dimethyl)silyl]oxymethyl]-2-methoxy-phenyl]-1H-pyrazol-3-yl]amino]pyrazine-2-carbonitrile (0.6 g, 1.4 mmol) in THF (12 mL) at 0° C. The resulting solution was allowed to warm to room temperature and stirring continued for one hour then the mixture was poured into water (40 mL) and extracted with EtOAc (2×100 mL). The combined organic extracts were washed with brine (10

123F. 5-[[5-(4-Formyl-2-methoxy-phenyl)-1H-pyrazol-3-yl]amino]pyrazine-2-carbonitrile Dess-Martin periodinane (3.69 g, 8.7 mmol) was added in portions to a stirred solution of 5-[[5-[4-(hydroxymethyl)-2-methoxy-phenyl]-1H-pyrazol-3-yl]amino]pyrazine-2-carbonitrile (0.92 g, 2.9 mmol) in THF (50 mL) under a nitrogen atmosphere. The solution was stirred for one hour then filtered through a pad of celite washing with THF (50 mL). The filtrate was evaporated under reduced pressure to leave a residue which was purified by column chromatography on neutral silica gel using 1.8% MeOH/CHCl$_3$ as the eluent to give the title compound (0.3 g, 33%).

123G. 5-[[5-[4-[[(3R)-3-fluoropyrrolidin-1-yl]methyl]-2-methoxy-phenyl]-1H-pyrazol-3-yl]amino]pyrazine-2-carbonitrile hydrochloride Diisopropylethylamine (0.16 mL, 0.94 mmol) was added to a stirred suspension of (3R)-3-fluoropyrrolidine hydrochloride (0.12 g, 0.94 mmol) in 1,2-dichloroethane (6 mL) and the mixture stirred for 20 minutes resulting in a colourless solution. 5-[[5-(4-Formyl-2-methoxy-phenyl)-1H-pyrazol-3-yl]amino]pyrazine-2-carbonitrile (0.15 g, 0.47 mmol) and glacial acetic acid (0.056 g, 0.94 mmol) were added and the mixture stirred for 30 minutes then cooled to 0° C. and NaBH(OAc)$_3$ (0.32 g, 1.5 mmol) was added in portions over 10 minutes. The mixture was allowed to warm to room temperature and stirred for a further 30 minutes then poured into ice-water (30 mL) and solid NaHCO$_3$ was added to adjust the pH of the solution to 8. The mixture was extracted with EtOAc (2×25 mL) and the combined organic extracts were washed with brine (20 mL), dried (Na$_2$SO$_4$) and evaporated under reduced pressure to leave a solid which was triturated with Et$_2$O (3×5 mL). The resulting solid was dissolved in a mixture of THF (1 mL) and MeCN (1 mL) and a solution of 4N HCl in dioxane (1 mL) was added and the resulting mixture stirred for 30 minutes. The solvents were evaporated under reduced pressure to leave a solid that was triturated with Et$_2$O (3×5 mL) and dried to give the title compound (76 mg, 38%) as an off-white solid.

Synthetic Route R

Illustrated with Reference to Example 140

Example 140

5-[[5-[4-[[(3R)-1-ethylpyrrolidin-3-yl]oxymethyl]-2-methoxy-phenyl]-1H-pyrazol-3-yl]amino]pyrazine-2-carbonitrile hydrochloride)

140A. tert-Butyl (3R)-3-[(3-methoxy-4-methoxycarbonyl-phenyl)methoxy]pyrrolidine-1-carboxylate A solution of tert-butyl (3R)-3-hydroxypyrrolidine-1-carboxylate (2.9 g, 15.5 mmoL) in DMF (8 mL) was added to a stirred slurry of sodium hydride (60% in mineral oil, 1.86 g, 4.65 mmol) in DMF (10 mL) at 0° C. under a nitrogen atmosphere and the resulting mixture stirred for 10 minutes. A solution of methyl 4-(bromomethyl)-2-methoxy-benzoate (4.0 g, 15.5 mmol) in DMF (7 mL) was added dropwise over 20 minutes maintaining the temperature at 0° C. The resulting mixture was allowed to warm to room temperature and stirring continued for 30 minutes before cooling back to 0° C. Methyl iodide (2.9 mL, 4.65 mmol) was added and the solution was allowed to warm to room temperature and stirring continued for one hour then the mixture was poured into ice cold water (100 mL) and extracted with EtOAc (3×100 mL). The combined organic extracts were washed with brine (10 mL), dried (Na$_2$SO$_4$) and evaporated under reduced pressure to leave a residue which was purified by column chromatography on neutral silica gel using 20% EtOAc/hexane as the eluent to give the title compound (4.3 g, 76%).

140B. tert-Butyl (3R)-3-[[4-(2-cyanoacetyl)-3-methoxy-phenyl]methoxy]pyrrolidine-1-carboxylate A solution of LiHMDS (1.0M in hexane, 42 mL, 42.0 mmol) was added dropwise over 20 minutes to a stirred solution of acetonitrile (3.2 mL, 60 mmol) in dry THF (50 mL) at −78° C. under a nitrogen atmosphere. Stirring was continued for 30 minutes then a solution of tert-butyl (3R)-3-[(3-methoxy-4-methoxycarbonyl-phenyl)methoxy]pyrrolidine-1-carboxylate (4.3 g, 12.0 mmol) in THF (50 mL) was added dropwise over 30 minutes maintaining the temperature at −78° C. The mixture was stirred at −78° C. for 30 minutes then allowed to warm to room temperature and stirring continued for one hour. The mixture was poured into cold saturated ammonium chloride solution (50 mL) and extracted with EtOAc (4×100 mL). The combined organic extracts were washed with brine (50 mL), dried (Na$_2$SO$_4$) and evaporated under reduced pressure to leave the title compound (4.4 g) which was used without further purification.

140C. tert-Butyl (3R)-3-[[4-(3-amino-1H-pyrazol-5-yl)-3-methoxy-phenyl]methoxy]pyrrolidine-1-carboxylate A solution of tert-butyl (3R)-3-[[4-(2-cyanoacetyl)-3-methoxy-phenyl]methoxy]pyrrolidine-1-carboxylate (4.4 g, 12.0 mmol) and hydrazine hydrate (99% in water, 1.2 g, 24.0 mmol) in ethanol (45 mL) was heated to reflux for 18 hours. The mixture was allowed to cool to room temperature and the solvents evaporated under reduced pressure to leave a residue which was purified by column chromatography on neutral silica gel using 3% MeOH/CHCl$_3$ as the eluent to give the title compound (2.6 g, 57%).

140D. tert-Butyl (3R)-3-[[4-[3-[(5-cyanopyrazin-2-yl)amino]-1H-pyrazol-5-yl]-3-methoxy-phenyl]methoxy]pyrrolidine-1-carboxylate A stirred solution of tert-butyl (3R)-3-[[4-(3-amino-1H-pyrazol-5-yl)-3-methoxy-phenyl]methoxy]pyrrolidine-1-carboxylate (1.0 g, 2.6 mmol), diisopropylethylamine (1.4 mL, 7.8 mmol) and 5-bromopyrazine-2-carbonitrile (1.43 g, 7.8 mmol) in dry 1,4-dioxane (20 mL) was heated to 80° C. for 48 hours. After cooling to room temperature the reaction mixture was poured into ice-water (50 mL) and extracted with EtOAc (4×50 mL). The combined organic extracts were washed with brine (30 mL), dried (Na$_2$SO$_4$) and evaporated under reduced pressure to leave a residue which was purified by column chromatography on neutral silica gel using 2% MeOH/DCM as the eluent to give the title compound (0.90 g, 71%).

140E. 5-[[5-[2-Methoxy-4-[[(3R)-pyrrolidin-3-yl]oxymethyl]phenyl]-1H-pyrazol-3-yl]amino]pyrazine-2-carbonitrile hydrochloride 4N HCl in dioxane (3 mL) was added to a stirred solution of tert-butyl (3R)-3-[[4-[3-[(5-cyanopyrazin-2-yl)amino]-1H-pyrazol-5-yl]-3-methoxy-phenyl]methoxy]pyrrolidine-1-carboxylate (0.90 g, 1.8 mmol) in a mixture of dry MeCN (10 mL) and dry THF (10 mL) and the resulting mixture stirred at room temperature for 3 hours. The solvents were evaporated under reduced pressure to leave a solid that was triturated with Et₂O (3×2 mL) followed by n-pentane (2×5 mL) and dried to give the title compound (0.8 g, 100%) as an off-white solid.

140F. 5-[[5-[4-[[(3R)-1-ethylpyrrolidin-3-yl]oxymethyl]-2-methoxy-phenyl]-1H-pyrazol-3-yl]amino]pyrazine-2-carbonitrile Diisopropylethylamine (0.08 mL, 0.46 mmol) was added to a stirred suspension of 5-[[5-[2-methoxy-4-[[(3R)-pyrrolidin-3-yl]oxymethyl]phenyl]-1H-pyrazol-3-yl]amino]pyrazine-2-carbonitrile hydrochloride (0.5 g, 1.2 mmol) in a mixture of MeOH (10 mL) and MeCN (15 mL) and the mixture stirred for 20 minutes at room temperature under a nitrogen atmosphere. Acetaldehyde (0.35 mL, 6.0 mmol) was added and the mixture stirred for a further 30 minutes then the mixture was cooled to 0° C. and NaBH(OAc)₃ (0.81 g, 3.8 mmol) was added in portions over 10 minutes. The mixture was allowed to warm to room temperature and stirred for a further 30 minutes then poured into ice-water (30 mL) and solid NaHCO₃ was added to adjust the pH to 8. The mixture was extracted with EtOAc (4×50 mL) and the combined organic extracts were washed with brine (20 mL), dried (Na₂SO₄) and evaporated under reduced pressure. The residue was purified by column chromatography on neutral silica gel using 10% MeOH/CHCl₃ as the eluent to leave a solid. The solid was dissolved in a mixture of THF (2 mL) and MeCN (2 mL) and a solution of 4N HCl in dioxane (0.5 mL) was added and the resulting mixture stirred for one hour. The solvents were evaporated under reduced pressure to leave a solid that was triturated with Et₂O (3×5 mL) and dried to give the title compound (66 mg, 12%) as an off-white solid.

Synthetic Route S

Illustrated with Reference to Example 143

Example 143

5-[[5-[4-[(1-Ethyl-4-piperidyl)methyl]-2-methoxy-phenyl]-1H-pyrazol-3-yl]amino]pyrazine-2-carbonitrile hydrochloride)

143A. Methyl 4-(diethoxyphosphorylmethyl)-2-methoxy-benzoate

A solution of methyl 4-(bromomethyl)-2-methoxy-benzoate (6.0 g, 23.3 mmol) in triethyl phosphite (12 mL) was heated to 100° C. in a sealed tube for 12 hours. The solution was allowed to cool to room temperature and evaporated under reduced pressure to leave the title compound (7.2 g, 98%) as a yellow solid which was used without further purification.

143B. tert-Butyl 4-[(3-methoxy-4-methoxycarbonyl-phenyl)methylene]piperidine-1-carboxylate A solution of methyl 4-(diethoxyphosphorylmethyl)-2-methoxy-benzoate (7.0 g, 22.1 mmol) in anhydrous THF (25 mL) was added dropwise over 10 minutes to a stirred slurry of sodium hydride (60% dispersion in oil, 2.65 g, 66.3 mmol) in anhydrous THF (50 mL) at 0° C. under a nitrogen atmosphere. The resulting mixture was stirred for 30 minutes then a solution of tert-butyl 4-oxopiperidine-1-carboxylate (4.4 g, 22.1 mmol) in THF (25 mL) was added dropwise over 10 minutes. The mixture was allowed to warm to room temperature and stirring continued for one hour then the mixture was poured into ice-water (100 mL) and extracted with EtOAc (4×100 mL). The combined organic extracts were washed with brine (10 mL), dried (Na₂SO₄) and evaporated under reduced pressure to leave the title compound (7.0 g, 91%) which was used without further purification.

143C. tert-Butyl 4-[(3-methoxy-4-methoxycarbonyl-phenyl)methyl]piperidine-1-carboxylate A suspension of tert-butyl 4-[(3-methoxy-4-methoxycarbonyl-phenyl)methylene]piperidine-1-carboxylate (7.0 g, 19.4 mmoL) and 10% Pd on carbon (1.6 g) in MeOH (140 mL) was stirred under a hydrogen atmosphere for 3 hours. The mixture was filtered through a pad of celite and evaporated under reduced pressure. The residue was purified by column chromatography on neutral silica gel using 30% EtOAc/hexane as the eluent to give the title compound (6.0 g, 85%).

143D. tert-butyl 4-[[4-(2-cyanoacetyl)-3-methoxy-phenyl]methyl]piperidine-1-carboxylate A solution of LiHMDS (1.0M in hexane, 29 mL, 29.0 mmol) was added dropwise over 20 minutes to a stirred solution of acetonitrile (2.2 mL, 41.5 mmol) in dry THF (30 mL) at −78° C. under a nitrogen atmosphere. Stirring was continued for 30 minutes then a solution of tert-butyl 4-[(3-methoxy-4-methoxycarbonyl-phenyl)methyl]piperidine-1-carboxylate (3.0 g, 8.3 mmol) in THF (30 mL) was added dropwise over 30 minutes maintaining the temperature at −78° C. The mixture was stirred at −78° C. for 30 minutes then allowed to warm to room temperature and stirring continued for 30 minutes. The mixture was poured into cold saturated ammonium chloride solution (50 mL) and extracted with EtOAc (3×100 mL). The combined organic extracts were washed with brine (50 mL), dried (Na₂SO₄) and evaporated under reduced pressure to leave the title compound (3.0 g, 98%) which was used without further purification.

143E. tert-Butyl 4-[[4-(3-amino-1H-pyrazol-5-yl)-3-methoxy-phenyl]methyl]piperidine-1-carboxylate A solution of tert-butyl 4-[[4-(2-cyanoacetyl)-3-methoxy-phenyl]methyl]piperidine-1-carboxylate (3.0 g, 8.1 mmol) and hydrazine hydrate (99% in water, 2.1 mL, 40.5 mmol) in ethanol (30 mL) was heated to reflux for 6 hours. The mixture was allowed to cool to room temperature and the solvents evaporated under reduced pressure to leave a residue which was purified by column chromatography on neutral silica gel using 2% MeOH/CHCl₃ as the eluent to give the title compound (1.3 g, 42%).

143F. tert-Butyl 4-[[4-[3-[(5-cyanopyrazin-2-yl) amino]-1H-pyrazol-5-yl]-3-methoxy-phenyl]methyl] piperidine-1-carboxylate A stirred solution of tert-butyl 4-[[4-(3-amino-1H-pyrazol-5-yl)-3-methoxy-phenyl]methyl]piperidine-1-carboxylate (1.0 g, 2.6 mmol), diisopropylethylamine (1.4 mL, 7.8 mmol) and 5-bromopyrazine-2-carbonitrile (1.43 g, 7.8 mmol) in dry 1,4-dioxane (10 mL) was heated to 80° C. for 15 hours. After cooling to room temperature the reaction mixture was poured into ice-water (50 mL) and extracted with EtOAc (2×100 mL). The combined organic extracts were washed with brine (30 mL), dried ($Na_2SO_4$) and evaporated under reduced pressure to leave a residue which was purified by column chromatography on neutral silica gel using 1.5% MeOH/DCM as the eluent to give the title compound (0.70 g, 55%).

143G. 5-[[5-[2-Methoxy-4-(4-piperidylmethyl)phenyl]-1H-pyrazol-3-yl]amino]pyrazine-2-carbonitrile hydrochloride 4N HCl in dioxane (5 mL) was added to a stirred solution of tert-butyl 4-[[4-[3-[(5-cyanopyrazin-2-yl)amino]-1H-pyrazol-5-yl]-3-methoxy-phenyl]methyl]piperidine-1-carboxylate (0.70 g, 1.4 mmol) in a mixture of dry MeCN (10 mL) and dry THF (10 mL) and the resulting mixture stirred at room temperature for 2 hours. The solvents were evaporated under reduced pressure to leave a solid that was triturated with $Et_2O$ (3×2 mL) and dried to give the title compound (0.6 g, 99%) as an off-white solid.

143H. 5-[[5-[4-[(1-ethyl-4-piperidyl)methyl]-2-methoxy-phenyl]-1H-pyrazol-3-yl]amino]pyrazine-2-carbonitrile hydrochloride Diisopropylethylamine (0.23 mL, 1.3 mmol) was added to a stirred suspension of 5-[[5-[2-methoxy-4-(4-piperidylmethyl)phenyl]-1H-pyrazol-3-yl]amino]pyrazine-2-carbonitrile hydrochloride (0.28 g, 0.65 mmol) in a mixture of MeOH (10 mL) and THF (10 mL) and the mixture stirred for 20 minutes at room temperature under a nitrogen atmosphere. Acetaldehyde (0.18 mL, 3.2 mmol) was added and the mixture stirred for a further 20 minutes then the mixture was cooled to 0° C. and $NaBH(OAc)_3$ (0.44 g, 2.08 mmol) was added in portions over 10 minutes. The mixture was allowed to warm to room temperature and stirred for a further 30 minutes then poured into ice-water (30 mL) and solid $NaHCO_3$ was added to adjust the pH of the solution to 8. The mixture was extracted with EtOAc (3×50 mL) and the combined organic extracts were washed with brine (20 mL), dried ($Na_2SO_4$) and evaporated under reduced pressure. The residue was purified by column chromatography on neutral silica gel using 9% MeOH/DCM as the eluent. The resulting solid was dissolved in a mixture of THF (10 mL) and MeCN (10 mL) and a solution of 4N HCl in dioxane (0.5 mL) was added and the resulting mixture stirred for 30 minutes. The solvents were evaporated under reduced pressure to leave a solid that was triturated with $Et_2O$ (3×10 mL) and dried to give the title compound (0.18 g, 60%) as a pale yellow solid.

Synthetic Route T

Illustrated with Reference to Example 149

Example 149

5-[[5-[4-[[(2R)-1-ethylpyrrolidin-2-yl]methyl]-2-methoxy-phenyl]-1H-pyrazol-3-yl]amino]pyrazine-2-carbonitrile hydrochloride)

149A. tert-Butyl (2R)-2-formylpyrrolidine-1-carboxylate

Dess-Martin periodinane (15.9 g, 37.4 mmol) was added in portions over 5 minutes to a stirred solution of tert-butyl (2R)-2-(hydroxymethyl)pyrrolidine-1-carboxylate (5.0 g, 24.9 mmol) in DCM (75 mL) under a nitrogen atmosphere. The resulting suspension was stirred for one hour then filtered through a pad of celite washing with DCM (100 mL). The filtrate was evaporated under reduced pressure to leave a residue which was purified by column chromatography on neutral silica gel using 12% EtOAc/hexanes as the eluent to give the title compound (4.4 g, 89%).

149B. tert-Butyl (2R)-2-[(E)-(p-tolylsulfonylhydrazono)methyl]pyrrolidine-1-carboxylate 4-Methylbenzenesulfonohydrazide (3.7 g, 22.1 mmol) was added to a stirred solution of tert-butyl (2R)-2-formylpyrrolidine-1-carboxylate (4.4 g, 22.1 mmol) in EtOH (45 mL) and the resulting solution was heated to 90° C. for 2 hours. The mixture was allowed to cool to room temperature and the solvents evaporated under reduced pressure to leave a solid that was recrystallized from EtOH to give the title compound (5.1 g, 63%).

149C. tert-Butyl (2R)-2-[(4-acetyl-3-methoxy-phenyl)methyl]pyrrolidine-1-carboxylate A mixture of tert-butyl (2R)-2-[(E)-(p-tolylsulfonylhydrazono)methyl]pyrrolidine-1-carboxylate (1.7 g, 4.6 mmol), (3-methoxy-4-methoxycarbonyl-phenyl)boronic acid (1.16 g, 5.5 mmol) and $K_2CO_3$ (0.95 g, 6.9 mmol) in 1,4-dioxane (45 mL) was stirred at 110° C. for 3 hours. The cooled reaction mixture was evaporated under reduced pressure to leave a residue which was purified by column chromatography on neutral silica gel using 13% EtOAc/hexanes as the eluent to give the title compound (1.4 g, 87%).

149D. tert-Butyl (2R)-2-[[4-(2-cyanoacetyl)-3-methoxy-phenyl]methyl]pyrrolidine-1-carboxylate A solution of LiHMDS (1.0M in hexane, 14 mL, 14.0 mmol) was added dropwise over 30 minutes to a stirred solution of acetonitrile (0.8 g, 20.0 mmol) in dry THF (70 mL) at −78° C. under a nitrogen atmosphere. Stirring was continued for 30 minutes then a solution of tert-butyl (2R)-2-[(4-acetyl-3-methoxy-phenyl)methyl]pyrrolidine-1-carboxylate (1.4 g, 4.0 mmol) in THF (70 mL) was added dropwise over 30 minutes maintaining the temperature at −78° C. The mixture was stirred at −78° C. for 30 minutes then allowed to warm to room temperature and stirring continued for 30 minutes. The mixture was poured into cold saturated ammonium chloride solution (50 mL) and extracted with EtOAc (4×100 mL). The combined organic extracts were washed with brine (50 mL), dried ($Na_2SO_4$)

149E. tert-Butyl (2R)-2-[[4-(3-amino-1H-pyrazol-5-yl)-3-methoxy-phenyl]methyl]pyrrolidine-1-carboxylate A solution of tert-butyl (2R)-2-[[4-(2-cyanoacetyl)-3-methoxy-phenyl]methyl]pyrrolidine-1-carboxylate (1.8 g, 5.2 mmol) and hydrazine hydrate (99% in water, 1.04 g, 20.8 mmol) in ethanol (20 mL) was heated to reflux for 16 hours. The mixture was allowed to cool to room temperature and the solvents evaporated under reduced pressure to leave a residue which was purified by column chromatography on neutral silica gel using 2% MeOH/CHCl$_3$ as the eluent to give the title compound (1.0 g, 52%).

149F. tert-Butyl (2R)-2-[[4-[3-[(5-cyanopyrazin-2-yl)amino]-1H-pyrazol-5-yl]-3-methoxy-phenyl]methyl]pyrrolidine-1-carboxylate A stirred solution of tert-butyl (2R)-2-[[4-(3-amino-1H-pyrazol-5-yl)-3-methoxy-phenyl]methyl]pyrrolidine-1-carboxylate (1.0 g, 2.7 mmol), diisopropylethylamine (1.4 mL, 8.1 mmol) and 5-bromopyrazine-2-carbonitrile (1.5 g, 8.1 mmol) in dry 1,4-dioxane (11 mL) was heated to 70° C. for 16 hours. After cooling to room temperature the reaction mixture was poured into ice-water (50 mL) and extracted with EtOAc (2×100 mL). The combined organic extracts were washed with brine (30 mL), dried (Na$_2$SO$_4$) and evaporated under reduced pressure to leave a residue which was purified by column chromatography on neutral silica gel using 45% EtOAc/hexanes as the eluent to give the title compound (0.70 g, 55%).

149G. 5-[[5-[2-Methoxy-4-[[(2R)-pyrrolidin-2-yl]methyl]phenyl]-1H-pyrazol-3-yl]amino]pyrazine-2-carbonitrile hydrochloride 4N HCl in dioxane (2 mL) was added to a stirred solution of tert-butyl (2R)-2-[[4-[3-[(5-cyanopyrazin-2-yl)amino]-1H-pyrazol-5-yl]-3-methoxy-phenyl]methyl]pyrrolidine-1-carboxylate (0.70 g, 1.4 mmol) in a mixture of dry MeCN (10 mL) and dry THF (10 mL) and the resulting mixture stirred at room temperature for 2 hours. The solvents were evaporated under reduced pressure to leave a solid that was triturated with EtOAc (3×2 mL) and dried to give the title compound (0.55 g, 91%) as an off-white solid.

149H. 5-[[5-[4-[[(2R)-1-Ethylpyrrolidin-2-yl]methyl]-2-methoxy-phenyl]-1H-pyrazol-3-yl]amino]pyrazine-2-carbonitrile hydrochloride Diisopropylethylamine (0.18 mL, 1.0 mmol) was added to a stirred suspension of 5-[[5-[2-methoxy-4-[[(2R)-pyrrolidin-2-yl]methyl]phenyl]-1H-pyrazol-3-yl]amino]pyrazine-2-carbonitrile hydrochloride (0.22 g, 0.53 mmol) in a mixture of MeOH (5 mL) and THF (5 mL) and the mixture stirred for 20 minutes at room temperature under a nitrogen atmosphere. Acetaldehyde (0.12 mL, 2.1 mmol) was added and the mixture stirred for a further 30 minutes then the mixture was cooled to 0° C. and NaBH(OAc)$_3$ (0.36 g, 1.7 mmol) was added in portions over 10 minutes. The mixture was allowed to warm to room temperature and stirred for a further one hour then poured into ice-water (30 mL) and solid NaHCO$_3$ was added to adjust the pH of the solution to 8. The mixture was extracted with EtOAc (5×50 mL) and the combined organic extracts were washed with brine (20 mL), dried (Na$_2$SO$_4$) and evaporated under reduced pressure. The residue was purified by column chromatography on neutral silica gel using 4% MeOH/DCM as the eluent. The resulting solid was dissolved in a mixture of THF (5 mL) and MeCN (5 mL) and a solution of 4N HCl in dioxane (0.2 mL) was added and the resulting mixture stirred for 30 minutes. The solvents were evaporated under reduced pressure to leave a solid that was triturated with Et$_2$O (3×10 mL) and dried to give the title compound (84 mg, 36%) as a light brown solid.

Biological Activity

Example A

Chk-1 Kinase Inhibiting Activity
The compounds of the invention were tested for activity against Chk-1 kinase using the materials and protocols set out below.
Reaction Buffer:
  Base Reaction buffer: 20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO
  *Required cofactors are added individually to each kinase reaction
Reaction Procedure:
(i) Prepare indicated substrate in freshly prepared Base Reaction Buffer
(ii) Deliver any required cofactors to the substrate solution above
(iii) Deliver indicated kinase into the substrate solution and gently mix
(iv) Deliver compounds in DMSO into the kinase reaction mixture
(v) Deliver $^{33}$P-ATP (specific activity 0.01 µCi/µl final) into the reaction mixture to initiate the reaction.
(vi) Incubate kinase reaction for 120 minutes at room temperature
(vii) Reactions are spotted onto P81 ion exchange paper (Whatman #3698-915)
(viii) Wash filters extensively in 0.1% phosphoric acid.
(ix) Dry filters and measure counts in scintillation counter
Kinase Information:
CHK-1—Genbank Accession # AF016582
Recombinant full length construct, N-terminal GST tagged, purified from insect cells.
No special measures were taken to activate this kinase.
Final concentration in assay=0.5 nM
Substrate: CHKtide
Peptide sequence: [KKKVSRSGLYRSPSMPENLNRPR]
Final concentration in assay=20 µM
No additional cofactors are added to the reaction mixture
From the results obtained by following the above protocol, the IC$_{50}$ values against Chk-1 kinase of each of the compounds of Examples 1-153 were determined and these are shown in Table 3.

TABLE 3

| Example | IC$_{50}$ (µM) |
|---|---|
| 1 | 0.0028 |
| 2 | 0.0027 |
| 3 | 0.00021 |
| 4 | 0.00019 |
| 5 | 0.0020 |

TABLE 3-continued

| Example | IC$_{50}$ (μM) |
|---|---|
| 6 | 0.000097 |
| 7 | 0.00010 |
| 8 | 0.000058 |
| 9 | 0.000077 |
| 10 | 0.011 |
| 11 | 0.000048 |
| 12 | 0.000034 |
| 13 | 0.00059 |
| 14 | 0.000026 |
| 15 | 0.00030 |
| 16 | 0.000085 |
| 17 | 0.00029 |
| 18 | 0.00017 |
| 19 | 0.00029 |
| 20 | 0.00029 |
| 21 | 0.0024 |
| 22 | 0.000026 |
| 23 | 0.00012 |
| 24 | 0.00024 |
| 25 | 0.014 |
| 26 | 0.010 |
| 27 | 0.0036 |
| 28 | 0.00013 |
| 29 | 0.000068 |
| 30 | 0.017 |
| 31 | 0.00037 |
| 32 | 0.00026 |
| 33 | 0.000074 |
| 34 | 0.00014 |
| 35 | 0.00014 |
| 36 | 0.000095 |
| 37 | 0.00011 |
| 38 | 0.00088 |
| 39 | 0.00018 |
| 40 | 0.00014 |
| 41 | 0.00051 |
| 42 | 0.00021 |
| 43 | 0.00073 |
| 44 | 0.00069 |
| 45 | >0.1 |
| 46 | 0.000054 |
| 47 | 0.00023 |
| 48 | 0.0015 |
| 49 | 0.036 |
| 50 | 0.020 |
| 51 | 0.0063 |
| 52 | 0.00046 |
| 53 | 0.0031 |
| 54 | 0.00012 |
| 55 | 0.227 |
| 56 | 0.183 |
| 57 | 0.000071 |
| 58 | 0.00054 |
| 59 | 0.000071 |
| 60 | 0.00010 |
| 61 | 0.00010 |
| 62 | 0.000084 |
| 63 | 0.000052 |
| 64 | 0.00015 |
| 65 | 0.000022 |
| 66 | 0.00014 |
| 67 | 0.0018 |
| 68 | 0.0029 |
| 69 | 0.0079 |
| 70 | 0.010 |
| 71 | >0.1 |
| 72 | 0.00016 |
| 73 | 0.00028 |
| 74 | 0.00035 |
| 75 | 0.00055 |
| 76 | 0.00011 |
| 77 | 0.00014 |
| 78 | 0.00069 |
| 79 | 0.00040 |
| 80 | 0.00019 |
| 81 | 0.00015 |
| 82 | 0.000016 |
| 83 | 0.00011 |
| 84 | 0.00014 |
| 85 | 0.00025 |
| 86 | 0.00012 |
| 87 | 0.000059 |
| 88 | 0.000079 |
| 89 | 0.000051 |
| 90 | 0.000058 |
| 91 | 0.00033 |
| 92 | 0.000016 |
| 93 | 0.000016 |
| 94 | 0.00018 |
| 95 | 0.00015 |
| 96 | 0.00040 |
| 97 | 0.0011 |
| 98 | 0.0018 |
| 99 | 0.00015 |
| 100 | 0.000053 |
| 101 | 0.000055 |
| 102 | 0.00016 |
| 103 | 0.000109 |
| 104 | 0.00012 |
| 105 | 0.000 |
| 106 | 0.00017 |
| 107 | 0.000081 |
| 108 | 0.000043 |
| 109 | 0.000087 |
| 110 | 0.0000069 |
| 111 | 0.0000052 |
| 112 | 0.0000042 |
| 113 | 0.00027 |
| 114 | 0.00020 |
| 115 | 0.00024 |
| 116 | 0.000077 |
| 117 | 0.000027 |
| 118 | 0.000022 |
| 119 | ND |
| 120 | ND |
| 121 | 0.00015 |
| 122 | 0.00014 |
| 123 | 0.00016 |
| 124 | 0.00025 |
| 125 | 0.00028 |
| 126 | 0.000056 |
| 127 | 0.000044 |
| 128 | 0.000023 |
| 129 | 0.000046 |
| 130 | 0.000025 |
| 131 | 0.00010 |
| 132 | 0.00011 |
| 133 | 0.00012 |
| 134 | 0.00011 |
| 135 | 0.000054 |
| 136 | 0.000053 |
| 137 | 0.000048 |
| 138 | 0.000041 |
| 139 | 0.000027 |
| 140 | 0.000021 |
| 141 | 0.000019 |
| 142 | 0.000082 |
| 143 | 0.000021 |
| 144 | 0.000026 |
| 145 | 0.0000084 |
| 146 | 0.000012 |
| 147 | 0.00016 |
| 148 | 0.000031 |
| 149 | ND |
| 150 | ND |
| 151 | ND |
| 152 | ND |
| 153 | 0.0038 |

ND = Not determined

Example B

Gemcitabine Combination Cell Assay

Exponentially growing MIA PaCa-2 (ATCC CRL-1420) cells are treated with trypsin to remove cells from the plate surface. Approximately 10,000 cells/well are plated in 96 well plates in RPMI containing 10% fetal bovine serum, 1% sodium pyruvate and 1% L-GlutaMax. Cells are allowed to adhere to the plate surface overnight. Serial half-log dilutions of Chk1 inhibitor test compounds and gemcitabine are made with a final highest concentration of 3000 nM and 100 nM, respectively. Chk1 inhibitors and gemcitabine are combined so that each concentration of Chk1 inhibitor is added to each concentration of gemcitabine. Each drug is also tested as a single agent. Drugs are added to adherent cells (in duplicate) and incubated for 72 h. At 72 h the cells are treated with Promega Cell Titer Glo reagent for approximately 15 minutes. Luminescence (relative light units, RLU) is recorded using a BMG Polarstar Omega plate reader. The single agent concentration that results in a 50% reduction in total signal ($IC_{50}$) is calculated using PRISM software and a four-parameter non-linear regression curve fit. For combination studies the RLUs are plotted using PRISM on an XY plot with the gemcitabine concentration on the X axis and RLU on the Y axis. The RLU for each concentration of Chk1 inhibitor is plotted as a function of gemcitabine concentration. The IC50 for gemcitabine alone and at each concentration of Chk1 is determined using a four-parameter non-linear regression curve fit. The approximate concentration of Chk1 inhibitor that results in a two and ten-fold reduction in the $IC_{50}$ of gemcitabine alone is calculated as an indication of synergistic potency.

From the results obtained by following the above protocol, the $IC_{50}$ values against MIAPaca-2 cells of the Chk1 inhibitor alone (Chk1 $IC_{50}$), the approximate concentration of Chk1 inhibitor that results in a two-fold (2×LS) and a 10-fold (10×LS) reduction in the $IC_{50}$ of gemcitabine alone of each of the compounds of Examples 1-154 are shown in Table 4.

TABLE 4

| Example | Chk1 $IC_{50}$ (nM) | 2xLS (nM) | 10xLS (nM) |
| --- | --- | --- | --- |
| 1 | 5386 | 100 | 1000 |
| 2 | 1411 | 100 | 1000 |
| 3 | 275 | 10 | 100 |
| 4 | ND | ND | ND |
| 5 | ND | ND | ND |
| 6 | 338 | 30 | 300 |
| 7 | 208 | 10 | ~200 |
| 8 | 259 | 10 | ~200 |
| 9 | 227 | 3 | 100 |
| 10 | >3000 | 1000 | >3000 |
| 11 | 214 | 3 | <100 |
| 12 | 264 | <3 | ~50 |
| 13 | >3000 | ~20 | 300 |
| 14 | 894 | <3 | ~50 |
| 15 | 2207 | ~5 | ~3000 |
| 16 | 1798 | <3 | 100 |
| 17 | 1819 | 10 | 300 |
| 18 | 1610 | ~5 | ~200 |
| 19 | 1608 | 3 | ~200 |
| 20 | 1111 | ~5 | 100 |
| 21 | 3181 | 100 | 1000 |
| 22 | 88 | <3 | <30 |
| 23 | 266 | <3 | <100 |
| 24 | 934 | 10 | 300 |
| 25 | >3000 | 300 | >3000 |
| 26 | 5585 | 1000 | >3000 |
| 27 | 5753 | 300 | 3000 |
| 28 | 279 | <3 | <100 |
| 29 | 176 | 3 | 100 |
| 30 | >3000 | 1000 | >3000 |
| 31 | 838 | 3 | 100 |
| 32 | 784 | 30 | 300 |
| 33 | 62 | <3 | <30 |
| 34 | 183 | 3 | 100 |
| 35 | 217 | 3 | 100 |
| 36 | 281 | 3 | 100 |
| 37 | 182 | 3 | <100 |
| 38 | 2754 | 100 | 1000 |
| 39 | 168 | <3 | 30 |
| 40 | 188 | <3 | 30 |
| 41 | 1114 | 30 | 300 |
| 42 | 73 | <3 | <30 |
| 43 | 1329 | 100 | 1000 |
| 44 | 1264 | 100 | 1000 |
| 45 | ND | ND | ND |
| 46 | 442 | <3 | <30 |
| 47 | 235 | 3 | 100 |
| 48 | 2021 | 100 | 1000 |
| 49 | 3566 | 1000 | <3000 |
| 50 | >3000 | 300 | 3000 |
| 51 | >3000 | 300 | 3000 |
| 52 | 953 | 30 | 300 |
| 53 | 2296 | 100 | 1000 |
| 54 | 137 | <3 | 30 |
| 55 | >3000 | 1000 | >3000 |
| 56 | >3000 | 1000 | >3000 |
| 57 | 337 | 3 | 100 |
| 58 | 676 | 30 | 300 |
| 59 | 263 | 3 | 100 |
| 60 | 329 | 3 | 100 |
| 61 | 251 | 2 | 100 |
| 62 | 875 | 10 | 300 |
| 63 | 600 | <3 | 100 |
| 64 | 144 | 3 | 100 |
| 65 | 144 | 3 | <100 |
| 66 | 111 | <3 | 30 |
| 67 | 1320 | 100 | 1000 |
| 68 | 1384 | 100 | 1000 |
| 69 | 2202 | 100 | 1000 |
| 70 | 2621 | 300 | 3000 |
| 71 | >3000 | >3000 | >3000 |
| 72 | 173 | 10 | 100 |
| 73 | 354 | 10 | 300 |
| 74 | 282 | 3 | 100 |
| 75 | >3000 | >3000 | >3000 |
| 76 | 482 | 10 | 300 |
| 77 | 164 | <3 | <100 |
| 78 | 136 | 10 | 100 |
| 79 | 478 | 3 | 100 |
| 80 | 36 | <3 | 10 |
| 81 | 36 | <3 | <30 |
| 82 | 74 | <3 | <30 |
| 83 | 107 | <3 | <100 |
| 84 | 62 | <3 | <100 |
| 85 | 138 | 3 | 100 |
| 86 | 239 | <3 | <100 |
| 87 | 540 | 10 | 300 |
| 88 | 424 | 10 | 300 |
| 89 | 193 | <3 | 100 |
| 90 | 390 | 10 | <300 |
| 91 | 411 | <3 | <100 |
| 92 | 132 | <3 | 30 |
| 93 | 99 | <3 | <30 |
| 94 | 475 | 3 | 100 |
| 95 | 183 | <3 | <100 |
| 96 | 730 | 10 | <300 |
| 97 | 1495 | 10 | 300 |
| 98 | 1778 | 10 | <1000 |
| 99 | 233 | <3 | 30 |
| 100 | 247 | 3 | <100 |
| 101 | 199 | 3 | <100 |
| 102 | 957 | 10 | 300 |
| 103 | 184 | 3 | 300 |
| 104 | 214 | 3 | 100 |
| 105 | 2303 | 30 | 1000 |
| 106 | 441 | 3 | 100 |
| 107 | 160 | 3 | 100 |
| 108 | 77 | <3 | 30 |
| 109 | 82 | <3 | <30 |
| 110 | 192 | 3 | 100 |

TABLE 4-continued

| Example | Chk1 IC$_{50}$ (nM) | 2xLS (nM) | 10xLS (nM) |
|---|---|---|---|
| 111 | 184 | <3 | 100 |
| 112 | 253 | <3 | 100 |
| 113 | 531 | 3 | 300 |
| 114 | 469 | 3 | <300 |
| 115 | 515 | 3 | <300 |
| 116 | 209 | 3 | 100 |
| 117 | 1890 | 10 | 1000 |
| 118 | 1198 | 3 | 300 |
| 119 | 687 | 10 | <300 |
| 120 | 397 | 3 | 100 |
| 121 | 177 | 3 | <100 |
| 122 | 136 | 3 | <100 |
| 123 | 440 | 3 | <300 |
| 124 | 322 | 3 | <300 |
| 125 | 550 | 10 | <300 |
| 126 | 210 | 3 | <100 |
| 127 | 169 | <3 | <100 |
| 128 | 158 | <3 | <100 |
| 129 | 278 | <3 | <100 |
| 130 | 142 | 3 | <100 |
| 131 | 592 | 3 | 100 |
| 132 | 411 | 3 | <300 |
| 133 | 139 | <3 | 30 |
| 134 | 352 | 3 | 100 |
| 135 | 334 | <3 | 100 |
| 136 | 228 | 3 | 100 |
| 137 | 256 | <3 | <100 |
| 138 | 836 | <10 | 300 |
| 139 | 743 | 10 | 300 |
| 140 | 618 | <10 | <300 |
| 141 | 970 | <10 | <300 |
| 142 | 306 | 3 | 100 |
| 143 | 820 | <10 | <300 |
| 144 | 829 | 10 | <300 |
| 145 | 267 | <3 | <100 |
| 146 | 433 | 3 | 100 |
| 147 | 1205 | 10 | 300 |
| 148 | 254 | <3 | <100 |
| 149 | 188 | <3 | 30 |
| 150 | 259 | 3 | 100 |
| 151 | 101 | <3 | <30 |
| 152 | 428 | 3 | 100 |
| 153 | 1197 | 100 | 1000 |
| 154 | 395 | 3 | 100 |

ND = Not determined

Example C

Pharmaceutical Formulations (i) Tablet Formulation

A tablet composition containing a compound of the formula (I) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (I) with 100 mg lactose and filling the resulting mixture into standard opaque hard gelatin capsules.

(iii) Injectable Formulation I

A parenteral composition for administration by injection can be prepared by dissolving a compound of the formula (0) or formula (1) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (0) or formula (1) (e.g. in salt form) (2 mg/ml) and mannitol (50 mg/ml), sterile filtering the solution and filling into sealable 1 ml vials or ampoules.

v) Injectable Formulation III

A formulation for i.v. delivery by injection or infusion can be prepared by dissolving the compound of formula (0) or formula (1) (e.g. in a salt form) in water at 20 mg/ml. The vial is then sealed and sterilised by autoclaving.

vi) Injectable Formulation IV

A formulation for i.v. delivery by injection or infusion can be prepared by dissolving the compound of formula (0) or formula (1) (e.g. in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the formula (0) or formula (1) with pharmaceutical grade corn oil to give a concentration of 5 mg/ml. The composition is sterilised and filled into a suitable container.

viii) Lyophilised Formulation

Aliquots of formulated compound of formula (0) or formula (1) are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A compound of the formula (0):

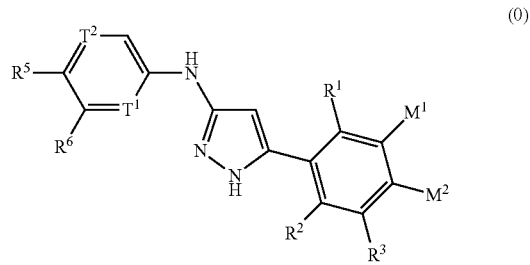

or a salt, N-oxide or tautomer thereof, wherein:

$T^1$ and $T^2$ are N;

$R^1$ is selected from hydrogen, fluorine, $C_{1-4}$ hydrocarbyl and $C_{1-4}$ hydrocarbyloxy;

$R^2$ is selected from hydrogen, fluorine, $C_{1-4}$ hydrocarbyl and $C_{1-4}$ hydrocarbyloxy;

$R^3$ is selected from hydrogen, methyl, fluorine, chlorine and bromine;

one of $M^1$ and $M^2$ is a group $R^4$ selected from hydrogen, methyl, fluorine, chlorine and bromine;

and the other of $M^1$ and $M^2$ is a moiety —A—$R^7$;

$R^5$ is selected from hydrogen, cyano, $C_{1-3}$ alkyl, cyclopropyl, chlorine, carboxy, and $C_{1-3}$-alkoxy-carbonyl;

$R^6$ is selected from hydrogen, fluorine, $C_{1-4}$ alkyl; and $C_{1-4}$ alkoxy optionally substituted with $NR^dR^e$ wherein $R^d$ and $R^e$ are the same or different and each is selected from hydrogen and $C_{1-4}$ alkyl, or $NR^dR^e$ forms a 4 to 7 membered saturated heterocyclic ring optionally containing a second heteroatom ring member selected from N, O and S and oxidized forms of S, the saturated heterocyclic ring being optionally substituted with one or more substituents selected from oxo, methyl, hydroxy and fluorine;

A is selected from:
(i) a bond;
(ii) $(CR^pR^q)_x$ wherein $R^p$ and $R^q$ are each independently hydrogen or methyl and x is 1 to 4;
(iii) an oxygen atom;
(iv) a group $NR^r$ wherein $R^r$ is hydrogen or methyl; and
(v) a saturated chain of 2 to 10 chain members in length containing at least one carbon atom chain member, at least one heteroatom chain member selected from nitrogen and oxygen, and optionally one or more further carbon atom chain members and/or heteroatom chain members selected from nitrogen, oxygen, sulfur, sulfinyl and sulfonyl; the saturated chain being optionally substituted with one or more substituents selected from =O, $C_{1-4}$ hydrocarbyl, fluoro-$C_{1-4}$ hydrocarbyl, hydroxy-$C_{1-4}$ hydrocarbyl, $C_{1-2}$-alkoxy-$C_{1-4}$ hydrocarbyl, and fluorine wherein two hydrocarbyl substituents on the same carbon atom may optionally link to form a ring of three to five ring members;

$R^7$ is a group $Cyc^1$ wherein $Cyc^1$ is a carbocyclic or heterocyclic non-aromatic group of 3 to 10 ring members of which 0 to 3 are selected from O, N and S and oxidized forms thereof, the carbocyclic or heterocyclic non-aromatic group being optionally substituted with one or more substituents $R^8$;

$R^8$ is selected from:
halogen;
oxo;
cyano;
nitro;
a carbocyclic or heterocyclic group having from 3 to 12 ring members, of which 0, 1, 2, 3 or 4 are heteroatom ring members selected from O, N and S and oxidized forms thereof, the carbocyclic or heterocyclic group being optionally substituted with one or more substituents $R^9$; and
a group $R^a$-$R^b$;

$R^a$ is a bond, O, CO, $X^1C(X^2)$, $C(X^2)X^1$, $X^1C(X^2)X^1$, S, SO, $SO_2$, $NR^c$, $SO_2NR^c$ or $NRcSO_2$;

$R^b$ is selected from:
hydrogen;
a carbocyclic or heterocyclic group having from 3 to 12 ring members, of which 0, 1, 2, 3 or 4 are heteroatom ring members selected from O, N and S and oxidized forms thereof, the carbocyclic or heterocyclic group being optionally substituted with one or more substituents $R^9$;
an acyclic $C_{1-12}$ hydrocarbyl group optionally substituted with one or more substituents selected from hydroxy; oxo; halogen; cyano; nitro; carboxy; amino; mono- or di-$C_{1-8}$ non-aromatic hydrocarbylamino; and carbocyclic or heterocyclic groups having from 3 to 12 ring members, of which 0, 1, 2, 3 or 4 are heteroatom ring members selected from O, N and S and oxidized forms thereof, the carbocyclic or heterocyclic group being optionally substituted with one or more substituents $R^9$; wherein one or more but not all of the carbon atoms of the acyclic $C_{1-12}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is selected from:
hydrogen;
a carbocyclic or heterocyclic group having from 3 to 12 ring members, of which 0, 1, 2, 3 or 4 are heteroatom ring members selected from O, N and S and oxidized forms thereof, the carbocyclic or heterocyclic group being optionally substituted with one or more substituents $R^9$;
an acyclic $C_{1-12}$ hydrocarbyl group optionally substituted with one or more substituents selected from hydroxy; oxo; halogen; cyano; nitro; carboxy; amino; mono- or di-$C_{1-8}$ non-aromatic hydrocarbylamino; and carbocyclic or heterocyclic groups having from 3 to 12 ring members, of which 0, 1, 2, 3 or 4 are heteroatom ring members selected from O, N and S and oxidized forms thereof, the carbocyclic or heterocyclic group being optionally substituted with one or more substituents $R^9$; wherein one or more but not all of the carbon atoms of the acyclic $C_{1-12}$ hydrocarbyl group may optionally be replaced by O, S, SO, $SO_2$, NH, N—$C_{1-4}$ alkyl, C(O)O, OC(O), NH(CO), C(O)NH, NH(CO)NH, N($C_{1-4}$ alkyl)C(O), C(O)N($C_{1-4}$ alkyl)

$X^1$ is O, S or $NR^c$; and $X^2$ is =O, =S or =$NR^c$;

wherein $R^9$ is selected from $R^8$ provided that when the substituents $R^9$ contain a carbocyclic or heterocyclic group, the said carbocyclic or heterocyclic group is unsubstituted or substituted with one or more substituents $R^{10}$;

$R^{10}$ is selected from halogen, oxo, cyano, and an acyclic $C_{1-6}$ hydrocarbyl group optionally substituted with one or more substituents selected from hydroxy; oxo; halogen; cyano; carboxy; amino; mono- or di-$C_{1-2}$ alkylamino; wherein one but not all of the carbon atoms of the acyclic $C_{1-6}$ hydrocarbyl group may optionally be replaced by O, S, SO, $SO_2$, NH or NMe;

$R^{11}$ is selected from amino, $Hyd^1$, NH-$Hyd^1$, N($Hyd^1$)$_2$; and $Cyc^1$;

$Hyd^1$ is a non-aromatic $C_{1-6}$ hydrocarbyl group optionally substituted by one or more substituents selected from halogen, cyano, hydroxy, amino and $Cyc^1$, wherein one or two of the carbon atoms of the non-aromatic $C_{1-6}$ hydrocarbyl group may optionally be replaced by O, NH, N-$Hyd^2$, C(=O), S, SO or $SO_2$, provided that at least one carbon atom of the hydrocarbyl group remains;

$Hyd^2$ is a $C_{1-4}$ hydrocarbyl group;

and wherein in any group consisting of or containing a hydrocarbyl moiety, the hydrocarbyl moiety is a hydrocarbon group optionally containing one or more single, double or triple carbon-carbon bonds or combinations thereof.

2. A compound according to claim 1 having the formula (1):

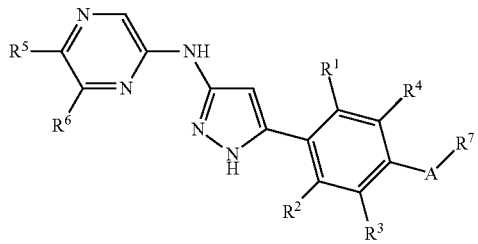

or a salt, N-oxide or tautomer thereof, wherein:

A is selected from:
(i) a bond; and
(ii) a saturated chain of 2 to 10 chain members in length containing at least one carbon atom chain member, at least one heteroatom chain member selected from nitrogen and oxygen, and optionally one or more further carbon atom chain members and/or heteroatom chain members selected from nitrogen, oxygen, sulfur, sulfinyl and sulfonyl; the saturated chain being optionally substituted with one or more substituents selected from =O, $C_{1-4}$ hydrocarbyl and fluorine wherein two hydrocarbyl substituents on the same carbon atom may optionally link to form a ring of three to five ring members;

$R^1$ is selected from hydrogen, fluorine, $C_{1-4}$ hydrocarbyl and $C_{1-4}$ hydrocarbyloxy;

$R^2$ is selected from hydrogen, fluorine, $C_{1-4}$ hydrocarbyl and $C_{1-4}$ hydrocarbyloxy;

$R^3$ is selected from hydrogen, methyl, chlorine and bromine;

$R^4$ is selected from hydrogen, methyl, chlorine and bromine;

$R^5$ is selected from hydrogen, cyano and methyl;

$R^6$ is selected from hydrogen, $C_{1-4}$ alkyl; and $C_{1-4}$ alkoxy optionally substituted with $NR^dR^e$ wherein $R^d$ and $R^e$ are the same or different and each is selected from hydrogen and $C_{1-4}$ alkyl, or $NR^dR^e$ forms a 4 to 7 membered saturated heterocyclic ring optionally containing a second heteroatom ring member selected from N, O and S and oxidized forms of S, the saturated heterocyclic ring being optionally substituted with one or more substituents selected from oxo, methyl, hydroxy and fluorine;

$R^7$ is a group $Cyc^1$ wherein $Cyc^1$ is a carbocyclic or heterocyclic non-aromatic group of 3 to 10 ring members of which 0 to 3 are selected from O, N and S and oxidized forms thereof, the carbocyclic or heterocyclic non-aromatic group being optionally substituted with one or more substituents $R^8$;

$R^8$ is selected from:
halogen;
oxo;
cyano;
nitro;
a carbocyclic or heterocyclic group having from 3 to 12 ring members, of which 0, 1, 2, 3 or 4 are heteroatom ring members selected from O, N and S and oxidized forms thereof, the carbocyclic or heterocyclic group being optionally substituted with one or more substituents $R^9$; and
a group $R^a$-$R^b$;

$R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$;

$R^b$ is selected from:
hydrogen;
a carbocyclic or heterocyclic group having from 3 to 12 ring members, of which 0, 1, 2, 3 or 4 are heteroatom ring members selected from O, N and S and oxidized forms thereof, the carbocyclic or heterocyclic group being optionally substituted with one or more substituents $R^9$; and
an acyclic $C_{1-12}$ hydrocarbyl group optionally substituted with one or more substituents selected from hydroxy; oxo; halogen; cyano; nitro; carboxy; amino; mono- or di-$C_{1-8}$ non-aromatic hydrocarbylamino; and carbocyclic or heterocyclic groups having from 3 to 12 ring members, of which 0, 1, 2, 3 or 4 are heteroatom ring members selected from O, N and S and oxidized forms thereof, the carbocyclic or heterocyclic group being optionally substituted with one or more substituents $R^9$; wherein one or more but not all of the carbon atoms of the acyclic $C_{1-12}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is selected from:
hydrogen;
a carbocyclic or heterocyclic group having from 3 to 12 ring members, of which 0, 1, 2, 3 or 4 are heteroatom ring members selected from O, N and S and oxidized forms thereof, the carbocyclic or heterocyclic group being optionally substituted with one or more substituents $R^9$; and
an acyclic $C_{1-12}$ hydrocarbyl group optionally substituted with one or more substituents selected from hydroxy; oxo; halogen; cyano; nitro; carboxy; amino; mono- or di-$C_{1-8}$ non-aromatic hydrocarbylamino; and carbocyclic or heterocyclic groups having from 3 to 12 ring members, of which 0, 1, 2, 3 or 4 are heteroatom ring members selected from O, N and S and oxidized forms thereof, the carbocyclic or heterocyclic group being optionally substituted with one or more substituents $R^9$; wherein one or more but not all of the carbon atoms of the acyclic $C_{1-12}$ hydrocarbyl group may optionally be replaced by O, S, SO, $SO_2$, NH, N—$C_{1-4}$ alkyl, C(O)O, OC(O), NH(CO), C(O)NH, NH(CO)NH, N($C_{1-4}$alkyl)C(O), C(O)N($C_{1-4}$ alkyl)

$X^1$ is O, S or $NR^c$; and
$X^2$ is =O, =S or =$NR^c$;

wherein $R^9$ is selected from $R^8$ provided that when the substituents $R^9$ contain a carbocyclic or heterocyclic group, the said carbocyclic or heterocyclic group is unsubstituted or substituted with one or more substituents $R^{10}$;

$R^{10}$ is selected from halogen, oxo, cyano, and an acyclic $C_{1-6}$ hydrocarbyl group optionally substituted with one or more substituents selected from hydroxy; oxo; halogen; cyano; carboxy; amino; mono- or di-$C_{1-2}$ alkylamino; wherein one but not all of the carbon atoms of the acyclic $C_{1-6}$ hydrocarbyl group may optionally be replaced by O, S, SO, $SO_2$, NH or NMe;

$R^{11}$ is selected from amino, $Hyd^1$, NH-$Hyd^1$, N($Hyd^1$)$_2$; and $Cyc^1$;

Hyd¹ is a non-aromatic $C_{1-6}$ hydrocarbyl group optionally substituted by one or more substituents selected from halogen, cyano, hydroxy, amino and Cyc¹, wherein one or two of the carbon atoms of the non-aromatic $C_{1-6}$ hydrocarbyl group may optionally be replaced by O, NH, N-Hyd², C(=O), S, SO or $SO_2$, provided that at least one carbon atom of the hydrocarbyl group remains;

Hyd² is a $C_{1-4}$ hydrocarbyl group;

and wherein in any group consisting of or containing a hydrocarbyl moiety, the hydrocarbyl moiety is a hydrocarbon group optionally containing one or more single, double or triple carbon-carbon bonds or combinations thereof.

3. A compound according to claim 1 wherein $R^1$ is selected from hydrogen and methoxy.

4. A compound according to claim 1 wherein $R^2$ is selected from hydrogen and methoxy.

5. A compound according to claim 1 wherein both of $R^3$ and $R^4$ are hydrogen.

6. A compound according to claim 1 wherein $R^5$ is selected from hydrogen and cyano.

7. A compound according to claim 6 wherein $R^5$ is cyano.

8. A compound according to claim 1 wherein $R^6$ is hydrogen.

9. A compound according to claim 1 wherein A is selected from a bond; —NH—CH₂—; —(CH₂)—NH—(CH₂)—; —(CH₂)—NH—(CH₂)—(CH₂)—; —(CH₂)—(CH₂)—NH—(CH₂)—; and —(CH₂)—NH—(CHMe).

10. A compound according to claim 1 wherein $R^8$ is absent or is selected from $C_{1-4}$ hydrocarbyl, $C_{1-4}$hydrocarbylsulfonyl, oxo, di-$C_{1-4}$hydrocarbylamino-$C_{1-4}$alkanoyl; and $C_{1-4}$ hydrocarbylcarbonyl.

11. A compound according to claim 1 wherein $R^7$ is selected from 4-morpholinyl, 1-methyl-4-piperidinyl and 1-cyclopropylcarbonyl-piperidin-4-yl.

12. A compound according to claim 1 wherein:
$R^1$ is hydrogen or methoxy;
$R^2$ is hydrogen or methoxy;
$R^3$ is hydrogen;
$R^4$ is hydrogen;
$R^5$ is hydrogen or cyano;
$R^6$ is hydrogen;
A is selected from a bond; —NH—CH₂—; —(CH₂)—NH—(CH₂)—; —(CH₂)—NH—(CH₂)—(CH₂)—; —(CH₂)—(CH₂)—NH—(CH₂)—; and —(CH₂)—NH—(CHMe)—; and
$R^7$ is selected from morpholinyl, 1-methyl-4-piperidinyl and 1-cyclopropylcarbonyl-piperidin-4-yl.

13. A compound according to claim 1 wherein:
$R^1$ is methoxy;
$R^2$ is hydrogen or methoxy;
$R^3$ is hydrogen;
$R^4$ is hydrogen;
$R^5$ is cyano;
$R^6$ is hydrogen; and
(i) when A is a bond, $R^7$ is 1-methyl-4-piperidinyl; or
(ii) when A is —(CH₂)—NH—(CH₂)—, $R^7$ is 1-cyclopropylcarbonyl-piperidin-4-yl; or
(iii) when A is (CH₂)—NH—(CH₂)—(CH₂)—, $R^7$ is 4-morpholinyl.

14. A compound according to claim 1 that is selected from:
5-(5-{2-methoxy-4-[(2-morpholin-4-yl-ethylamino)-methyl]-phenyl}-1H-pyrazol-3-ylamino)-pyrazine-2-carbonitrile;

(5-{2-methoxy-4-[(2-morpholin-4-yl-ethylamino)-methyl]-phenyl}-1H-pyrazol-3-yl)-pyrazin-2-ylamine;

5-{5-[2-methoxy-4-(1-methyl-piperidin-4-yl)-phenyl]-1H-pyrazol-3-ylamino}-pyrazine-2-carbonitrile;

5-[5-(4-{[(1-cyclopropane-carbonyl-piperidin-4-ylmethyl)-amino]-methyl}-2-methoxy-phenyl)-1H-pyrazol-3-ylamino]-pyrazine-2-carbonitrile;

N-[[4-[3-[(5-cyanopyrazin-2-yl)amino]-1H-pyrazol-5-yl]-3-methoxy-phenyl]methyl]cyclopropanecarboxamide;

5-[[5-[2-methoxy-4-[(tetrahydropyran-4-ylamino)methyl]phenyl]-1H-pyrazol-3-yl]amino]pyrazine-2-carbonitrile;

5-[[5-[2-methoxy-4-[[methyl(2-morpholinoethyl)amino]methyl]phenyl]-1H-pyrazol-3-yl]amino]pyrazine-2-carbonitrile;

5-[[5-[2-methoxy-4-(2-morpholinoethylamino)phenyl]-1H-pyrazol-3-yl]amino]pyrazine-2-carbonitrile;

5-[[5-[4-[1-[2-(dimethylamino)acetyl]-4-piperidyl]-2-methoxy-phenyl]-1H-pyrazol-3-yl]amino]pyrazine-2-carbonitrile;

5-[[5-[2-methoxy-4-[[[(1R)-1-methyl-2-morpholino-ethyl]amino]methyl]phenyl]-1H-pyrazol-3-yl]amino]pyrazine-2-carbonitrile;

5-[[5-[4-[[(1,1-dimethyl-2-morpholino-ethyl)amino]methyl]-2-methoxy-phenyl]-1H-pyrazol-3-yl]amino]pyrazine-2-carbonitrile;

5-[[5-[2-methoxy-4-(4-piperidyl)phenyl]-1H-pyrazol-3-yl]amino]pyrazine-2-carbonitrile;

5-[[5-[2-fluoro-4-(1-methyl-4-piperidyl)phenyl]-1H-pyrazol-3-yl]amino]pyrazine-2-carbonitrile;

5-[[5-[2-methoxy-4-(4-methylpiperazin-1-yl)phenyl]-1H-pyrazol-3-yl]amino]pyrazine-2-carbonitrile;

5-[[5-[2-methoxy-4-(4-methyl-1,4-diazepan-1-yl)phenyl]-1H-pyrazol-3-yl]amino]pyrazine-2-carbonitrile;

N-[5-[2-methoxy-4-(1-methyl-4-piperidyl)phenyl]-1H-pyrazol-3-yl]-5-methyl-pyrazin-2-amine;

5-[[5-[4-(1-methyl-4-piperidyl)phenyl]-1H-pyrazol-3-yl]amino]pyrazine-2-carbonitrile;

5-[[5-[2-methoxy-4-[(1-methyl-4-piperidyl)oxy]phenyl]-1H-pyrazol-3-yl]amino]pyrazine-2-carbonitrile;

5-[[5-[2-methoxy-4-[(1-methyl-4-piperidyl)methoxy]phenyl]-1H-pyrazol-3-yl]amino]pyrazine-2-carbonitrile;

5-[[5-[5-fluoro-2-methoxy-4-(1-methyl-4-piperidyl)phenyl]-1H-pyrazol-3-yl]amino]pyrazine-2-carbonitrile;

5-[[5-[2-methoxy-4-[(3S)-pyrrolidin-3-yl]oxy-phenyl]-1H-pyrazol-3-yl]amino]pyrazine-2-carbonitrile;

5-[[5-[2-methoxy-4-(pyrrolidin-2-ylmethoxy)phenyl]-1H-pyrazol-3-yl]amino]pyrazine-2-carbonitrile;

5-[[5-[2-methoxy-4-[(1-methylpyrrolidin-2-yl)methoxy]phenyl]-1H-pyrazol-3-yl]amino]pyrazine-2-carbonitrile;

5-[[5-[2-methoxy-4-(4-piperidylmethoxy)phenyl]-1H-pyrazol-3-yl]amino]pyrazine-2-carbonitrile;

5-[[5-[2-methoxy-4-[[(1-methyl-4-piperidyl)amino]methyl]phenyl]-1H-pyrazol-3-yl]amino]pyrazine-2-carbonitrile;

5-[[5-[2-isopropoxy-4-(1-methyl-4-piperidyl)phenyl]-1H-pyrazol-3-yl]amino]pyrazine-2-carbonitrile;

5-[[5-[2-methoxy-4-(3-piperidyl)phenyl]-1H-pyrazol-3-yl]amino]pyrazine-2-carbonitrile;

5-[[5-[2-methoxy-4-(1-methyl-3-piperidyl)phenyl]-1H-pyrazol-3-yl]amino]pyrazine-2-carbonitrile;

5-[[5-[2-methoxy-4-(1-methyl-2-piperidyl)phenyl]-1H-pyrazol-3-yl]amino]pyrazine-2-carbonitrile;

5-[[5-[2-methoxy-4-[(3S)-1-methylpyrrolidin-3-yl]oxy-phenyl]-1H-pyrazol-3-yl]amino]pyrazine-2-carbonitrile;
5-chloro-N-[5-[2-methoxy-4-(4-piperidyl)phenyl]-1H-pyrazol-3-yl]pyrazin-2-amine;
5-chloro-N-[5-[2-methoxy-4-(1-methyl-4-piperidyl)phenyl]-1H-pyrazol-3-yl]pyrazin-2-amine;
5-[[5-[2-methoxy-4-(4-piperidyl)phenyl]-1H-pyrazol-3-yl]amino]pyrazine-2-carboxylic acid;
5-[[5-(2-methoxy-4-piperazin-1-yl-phenyl)-1H-pyrazol-3-yl]amino]pyrazine-2-carbonitrile;
5-[[5-[4-[(2S,6S)-2,6-dimethyl-4-piperidyl]-2-methoxy-phenyl]-1H-pyrazol-3-yl]amino]pyrazine-2-carbonitrile;
5-[[5-(2-methoxy-4-tetrahydropyran-4-yl-phenyl)-1H-pyrazol-3-yl]amino]pyrazine-2-carbonitrile;
5-[[5-[2-fluoro-4-(4-piperidyl)phenyl]-1H-pyrazol-3-yl]amino]pyrazine-2-carbonitrile;
5-[[5-[2-isopropoxy-4-(4-piperidyl)phenyl]-1H-pyrazol-3-yl]amino]pyrazine-2-carbonitrile;
5-[[5-[4-(1,4-diazepan-1-yl)-2-methoxy-phenyl]-1H-pyrazol-3-yl]amino]pyrazine-2-carbonitrile;
N-[5-[2-methoxy-4-(4-piperidyl)phenyl]-1H-pyrazol-3-yl]-5-methyl-pyrazin-2-amine;
5-[[5-[4-(4-piperidyl)phenyl]-1H-pyrazol-3-yl]amino]pyrazine-2-carbonitrile;
5-[[5-[2-methoxy-4-(4-piperidyloxy)phenyl]-1H-pyrazol-3-yl]amino]pyrazine-2-carbonitrile;
5-[[5-[5-fluoro-2-methoxy-4-(4-piperidyl)phenyl]-1H-pyrazol-3-yl]amino]pyrazine-2-carbonitrile;
5-[[5-[4-(1-ethyl-4-piperidyl)-2-methoxy-phenyl]-1H-pyrazol-3-yl]amino]pyrazine-2-carbonitrile;
5-[[5-[4-(1-isopropyl-4-piperidyl)-2-methoxy-phenyl]-1H-pyrazol-3-yl]amino]pyrazine-2-carbonitrile;
2-[4-[4-[3-[(5-cyanopyrazin-2-yl)amino]-1H-pyrazol-5-yl]-3-methoxy-phenyl]-1-piperidyl]acetamide;
5-[[5-[2-methoxy-4-[[methyl(tetrahydropyran-4-yl)amino]methyl]phenyl]-1H-pyrazol-3-yl]amino]pyrazine-2-carbonitrile;
5-[[5-[4-(4-fluoro-1-methyl-4-piperidyl)-2-methoxy-phenyl]-1H-pyrazol-3-yl]amino]pyrazine-2-carbonitrile;
5-[[5-[2-methoxy-4-(1-methylazetidin-3-yl)phenyl]-1H-pyrazol-3-yl]amino]pyrazine-2-carbonitrile;
5-[[5-[4-(3-fluoro-1-methyl-azetidin-3-yl)-2-methoxy-phenyl]-1H-pyrazol-3-yl]amino]pyrazine-2-carbonitrile;
5-[[5-[5-chloro-2-methoxy-4-(1-methyl-4-piperidyl)phenyl]-1H-pyrazol-3-yl]amino]pyrazine-2-carbonitrile;
5-[[5-[5-chloro-2-methoxy-4-(4-piperidyl)phenyl]-1H-pyrazol-3-yl]amino]pyrazine-2-carbonitrile;
5-[[5-[3-chloro-2-methoxy-4-(1-methyl-4-piperidyl)phenyl]-1H-pyrazol-3-yl]amino]pyrazine-2-carbonitrile;
5-[[5-[3-chloro-2-methoxy-4-(4-piperidyl)phenyl]-1H-pyrazol-3-yl]amino]pyrazine-2-carbonitrile;
methyl 5-[[5-[2-methoxy-4-(4-piperidyl)phenyl]-1H-pyrazol-3-yl]amino]pyrazine-2-carboxylate;
5-[[5-[2-methoxy-4-[(tetrahydrofuran-3-ylamino)methyl]phenyl]-1H-pyrazol-3-yl]amino]pyrazine-2-carbonitrile;
5-[[5-[2-methoxy-4-[[methyl(tetrahydrofuran-3-yl)amino]methyl]phenyl]-1H-pyrazol-3-yl]amino]pyrazine-2-carbonitrile;
5-[[5-[2-methoxy-4-(tetrahydropyran-4-ylmethylamino)phenyl]-1H-pyrazol-3-yl]amino]pyrazine-2-carbonitrile;
5-[[5-[2-methoxy-4-(tetrahydropyran-4-ylmethoxy)phenyl]-1H-pyrazol-3-yl]amino]pyrazine-2-carbonitrile;
5-[[5-[4-(4-fluoro-4-piperidyl)-2-methoxy-phenyl]-1H-pyrazol-3-yl]amino]pyrazine-2-carbonitrile;
5-[[5-[4-(3-fluoroazetidin-3-yl)-2-methoxy-phenyl]-1H-pyrazol-3-yl]amino]pyrazine-2-carbonitrile;
5-[[5-[2-methoxy-4-[(3R)-1-methylpyrrolidin-3-yl]oxy-phenyl]-1H-pyrazol-3-yl]amino]pyrazine-2-carbonitrile;
5-[[5-(2-methoxy-4-morpholino-phenyl)-1H-pyrazol-3-yl]amino]pyrazine-2-carbonitrile;
5-[[5-[4-(4-ethylpiperazin-1-yl)-2-methoxy-phenyl]-1H-pyrazol-3-yl]amino]pyrazine-2-carbonitrile;
5-[[5-[4-(4-isopropylpiperazin-1-yl)-2-methoxy-phenyl]-1H-pyrazol-3-yl]amino]pyrazine-2-carbonitrile;
5-[[5-[2-methoxy-4-[(3R)-3-methylpiperazin-1-yl]phenyl]-1H-pyrazol-3-yl]amino]pyrazine-2-carbonitrile;
5-[[5-[4-(4-ethyl-1,4-diazepan-1-yl)-2-methoxy-phenyl]-1H-pyrazol-3-yl]amino]pyrazine-2-carbonitrile;
5-[[5-[4-(4-isopropyl-1,4-diazepan-1-yl)-2-methoxy-phenyl]-1H-pyrazol-3-yl]amino]pyrazine-2-carbonitrile;
5-[[5-[4-(1-ethyl-4-fluoro-4-piperidyl)-2-methoxy-phenyl]-1H-pyrazol-3-yl]amino]pyrazine-2-carbonitrile;
5-[[5-[4-(4-fluoro-1-isopropyl-4-piperidyl)-2-methoxy-phenyl]-1H-pyrazol-3-yl]amino]pyrazine-2-carbonitrile;
5-[[5-[4-(1-ethyl-3-fluoro-4-piperidyl)-2-methoxy-phenyl]-1H-pyrazol-3-yl]amino]pyrazine-2-carbonitrile;
5-[[5-[4-(3-fluoro-1-isopropyl-4-piperidyl)-2-methoxy-phenyl]-1H-pyrazol-3-yl]amino]pyrazine-2-carbonitrile;
5-[[5-[2-methoxy-4-[1-(2-methoxyethyl)-4-piperidyl]phenyl]-1H-pyrazol-3-yl]amino]pyrazine-2-carbonitrile;
5-[[5-[4-[(cyclopropylamino)methyl]-2-methoxy-phenyl]-1H-pyrazol-3-yl]amino]pyrazine-2-carbonitrile;
5-[[5-[4-[(3R)-3,4-dimethylpiperazin-1-yl]-2-methoxy-phenyl]-1H-pyrazol-3-yl]amino]pyrazine-2-carbonitrile;
5-[[5-[4-[(3R)-4-ethyl-3-methyl-piperazin-1-yl]-2-methoxy-phenyl]-1H-pyrazol-3-yl]amino]pyrazine-2-carbonitrile;
5-[[5-[4-[(3S)-1-isopropylpyrrolidin-3-yl]oxy-2-methoxy-phenyl]-1H-pyrazol-3-yl]amino]pyrazine-2-carbonitrile;
5-[[5-[4-[(3R)-1-isopropylpyrrolidin-3-yl]oxy-2-methoxy-phenyl]-1H-pyrazol-3-yl]amino]pyrazine-2-carbonitrile;
5-[[5-[4-[(3(R,S),4(R,S))-3-fluoro-1-methyl-4-piperidyl]-2-methoxy-phenyl]-1H-pyrazol-3-yl]amino]pyrazine-2-carbonitrile;
5-[[5-[4-(3,3-difluoro-1-methyl-4-piperidyl)-2-methoxy-phenyl]-1H-pyrazol-3-yl]amino]pyrazine-2-carbonitrile;
5-[[5-[4-(1-ethyl-3,3-difluoro-4-piperidyl)-2-methoxy-phenyl]-1H-pyrazol-3-yl]amino]pyrazine-2-carbonitrile;
5-[[5-[4-[1-(2-hydroxyethyl)-4-piperidyl]-2-methoxy-phenyl]-1H-pyrazol-3-yl]amino]pyrazine-2-carbonitrile;
5-[[5-[2-methoxy-4-(pyrrolidin-1-ylmethyl)phenyl]-1H-pyrazol-3-yl]amino]pyrazine-2-carbonitrile;
5-[[5-[2-methoxy-4-(morpholinomethyl)phenyl]-1H-pyrazol-3-yl]amino]pyrazine-2-carbonitrile;
5-[[5-[2-methoxy-4-[[(2R)-1-methylpyrrolidin-2-yl]methoxy]phenyl]-1H-pyrazol-3-yl]amino]pyrazine-2-carbonitrile hydrochloride;

5-[[5-[2-methoxy-4-[[(2S)-1-methylpyrrolidin-2-yl] methoxy]phenyl]-1H-pyrazol-3-yl]amino]pyrazine-2-carbonitrile hydrochloride;

5-[[5-[4-[1-(2-fluoroethyl)-4-piperidyl]-2-methoxy-phenyl]-1H-pyrazol-3-yl]amino]pyrazine-2-carbonitrile;

5-[[5-[2-methoxy-4-[(1-methyl-4-piperidyl)methylamino]phenyl]-1H-pyrazol-3-yl]amino]pyrazine-2-carbonitrile;

5-[[5-[4-[(1-ethyl-4-piperidyl)methylamino]-2-methoxy-phenyl]-1H-pyrazol-3-yl]amino]pyrazine-2-carbonitrile;

5-[[5-[4-[(1-isopropyl-4-piperidyl)methylamino]-2-methoxy-phenyl]-1H-pyrazol-3-yl]amino]pyrazine-2-carbonitrile;

5-[[5-[2-methoxy-4-[(1-methyl-4-piperidyl)amino]phenyl]-1H-pyrazol-3-yl]amino]pyrazine-2-carbonitrile;

5-[[5-[4-[(1-ethyl-4-piperidyl)amino]-2-methoxy-phenyl]-1H-pyrazol-3-yl]amino]pyrazine-2-carbonitrile;

5-[[5-[4-[(1-isopropyl-4-piperidyl)amino]-2-methoxy-phenyl]-1H-pyrazol-3-yl]amino]pyrazine-2-carbonitrile;

5-[[5-[2-methoxy-4-[(1-methyl-4-piperidyl)oxymethyl] phenyl]-1H-pyrazol-3-yl]amino]pyrazine-2-carbonitrile;

5-[[5-[4-[(1-ethyl-4-piperidyl)oxymethyl]-2-methoxy-phenyl]-1H-pyrazol-3-yl]amino]pyrazine-2-carbonitrile;

5-[[5-[4-[(1-isopropyl-4-piperidyl)oxymethyl]-2-methoxy-phenyl]-1H-pyrazol-3-yl]amino]pyrazine-2-carbonitrile;

5-[[5-(2-fluoro-6-methoxy-4-piperazin-1-yl-phenyl)-1H-pyrazol-3-yl]amino]pyrazine-2-carbonitrile;

5-[[5-[2-methoxy-4-[(2R)-4-methylmorpholin-2-yl]phenyl]-1H-pyrazol-3-yl]amino]pyrazine-2-carbonitrile;

5-[[5-[2-methoxy-4-[(2R)-4-ethylmorpholin-2-yl]phenyl]-1H-pyrazol-3-yl]amino]pyrazine-2-carbonitrile;

5-[[5-[2-methoxy-4-[(2S)-4-methylmorpholin-2-yl]phenyl]-1H-pyrazol-3-yl]amino]pyrazine-2-carbonitrile;

5-[[5-[2-methoxy-4-[(2S)-4-ethylmorpholin-2-yl]phenyl]-1H-pyrazol-3-yl]amino]pyrazine-2-carbonitrile;

5-[[5-(2, 6-dimethoxy-4-piperazin-1-yl-phenyl)-1H-pyrazol-3-yl]amino]pyrazine-2-carbonitrile;

5-[[5-[2,6-dimethoxy-4-(4-methylpiperazin-1-yl)phenyl]-1H-pyrazol-3-yl]amino]pyrazine-2-carbonitrile;

5-[[5-[4-[[(3R)-3-fluoropyrrolidin-1-yl]methyl]-2-methoxy-phenyl]-1H-pyrazol-3-yl]amino]pyrazine-2-carbonitrile;

5-[[5-[2-methoxy-4-[[(3S)-3-methoxypyrrolidin-1-yl] methyl]phenyl]-1H-pyrazol-3-yl]amino]pyrazine-2-carbonitrile;

5-[[5-[2-methoxy-4-[[(3R)-3-methoxypyrrolidin-1-yl] methyl]phenyl]-1H-pyrazol-3-yl]amino]pyrazine-2-carbonitrile;

5-[[5-[4-[[(2R)-1-ethylpyrrolidin-2-yl]methoxy]-2-methoxy-phenyl]-1H-pyrazol-3-yl]amino]pyrazine-2-carbonitrile;

5-[[5-[4-[[(2R)-1-isopropylpyrrolidin-2-yl]methoxy]-2-methoxy-phenyl]-1H-pyrazol-3-yl]amino]pyrazine-2-carbonitrile;

5-[[5-[4-[[(2S)-1-ethylpyrrolidin-2-yl]methoxy]-2-methoxy-phenyl]-1H-pyrazol-3-yl]amino]pyrazine-2-carbonitrile;

5-[[5-[4-[[(2S)-1-isopropylpyrrolidin-2-yl]methoxy]-2-methoxy-phenyl]-1H-pyrazol-3-yl]amino]pyrazine-2-carbonitrile;

5-[[5-[4-[(cyclopropylmethylamino) methyl]-2-methoxy-phenyl]-1H-pyrazol-3-yl]amino]pyrazine-2-carbonitrile;

5-[[5-[2-methoxy-4-[[[(3R)-tetrahydrofuran-3-yl]amino] methyl]phenyl]-1H-pyrazol-3-yl]amino]pyrazine-2-carbonitrile;

5-[[5-[2-methoxy-4-[[[(3S)-tetrahydrofuran-3-yl]amino] methyl]phenyl]-1H-pyrazol-3-yl]amino]pyrazine-2-carbonitrile;

5-[[5-[4-[(3R)-4-isopropyl-3-methyl-piperazin-1-yl]-2-methoxy-phenyl]-1H-pyrazol-3-yl]amino]pyrazine-2-carbonitrile;

5-[[5-[4-[(1-ethyl-4-piperidyl)oxy]-2-methoxy-phenyl]-1H-pyrazol-3-yl]amino]pyrazine-2-carbonitrile;

5-[[5-[4-[(1-isopropyl-4-piperidyl)oxy]-2-methoxy-phenyl]-1H-pyrazol-3-yl]amino]pyrazine-2-carbonitrile;

5-[[5-[4-(4-ethylpiperazin-1-yl)-2-fluoro-6-methoxy-phenyl]-1H-pyrazol-3-yl]amino]pyrazine-2-carbonitrile;

5-[[5-[4-(4-isopropylpiperazin-1-yl)-2-fluoro-6-methoxy-phenyl]-1H-pyrazol-3-yl]amino]pyrazine-2-carbonitrile;

5-[[5-[4-[[(3S)-1-ethylpyrrolidin-3-yl]oxymethyl]-2-methoxy-phenyl]-1H-pyrazol-3-yl]amino]pyrazine-2-carbonitrile;

5-[[5-[4-[[(3S)-1-isopropylpyrrolidin-3-yl]oxymethyl]-2-methoxy-phenyl]-1H-pyrazol-3-yl]amino]pyrazine-2-carbonitrile;

5-[[5-[4-[[(3R)-1-ethylpyrrolidin-3-yl]oxymethyl]-2-methoxy-phenyl]-1H-pyrazol-3-yl]amino]pyrazine-2-carbonitrile;

5-[[5-[4-[[(3R)-1-isopropylpyrrolidin-3-yl]oxymethyl]-2-methoxy-phenyl]-1H-pyrazol-3-yl]amino]pyrazine-2-carbonitrile;

5-[[5-[4-(4-isobutylpiperazin-1-yl)-2-methoxy-phenyl]-1H-pyrazol-3-yl]amino]pyrazine-2-carbonitrile;

5-[[5-[4-[(1-ethyl-4-piperidyl)methyl]-2-methoxy-phenyl]-1H-pyrazol-3-yl]amino]pyrazine-2-carbonitrile;

5-[[5-[4-[(1-isopropyl-4-piperidyl)methyl]-2-methoxy-phenyl]-1H-pyrazol-3-yl]amino]pyrazine-2-carbonitrile;

5-[[5-[4-[(1-ethyl-4-piperidyl)methyl-methyl-amino]-2-methoxy-phenyl]-1H-pyrazol-3-yl]amino]pyrazine-2-carbonitrile;

5-[[5-[4-[(2R)-4-isopropylmorpholin-2-yl]-2-methoxy-phenyl]-1H-pyrazol-3-yl]amino]pyrazine-2-carbonitrile;

5-[[5-[4-[(1-isopropyl-4-piperidyl)methyl-methyl-amino]-2-methoxy-phenyl]-1H-pyrazol-3-yl]amino] pyrazine-2-carbonitrile;

5-[[5-[4-[[(2R)-1-ethylpyrrolidin-2-yl]methyl]-2-methoxy-phenyl]-1H-pyrazol-3-yl]amino]pyrazine-2-carbonitrile;

5-[[5-[4-[(2S)-4-isopropylmorpholin-2-yl]-2-methoxy-phenyl]-1H-pyrazol-3-yl]amino]pyrazine-2-carbonitrile;

5-[[5-[4-[[(2R)-1-isopropylpyrrolidin-2-yl]methyl]-2-methoxy-phenyl]-1H-pyrazol-3-yl]amino]pyrazine-2-carbonitrile;

5-[[5-[4-[[(2S)-1-ethylpyrrolidin-2-yl]methyl]-2-methoxy-phenyl]-1H-pyrazol-3-yl]amino]pyrazine-2-carbonitrile;

5-[[5-(2-methoxy-4-piperazin-1-yl-phenyl)-1H-pyrazol-3-yl]amino]pyrazine-2-carbonitrile;

5-[[5-[4-[[(2S)-1-isopropylpyrrolidin-2-yl]methyl]-2-methoxy-phenyl]-1H-pyrazol-3-yl]amino]pyrazine-2-carbonitrile;

5-[[5-[4-[[(3S)-1-isopropylpyrrolidin-3-yl]amino]-2-methoxy-phenyl]-1H-pyrazol-3-yl]amino]pyrazine-2-carbonitrile;

5-[[5-[4-[[(3R)-1-isopropylpyrrolidin-3-yl]amino]-2-methoxy-phenyl]-1H-pyrazol-3-yl]amino]pyrazine-2-carbonitrile;

5-[[5-[4-[[(3R)-1-ethylpyrrolidin-3-yl]amino]-2-methoxy-phenyl]-1H-pyrazol-3-yl]amino]pyrazine-2-carbonitrile;

5-[[5-[4-[[(3S)-1-ethylpyrrolidin-3-yl]amino]-2-methoxy-phenyl]-1H-pyrazol-3-yl]amino]pyrazine-2-carbonitrile;

5-[[5-[2-methoxy-4-[(3S)-3-methylpiperazin-1-yl]phenyl]-1H-pyrazol-3-yl]amino]pyrazine-2-carbonitrile;

5-[[5-[4-[(3R)-3-ethylpiperazin-1-yl]-2-methoxy-phenyl]-1H-pyrazol-3-yl]amino]pyrazine-2-carbonitrile;

5-[[5-[4-[(3S)-3-isopropylpiperazin-1-yl]-2-methoxy-phenyl]-1H-pyrazol-3-yl]amino]pyrazine-2-carbonitrile;

5-[[5-[4-[(3R)-3-isopropylpiperazin-1-yl]-2-methoxy-phenyl]-1H-pyrazol-3-yl]amino]pyrazine-2-carbonitrile;

5-[[5-[4-(3,3-dimethylpiperazin-1-yl)-2-methoxy-phenyl]-1H-pyrazol-3-yl]amino]pyrazine-2-carbonitrile;

and salts and tautomers thereof.

15. A pharmaceutical composition comprising the compound as defined in claim 1 and a pharmaceutically acceptable excipient.

16. A combination comprising the compound as defined in claim 1 and another chemotherapeutic agent.

17. A compound according to claim 2 wherein $R^1$ is selected from hydrogen and methoxy.

18. A compound according to claim 17 wherein:
$R^2$ is hydrogen or methoxy;
$R^3$ is hydrogen;
$R^4$ is hydrogen;
$R^5$ is hydrogen or cyano;
$R^6$ is hydrogen;
A is selected from a bond, —NH—CH$_2$; —(CH$_2$)—NH—(CH$_2$)—; —(CH$_2$)—NH—(CH$_2$)—(CH$_2$)—; —(CH$_2$)—(CH$_2$)—NH—(CH$_2$)—; and —(CH$_2$)—NH—(CHMe)—; and
$R^7$ is selected from 4-morpholinyl, 1-methyl-4-piperidinyl and
1-cyclopropylcarbonyl-piperidin-4-yl.

19. A compound according to claim 17 wherein:
$R^1$ is methoxy;
$R^2$ is hydrogen or methoxy;
$R^3$ is hydrogen;
$R^4$ is hydrogen;
$R^5$ is cyano;
$R^6$ is hydrogen; and
(i) when A is a bond, $R^7$ is 1-methyl-4-piperidinyl; or
(ii) when A is —(CH$_2$)—NH—(CH$_2$)—, $R^7$ is cyclopropylcarbonyl-piperidin-4-yl; or
(iii) when A is (CH$_2$)—NH—(CH$_2$)—(CH$_2$)—, $R^7$ is 4-morpholinyl.

20. The compound of claim 14 wherein the compound is a hydrochloride salt.

21. The compound of claim 14 wherein the compound is 5-[[5-[4-(4-fluoro-1-methyl-4-piperidyl)-2-methoxy-phenyl]-1H-pyrazol-3-yl]amino]pyrazine-2-carbonitrile or a salt thereof.

22. The compound of claim 14 wherein the compound is 5-[[5-[4-(4-isopropylpiperazin-1-yl)-2-methoxy-phenyl]-1H-pyrazol-3-yl]amino]pyrazine-2-carbonitrile or a salt thereof.

23. The compound of claim 14 wherein the compound is 5-[[5-[4-(4-ethylpiperazin-1-yl)-2-fluoro-6-methoxy-phenyl]-1H-pyrazol-3-yl]amino]pyrazine-2-carbonitrile or a salt thereof.

* * * * *

UNITED STATES PATENT AND TRADEMARK OFFICE
CERTIFICATE OF CORRECTION

PATENT NO. : 10,010,547 B2
APPLICATION NO. : 15/118072
DATED : July 3, 2018
INVENTOR(S) : Robert George Boyle et al.

Page 1 of 1

It is certified that error appears in the above-identified patent and that said Letters Patent is hereby corrected as shown below:

In the Claims

In Column 200, Lines 51-52, Claim 2: please delete "$C_{1-4}$alkyl" and insert --$C_{1-4}$ alkyl--.

In Column 201, Lines 31-33, Claim 10: please delete "$C_{1-4}$hydrocarbylsulfonyl, oxo, di-$C_{1-4}$hydrocarbylamino-$C_{1-4}$alkanoyl;" and insert --$C_{1-4}$ hydrocarbylsulfonyl, oxo, di-$C_{1-4}$ hydrocarbylamino-$C_{1-4}$ alkanoyl;--.

Signed and Sealed this
Sixteenth Day of October, 2018

Andrei Iancu
*Director of the United States Patent and Trademark Office*